US009885055B2

(12) United States Patent
Daniell

(10) Patent No.: US 9,885,055 B2
(45) Date of Patent: Feb. 6, 2018

(54) CHLOROPLASTS ENGINEERED TO EXPRESS PHARMACEUTICAL PROTEINS

(75) Inventor: Henry Daniell, Winter Park, FL (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 13/558,511

(22) Filed: Jul. 26, 2012

(65) Prior Publication Data
US 2013/0058969 A1 Mar. 7, 2013

Related U.S. Application Data

(63) Continuation of application No. 11/915,666, filed as application No. PCT/US2006/021024 on May 30, 2006, now abandoned.

(60) Provisional application No. 60/685,734, filed on May 27, 2005.

(51) Int. Cl.

| | |
|---|---|
| *C07K 14/62* | (2006.01) |
| *C12N 15/82* | (2006.01) |
| *A61K 39/07* | (2006.01) |
| *A61K 39/12* | (2006.01) |
| *A61K 39/15* | (2006.01) |
| *A61K 39/29* | (2006.01) |
| *C07K 14/56* | (2006.01) |
| *A61K 39/00* | (2006.01) |

(52) U.S. Cl.

CPC ...... *C12N 15/8257* (2013.01); *A61K 39/0008* (2013.01); *A61K 39/07* (2013.01); *A61K 39/12* (2013.01); *A61K 39/15* (2013.01); *A61K 39/29* (2013.01); *C07K 14/56* (2013.01); *C12N 15/8214* (2013.01); *C12N 15/8258* (2013.01); *A61K 39/00* (2013.01); *A61K 2039/517* (2013.01); *A61K 2039/542* (2013.01); *A61K 2039/6037* (2013.01); *C07K 2319/55* (2013.01); *C07K 2319/60* (2013.01); *C12N 2720/12334* (2013.01); *C12N 2770/24234* (2013.01)

(58) Field of Classification Search
CPC C12N 15/8257; C12N 15/8214; C07K 14/62; A61K 9/1274
See application file for complete search history.

(56) References Cited

U.S. PATENT DOCUMENTS

| | | | | |
|---|---|---|---|---|
| 5,693,507 A | 12/1997 | Daniell | | |
| 5,877,402 A | 3/1999 | Maliga | | |
| 5,932,479 A | 8/1999 | Daniell | | |
| 6,642,053 B1 | 11/2003 | Daniell | | |
| 6,680,426 B2 | 1/2004 | Daniell | | |
| 7,129,391 B1 * | 10/2006 | Daniell | | 800/278 |
| 2002/0162135 A1 | 10/2002 | Daniell | | |
| 2004/0177402 A1 | 9/2004 | Daniell | | |
| 2005/0108792 A1 | 5/2005 | Daniell | | |
| 2006/0246489 A1 * | 11/2006 | Svetlov | C12Q 1/00 | 435/6.16 |

FOREIGN PATENT DOCUMENTS

| | | |
|---|---|---|
| WO | 1999010513 | 3/1999 |
| WO | 2001064850 | 9/2001 |
| WO | 2001064927 | 9/2001 |
| WO | 2001064929 | 9/2001 |
| WO | 2001072959 | 10/2001 |
| WO | 2003057834 | 7/2003 |
| WO | 2004005467 | 1/2004 |
| WO | 2004005480 | 1/2004 |
| WO | 2004005521 | 1/2004 |

OTHER PUBLICATIONS

Arakawa et al. (Nature Biotechnology, 1998, vol. 16, p. 934-938).*
Groskreutz et al. (Journal of Biological Chemistry, 1994, vol. 269, p. 6241-6245).*
Riedl et al. (Nature Reviews, 2004, vol. 5, p. 897-907).*
Daniell et al., Multigene engineering: dawn of an exciting new era in biotechnology, Curr Opin Biotechnol., 2002, 136-41, 13(2).
Daniell et al., Milestones in chloroplast genetic engineering: an environmentally friendly era in biotechnology, Trends Plant Sci., 2002, 84-91, 7(2).
Watson et al., Expression of Bacillus anthracis protective antigen in transgenic chloroplasts of tobacco, a non-food/feed crop, Vaccine, 2004, 4374-84, 22(31-32).

Kumar et al., Plastid-expressed betaine aldehyde dehydrogenase gene in carrot cultured cells, roots, and leaves confers enhanced salt tolerance, Plant Physiol., 2004, 2843-54, 136(1).

Kumar et al., Stable transformation of the cotton plastid genome and maternal inheritance of transgenes, Plant Mol Biol., 2004, 203-16, 56(2).

Quesada-Vargas et al., Characterization of heterologous multigene operons in transgenic chloroplasts: transcription, processing, and translation, Plant Physiol., 2005, 1746-62, 138(3).

Koya et al., Plant-based vaccine: mice immunized with chloroplast-derived anthrax protective antigen survive anthrax lethal toxin challenge, Infect Immun., 2005, 8266-74, 73(12).

Daniell et al., Breakthrough in chloroplast genetic engineering of agronomically important crops, Trends Biotechnol., 2005, 238-45, 23(5).

* cited by examiner

*Primary Examiner* — Agnieszka Boesen

(74) *Attorney, Agent, or Firm* — Kathleen D. Rigaut; Dann, Dorfman, Herrell and Skillman, P.C.

(57) ABSTRACT

Vaccines for conferring immunity in mammals to infective pathogens are provided, as well as vectors and methods for plastid transformation of plants to produce protective antigens and vaccines for oral delivery. The vaccines are operative by parenteral administration as well. The invention also extends to the transformed plants, plant parts, and seeds and progeny thereof. The invention is applicable to monocot and dicot plants.

5 Claims, 52 Drawing Sheets

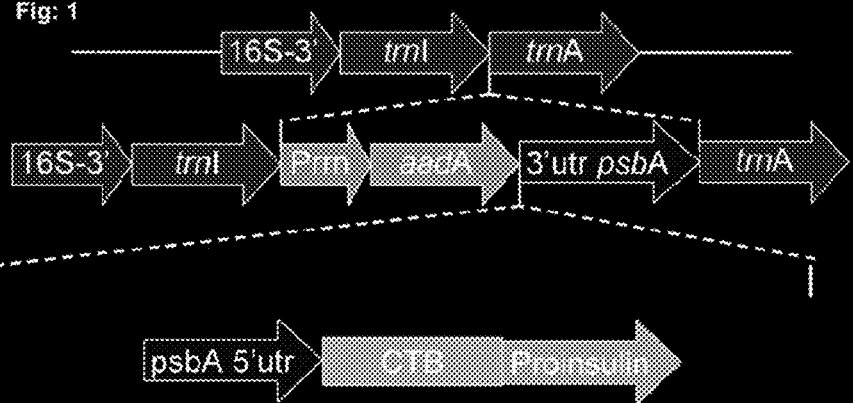
Fig: 1
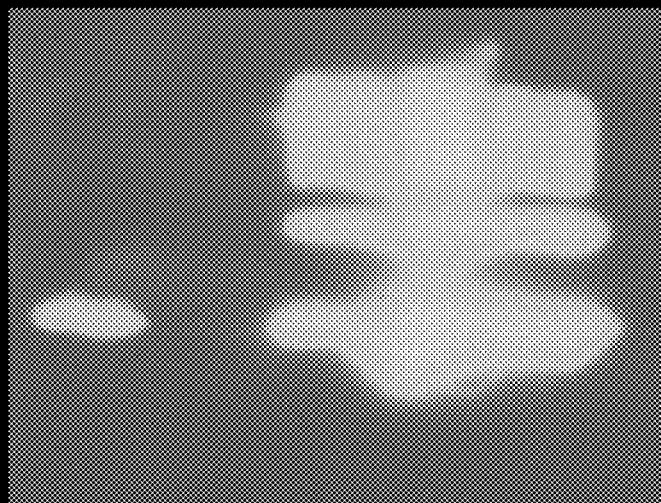
Fig: 2

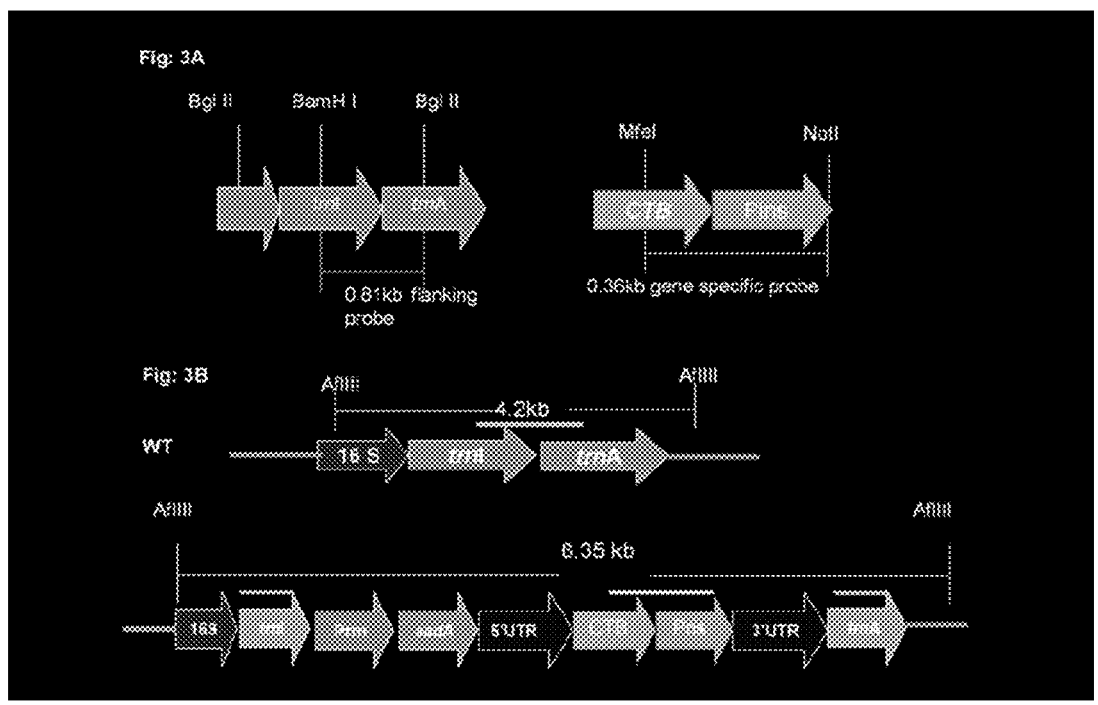

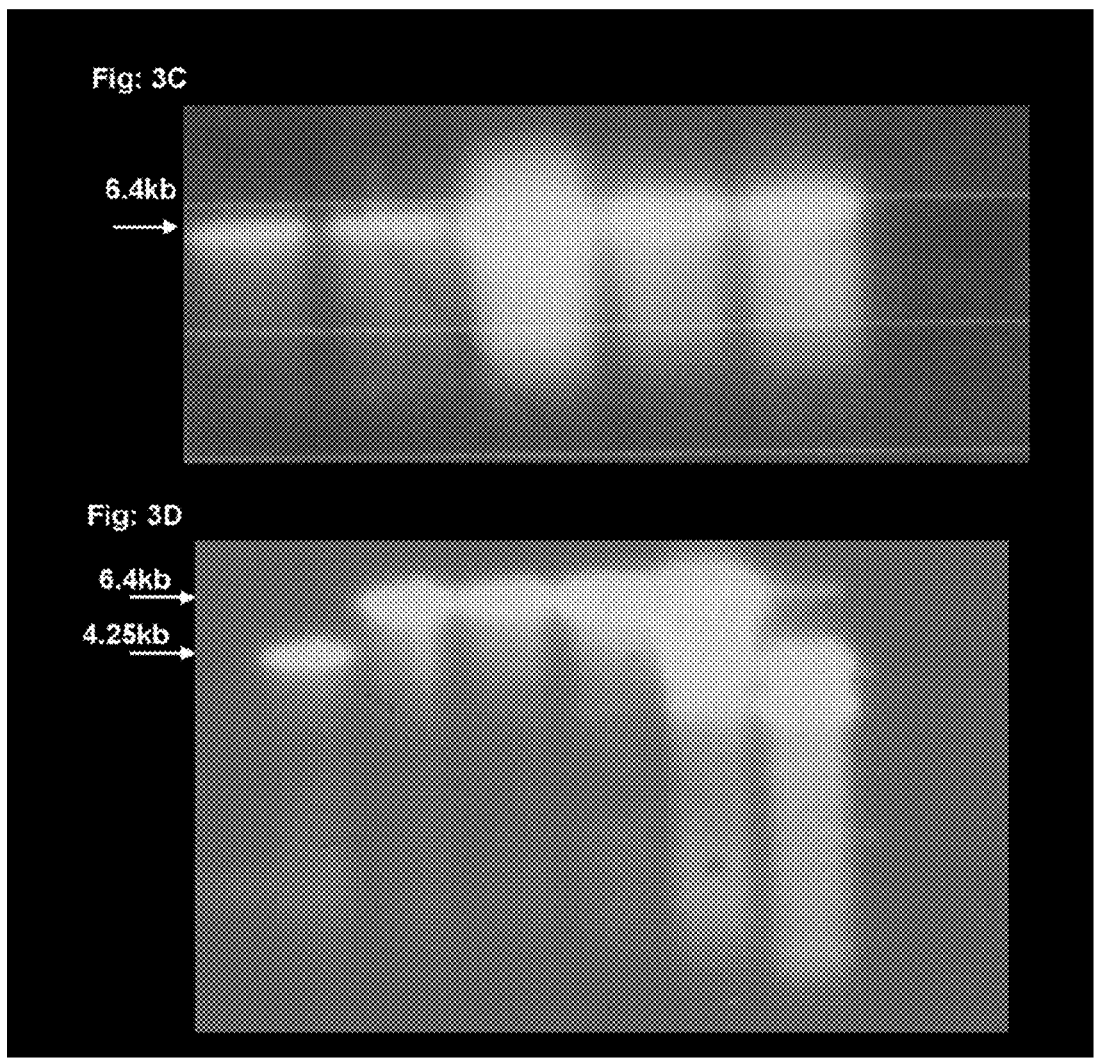

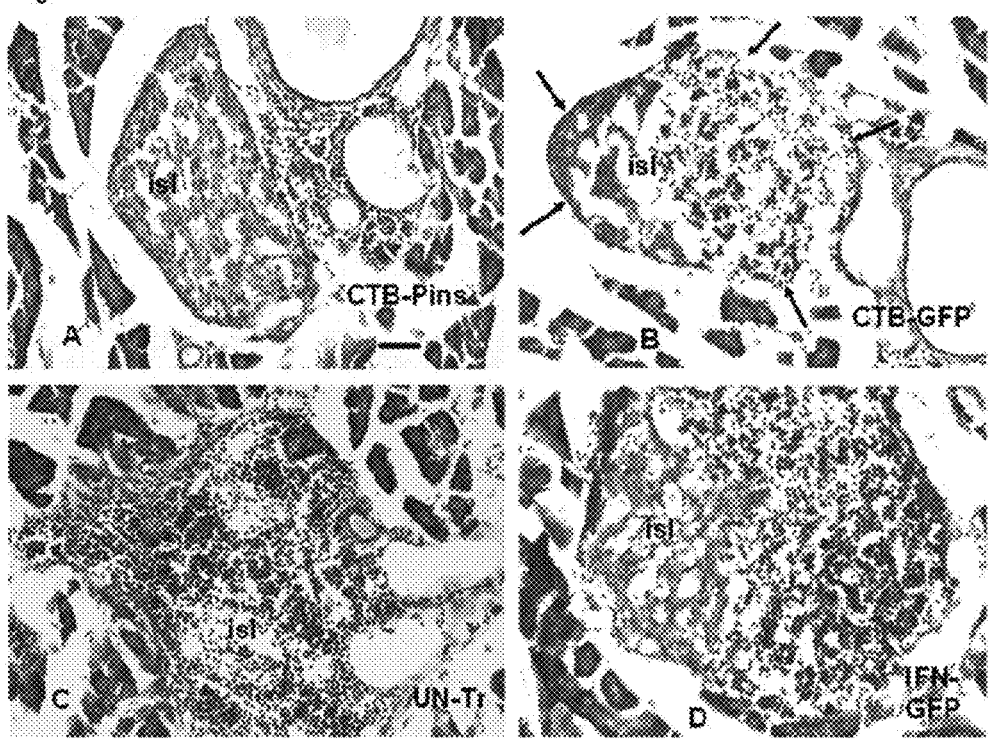

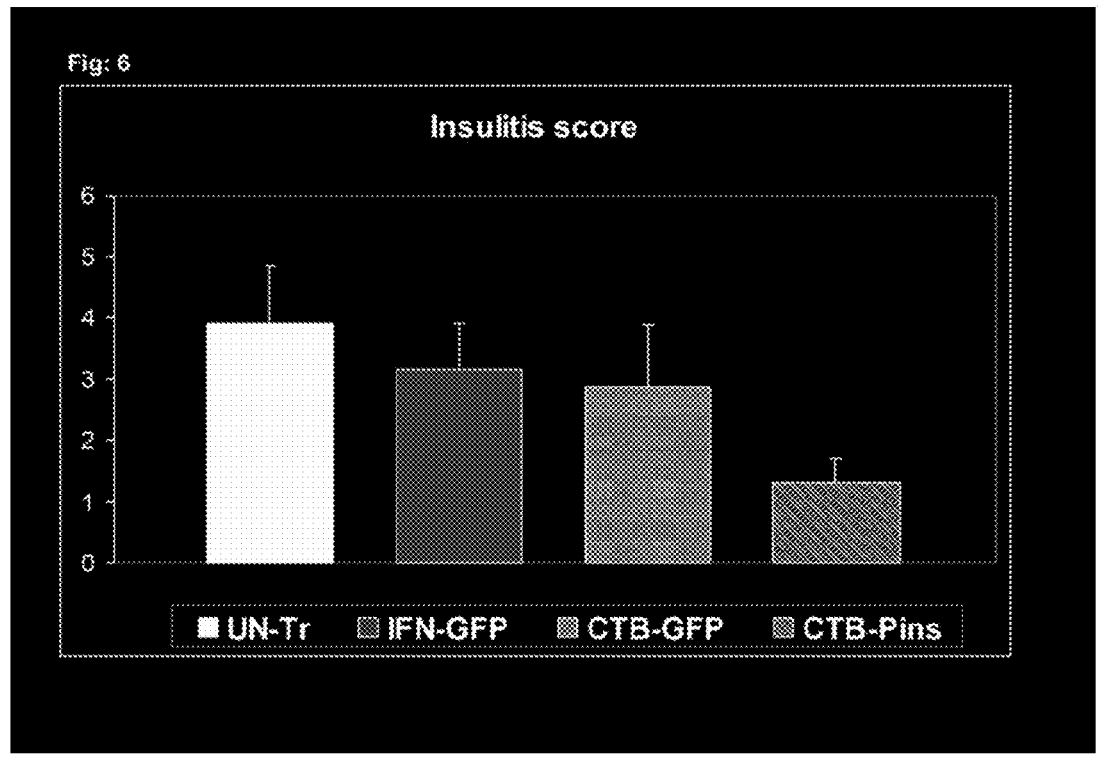
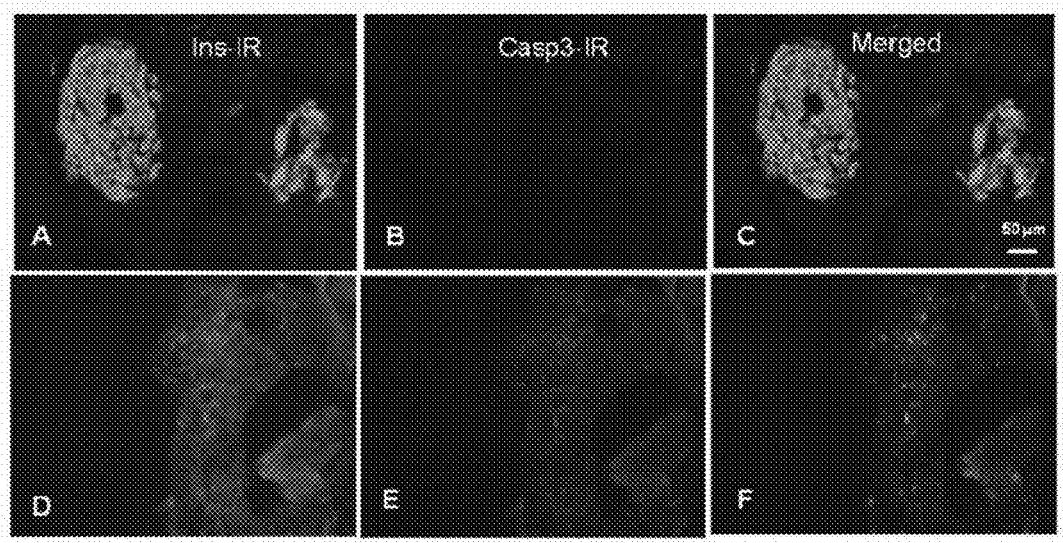

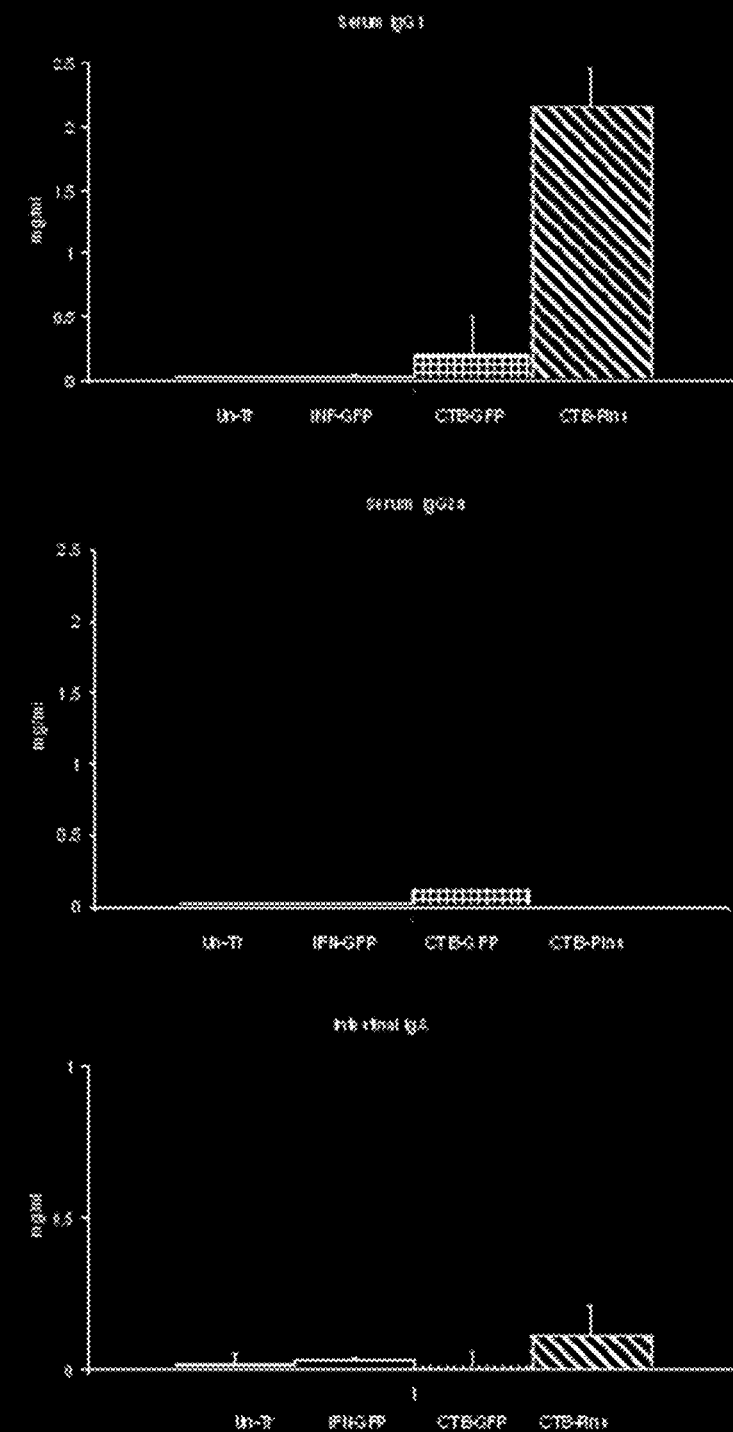

A. 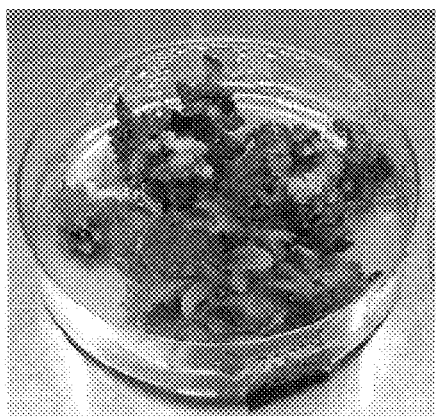 B. 
FIG. 19
A.  B.
FIG. 20

A.
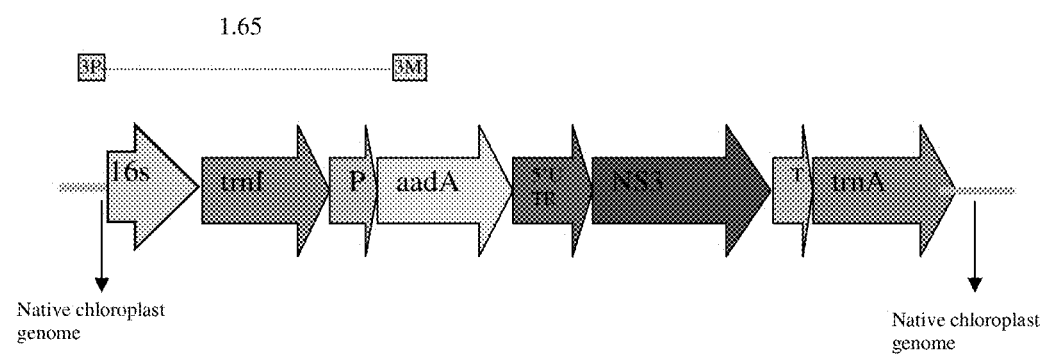
B.
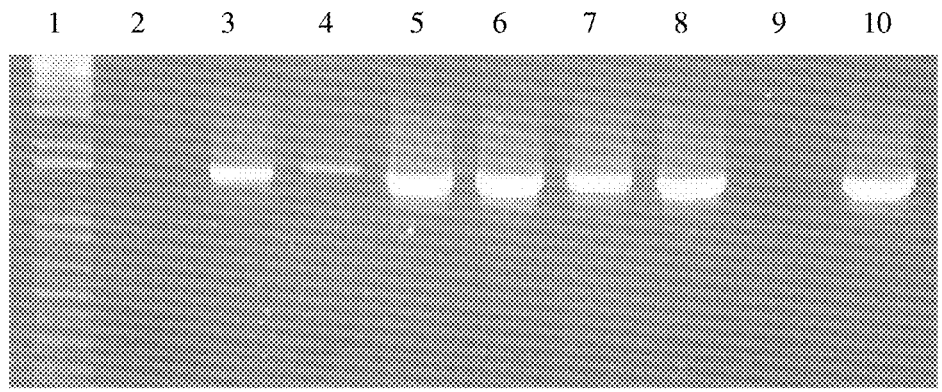
FIG. 21

A.
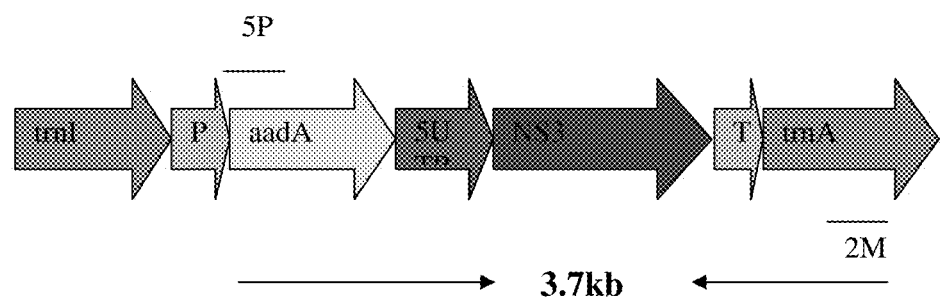
B.
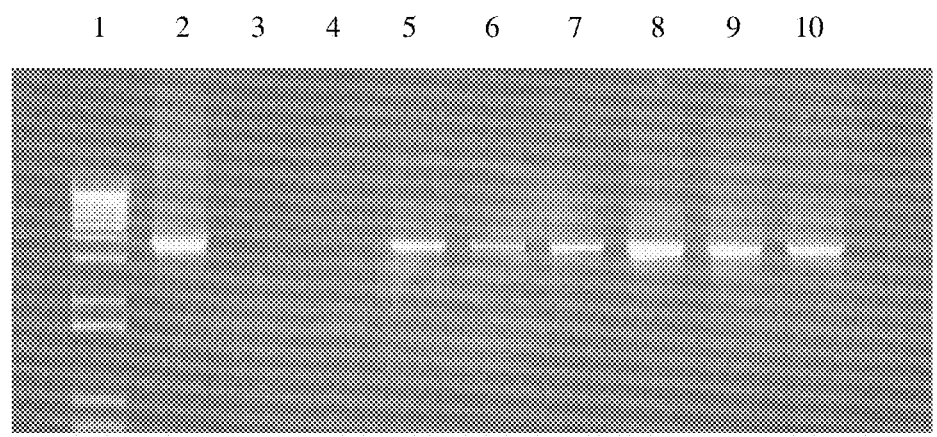
FIG. 22

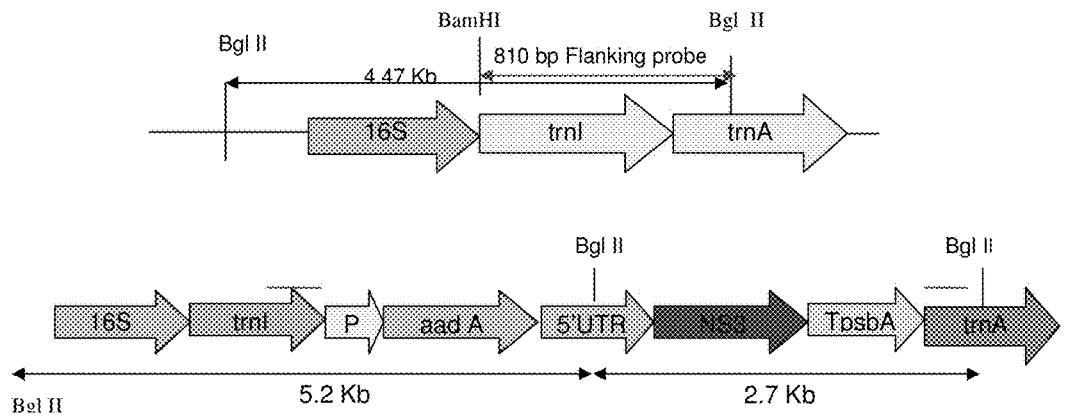
A.
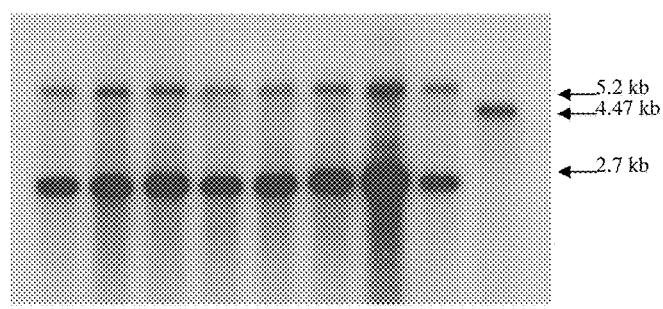
FIG. 23
B.

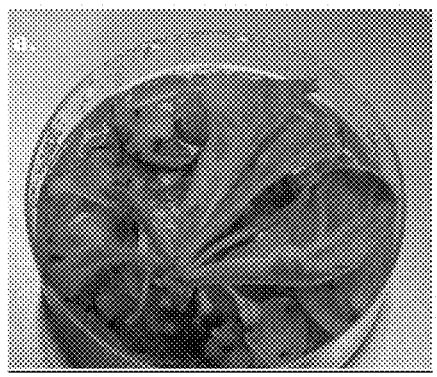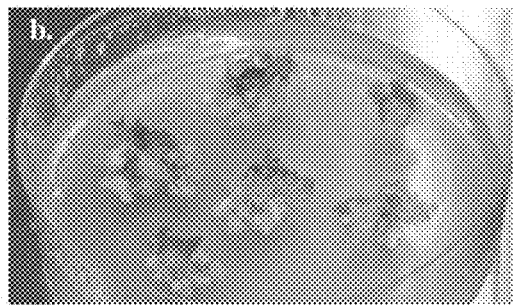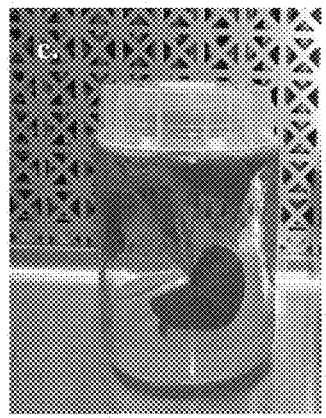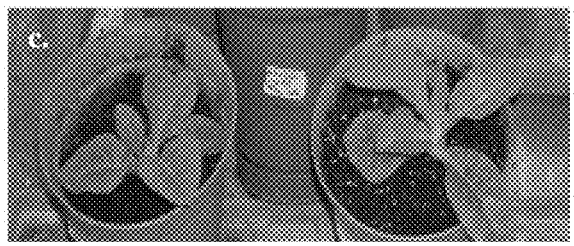
FIG. 31.

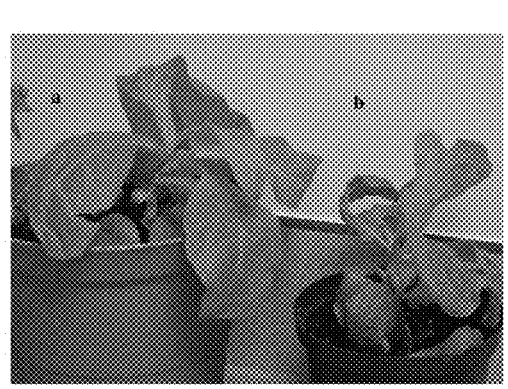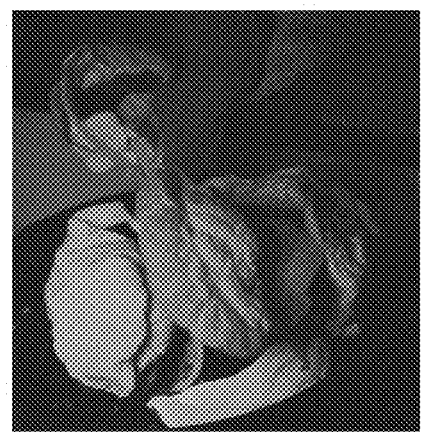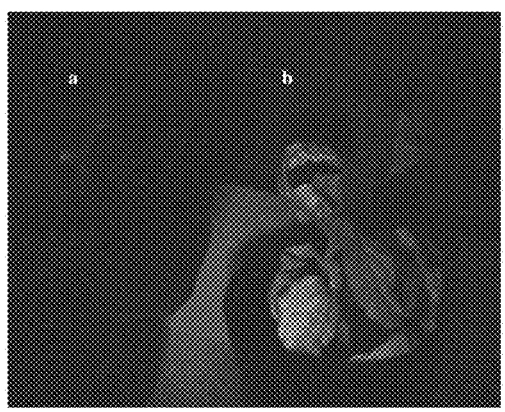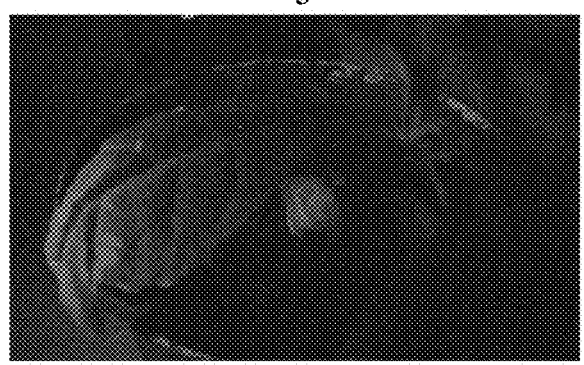
FIG. 36.

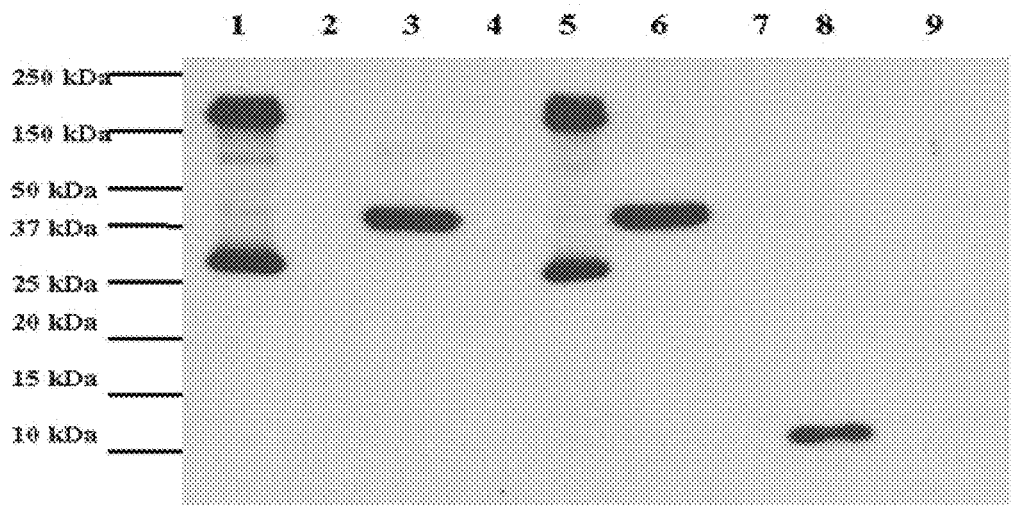
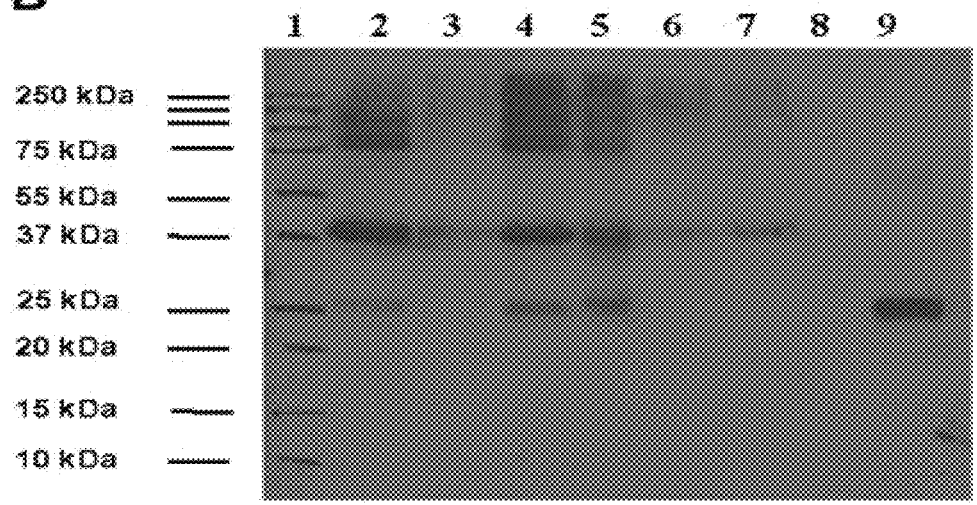
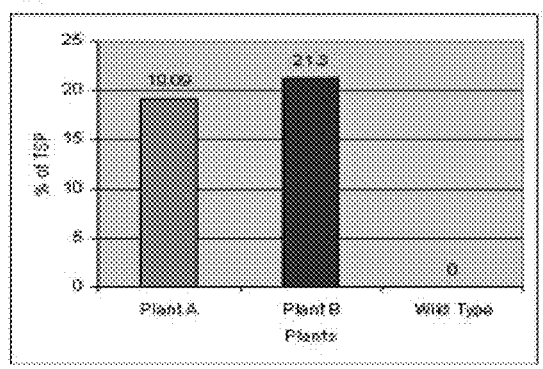
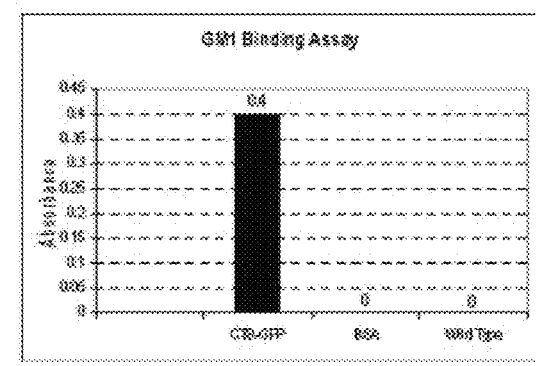
FIG. 41

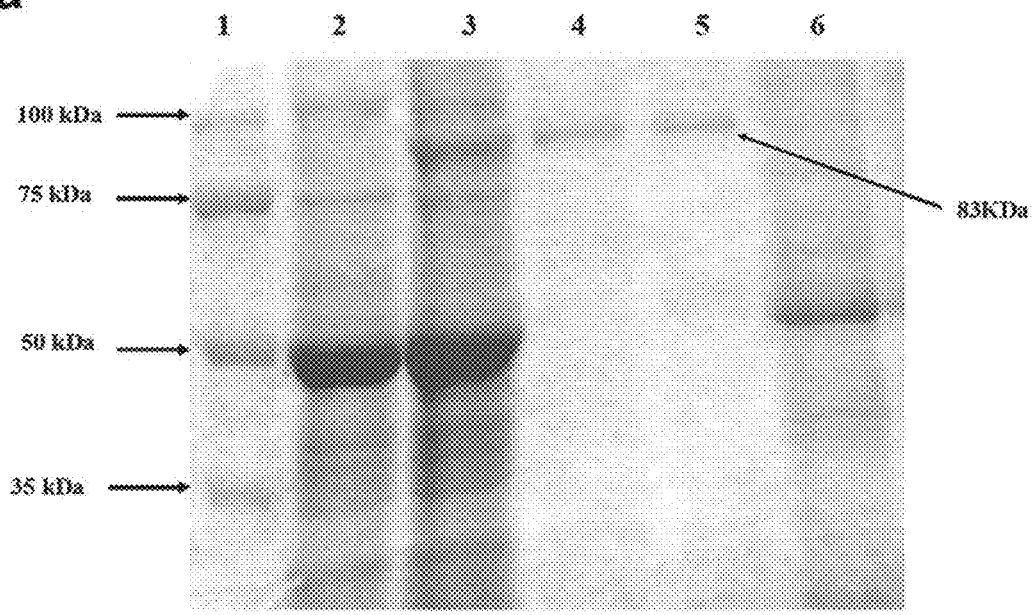
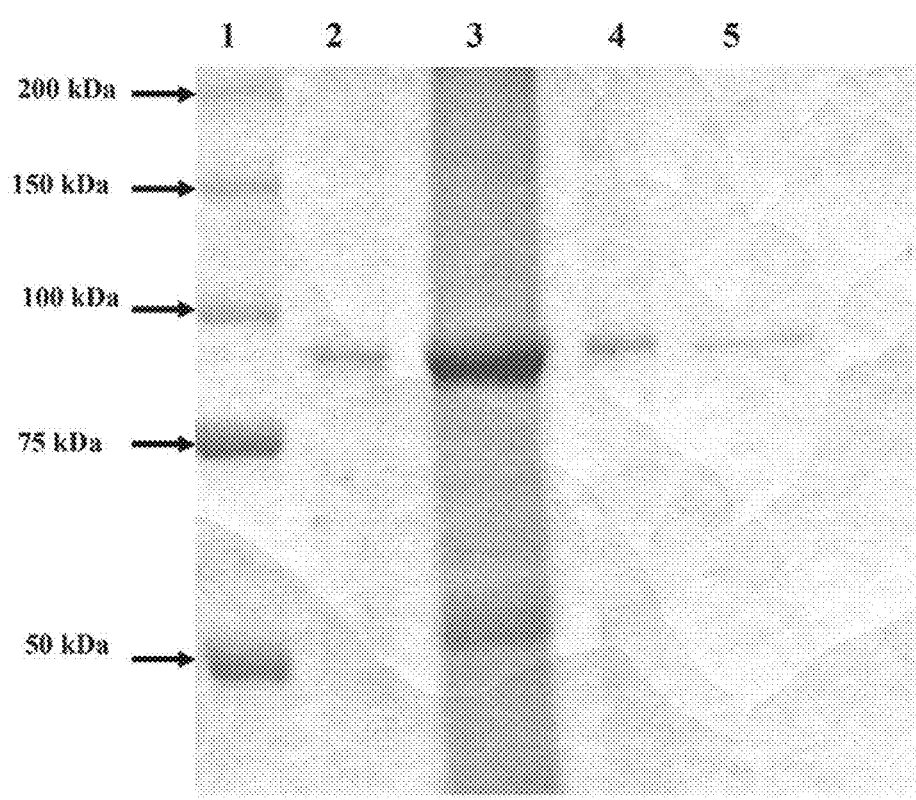
FIG. 54

SEQUENCE LISTING

<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      hinge region peptide

<400> SEQUENCE: 1

Gly Pro Gly Pro
1

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer 3P

<400> SEQUENCE: 2
aaaacccgtc ctcgttcgga ttgc                                          24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer 3M

<400> SEQUENCE: 3
ccgcgttgtt tcatcaagcc ttacg                                         25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer 5P

<400> SEQUENCE: 4
ctgtagaagt caccattgtt gtgc                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer 2M

<400> SEQUENCE: 5
gactgcccac ctgagagcgg aca                                           23

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer NS3-F

<400> SEQUENCE: 6
cagtgtggag ctcttgtacg taccaccatg gcg                                33

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer NS3

<400> SEQUENCE: 7
tggagagcac ctgcggccgc ccatcgacct gg                                 32

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer M13 forward

<400> SEQUENCE: 8
tgaccggcag caaaatg                                                  17

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer M13 reverse

<400> SEQUENCE: 9
ggaaacagct atgaccatg                                                19

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      furin cleavage site peptide

<400> SEQUENCE: 10

Pro Arg Ala Arg Arg
1               5

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaacccgtc ctccgttcgg attgc                                         25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
tgactgccca cctgagagcg gaca                                          24
```

```
<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      cleavage site peptide

<400> SEQUENCE: 13

Arg Ala Arg Arg
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```

CHLOROPLASTS ENGINEERED TO EXPRESS PHARMACEUTICAL PROTEINS

RELATED APPLICATIONS

This application is a continuation of U.S. Ser. No. 11/915,666 filed Nov. 27, 2007, which claims priority to PCT/US06/21024 filed May 30, 2006, which claims the benefit of U.S. Ser. No. 60/685,734, filed May 27, 2005, which are incorporated herein in their entirety by reference.

SEQUENCE LISTING

The instant application contains a Sequence Listing which has been submitted in ASCII format via EFS-Web and is hereby incorporated by reference in its entirety. Said ASCII copy, created on Nov. 8, 2012, is named 166912US.txt and is 3,473 bytes in size.

STATEMENT REGARDING FEDERALLY SPONSORED RESEARCH

This invention was made with government support under grant no. 58-3611-2-106 awarded by the United States Department of Agriculture/Agricultural Research Service. The government has certain rights in the invention.

BACKGROUND

Progress has been made in engineering plant cells to produce useful proteins. For example, plants have been shown to express potentially medically important proteins that may be used for immunization against pathogens. Many infectious diseases require booster vaccinations or multiple antigens to induce and maintain protective immunity. Advantages of plant-derived vaccines include the delivery of multiple antigens, low cost of production, storage & transportation, elimination of medical personnel and sterile injections, heat stability, antigen protection through bioencapsulation, the generation of systemic & mucosal immunity and improved safety via the use of a subunit vaccine and absence of human pathogens. Despite cases of successful expression of proteins, the development of plant derived medically important compositions is still in its formative stages.

BRIEF DESCRIPTION OF THE DRAWINGS

FIG. 1: CTB-Pris Construct and Site of Integration into the Chloroplast Genome: Insertion of 5'UTR-CTB-human proinsulin into the chloroplast transformation vector pLD and the site of integration into the chloroplast genome between the trnI and trnA genes.

FIG. 2: Western blot analysis of chloroplast transgenic lines probed with proinsulin antibody: Lane 1 *E. coli* crude extract expressing CTB-Pins, lane 2 untransformed plant extract, lanes 3-5 plant extract of transgenic lines.

FIG. 3A: Southern blot probed with BamHI/BglII 0.81 kb flanking sequence. Gene specific probe (0.36 kb) was obtained by MfeI/NotI digestion of pLD-5CP vector. 3B: Illustration of untransformed and transformed chloroplast genomes at the site of integration of transgenes. Untransformed & transformed plant DNA was digested with AflIII and AflIII. The expected size for each fragment is shown along with the hybridization site for the flanking sequence probe and gene specific probe. 3C: Southern Blot with gene specific probe: Lanes 1-5: DNA from transgenic lines; lane 6: untransformed wild type. 3D: Southern Blot with flanking sequence probe: Lane 1: untransformed wild type, lanes 2-6: transgenic lines.

FIG. 4: A) Haematoxylin & Eosin staining of a section of the pancreas (showing an islet: isl) of a mouse treated with CTB-Pins for 7 weeks. There is no cellular infiltration inside the islet. Lymphocytes are shown outside the islet (arrow in A). In 4 B) arrows indicate the borders of an islet in the pancreas of a mouse treated with CTB-GFP (a control group). Blue dots show cellular infiltration of the islet. FIG. 4C shows a big islet with severe lymphocytic infiltration in a mouse treated with untransformed (UN-Tr) plant leaf material. In 4 D) a severe lymphocytic infiltration in a mouse treated with interferon-GFP (IFN-GFP) is shown.

FIG. 6: Lymphocytic infiltrations (insulitis) were scored by blindly evaluating 50 sections per pancreas of each animal in different experimental groups as indicated. The NOD mice treated with CTB-Pins scored significantly lower ($P<0.05$) than the untransformed (UN-Tr) plant, interferon-GFP (IFN-GFP), or CTB-GFP plant treated groups. ANOVA was done through Excel, and the P value is less that 0.001. The bars represent the standard deviation.

FIG. 7: Insulin immunoreactivity in Langerhans islets of a mouse treated with CTBPins (A). In 7 B, Caspase-3 immunostaining in the same section is shown in the red channel. Merged picture of A and B is shown in 7C. 7D) A view of the pancreas which shows the remnant of a large langerhans islet of the mouse treated with untransformed plant leaf material. E) shows the Caspase-3 immunoreactivity in the same section taken in red channel. F) shows the merged picture of D and E; here, all the remaining cells which are also depleted of insulin, are expressing the active caspase-3.

FIG. 10: Serum levels of IgG1 in NOD mice treated with CTB-Pins expressing plant leaf material as compared to the control groups treated with untransformed plant, the CTB-IFN or CTB-GFP plant expressing leaf material.

regulatory sequences into the chloroplast genome by two homologous recombination events.

Figure 30:
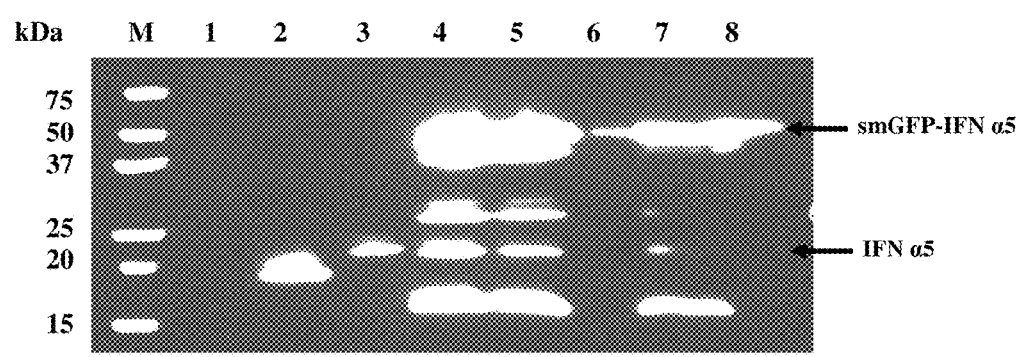
Figure 32:
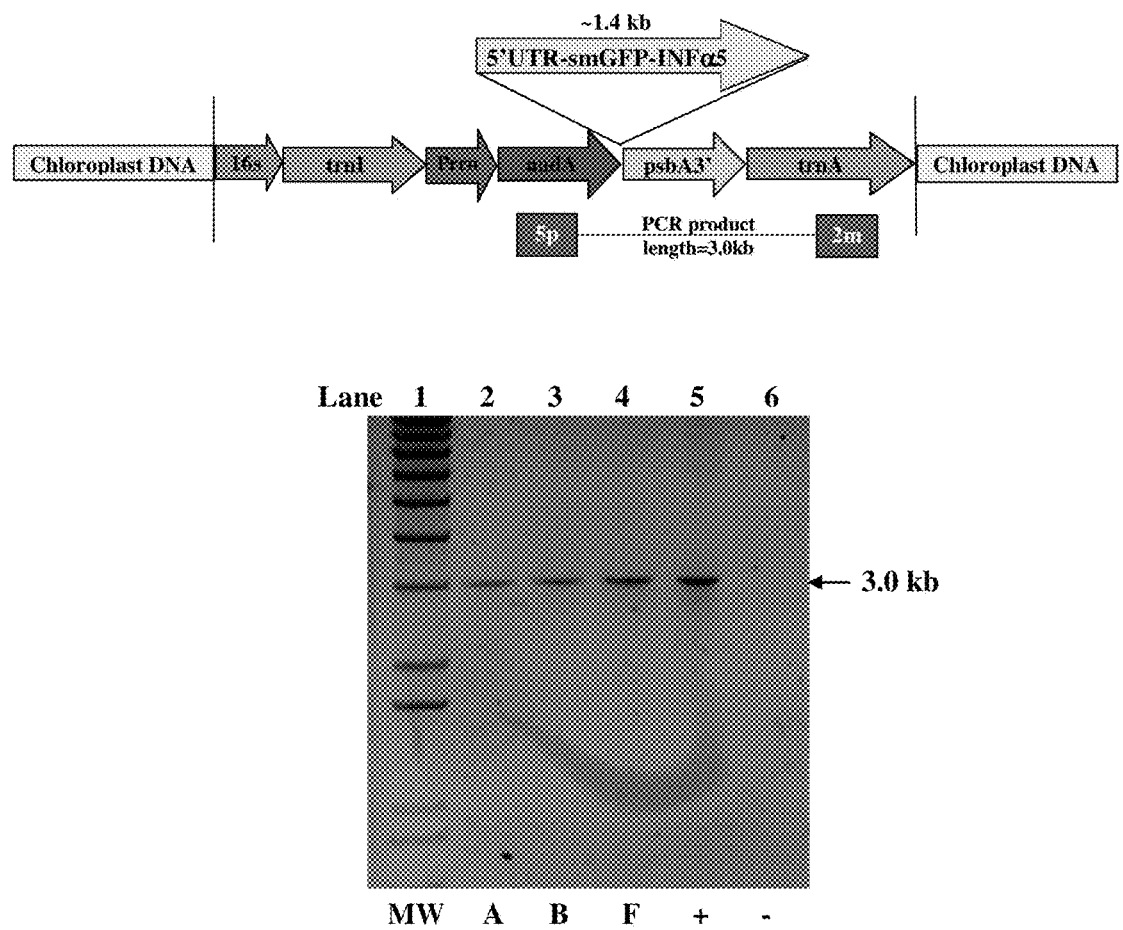
Figure 33:
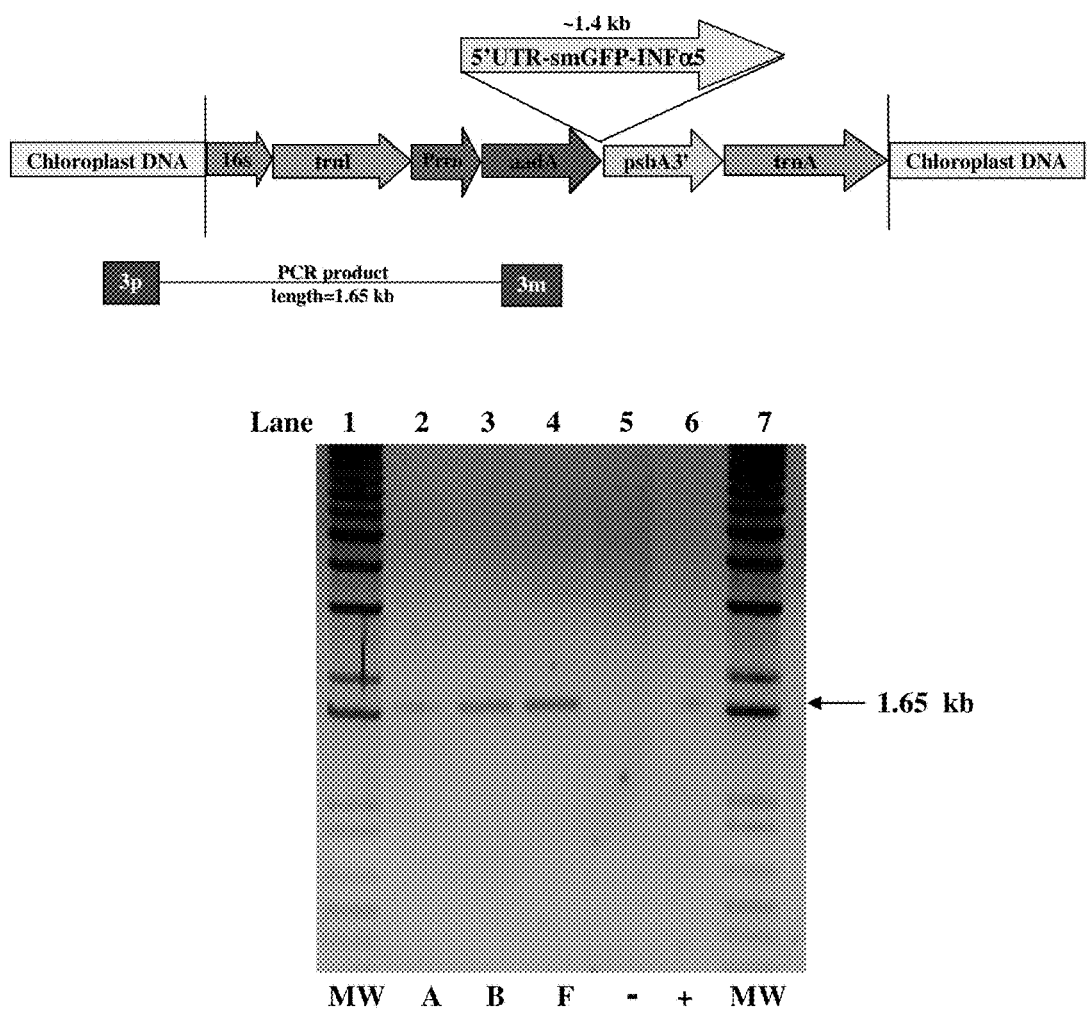
Figure 34:
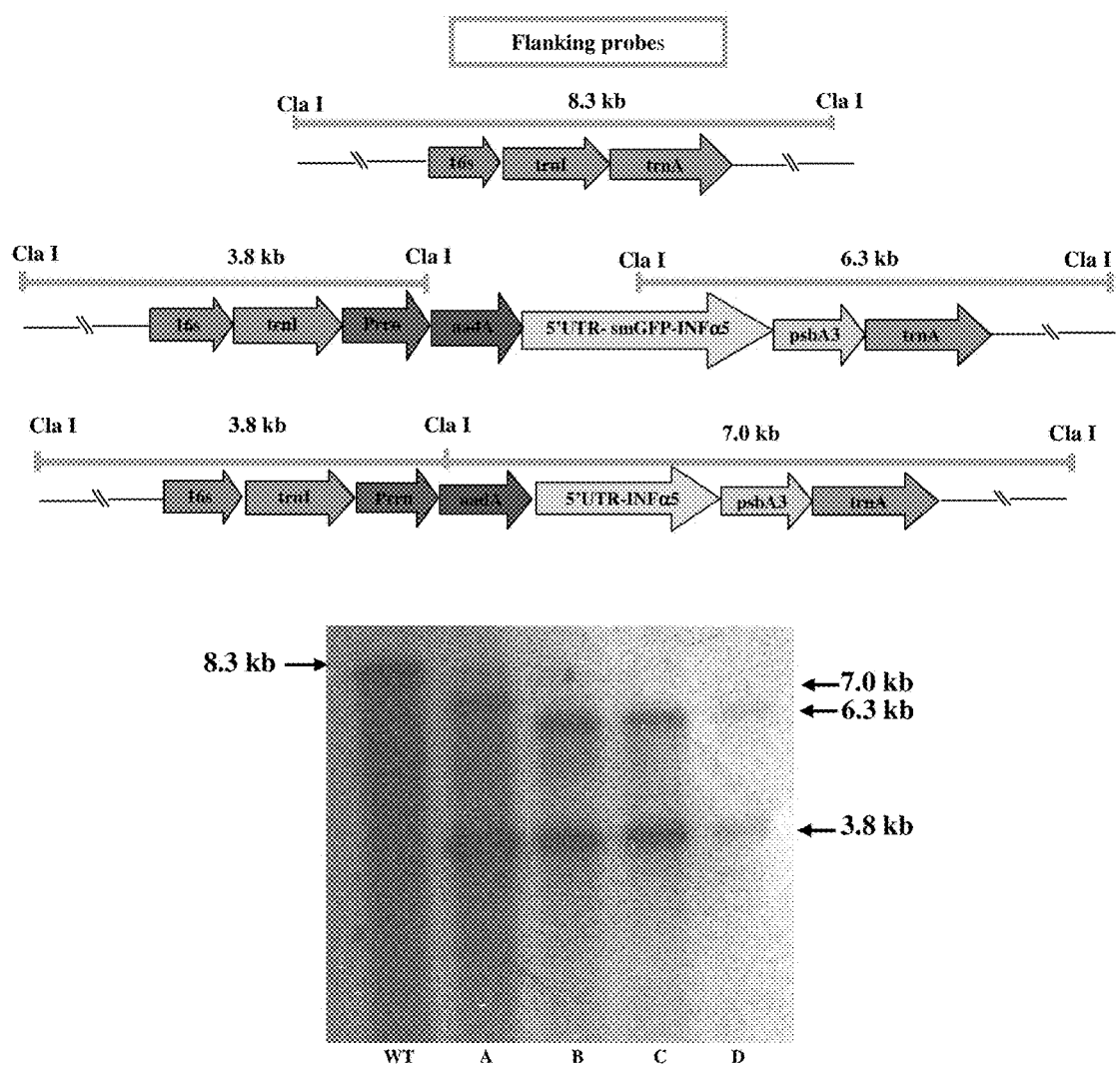
Figure 35:
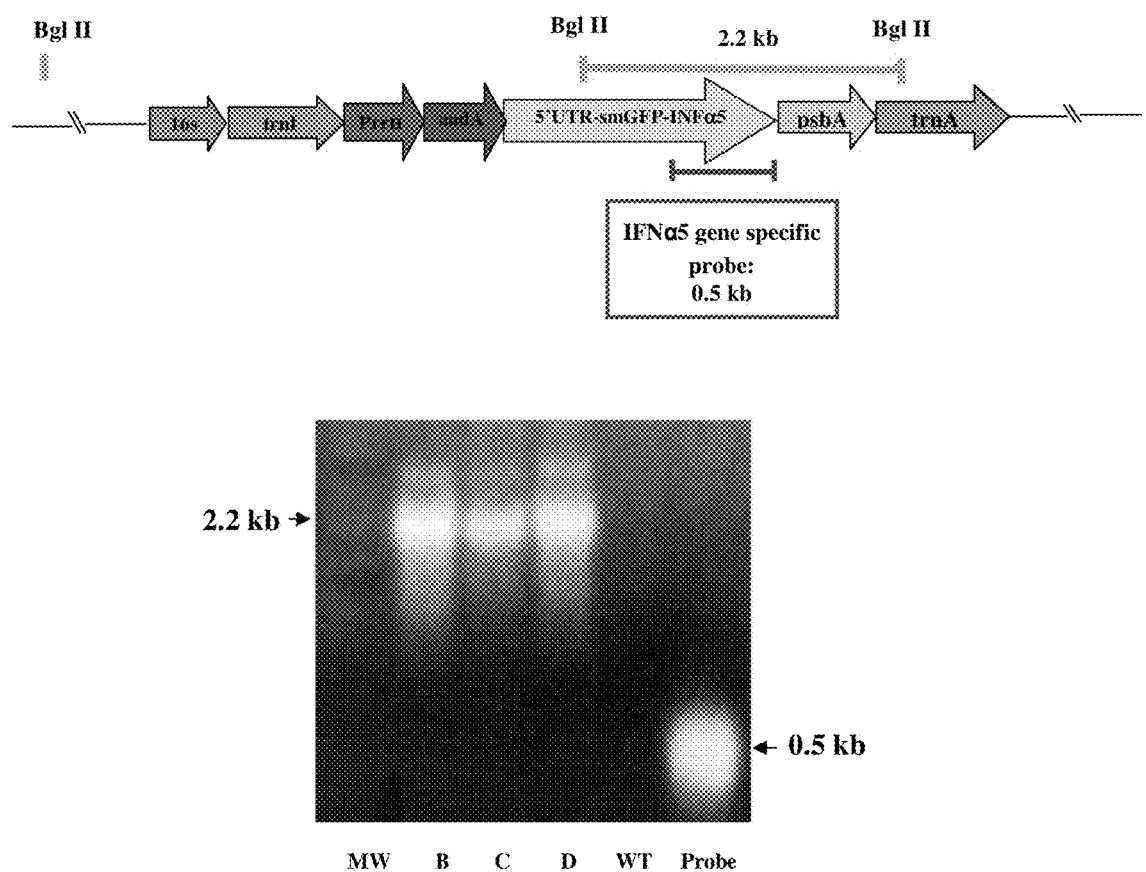
Figure 37:
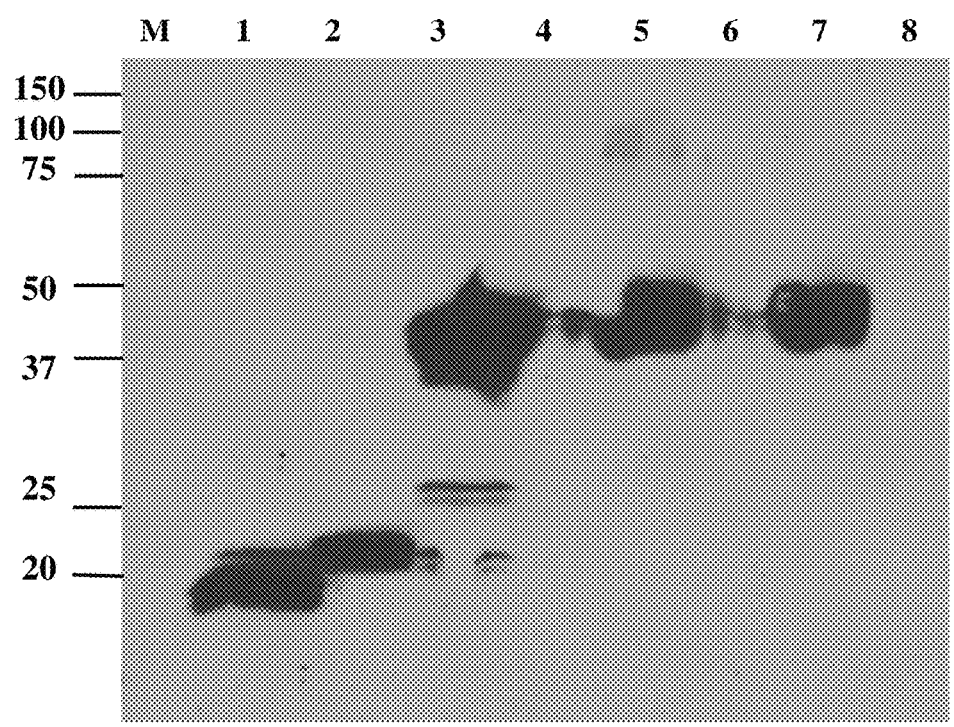
Figure 38:
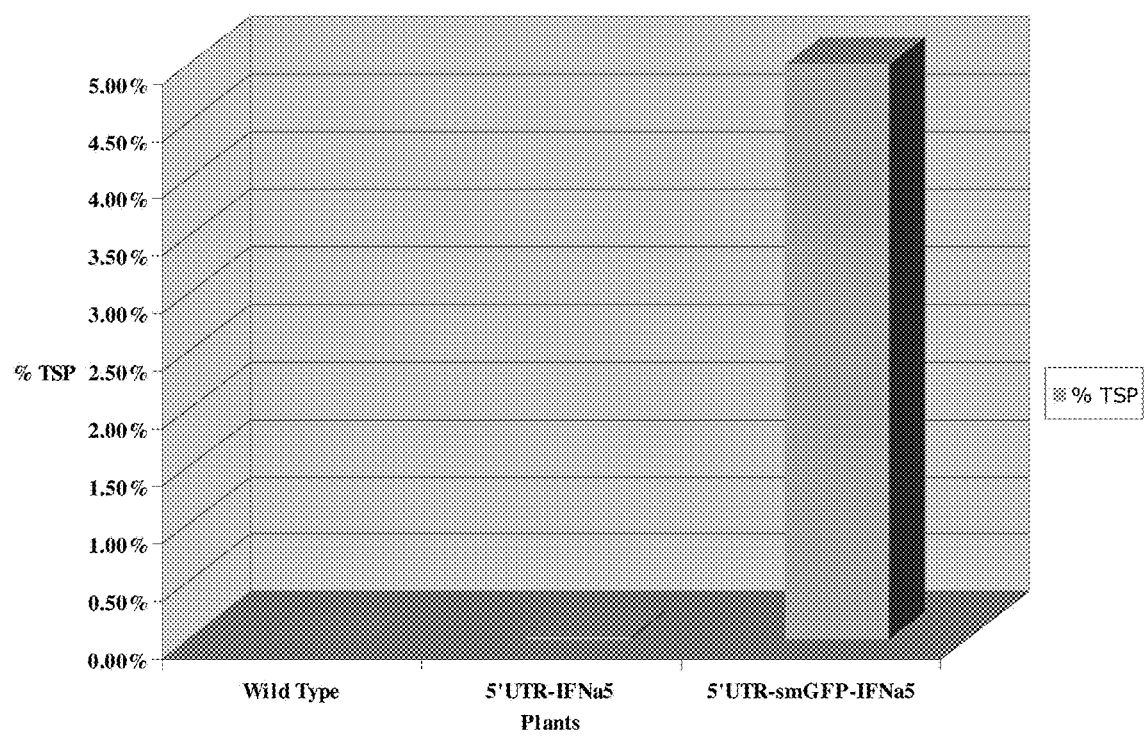

FIG. 30. Expression of smGFP-IFNα5 in *E. coli* and Immunoblot Anal

F) Section of the liver from a mouse fed by wild-type (untransformed) plant. G) Section of the liver from a mouse fed by IFN-GFP expressing plant. H) GFP-immunoreactivity in the spleen of mouse fed orally by CTB-GFP expressing plant. Arrows indicate various cells with a higher GFP content. I) Section of the spleen from a mouse fed by wild-type (untransformed) plant. J) Section of the spleen from a mouse fed by wild-type (untransformed) plant. Scale bar for A-D_50 µm, Scale bar for E-J_25 µm.

Figure 44:
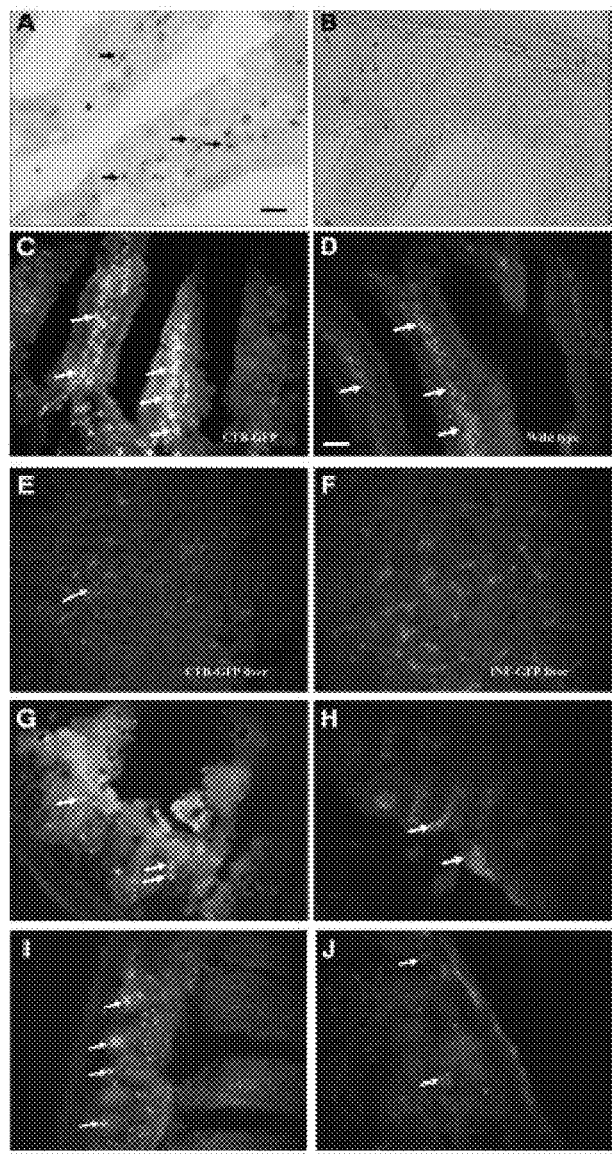

FIG. 44. Immunohistochemistry of ileum, liver, and spleen tissues of mice fed with CTBGFP expressing leaves or IFN-GFP expressing leaves or wild-type leaves. A) Shows a section of the intestine of a CTB-GFP treated mouse. The arrows indicate CTB in the submucosa of the intestinal villi. B) Shows a section of mouse ileum fed with wild-type plant, immunostained for CTB. C-F) Double staining for macrophage (red) and CTB (green) in mouse intestine and liver. C) Arrows show macrophages in the submucosa of the intestine containing CTB, in a mouse fed with CTB-GFP expressing plant leaf material. The merged color is yellow. D) Arrows indicate F4/80-positive cells (macrophages, in red) in a merged picture in the intestine of a mouse fed with WT leaf material. E) A merged picture showing double staining for macrophage (Kupffer cells) and CTB in mouse liver. Arrows show macrophages (red) in the liver. No sign of CTB (green) was found in the liver of a CTB-GFP fed mouse. F) Liver section of an IFN-GFP fed mouse used as a negative control for CTB. Macrophages are seen in red. G) F4/80 Ab was used as a marker of macrophages in the intestine. Arrows indicate macrophages, which have entrapped GFP (yellow after merging the red and the green). Many of the macrophages are not associated with GFP. H) Many macrophages are seen in the intestine of mouse fed with IFN-GFP expressing plant leaf material, which do not show GFP immunoreactivity. I, J) CD11c (red) and GFP (green) immunoreactivities in the mouse intestine. I) Arrows indicate CD11c (red, presumably dendritic cells, due to having a star shape morphology) with internalized GFP (green), which can be seen in yellow color when the red and green channels were merged. J) Arrows indicate CD11c-positive cells in intestine of mice fed with IFN-GFP expressing plant leaf material. Scale bar for A and B_25 µm. Scale bar for C-J_50 µm.

Figure 45:
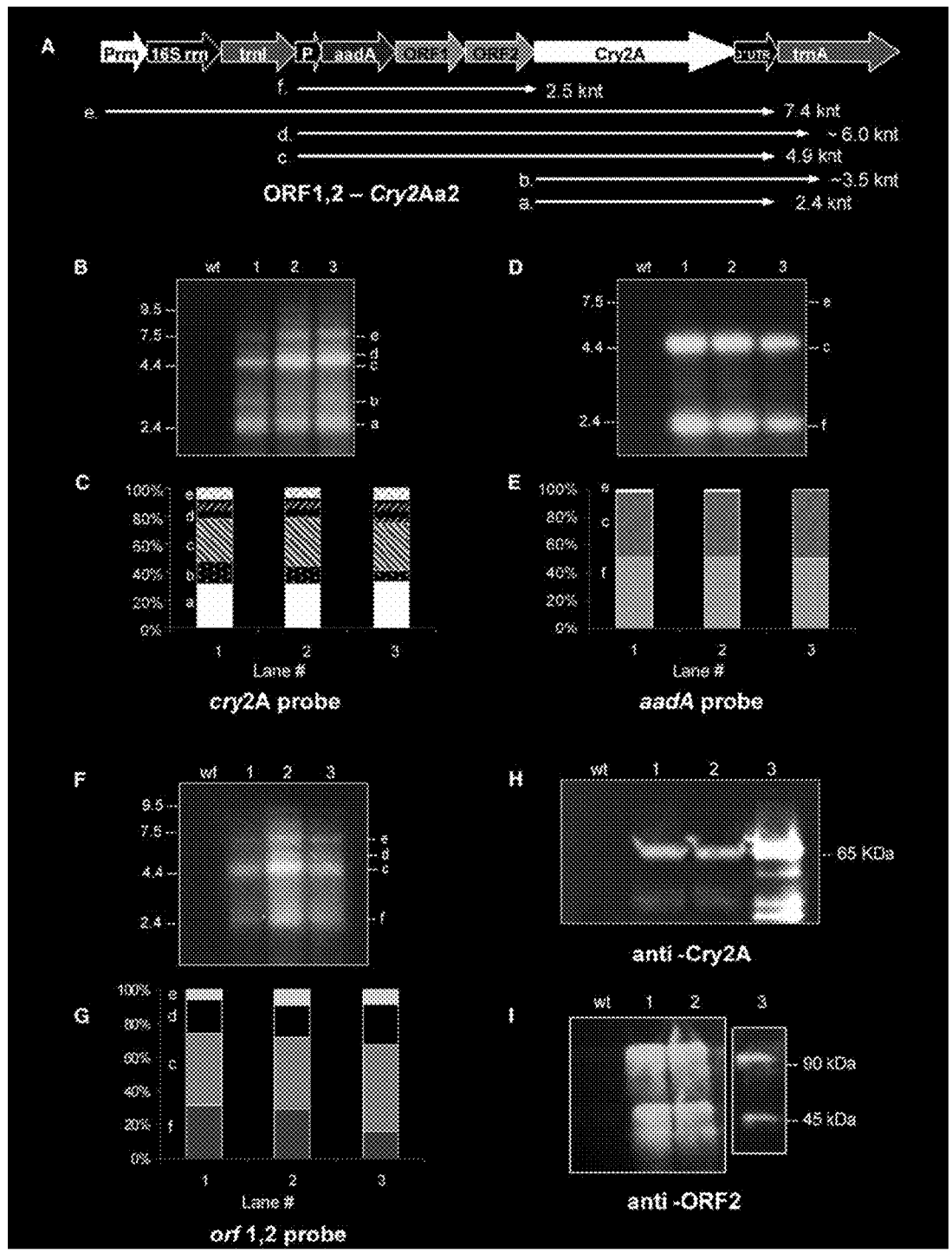

FIG. 45: Transcriptional and translational analysis of the Cry2Aa2 operon: A. Schematic representation of the orf1-orf2-cry2Aa2 operon in transgenic lines, including the aadA gene and the upstream Prrn promoter (P); upstream native chloroplast 16S ribosomal RNA gene with its respective promoter (Pan) and the trnI and trnA are shown. Arrows represent expected transcripts and their respective sizes. B. RNA hybridized with the cry2A probe, loaded as follows: wt: wild type control; lanes 1, 2 and 3: cry2Aa2 operon transgenic lines. Transcripts of the cry2Aa2 operon are indicated by lowercase letters and correspond to the transcripts depicted in A. C. Relative heterologous transcript abundance within each line hybridized with the cry2A probe. D. Transcript analysis showing RNA hybridization with the aadA probe, loaded as follows: wt: wild type control, lanes 1-3: cry2Aa2 operon transgenic lines. Transcripts of the cry2Aa2 operon are of sizes as described for the cry2Aa2 probe; f is aadA/orf1/orf2 tricistron, 2,5 knt. E. Heterologous transcript quantification for samples hybridized with the aadA probe. F. RNA hybridization using the orf1,2 probe. Samples were loaded in the same order as in D and predicted transcript sizes correspond to those observed in D. G. Relative transcript abundance within each transgenic line obtained by hybridization with the orf1,2 probeH. Western blot analysis using the Cry2Aa2 antibody. wt: wild type control; lanes 1 and 2: cry2Aa2 operon transgenic lines; lane 3: positive control (Cry2Aa2 protein). The expected polypeptide of 65 kDa is shown in both transgenic plants and the positive control. I. Western blot analysis using the ORF2 antibody. wt: wild type control; lanes 1 and 2: cry2Aa2 operon transgenic lines; lane 3: positive control (ORF2 protein). The expected polypeptide of 45 kDa is shown in both transgenic plants and the positive control.

Figure 46:
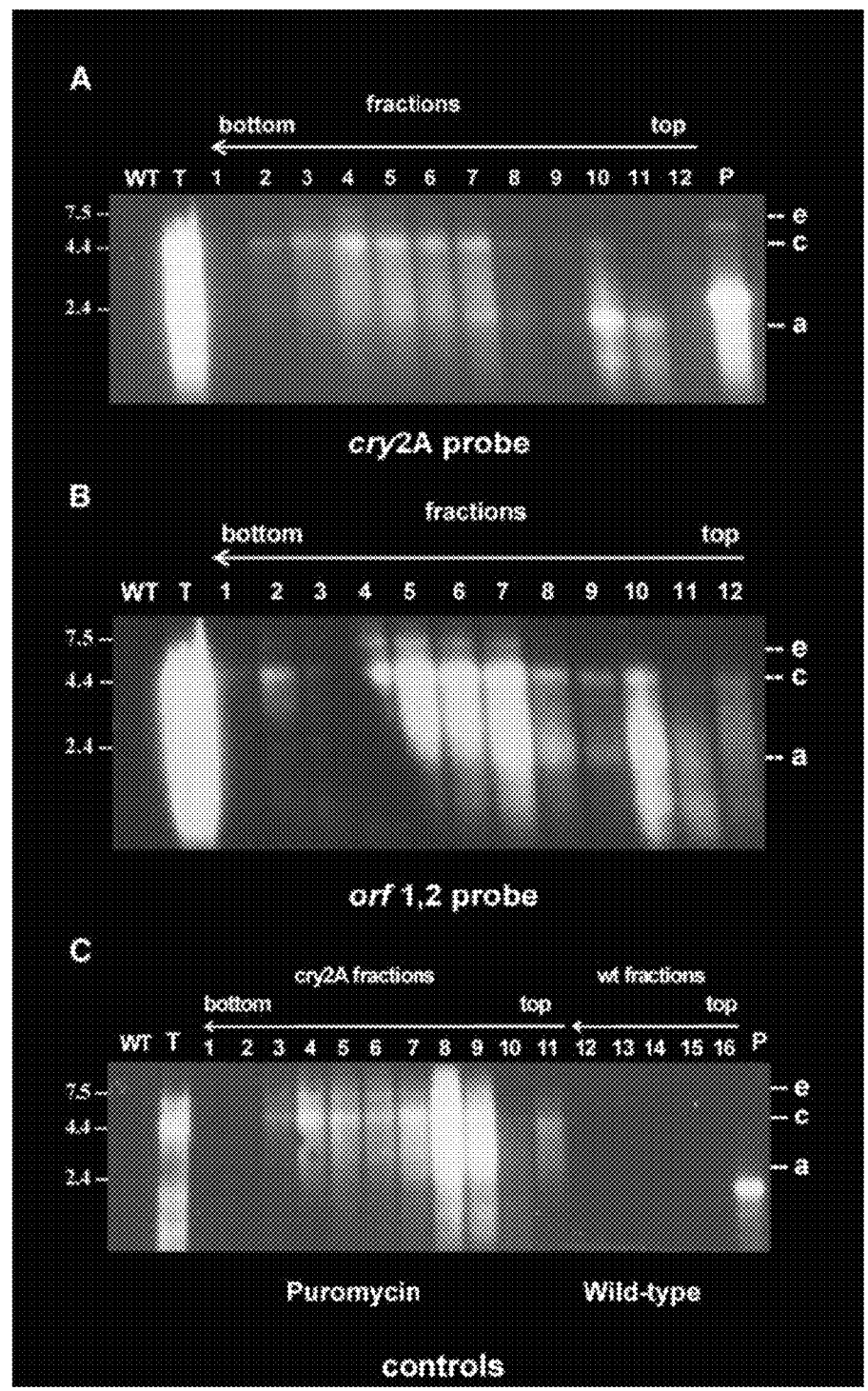

FIG. 46: Polysome fractionation assays of the cry2Aa2 operon

A. RNA hybridized with the cry2A probe after fractionation through a sucrose gradient. WT: wild type control, T: total RNA sample, lanes 1-12: RNA collected from the different fractions of the gradient. Lower fractions correspond to the bottom of the sucrose gradient (polysomal fractions). P: cry2Aa2 probe. c: transcript "c" (aadA-orf1-orf2-cry2A polycistron) described in FIG. 1A. B. Same RNA blot after stripping and re-hybridizing with orf1,2 probe. Lane P is omitted because no orf1,2 probe was loaded. C. Puromycin release and wild-type controls. Cry2Aa2 samples were treated with puromycin before loading onto sucrose gradients, whereas an additional wild-type sample was loaded onto sucrose gradients and used as a negative control. RNA was hybridized with the aadA probe. The gel was loaded as follows: WT: wild-type RNA; T: total RNA; 1-11: RNA collected from the different fractions of the sucrose gradient and hybridized with the aadA probe. Lanes 12-16: wild-type RNA from fractions 2, 4, 6, 8 and 10 collected from the sucrose gradient. P: aadA probe. c: transcript "c" (aadA-orf1-orf2-cry2A polycistron) described in FIG. 1A.

Figure 47:
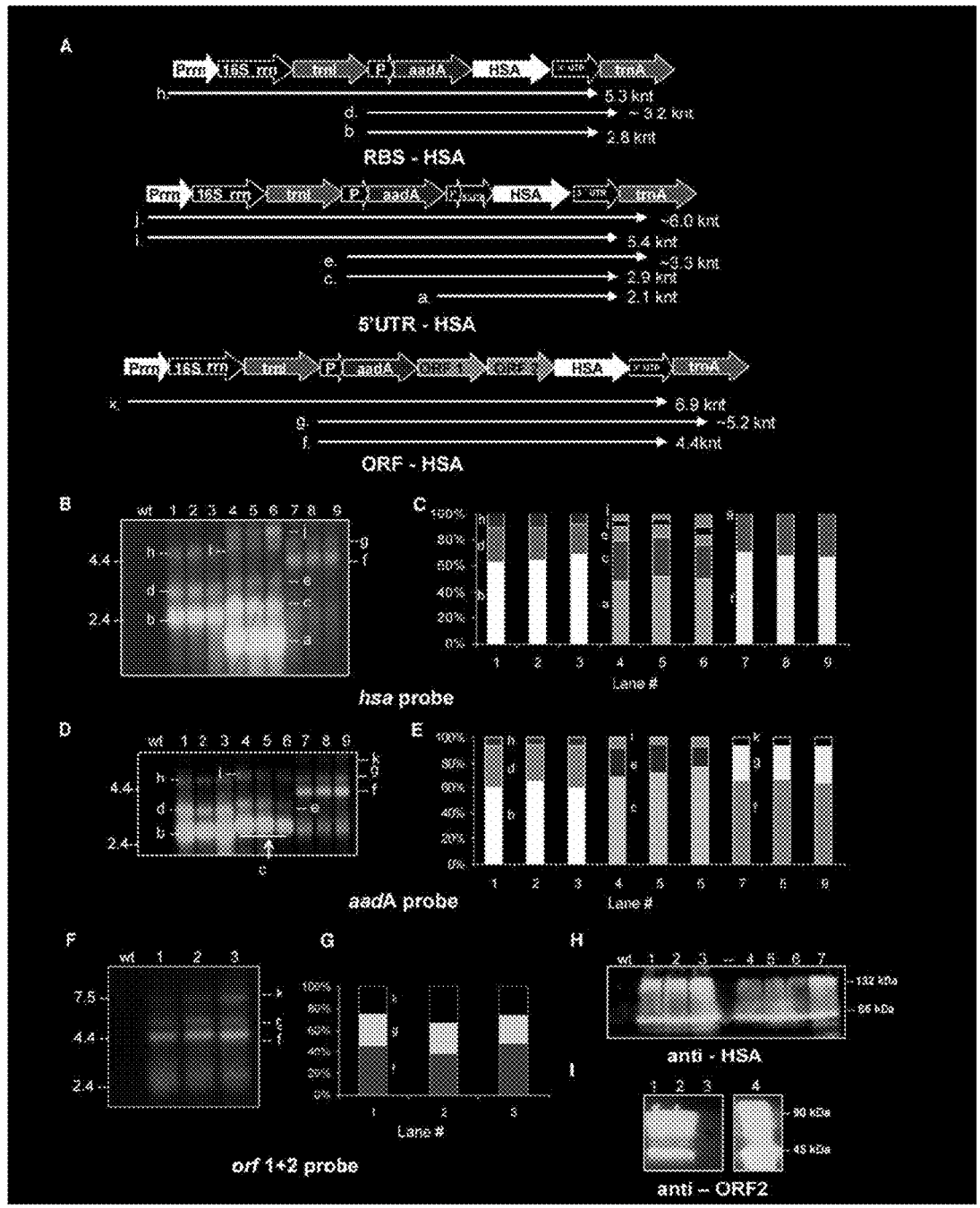

FIG. 47: Transcriptional and translational analysis of the hsa operons

A. Schematic representation of the hsa operons (rbs-hsa, 5'UTR-hsa, orf1-orf2-hsa) in transgenic lines, including the aadA gene and upstream Prrn promoter (P); upstream native chloroplast 16S ribosomal RNA gene and promoter (Prrn) as well as trnI/trnA genes are shown. Arrows represent expected transcripts and their respective sizes. B. RNA hybridization with the hsa probe. wt: wild type; lanes 1-3: rbs-hsa transgenic lines; lanes 4-6: 5'UTR-hsa transgenic lines; lanes 7-9: orf1,2-hsa transgenic lines. Lowercase letters correspond to the transcripts predicted in A. C. Relative abundance of the transcripts obtained with the hsa probe. D. mRNA transcripts hybridized with the aadA probe and loaded in the same order as in B. Transcripts a-i corresponded to the same transcripts observed in B, "k" corresponds to the 16 rrn/hsa polycistron (6,9 knt). E. Quantification of relative heterologous transcript abundance obtained with the aadA probe. F. mRNA transcripts of wild-type (wt) and orf1,2-hsa transgenic lines (lanes 1-3) hybridized with the orf1,2 probe. G. Relative abundance obtained for the transcripts detected with the orf1,2 probe. H. Western blot analysis using the HSA antibody. wt: wild type control. Lanes 1-2: RBS-hsa transgenic lines; lanes 3-4: 5'UTR-hsa transgenic lines. Lanes 5 and 6 orf1,2-hsa transgenic lines. Lane 7: positive control (HSA protein). Lane marked with (–) was left blank. All samples presented 66 kDa and 132 kDa peptides, corresponding to the size of the HSA protein, and its dimeric form, respectively. I. Western blot analysis using the ORF2 antibody. Lanes 1-2: orf1,2-hsa transgenic lines; lane 3: wild type control; lane 4: positive control (ORF protein). 45 kDa ORF2 and 90 kDa dimer are shown.

Figure 48:
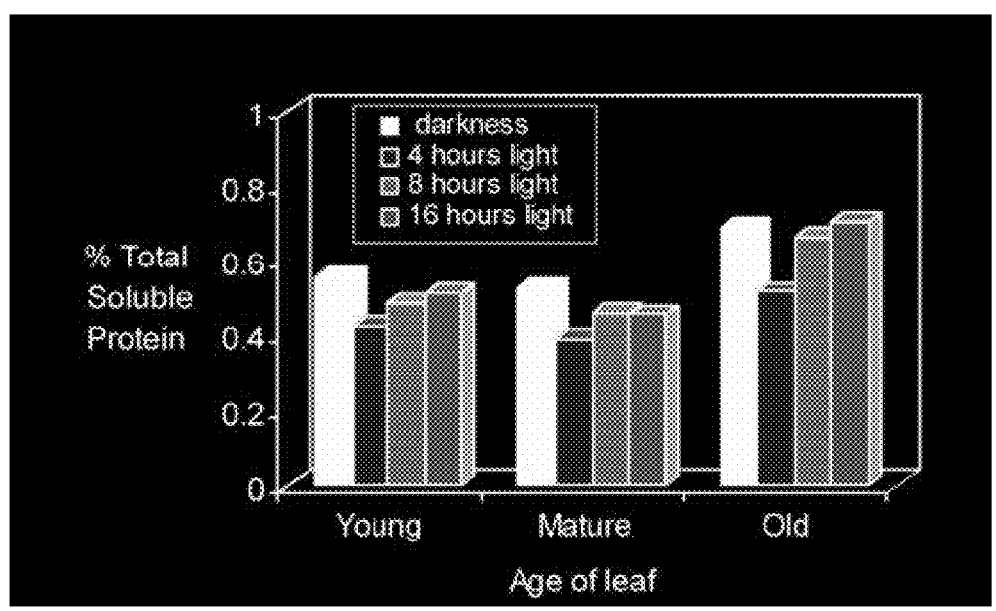

FIG. 48: ELISA analysis of the orf1-orf2-hsa transgenic line.

Total soluble protein content of young, mature and old leaf extracts of the orf1-orf2-hsa transgenic lines determined by ELISA analyses. Transgenic plants were subjected to the following light conditions: 4, 8, and 16 hours of light, as well as total darkness.

Figure 49:
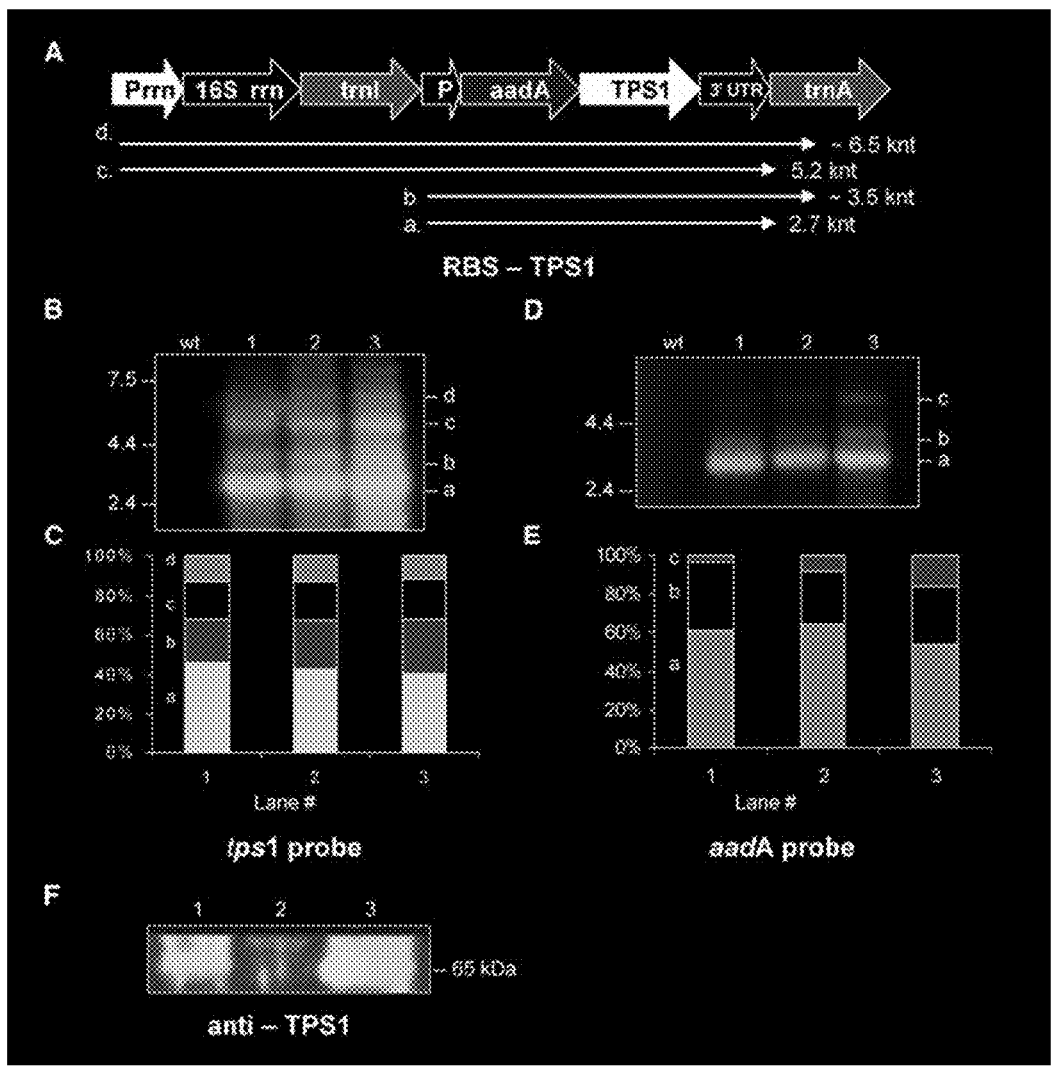

FIG. 49: Transcriptional and translational analysis of the tps1 operon

A. Schematic representation of the tps1 operon in transgenic lines, including the aadA gene and upstream Prrn promoter (P). Upstream native chloroplast 16S ribosomal RNA gene and promoter (Prrn) as well as trnI/trnA genes are shown. Arrows represent expected transcripts and their respective sizes. B. Northern blot analysis obtained by hybridization with the tps1 probe, loaded as follows: wt: wild type control; lanes 1, 2 and 3: tps1 transgenic lines. Transcripts of the tps1 operon correspond to those depicted in A, indicated with lowercase letters. C. Relative transcript abundance per transgenic line, obtained with the tps1 probe. D. RNA transcripts hybridized with the aadA probe, loaded as follows: wt: wild type control; lanes 1-3: tps1 transgenic lines. Transcript bands obtained for the tps1 operon are of sizes as described for tps1 probe (B). D. Relative abundance of transcripts in each sample after hybridization with the aadA probe. E. Western blot analysis using the TPS1 antibody. Lane 1: positive control (TPS1 protein); lane 2: wild type control; lane 3: tps1 transgenic line. A polypeptide of 65 kDa was observed in the transgenic clone, corresponding to the expected size of the TPS1 protein, as observed in the positive control.

Figure 50:
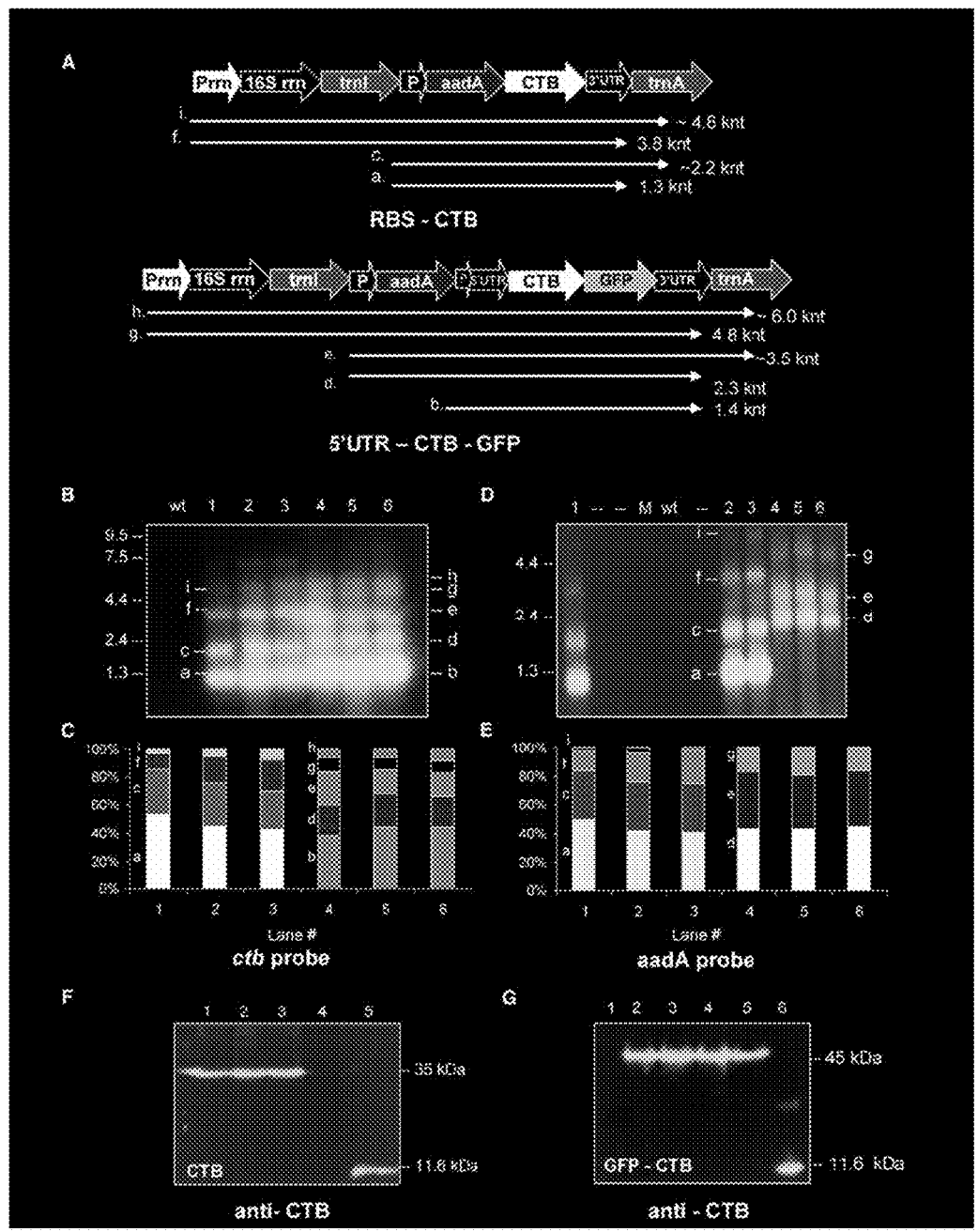

FIG. 50: Transcriptional and translational analysis of the CTB operons

A. Schematic representation of the 5'UTR-ctb-gfp and RBS-ctb operon in transgenic lines, including the aadA gene and the upstream Prrn promoter (P); upstream native chloroplast 16S ribosomal RNA gene with its respective promoter (Prrn) and the trnI and trnA are also shown. Arrows represent expected transcripts and their respective sizes. B. Northern blot analysis showing RNA hybridized with the CTB probe. Samples were loaded as follows: wt: wild type control; lanes 1-3: 5'UTR-ctb-gfp transgenic lines; lanes 4-6: rbs-ctb transgenic lines. The transcripts and respective sizes correspond to those indicated in A with lowercase letters. C. Relative transcript abundance, within each line, of the transcripts shown in B. D. RNA hybridization using the aadA probe, and loaded according to the following: M: molecular weight marker; wt: wild type control; lanes 1-3: RBS-ctb transgenic lines. Lanes 4-6: 5'UTR-ctb-gfp transgenic lines. Lanes marked with (—) were left blank. The transcripts observed correspond to the same as in B. E. Relative transcript abundance, per line, for the transcripts shown in C. F. Western blot analysis of the RBS-CTB transgenic lines using anti-CTB antibody. Lanes 1-3: transgenic clones; lane 4: wild type control; lane 5: positive control (CTB protein). CTB from transgenic lines is in trimeric form. E. Western blot analysis of the 5'UTR-ctb-gfp transgenic lines using the CTB antibody. Lane 1: Wild type control. Lanes 2-5: transgenic lines. Lane 6: positive control (CTB protein).

Figure 51:
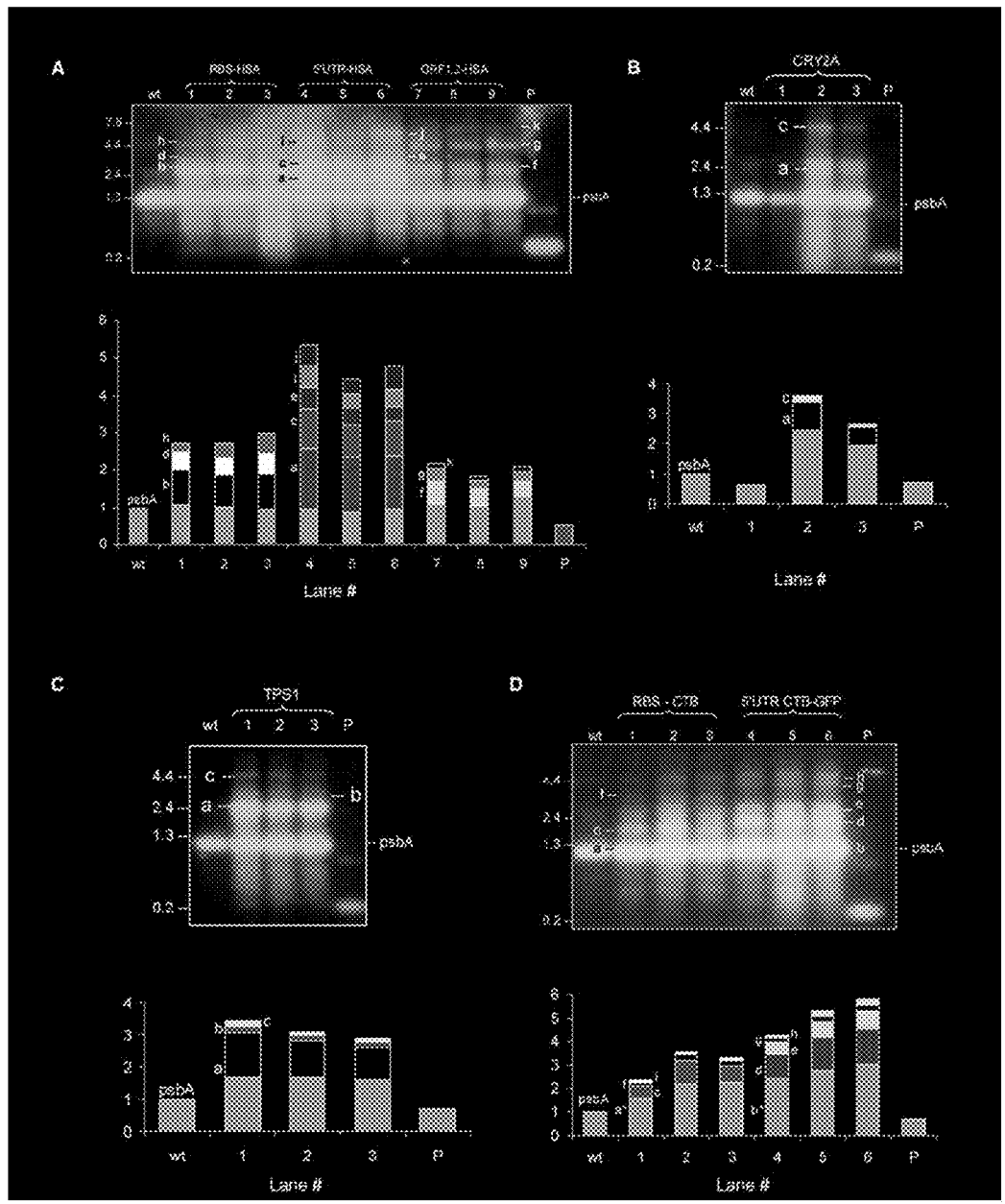

FIG. 51: Transcription of heterologous operons using the psbA 3'UTR probe.

A. Northern blot analysis and corresponding quantification of transcripts obtained from different HSA transgenic lines described in FIG. 3, as well as of the native psbA transcripts. The RNA gels were loaded as follows: wt: wild-type. Lanes 1-3: RBS-HSA transgenic lines. Lanes 4-6: 5'UTR-HSA transgenic lines. Lanes 7-9: ORF-1,2-HSA transgenic lines. P: psbA 3'UTR probe. Lowercase letters correspond to the same transcripts predicted in FIG. 3A. Transcript abundance was normalized against the wild-type psbA, to which a value of 1 was assigned. B. Northern blot analysis and corresponding transcript quantification of the cry2Aa2 operon. Gel loading was as follows: wt: wild-type RNA. Lanes 1-3: Cry2Aa2 transgenic lines. P: psbA 3'UTR probe. Lowercase letters correspond to transcripts predicted in FIG. 1A. Native psbA transcript is indicated. Transcript abundance was normalized against the wild-type psbA, to which a value of 1 was assigned. The low transcript abundance of lane 1 is due to partial RNA degradation in the sample. C. RNA blot and transcript quantification of the transgenic TPS1 lines. The RNA gel was loaded as follows: wt: wild-type. Lanes 1-3. TPS1 transgenic lines. P: psbA 3'UTR probe. Lowercase letters correspond to transcript sizes shown in FIG. 5A. Native psbA transcript is indicated Transcript abundance was normalized against the wild-type psbA, showing a value of 1. D. Northern blot analysis of the RBS-CTB and 5'UTR-CTB-GFP transgenic lines. Samples were loaded as follows: wt: wild-type. Lanes 1-3: RBS-CTB transgenic lines. Lanes 4-6: 5'UTR-CTB-GFP transgenic lines. P: psbA 3'UTR probe. Lowercase letters correspond to transcripts shown in FIG. 6A. Transcripts a* and b* are similar in size to the native psbA and therefore they cannot be distinguished from the native transcript. Because such transcripts were shown to be very abundant in FIG. 6B, and because of increase in transcript abundance in comparison to the wild-type psbA transcript, it is assumed that such transcripts are present. Transcript abundance was normalized against the wild-type psbA, to which a value of 1 was assigned.

Figure 52:
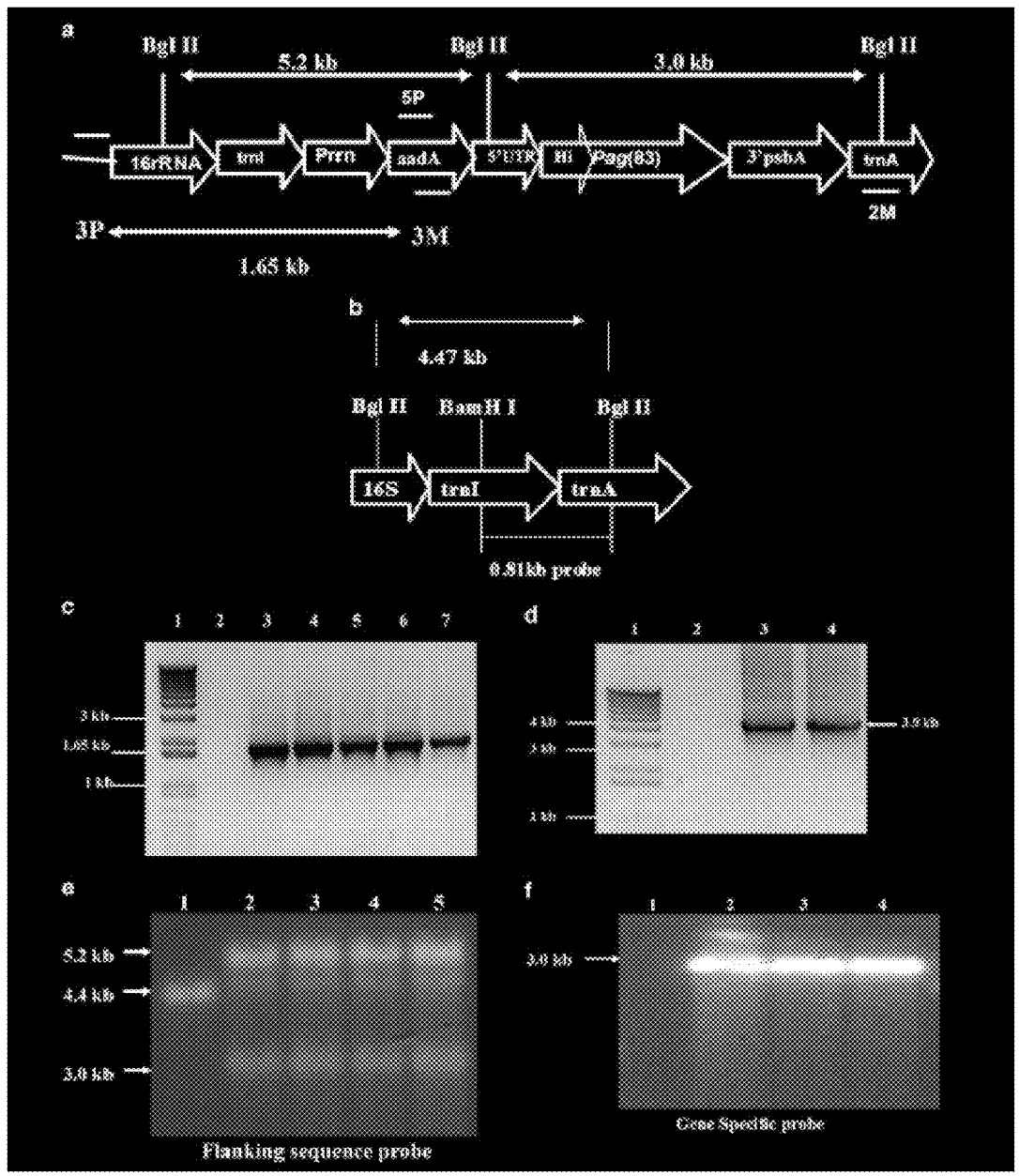

FIG. 52 Vector map and confirmation of transgene integration into chloroplast genome by PCR and Southern blotting. (a) Schematic representation of pLD-VK1 vector with protective antigen gene (pagA), aadA (selectable marker), 5'UTR, and chloroplast flanking sequences for site-specific integration with the primers 3P/3M and 5P/2M annealing sites within the native chloroplast genome and the schematic diagram of expected products from digestion of plants transformed with pLD-VK1. (b) Schematic diagram of expected products from digestion of wild-type untransformed plant. (c) Confirmation of site-specific transgene cassette integration by PCR using primers (3P/3M) to yield a 1.65-kb product. Lane 1, 1-kb DNA ladder; lane 2, wild type; lanes 3 to 6, pLD-VK1 transgenic lines; lane 7, positive control (interferon transgenes).

Figure 53:
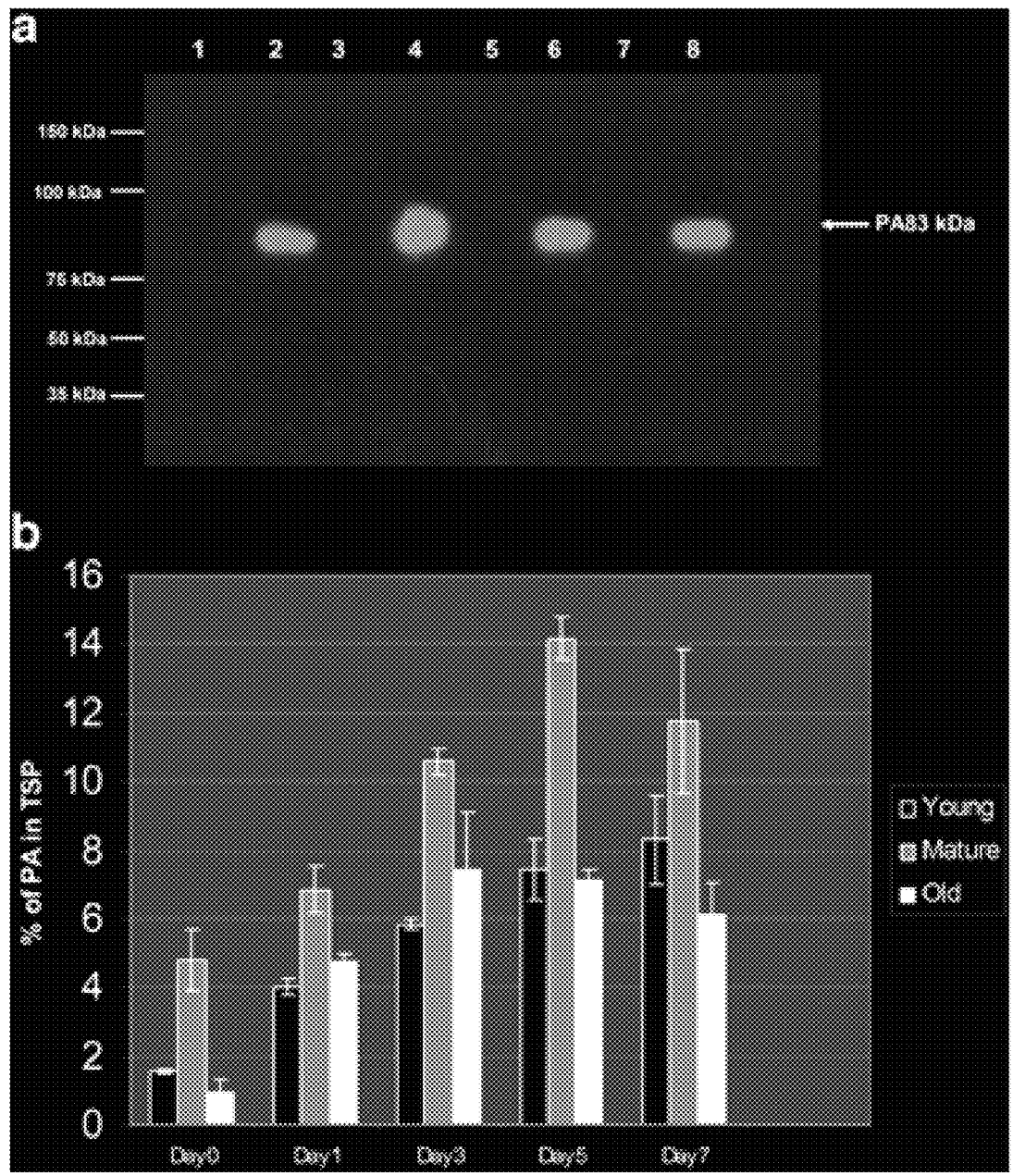

FIG. 53. Immunoblotting analysis and quantification of PA expressed in chloroplast of transgenic plants (pLD-VK1) in T0 generation. (a) Immunoblotting demonstrating the expression of PA in transgenic plant crude extracts. Lane 1, wild type; lane 2, 100-ng standard; lane 4, transgenic line 5; lane 6, transgenic line 7; lane 8, transgenic line 8; lanes 3, 5, and 7, empty. (b) Expression levels in percent TSP of PA-expressing leaves (young, mature, and old) under normal and continuous illumination observed for 0 to 7 days.

FIG. 54. Purification of PA by affinity chromatography from the crude extracts of plant leaves expressing PA. (a) Coomassie staining of the proteins in crude extract and purified protein: Lane 1, protein plus precision ladder; lane 2, wild-type leaf crude extract; lane 3, crude extract of transgenic plant expressing PA; lanes 4 and 5, purified chloroplast-derived PA; lane 6, flowthrough collected during purification. (b) Lane 1, ladder; lane 3, concentrated protein; lane 5, purified protein (before concentrating); lanes 2 and 4, overflow from lane 3.

Figures 55, 56:
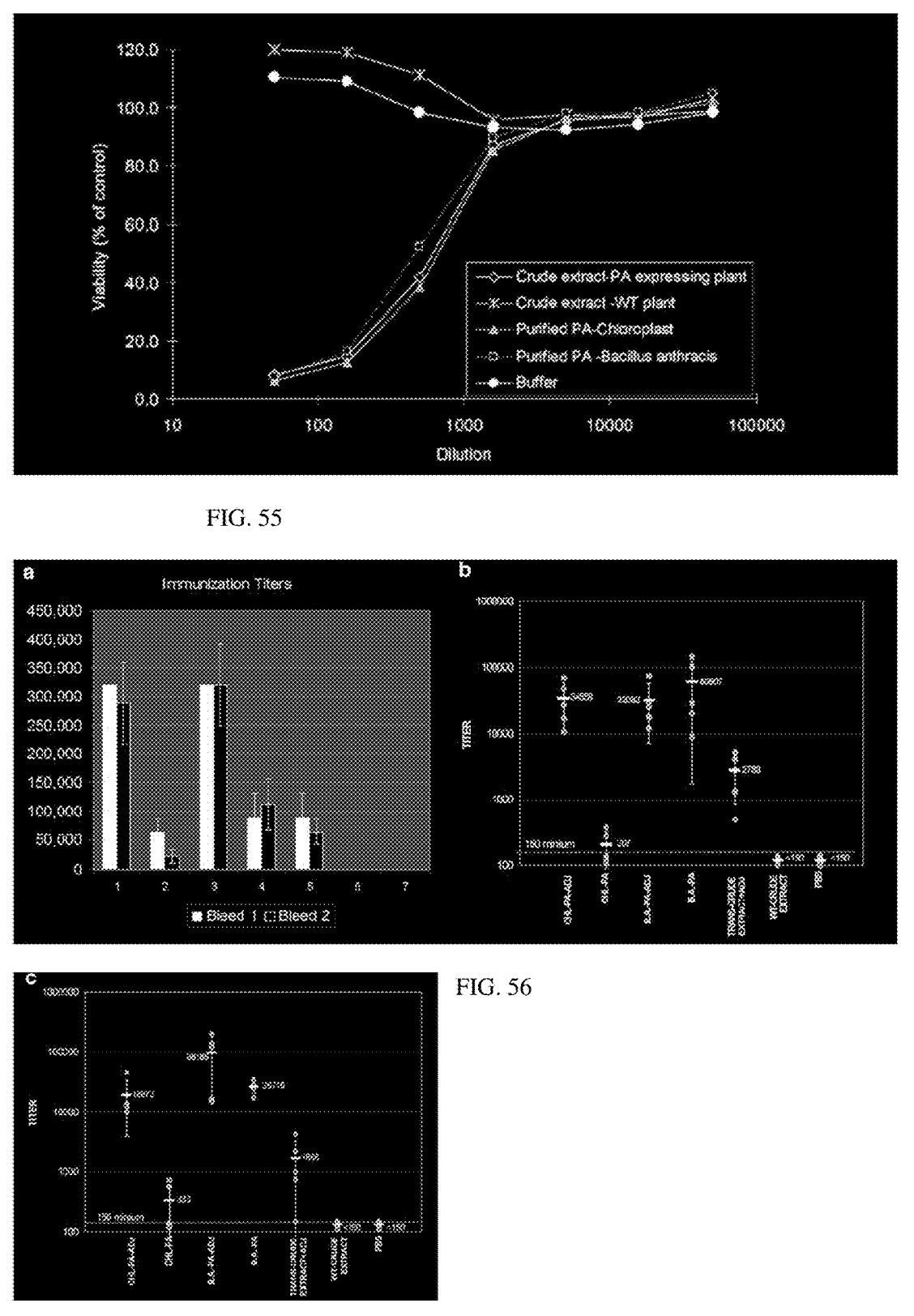

FIG. 55. Functional analysis of PA with macrophage cytotoxicity assay. The cytotoxicities of various PA preparations for mouse macrophage RAW264.7 cells were assayed in the presence of LF. Samples that were diluted serially were as follows: crude extract of plant leaves expressing PA with His tag, wild-type (WT) plant leaf crude extract, 20-μg/ml stock of purified chloroplast-derived PA, 20-μg/ml stock of purified PA derived from B. anthracis, and plant protein extraction buffer.

FIG. 56. IgG antibody titers and toxin neutralization assay titers in serum samples obtained from mice after third and fourth doses. (a) Comparison of immune responses in serum samples of mice administered subcutaneously with chloroplast-derived PA (CpPA) with adjuvant (column 1), chloroplast-derived PA (CpPA) alone (column 2), Std-PA derived from B. anthracis with adjuvant (column 3), Std-PA alone (column 4), PA plant leaf crude extract with adjuvant (column 5), wild-type plant leaf crude extract with adjuvant (column 6), and unimmunized mice (column 7). (b) Toxin neutralization titers of sera collected from the mice on day 43 of post-initial immunization. Each symbol represents average EC50 from three replicate assays of a single mouse serum. CHL, chloroplast; ADJ, adjuvant; B.A., B. anthracis; WT, wild type. (c) Toxin neutralization assays of serum samples collected from the mice on day 155 of post-initial immunization. Each symbol represents the average EC50 from three replicate assays of a single mouse serum.

Figure 57:
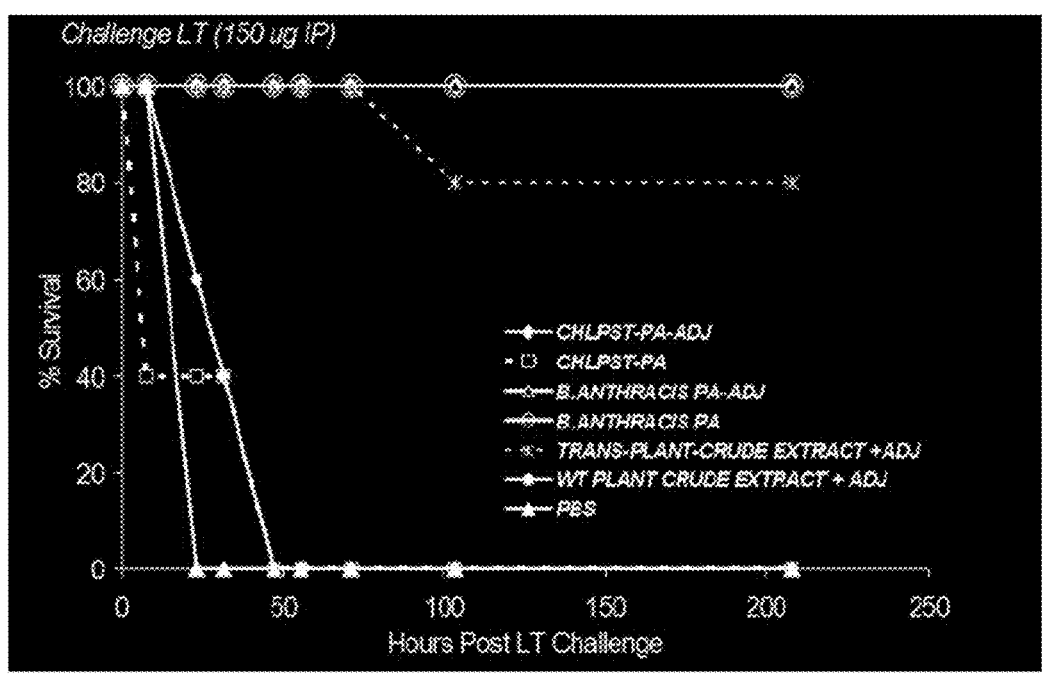

FIG. 57. Toxin challenge of the mice with systemic anthrax lethal toxin. Shown is survival over time for different groups of mice after challenge with a 150-μg dose of lethal toxin. IP, intraperitoneal; CHLPST, chloroplast; ADJ, adjuvant; WT, wild type.

DETAILED DESCRIPTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

Methods, vectors, and compositions for transforming plants and plant cells are taught for example in WO 01/72959; WO 03/057834; and WO 04/005467. WO 01/64023 discusses use of marker free gene constructs.

Proteins expressed in accord with certain embodiments taught herein may be used in vivo by administration to a subject, human or animal in a variety of ways. The pharmaceutical compositions may be administered orally or parenterally, i.e., subcutaneously, intramuscularly or intravenously. Thus, this invention provides compositions for parenteral administration which comprise a solution of the fusion protein (or derivative thereof) or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of fusion protein (or portion thereof) in these formulations can vary widely depending on the specific amino acid sequence of the subject proteins and the desired biological activity, e.g., from less than about 0.5%, usually at or at least about 1% to as much as 15 or 20% by weight and will be selected primarily based on fluid volumes, viscosities, etc., in accordance with the particular mode of administration selected.

Oral vaccines produced by embodiments of the present invention can be administrated by the consumption of the foodstuff that has been manufactured with the transgenic plant producing the antigenic like particles. The edible part of the plant is used as a dietary component while the vaccine is administrated in the process.

To evaluate the antigenicity of the expressed antigens, the level of immunoglobulin A in feces or immunoglobulin G in serum is measured, respectively, after test animals has been immunized with the antigen embodiments of the present invention by oral administration or peritoneal injection. The ability to elicit the antibody formation is measured by Enzyme-linked immunosorbent assay. In addition, the direct consumption of the transgenic plant producing the antigen induces the formation of antibodies against the specific antigen.

The vaccines of certain embodiments of the present invention may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the vaccine may contain minor amounts of auxiliary substances such as wetting or emulsifying agents, pH buffering agents, or adjuvants which enhance the effectiveness of the vaccines. The preparation for parental administration includes sterilized water, suspension, emulsion, and suppositories. For the emulsifying agents, propylene glycol, polyethylene glycol, olive oil, ethyloleate, etc. may be used. For suppositories, traditional binders and carriers may include polyalkene glycol, triglyceride, witepsol, macrogol, tween 61, cocoa butter, glycerogelatin, etc. In addition, pharmaceutical grades of mannitol, lactose, starch, magnesium stearate, sodium saccharine, cellulose, magnesium carbonate and the like can be used as excipients.

Antigen(s) may be administered by the consumption of the foodstuff that has been manufactured with the transgenic plant and the edible part of the plant is used directly as a dietary component while the vaccine is administrated in the process.

The vaccine may be provide with the juice of the transgenic plants for the convenience of administration. For said purpose, the plants to be transformed are preferably selected from the edible plants consisting of tomato, carrot and apple, which are consumed usually in the form of juice.

The vaccination will normally be taken at from two to twelve week intervals, more usually from three to hive week intervals. Periodic boosters at intervals of 1-5 years, usually three years, will be desirable to maintain protective levels of the antibodies. It will be desirable to have administrations of the vaccine in a dosage range of the active ingredients of about 100-500 µg/kg, preferably 200-400 µg/kg.

According to one embodiment, the subject invention relates to a vaccine derived from a plant transformed to express antigenic proteins capable of producing an immune response in a subject (human or non-human animal).

According to another embodiment, the subject invention pertains to a transformed chloroplast genome that has been transformed with a vector comprising a heterologous gene that expresses a peptide as disclosed herein.

Of particular present interest is a transformed chloroplast genome that has been transformed with a vector comprising a heterologous gene that expresses a peptide antigenic for rotavirus, hepatitis C or Anthrax. In a related embodiment, the subject invention pertains to a plant comprising at least one cell transformed to express a peptide as disclosed herein.

Accordingly, in one embodiment, a vaccine pertains to an administratable vaccine composition that comprises an antigen having been expressed by a plant and a plant remnant. A plant remnant may include one or more molecules (such as, but not limited to, proteins and fragments thereof, minerals, nucleotides and fragments thereof, plant structural components, etc.) derived from the plant in which the antigen was expressed. Accordingly, a vaccine pertaining to whole plant material (e.g., whole or portions of plant leafs, stems, fruit, etc.) or crude plant extract would certainly contain a high concentration of plant remnants, as well as a composition comprising purified antigen that has one or more detectable plant remnants.

Reference to specific polypeptide sequences herein (such as but not limited to, CTB, proinsulin, interferon alpha, GFP, NSP4, HCV NS3 protein, yeast trehalose phosphate synthase, human serum albumin, Cry2Aa2 protein, and/or protective antigen relate to the full length amino acid sequences as well as at least 12, 15, 25, 50, 75, 100, 125, 150, 175, 200, 225, 250 or 265 contiguous amino acids selected from such amino acid sequences, or biologically active variants thereof.

Variants which are biologically active, refer to those, in the case of immunization, confer an ability to induce serum antibodies which protect against infection against the pathogen from which polypeptide is derived, or, in the case of desiring the native function of the protein, is a variant which maintains the native function of the protein. Preferably, naturally or non-naturally occurring polypeptide variants have amino acid sequences which are at least about 55, 60, 65, or 70, preferably about 75, 80, 85, 90, 96, 96, or 98% identical to the full-length amino acid sequence or a fragment thereof. Percent identity between a putative polypeptide variant and a full length amino acid sequence is determined using the Blast2 alignment program (Blosum62, Expect 10, standard genetic codes).

Variations in percent identity can be due, for example, to amino acid substitutions, insertions, or deletions Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of polypeptide can be found using computer programs well known in the art, such as DNASTAR software. Whether an amino acid change results in a biologically active LecA polypeptide can readily be determined by assaying for native activity, as described for example, in the specific Examples, below.

Reference to genetic sequences herein refers to single- or double-stranded nucleic acid sequences and comprises a coding sequence or the complement of a coding sequence for polypeptide of interest. Degenerate nucleic acid sequences encoding polypeptides, as well as homologous nucleotide sequences which are at least about 50, 55, 60, 65, 60, preferably about 75, 90, 96, or 98% identical to the cDNA may be used in accordance with the teachings herein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of nucleic acid sequences which encode biologically active polypeptides also are useful polynucleotides.

Variants and homologs of the nucleic acid sequences described above also are useful nucleic acid sequences. Typically, homologous polynucleotide sequences can be identified by hybridization of candidate polynucleotides to known polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of polynucleotides referred to herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Nucleotide sequences which hybridize to polynucleotides of interest, or their complements following stringent hybridization and/or wash conditions also are also useful polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a polynucleotide of interest or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\% G+C) - 0.63(\% \text{ formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Relevant articles on genetic sequences is provided: proinsulin (Brousseau et al., *Gene*, 1982 March; 17(3):279-89; Narrang et al, *Can J Biochem Cell Biol.* 1984 April; 62(4): 209-16; and Georges et al, *Gene* 27 (2), 201-211 (1984)); GFP (Prasher et al., *Gene* 111, 229-233, (1992)); protective antigen (Welkos et al., *Gene.* 1988 Sep. 30; 69(2):287-300); alpha interferon (Strausberg et al., *Proc. Natl. Acad. Sci. U.S.A.* 99 (26), 16899-16903 (2002)); rotavirus (Kirkwood et al., *Virus Genes*, Volume 19, Issue 2, October 1999, Pages 113-122); hepatitis C NS3 (Lodrini et al., *J Biol Regul Homeost Agents.* 2003 April-June; 17(2):198-204); and CTB (Shi et al, *Sheng Wu Hua Hsuch Tsa Chih* 9 (No. 4), 395-399 (1993).

Example 1: Expression of Cholera Toxin B Subunit-Proinsulin Fusion Protein in Transgenic Tobacco Chloroplasts as a Treatment Against Development of Type-1 Autoimmune Diabetes Oral administration of disease specific autoantigens have been demonstrated to delay or even prevent the onset of disease symptoms, referred to as tolerance. The inventor has produced a *Nicotiana tabacum* cv. petit Havana chloroplast transgenic lines that expresses a cholera toxin B subunit (from *Vibrio Cholerae*)-human proinsulin (a and b chain) fusion protein, designated CTB-Pris. This approach has been previously demonstrated by nuclear expression in potato tubers, to prevent the onset of insulin-dependent diabetes mellitus (IDDM) in NOD mice, when delivered orally. The pLD-PW contains the CTB-Pris gene cloned into the universal chloroplast transformation vector pLD-ctv in which the 16S rRNA promoter drives the aadA gene selectable marker, which confers resistance to spectinomycin; the psbA 5' untanslated region (UTR) enhanced translation of CTB-Pris in the presence of light and the psbA 3'UTR conferred transcript stability. The trnI and trnA homologous flanking sequences facilitated site-specific integration of transgenes into the tobacco chloroplast genome. Site-specific integration was demonstrated by PCR and Southern blot analysis with probes for both CTB and Pris. Western Blot analysis has demonstrated the presence of abundant CTB-Pris in transgenic plants with both CTB polyclonal and proinsulin monoclonal antibodies. Southern blot analysis has also confirmed that homoplasmy had been achieved in the T0 generation. These chloroplast transgenic lines grew slowly although their appearance was normal. Quantification studies are conducted as well as animal studies on NOD mice in order to determine the ED50 for prevention of the onset of insulin-dependent diabetes mellitus. Techniques for plant transformation and processing and uses of expressed protein are discussed in WO 01/72959.

Diabetes is a disease in which the body does not produce or properly utilizeinsulin. Type 1 diabetes results from the autoimmune destruction of insulin-producing cells and a corresponding failure to produce adequate insulin. In 2002, the American Diabetes Association estimated that 18.2 million people in the United States, or 6.3% of the total population, have diabetes, with more than $120 billion in treatment costs each year. Complications that can arise from diabetes include: heart disease, nephropathy, retinopathy, neuropathy, hypertension, foot complications, skin problems, gastroparesis, and depression. In 2002, diabetes was the sixth leading cause of death in the U.S. contributing to 213,062 deaths. The only currently accepted form of treatment is the administration of recombinant insulin, which serves to temporarily replace the missing insulin in diabetic patients. Therefore, it is essential to find a prevention and cure for this dreadful disease.

Insulin is secreted by pancreatic β-cells and is regulated by a glucose-sensing system. The insulin polypeptide is made up of an A chain (21 amino acids) and a B chain (30 amino acids) that are bound together via disulfide bonds across cysteine residues. It is initially translated in the endoplasmic reticulum as preproinsulin, processed into proinsulin that is trafficked to the secretory granules of the β-cell, and finally processed into C-peptide and mature insulin (reviewed in Halban 1991). The function of C peptide, which is part of proinsulin prior to processing, has remained a mystery until recently, when human trials have demonstrated that the proinsulin C-peptide stimulates the activities of Na+,K+-ATPase and endothelial nitric oxide synthase, both of which are enzyme systems of importance for nerve function and known to be deficient in Type 1 diabetes (Ekberg et al., 2003). The major destruction of β-cells occurs predominantly from autoreactive T-cytotoxic cells (Nagata et al., 1994) and T-helper 1 cells (Ploix et al., 1999) reactive to β-cell autoantigens such as insulin.

Biopharmaceutical proteins expressed in plant cells should reduce their cost of production, purification, processing, cold storage, transportation and delivery. Integration of transgenes via the nuclear genome may have a few disadvantages. The chloroplast genetic engineering approach overcomes such concerns of transgene containment (Daniell 2002), low levels of transgene expression, gene silencing, position effect, pleiotropic effects, and presence of antibiotic resistant genes or vector sequences in transformed genomes (Daniell et al. 2002, 2004a-c, 2005a,b; Grevich & Daniell, 2005). This approach has been successfully used in our laboratory to confer desired plant traits (Daniell et al. 1998; Kota et al. 1999; DeGray et al. 2001; Lee et al. 2003; Kumar et al. 2004a; Ruiz et al. 2003). Employing knowledge gained through these studies, we have demonstrated expression and assembly of several vaccine antigens, including the cholera toxin B subunit (CTB, Daniell et al. 2001), the F1~V fusion antigen for plague (Singleton 2003; Daniell et al. 2005b), the 2L21 peptide from the canine parvovirus (CPV, Molina et al. 2004), the anthrax protective antigen (PA, Watson et al. 2004), and the NS3 protein as a vaccine antigen for hepatitis C (Bhati 2004). Cytotoxicity measurements in macrophage lysis assays showed that chloroplast-derived anthrax protective antigen (PA) was equal in potency to PA produced in *B. anthracis*. It was reported that one acre of land should produce 360 million doses of a purified vaccine free of the bacterial toxins (Koya et al. 2005) because of the large yield of biomass. In addition to its use for the hyper-expression of vaccine antigens, transgenic chloroplasts have been used in our lab for the production of valuable therapeutic proteins, such as human elastin-derived polymers for various biomedical applications (Guda et al. 2000); human serum albumin (Fernandez-San Millan et al. 2003); magainin, a broad spectrum topical agent, systemic antibiotic, wound healing stimulant and a potential anticancer agent (DeGray et al. 2001); various interferon α proteins (Daniell et al. 2004b, 2005b); and insulin-like growth factor 1 (Ruiz 2002). Several other laboratories have expressed other therapeutic proteins, including human somatotropin (Staub et al. 2000) and interferon γ-GUS fusion proteins (Leelavathi & Reddy 2003), and the C-terminus of Clostridium tetani (Tregoning et al. 2003) in transgenic chloroplasts. The successful expression and assembly of complex multi-subunit proteins has demonstrated that chloroplasts contain the machinery that allows for correct folding and disulfide bond formation, resulting in fully functional proteins (Daniell et al. 2004b, 2005b).

Oral delivery of biopharmaceutical proteins expressed in plant cells should reduce their cost of production, purification, processing, cold storage, transportation and delivery. However, poor intestinal absorption of intact proteins is a major challenge. To overcome this limitation, we investigated the concept of receptor-mediated oral delivery of transgenic proteins. Therefore, the transmucosal carrier cholera toxin B-subunit and green fluorescent protein (CTB-GFP), separated by a furin cleavage site, was expressed via the tobacco chloroplast genome. Following oral administration of CTBGFP expressing leaf material to mice, GFP was observed in the mice intestinal mucosa, liver and spleen in fluorescence and immunohistochemical studies, while CTB remained in the intestinal cell (Limaye et al., 2006). This report of receptor-mediated oral delivery of a foreign protein into the circulatory system brings the delivery of human therapeutic proteins one step closer to realization. Transformation of non-green tissue plastids (Kumar et al. 2004 a,b; Daniell et al., 2005a) was recently achieved, further facilitating the oral delivery of therapeutic proteins.

The non-obese diabetic (NOD) mouse is a useful animal model for research in human diabetes. About 60%-75% of NOD mice become diabetic by 40 weeks of age (Homann et al., 1999a). These mice show signs of insulitis due to lymphocytic infiltration of the endocrine part of the pancreas, which leads to decreased production of insulin and increased blood sugar with its consequent pathologies. In this study, we examine the effect of oral administration of chloroplast-derived proinsulin conjugated to CTB for the induction of oral tolerance towards insulin. Oral administration of small quantities of CTB-Proinsulin to NOD mice leads to its uptake by intestinal epithelial cells via the GM1 receptor. These cells then pass the antigen (proinsulin) to the underlying antigen presenting cells (APCs), such as macrophages or dendritic cells. These cells in turn activate lymphocytes to up-regulate the Th2 response, leading to the production of immune-suppressing cytokines such as interleukins 4 (IL-4) and 10 (IL-10), which suppress (reduce) the immune attack against the endocrine insulin-producing β-cells of the Langerhans islets of the pancreas.

Material and Methods

Vector Construction

The human proinsulin gene was synthesized by a method that utilized four overlapping oligos with a low annealing temperature (50° C.). The products were then used as templates for high annealing temp (65° C.) primers, thus synthesizing the required 258 bp gene (Protocol from Prodromou and Pearl, 1992). The PCR product was then subsequently cloned into the PCR 2.1 vector and the sequence verified. The psbA promoter and 5' untranslated region (UTR) was amplified from the tobacco chloroplast genome, followed by sub-cloning, and sequence verification. The promoter-5'UTR fragment was then spliced together with the cholera toxin B-subunit (CTB) and human proinsulin by a process that utilizes four primers (Splicing by Overlap Extension, Horton et al., 1989). Thus, the construct now contained the 5'UTR-CTB, and a GPGP (glycine-proline-glycine-proline) hinge region introduced by mutagenesis to allow for the proper folding of each protein by reducing steric hindrance, followed by human proinsulin; the final construct was termed 5CP. Following SalI/NotI digestion to release the fusion gene of interest, it was ligated into the pLD-ctv chloroplast transformation vector. The 5CP insert was ligated into the chloroplast transformation vector, pLD-ctv which was developed previously by the Daniell laboratory (Daniell et al., 1998; 2004c).

Bombardment and Selection of Transgenic Plants

The Bio-Rad PDS-1000/He biolistic device was used to bombard pLD-CTB-Pins onto sterile Nicotiana tabacum cv. Petit Havana tobacco leaves, on the abaxial side as has been previously described (Daniell, 1997; Daniell et al., 2004c). The bombarded leaves were incubated in the dark for 24 hours and then placed on shoot inducing media (RMOP) containing 500 µg/ml spectinomycin for two rounds of selection. This was followed by another round of selection on MSO, a root-inducing medium which contained 500 µg/ml spectinomycin.

Southern Blot Analysis

Total plant DNA was digested with AflIII, separated on a 0.7% agarose gel at 45V for 8 hours, and then transferred to a nylon membrane. The pUC-CT vector DNA was digested with BamHI and BglII to generate a 0.8 kb probe which was used as a flanking probe (Daniell et al., 2004c) and pLD-CTB-Pins was digested with MfeI and NotI to generate the 0.36 kb gene specific probe. After labeling the probe with P32, hybridization of the membranes was done using QUICK-HYB hybridization solution and protocol (Stratagene, La Jolla, Calif.).

Western Blot Analysis

Approximately 100 mg of leaf tissue was ground in liquid nitrogen and resuspended in 500 µl of plant extraction buffer (0.1% SDS, 100 mM NaCl, 200 mM Tris-HCl pH 8.0, 0.05% Tween 20, 400 mM sucrose, 2 mM PMSF). After centrifugation at 13,000 rpm for 5 minutes, the supernatant containing the soluble extracted protein was collected. The plant extract along with the sample loading buffer were boiled, and then run on a 13% SDS-PAGE gel for 40 mins at 50V and then 2 hours at 80V. The protein was then transferred to nitrocellulose membrane for 1 hour at 85V. After blocking the membranes with PTM (1×PBS, 0.05% Tween 20, and 3% dry milk) for 1 hour, mouse anti-proinsulin monoclonal antibody (Amersham Pharmacia) at a 1:20,000 dilution was added and incubated for 2 hours. Goat anti-mouse IgG antibody conjugated to horseradish peroxidase (Sigma) at a 1:15,000 dilution was used as a secondary antibody and incubated for 1.5 hours.

Quantification via ELISA

Approximately 100 mg of leaf tissue was ground in liquid nitrogen and resuspended in 500 µl of plant extraction buffer (15 mM Na2CO3, 35 mM NaHCO3, 3 mM NaN3, pH 9.6, 0.1% Tween 20 and 5 mM PMSF). Using the Total Proinsulin ELISA Kit (Linco Research, St Charles, Mo.) and following manufactures instructions, the Insulin present in the leaf was quantified. Ninety-six well plates were read on a plate reader (Dynex Technologies) at 450 nm.

Animal Studies

Four week old female non-obese diabetic (NOD) mice were purchased from The Jackson Laboratory (Bar Harbor, Me.). Mice were kept in the UCF Wild Animal Facility under normal light/dark cycle conditions and had access to food and water ad lib. Treatment by means of oral administration of Cholera toxin B subunit-Proinsulin (CTBPins) expressing transgenic or control plant leaf material began when animals were 5 weeks old, to allow the mice one week to acclimate to the facility. Mice were divided into the following groups: group 1 was fed untransformed plant leaf material; group 2 was fed transgenic plant leaf expressing Cholera toxin B subunit conjugated to GFP (CTB-GFP); group 3 was fed transgenic plant leaf expressing interferon conjugated to GFP (IFNGFP); and group 4 was fed CTB-Pins expressing transgenic plant leaf. Each group contained five animals, except the CTB-Pins group, which contained seven. Mice were fed 8 mg of the specified ground plant leaf material once a week for 7 weeks. The animals were sacrificed at 12 weeks of age, the pancreas and other tissues were collected, and both blood and urine glucose levels were measured.

Blood and Urine Glucose Levels

Blood and urine glucose levels were measured for two consequent weeks (11 and 12 weeks old) with urinary glucose test strips (Clinistix and Diastix, Bayer), and blood glucose was measured by bleeding from either the tail vein or the retro-bulbar vein (at week 12, before sacrificing) by blood glucose analyzer (Boehringer Mannheim). Blood glucose levels over 250 mg/dl were considered diabetic (Arakawa et al, 1998).

Histochemistry for Lymphocytic Infiltration and Insulitis

Following the 7 week treatment, mice were sacrificed and perfused transcardially with 10 ml of PBS followed by 50 ml of 4% paraformaldehyde in PBS. Fresh frozen sections of the pancreas were collected (Samsam et al., 2003). The pancreas was removed, post-fixed overnight, and then cryoprotected by serially passing through 10%, 20% and 30% sucrose solutions in PBS. The pancreatic tissue was then immersed in Tissue Tek freezing medium (Vector labs) and frozen in liquid nitrogen-cooled isomethylbuthane (isopathane, Sigma). Ten micrometer (nm) thick frozen sections of the pancreas were then prepared using a cryostat. Pancreas cryosections were stained with Hematoxillin and Eosin, dehydrated in serial graded alcohol solutions, and the slides were cover slid.

Insulitis levels were measured based on the extent of the lymphocyte infiltration of the islets of Langerhans. At least 50 sections per animal were scored, the degree of insulitis was scored based on a 5 level scale ranging from 1-5, where score 1 is a normal islet with no sign of T-cell infiltration, and score 5 indicates increasing of insulitis.

Immunohistochemistry for Insulin, Caspase-3, Interleukin (IL) 4 and IL10

Immunohistochemistry for the localization of insulin, caspase-3 (a final molecule of apoptosis), and the immunosuppressive cytokines IL4 and IL10 were performed on the pancreas cryosections. Sections were blocked with 10% BSA (bovine serum albumin) containing 0.3% Triton-X 100.

Polyclonal guinea pig anti-insulin, polyclonal rabbit anti-caspase-3, rat monoclonal anti-IL4 and anti-IL10 primary antibodies (Invitrogen) were diluted at a concentration of 1:300 in 1% BSA in PBS containing 0.3% Triton-X. Fluorescent conjugated secondary antibodies were goat anti-guinea pig-Alexa Fluor 488 (green), goat anti-rabbit-Alexa Fluor 555 (red), and goat anti-rat Alexa Fluor 555 (red, Invitrogen).

Antibody Titer

Serum and intestinal antibodies were assayed for the presence of anti-insulin and anti-CTB antibodies using colorimetric ELISA methods. Ninety-six well plates were coated with either CTB or human insulin (Sigma). Serial dilutions of serum or supernatants of fecal pellets collected from the different animal groups were added to the coated microtiter plate wells. Secondary antibodies were horseradish peroxidase (HRP)-conjugated anti-mouse IgG2a, IgG1, or IgA antibodies (BD Pharmingen, USA) at a concentration of 1:3000 in PBS containing 0.1% Tween-20 and 3% milk powder. The plates were washed with 200 µl of PBS, and the substrate tetra-methyl benzidine (TMB) was added to the wells and incubated in the dark at 37° C. for 20 minutes. The reaction was stopped by adding 50 µl of H2SO4 and the plates were read on a plate reader (Dynex Technologies) at 450 nm.

Results

Vector Construction of pLD-5'UTR-CTB-Human Proinsulin (5CP)

The CTB-Pris fusion gene was inserted into the chloroplast transformation vector pLD-ctv for homologous recombination into the tobacco chloroplast genome. The pLD vector contains the trnI and trnA flanking sequences utilized to facilitate homologous recombination into the inverted repeat region of the tobacco chloroplast genome. The 5CP construct was expressed under the control of the psbA 5'UTR/promoter in order to achieve hyper-expression as previously demonstrated (Fernandez San-Millan et al., 2003; Daniell et al., 2004c; Dhingra et al., 2004). The aadA gene confers resistance to spectinomycin in order to select for transformed shoots (Goldschmidt-Clermont 1991) and is regulated by the 16S rRNA promoter. The 3'UTR located at the 3' end of the introduced gene confers transcript stability (Stern and Gruissem 1987). The pLD vector also possesses the chloroplast origin of replication (autonomously replicating sequence) located within the trnI region (Kunnimalaiyaan and Nielsen, 1997) which promotes replication of the plasmid following bombardment (FIG. 1). Crude extracts from E. coli clones that contained the 5'UTR-CTB-proinsulin insert was subjected to SDS-PAGE/immunoblotting, along with untransformed E. coli that served as a negative control. Following immunoblot detection with the insulin antibody, the correct size (~22 kDa) CTBPro insulin fusion protein was confirmed (FIG. 2, Lane 1).

Analysis of the Transgenic Chloroplast Genome Reveals Homoplasmy

The chloroplast transgenic lines were subjected to Southern blot analysis in order to confirm site-specific integration and to determine whether they were homoplasmic or heteroplasmic. Homoplasmy is achieved when all the copies of the genome within the chloroplast have stably integrated transgenes. The gene-specific probe (CTB-proinsulin) that was taken from the pLD-5CP vector by MfeI/NotI digestion (FIG. 3A) (360 bp) bound to the proper transgenic plant fragment but not wild-type plant fragment (FIG. 3C) following digestion of transgenic plant DNA with AflIII (FIG. 3B). This indicates that the gene of interest was integrated into the correct region within the chloroplast genome and the untransformed plant DNA showed no such hybridization. The flanking sequence probe which contains the region of the trnI and trnA genes was obtained by digestion of pUC-ct vector by BglII/BamHI digestion (FIG. 3A). Chloroplast transgenic and untransformed plant DNA was digested with AflIII (FIG. 3B). Upon hybridization with the flanking sequence probe, transformed chloroplasts should yield a 6.4 kb fragment; untransformed plants, a 4.2 kb fragment. If the 4.2 kb fragment is not seen within the transgenic line, all the chloroplast genomes carry the gene of interest, and homoplasmy has been attained within our current limit of detection. Most of the lines tested showed only the 6.4 kb fragment when hybridized to transgenic plant DNA (FIG. 3D), indicating that homoplasmy was indeed achieved within limits of detection.

CTB-Proinsulin Pentamers were Assembled in Transgenic Chloroplasts

Immunoblots showed the presence of ~22 kDa fusion protein in the chloroplast transgenic lines. The formation of monomers, dimers, trimers, tetramers, and pentamers of the CTB-Pins fusion protein was also observed (FIG. 2). A similar banding pattern was observed by immunodetection with both the proinsulin monoclonal antibody (FIG. 2) and the CTB polyclonal antibody (data not shown). Quantification of the fusion protein on western blots was performed by comparing plant samples with a known quantity of purified CTB and reading them on an alpha imager by spot densitometry. Three different transgenic lines were found to contain 358 µg, 270 µg and 364.8 µg of CTB-proinsulin per 100 mg of leaf tissue, or approximately 30% of total soluble protein (tsp). Quantification by Total Proinsulin ELISA Kit of frozen plant tissue revealed that the same transgenic lines contained 145 µg, 95 µg and 194 µg of CTB-proinsulin per 100 mg of frozen leaf tissue, for a maximum of 13.8% tsp. Such variation could be due to the use of fresh versus frozen plant material for these assays or differences in sample preparation or growth conditions.

Blood Glucose Levels of NOD Mice Treated with CTB-Human Proinsulin were Lowered

We divided the NOD mice into four groups fed once a week for seven weeks beginning at week 5. Each group differed only by the plant material they were fed. We fed one group untransformed plant material to control for the potential effects of plant material alone. One group received transgenic plant material expressing Cholera toxin B subunit-GFP fusion protein (CTB-GFP; Limaye et al, 2006) to assess the effects of high levels of conjugated CTB. Another group received transgenic plant material expressing interferon alpha 5 conjugated to GFP (IFN-GFP) as yet another control of GFP without CTB. The last group received CTB-Pins, which we hypothesized would protect against the onset of insulitis in these mice.

Blood and urine glucose levels of the treated NOD mice were measured twice, at weeks 6 and 7. The blood glucose values of all groups in this study at both time points tested were below 200 mg/dl, and therefore considered to be within a normal, nondiabetic range. This was not an unforeseen possibility, since NOD mice typically do not develop high blood glucose until 12-15 weeks age (Arakawa et al, 1998). However, the CTB-Pins treated animals tended to have lower blood glucose values than the control groups (data not shown). Likewise, urine glucose values were also within normal limits.

Lymphocytic Infiltration of the Endocrine Part of Pancreas (Insulitis)

Insulitis is characterized by lymphocytic infiltration of the pancreatic islets, accompanied by the secretion of proinflammatory cytokines, which leads to the destruction of the pancreatic islets, including the insulin producing beta cells. We collected pancreata from twelve week old NOD mice from the different treatment groups to assess the degree of insulitis. Representative sections prepared from each treatment group showed that oral administration of transgenic plant material expressing CTB-Pins led to much less destructive cellular infiltration of the pancreatic islets as compared to the other experimental groups (FIG. 4).

Figure 5:
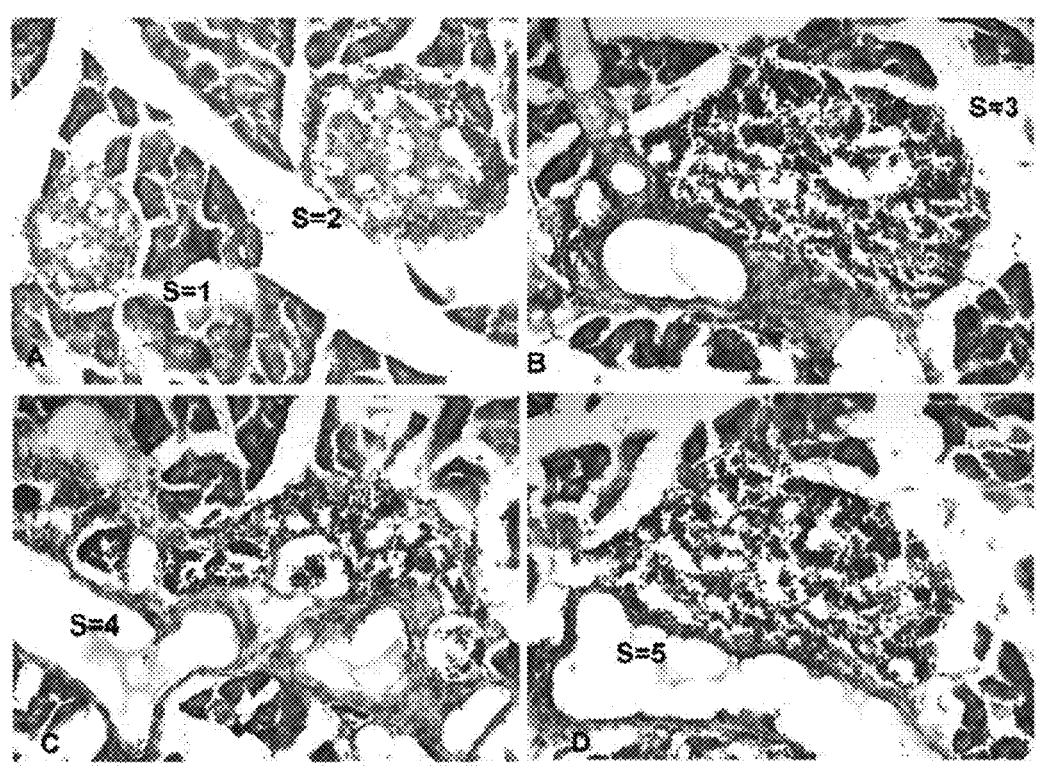
FIG. 5: Scoring (S) the insulitis according to the severity of the lymphocytic infiltration of the pancreas Langerhans islets. Score 1 indicates no or pre-islet infiltration, minimal infiltrations were scored 2, moderate infiltrations were scored 3 and severe infiltrations were scored 4. When more than 80% of the islets were infiltrated, the score was 5.

To quantify and compare the insulitis of each treatment group, cellular infiltrations were scored blindly according to the following: no islet cellular infiltration or pre-islet infiltration were scored 1, minimal infiltrations were scored 2, moderate infiltrations were scored 3, and severe infiltrations were scored 4 (FIG. 5). When more than 80% of the islets were infiltrated, the score was 5 (FIG. 5). Accordingly, fifty sections per animal were analyzed and the average score indicated that the pancreata from NOD mice administered CTB-Pins had minimal cellular infiltration, and this reduction in cellular infiltration is significantly less than all other treatment groups (FIG. 6).

Preservation of the Insulin Producing β-Cells Following Oral Delivery of CTB-Pins We next wanted to determine if the remaining β-cells represented in the pancreata of the different treatment groups were apoptotic. Because cellular infiltration can lead to apoptosis, this could be used as a hallmark to study type 1 diabetes. Therefore, we labeled sections with insulin and caspase-3, a known marker for apoptosis (Riedl & Shi, 2004). We found that the β-cells from NOD mice administered CTB-Pins rarely expressed caspase-3, suggesting that apoptosis was prevented in these cells (FIG. 7). In the other experimental groups, even the very few remaining insulin-producing β-cells expressed activated caspase-3, suggesting that they were undergoing apoptosis (FIG. 7).

Induction of Th2 Response and Production of Immunosuppressory Cytokines

Figure 8:
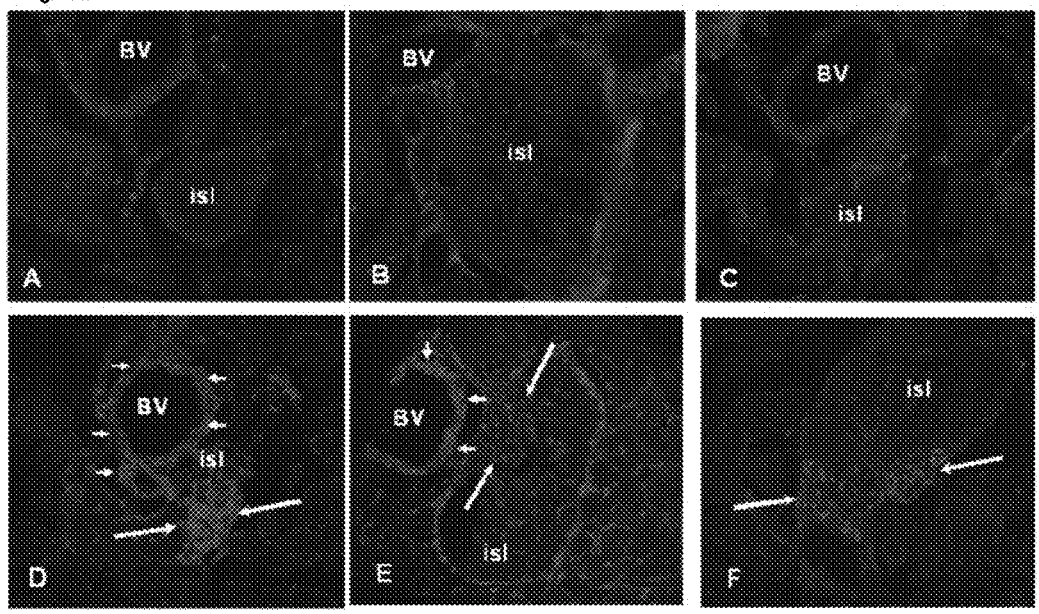
FIG. 8: Interleukin 10 (IL10) immunoreactivity in the pancreas of three mice treated with untransformed plant leaf material A, B, and C. Blood vessels (BV) and the langerhans islets (isl) are indicated. No significant IL10 immunostaining can bee seen in or around the islets or around the blood vessels. D, E, and F show the islets of mice treated with CTB-Proinsulin. Small arrows indicate perivascular infiltration of IL10 expressing lymphocytes. Large arrows indicate IL10 positive lymphocytes inside or around the islets.
Figure 9:
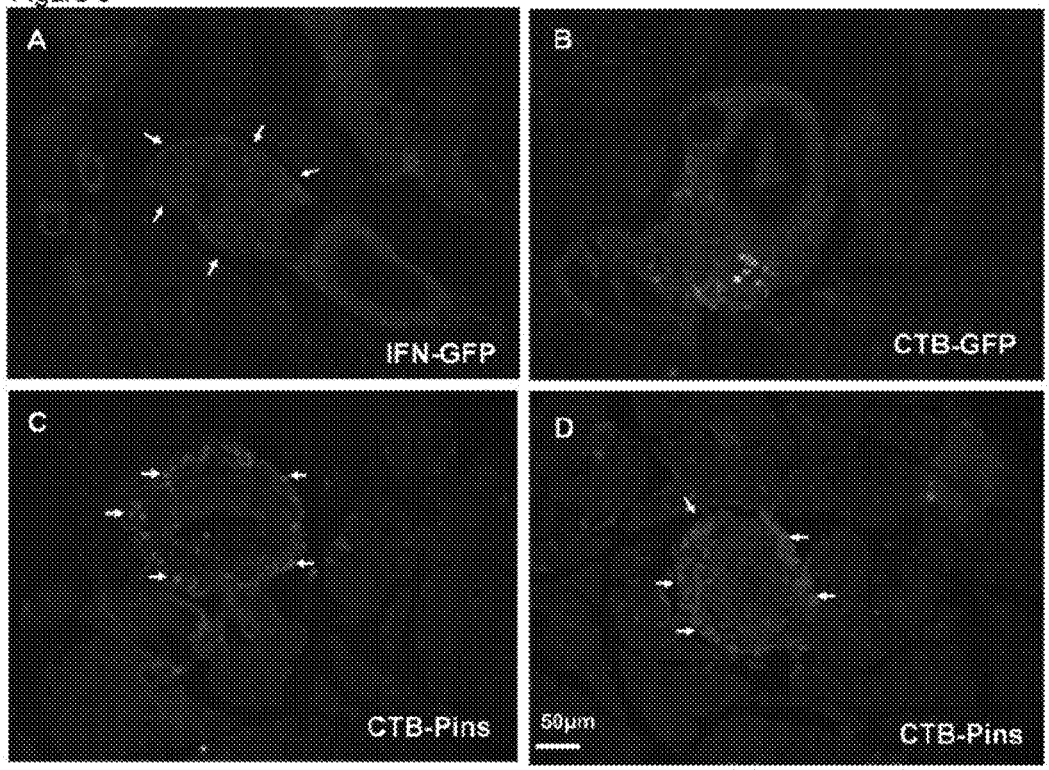
FIG. 9: Interleukin-4 (IL4) immunoreactivity in the pancreas of mice treated with IFNGFP or CTB-GFP or CTB-Pins plant leaf material. Blood vessels (BV) are free of perivascular lymphocytic infiltration and no significant IL4 positive cells can be seen around the islets (arrows demarcate the islets). A large number of IL4 positive cells are shown around the islets of CTB-Pins treated NOD mice.

Oral administration of CTB-Pins to the NOD mice led to an increased recruitment of immunosuppressive cytokine-producing cells (lymphocytes) to the pancreas. A large number of IL10- or IL4-producing cells are seen proximal to the pancreatic islets, which are recruited through the circulation (FIGS. 8 & 9). This process is supported by significant perivascular migration of IL4- and IL10-expressing cells seen in the pancreas of CTBPins treated NOD mice (FIGS. 8 & 9). Blood vessels were distinguished from ducts as follows. The internal layer lining the blood vessels is comprised of endothelium, a thin, flat layer different from the more cuboidal lining of the ducts. These latter structures are thicker with a narrower lumen. In addition, endocrine glands are ductless glands. Although the pancreas has both endocrine and exocrine parts, the blood vessels are more likely to be found close to the endocrine parts where the products are secreted out of the cell and absorbed into the blood vessels, which must be in close contact to the endocrine cells. The third reason to believe that blood vessels are depicted is that blood cells should be found in the blood vessels and not the ducts. Also, there are no reports of immune attack against or regulatory process in favor of the pancreatic ducts.

Serum and Intestinal Immunoglobulin Levels Following Oral Delivery of CTB-Pins

Serum and intestinal mucosal immunoglobulin (Ig) levels were determined by ELISA using CTB as the capture antigen. Serum levels of IgG1 increased in NOD mice treated with CTB-Pins expressing plant leaf material as compared to the control groups. There were low serum IgG2a and mucosal IgA levels against CTB observed among NOD mice treated with untransformed plant leaf material or plants expressing CTB-IFN or CTB-GFP or CTB-Pins (FIG. 10).

Discussion

Oral administration of antigens represents a potential way to induce oral tolerance. Tolerance refers to the state of lowered systemic responsiveness toward an antigen following oral delivery. Both active and passive forms of tolerance can be induced, dependent upon the dose of antigen and the route of administration. The passive form is the functional inactivation of antigen specific lymphocytes and is selective for only pre-existing effectors. The active form of tolerance operates through the action of regulatory lymphocytes that are able to down-modulate inflammation via bystander suppression of effector cells. Bystander suppression is viewed as a form of immunoregulation rather than tolerance (Homman et al., 1999b). Mucosal immunity generated by oral delivery is a protective immune response manifested by Th-2 type cytokines such as IL-4, IL 10, and TGF-β. Antigen taken orally leads to presentation in the intestinal mucosa, which is able to generate protective Th-2 cells in the gut associated lymphoid tissue (GALT), such as the Peyer's patches. The antigen utilized is important because its nature may determine the type of cytokines produced by the antigen specific T-cells, it must direct the mucosal-derived T-cells to migrate to the organ of interest, and it must then be able to down-regulate the localized immune response (Gottlieb and Eisenbarth 2001). Previous studies have demonstrated that insulin given orally to non-obese diabetic (NOD) mice reduced the level of diabetes by 50%, and the protection was associated with the development of a Th-3-type response, specifically TGF-β producing T-cells (Zhang et al., 1991).

Oral tolerance induced by autoantigens has been applied successfully as a therapeutic tool in experimental models of autoimmune diseases (Strobel et al., 1998). The basic mechanism of oral tolerance in humans is currently a work in progress, and oral antigen administration regimens have resulted in limited success when applied to patients (Garside et al., 1999, Pozzilli et al., 2000b, Chailous et al., 2000). A possible explanation for the limited success could be due to the fact that the doses of the orally administered antigens to humans was too low compared to those we delivered to mice, considering the surface area of the intestinal absorptive epithelium (Pozzilli et al., 2000a). In this case, CTB may serve as the necessary co-factor required to overcome the inefficient presentation of insulin to the mucosal T-cells, resulting from the limited transport of native insulin across the epithelial layer. In order for oral tolerance to become a realistic therapy for human autoimmune diseases, adjuvants that possess the ability to enhance the tolerogenic potential of orally delivered antigens need to be identified. The coupling of autoantigens—in this case, proinsulin—to the non-toxic Cholera toxin B subunit (CTB) dramatically increases their tolerogenic potential (Sun et al., 1994, Bergerot et al., 1997; Arakawa et al., 1998). This effect is mediated by the ability of CTB to act as a transmucosal carrier, although CTB may have a direct affect on the immune system (Burkart et al., 1999, Li et al., 1996). The current primary limitation in advancing this concept in clinical trials is the low levels of expression in transgenic plants (Bergerot et al., 1997). Therefore, this limitation can be overcome by the hyperexpression of CTB-proinsulin fusion protein in transgenic chloroplasts.

Previous studies to express CTB-proinsulin fusion protein in plants were performed with potato plants (Arakawa et al., 1998). Expression levels in nuclear transgenic potato plants were 0.05-0.1% total soluble protein (tsp). The low expression levels required feeding NOD mice with large amounts of fresh potatoes. In this study, we have expressed CTB-proinsulin fusion protein in transgenic tobacco chloroplasts to levels at least 130-300-fold greater than those in nuclear transgenic potatoes. As such, we fed the NOD mice 8 mg of leaf tissue per week, which is a 375-fold lesser amount of plant tissue compared to the 3 g per week used previously (Arakawa et al, 1998). Using these small concentrated doses reduces the possibility of potential confounding effects of leaf tissue and eliminates the need to process or purify the plant material. Such hyperexpression of CTB-Proinsulin should make this fusion protein abundantly available for animal studies in NOD mice. Expression of CTB-Proinsulin within transgenic chloroplasts also eliminates the detrimental effects that occurred to nuclear transgenic proteins in the cytoplasm (Mason et al., 1999). Secondly, the expression of the foreign gene within chloroplasts provides a safeguard for transgene containment due to maternal inheritance of the plastid genome (Daniell, 2002) and engineered cytoplasmic male sterility (Ruiz & Daniell, 2005). Oral delivery of biopharmaceutical proteins expressed in plant cells reduces their cost of production, purification, processing, cold storage, transportation and delivery.

Oral administration of self antigens such as insulin leads to their uptake by the gut associated lymphoid tissue (GALT), including the intestinal mucosal M cells, which pass the antigen to underlying antigen presenting cells, such as macrophages and dendritic cells (Limaye et al., 2006). This leads to the activation of T-cells and induction of a Th2 cell response, which is characterized by the up-regulation of immunosuppressive cytokines (such as IL10 and IL4) and serum antibodies (such as IgG1 but not IgG2a) (Salmound et al., 2002, Farmer and Weiner 2005). No significant increase in mucosal IgA was seen in our study in CTB-Pins treated mice versus the control groups.

The presence of CTB in the intestine ensures an effective receptor-mediated oral delivery of intact plant-derived fusion protein across the intestinal mucosa via binding of CTB to the GM1 ganglioside receptor and uptake by intestinal M cells and enterocytes. Taken together, the data presented here suggest that the suppression of the disease was mediated by regulatory Th-2-cells. Since T-cell regulation is a major player in mucosal immunity, oral administration of an autoantigen can be used to treat autoimmune diseases in animal models by generating active T-cell suppression. Mucosal autoantigen administration represents a potential way to establish tolerance towards autoantigens and the prevention of autoimmune diseases. Several autoimmune diseases and their antigens are known: Multiple Sclerosis (MBP and PLP), Arthritis (Type II collagen), Uvetis (S-antigen and IRBP), Myasthenia gravis (AChR) and Thyroiditis (Thyroglobin) (Hafler and Weiner 1997).

One previous human clinical study on the oral delivery of insulin was unsuccessful (Skyler et al., 2005) because insulin was not protected from digestive enzymes and acid hydrolysis. In this study, however, insulin was protected by bioecapsulation within plant chloroplasts. Future experiments involving the CTBPro insulin construct, including human clinical trials, will utilize cultured cells free of nicotine or other alkaloids instead of leaves, although the amount of nicotine present will be negligible. Additionally, we used 5-week old mice in this study to demonstrate the alleviation of symptomatic pancreatic insulitis and preservation of insulin-producing β-cells in mice, a condition that mimics human type 1 diabetes. Based on the success of the concept in older mice (Harrison et al., 1996), this strategy is likely to work not only prior to the onset of diabetes, but also at later stages of this autoimmune disease.

REFERENCES

Arakawa T, Yu J, Chong D, Hough J, Engen P, Langridge W. (1998). A plant-bases cholera toxin B subunit-insulin fusion protein protects against the development of autoimmune diabetes. Nature, 16: 934-38

Bergerot, IPloix, C., Petersen, J., Moulin. V., Rask, C., Fabien, N. (1997) A cholera toxoid-insulin conjugate as an oral vaccine against spontaneous autoimmune diabetes. Proc. Natl. Acad. Sci. USA 94:4610-4614.

Bhati A. (2005) Expression of Hepatitic C viral non structural 3 protein in transgenic chloroplast Master's Thesis, University of Central Florida Burkart V, Kim Y, Kauer M, Kolb H. (1999) Induction of tolerance in macrophages by cholera toxin B chain. Pathobiology. 67(5-6):314-7

Chaillous L, Lefevre H, Thivolet C, Boitard C, Lahlou N, Atlan-Gepner C, Bouhanick B, Mogenet A, Nicolino M, Carel J C, Lecomte P, Marechaud R, Bougneres P, Charbonnel B, Sai P: (2000) Oral insulin administration and residual beta-cell function in recent onset type 1 Diabetes: a multicentre randomised controlled trial. Diabete Insuline Orale group. *Lancet* 356: 545-549

Daniell, H. (1997). Transformation and foreign gene expression in plants mediated by microprojectile bombardment. *Meth Mol. Biol.* 62:453-488.

Daniell, H. (2002) Molecular strategies for gene containment in transgenic crops. *Nat. Biotechnol.* 20, 581-586.

Daniell, H. Datta, R. Varma, S. Gray, S, and Lee, S. B. (1998) Containment of herbicide resistance through genetic engineering of the chloroplast genome. *Nat. Biotechnol.* 16, 345-348.

Daniell, H. Lee, S. B. Panchal, T. and Wiebe, P. O. (2001) Expression of cholera toxin B subunit gene and assembly as functional oligomers in transgenic tobacco chloroplasts. *J. Mol. Biol.* 311, 1001-1009.

Daniell, H. Kahn, M. and Allison, L. (2002) Milestones in chloroplast genetic engineering: an environmentally friendly era in biotechnology. *Trends Plant Sci.* Vol. 7, No. 2 84-91.

Daniell H, Cohill P, Kumar S, Dufourmantel N, Dubald M. (2004a) Chloroplast genetic engineering. H Daniell and C Chase, eds, Molecular biology and biotechnology of plant organelles, Kluwer Academic Publishers, Dordrecht, pp. 423-468.

Daniell H, Carmona-Sanchez O, Burns B B. (2004b) Chloroplast derived antibodies, biopharmaceuticals and edible vaccines. In R Fischer and S Schillberg eds, Molecular Farming Weinheim: WILEY-VCH Verlag, pp. 113-133.

Daniell H, Ruiz O N, Dhingra A. (2004c) Chloroplast genetic engineering to improve agronomic traits. *Methods in Molecular Biology* 286: 111-137.

Daniell H, Kumar S, Dufourmantel N. (2005a) Breakthrough in chloroplast genetic engineering of agronomically important crops. *Trends Biotechnol.* 23:238-45

Daniell H, Chebolu S, Kumar S, Singleton M, Falconer R. (2005b) Chloroplast derived vaccine antigens and other therapeutic proteins. *Vaccine* 23:1779-1783.

DeGray, G. Rajasekaran, K. Smith, F. Sanford, J. and Daniell, H. (2001) Expression of an antimicrobial peptide via the chloroplast genome to control phytopathogenic bacteria and fungi. *Plant Physiology.* 127, 852-862.

Dhingra A, Portis A R Jr, Daniell H. (2004) Enhanced translation of a chloroplast expressed RbcS gene restores small subunit levels and photosynthesis in nuclear RbcS antisense plants. Proc Natl Acad Sci USA. 2004 Apr. 20; 101(16):6315-20. Epub April 5.

Ekberg K, Brismar T, Johansson B L, Jonsson B, Lindstrom P, Wahren J. (2003) Amelioration of sensory nerve dysfunction by C-Peptide in patients with type 1 diabetes. Diabetes. February; 52(2):536-41.

Faria A M, Weiner H L. (2005) Oral tolerance. Immunol Rev. August; 206:232-59. Review.

Fernandez-San Millan, A. Mingeo-Castel, A. M. Miller, M. and Daniell, H. (2003) A chloroplast transgenic approach to hyper-express and purify Human Serum Albumin, a protein highly susceptible to proteolytic degradation. *Plant Biotechnology Journal.* 1, 71-79.

Garside P, Mowat A M, Khoruts A. (1999) Oral tolerance in disease. Gut. January; 44(1):137-42. Review.

Goldschmidt-Clermont, M. (1991) Transgenic expression of aminoglycoside adenine transferase in the chloroplast: a selectable marker for site-directed transformation of *Chlamydomonas. Nucl. Acids Res.* 19, 4083-4089

Gottlieb P A., and Eisenbarth G S. (2002) Insulin-specific tolerance in diabetes. Clinical Immunology. 1: 2-11

Grevich, J. J. & Daniell, H. (2005) Chloroplast genetic engineering: Recent advances and future perspectives. *Critical reviews in Plant sciences.* 24: 83-107.

Guda, C. Lee, S. B. and Daniell, H. (2000) Stable expression of biodegradable protein based polymer in tobacco chloroplasts. *Plant Cell Rep.* 19, 25T262.

Hafler and Weiner (1997) Oral tolerance for the treatment of Autoimmune diseases. Novel therapeutic agents for the treatment of autoimmune diseases. Marcel Dekker inc. New York, Ch 17. pp. 201-220

Halban P A. (1991) Structural domains and molecular lifestyles of insulin and its precursors in the pancreatic beta-cell. Diabetologia. 1991 November; 34(11):767-78. Review Harrison L. C., Dempsey-Collier M., Kramer D R, Takahashi K. (1996) Insulin induces regulatory CD8 T Cells that prevent murine insulin-dependent diabetes. J. Exp. Med. Volume 184 December 2167-2174

Homann D., Dyrberg, T., Petersen, J., Oldstone M. B., and von Herrath M. G. (1999a) Insulin in oral immune (tolerance): a one-amino acid change in the B chain makes the difference, J. Immunol. 163 (4), pp. 1833-1838.

Homann D, Holz A, Bot A, Coon B, Wolfe T, Petersen J, Dyrberg T P, Grusby M J, von Herrath M G. (1999b) Autoreactive CD4+ T cells protect from autoimmune diabetes via bystander suppression using the IL-4/Stat6 pathway. *Immunity.* October; 11(4):463-72.

Horton R M, Hunt H D, Ho S N, Pullen J K, Pease L R. (1989) Engineering hybrid genes without the use of restriction enzymes: gene splicing by overlap extension. Gene. April 15; 77(1):61-8

Kota M, Daniell H, Varma S, Garczynski S F, Gould F, Moar W J. (1999) Overexpression of the *Bacillus thuringiensis* (Bt) Cry2Aa2 protein in chloroplasts confers resistance to plants against susceptible and Bt-resistant insects. Proc Natl Acad Sci USA. 1999 Mar. 2; 96(5):1840-5

Koya V, Moayeri M, Leppla S H, Daniell H. (2005) Plant-based vaccine: mice immunized with chloroplast-derived anthrax protective antigen survive anthrax lethal toxin challenge. Infect Immun. December; 73(12):8266-74

Kumar S, Dhingra A, Daniell H. (2004a) Plastid-expressed betaine aldehyde dehydrogenase gene in carrot cultured cells, roots, and leaves confer enhanced salt tolerance. *Plant Physiol* 136: 2843-2854

Kumar S, Dhingra A, Daniell H. (2004b) Stable transformation of the cotton plastid genome and maternal inheritance of transgenes. *Plant Mol Biol* 56:203-216.

Kunnimalaiyaan M, Nielsen B L. (1997) Fine mapping of replication origins (on A and on B) in *Nicotiana tabacum* chloroplast DNA. *Nucleic Acids Res.* September 15; 25(18):3681-6.

Lee, S. B. Kwon, H. B. Kwon, S. J. Park, S. C. Jeong, M. J. Han, S. E. Byun, M. O. and Daniell, H. (2003) Accumulation of trehalose within transgenic chloroplasts confers drought tolerance. *Mol. Breeding*. 11, 1-13.

Leelavathi S, Reddy V S. (2003) Chloroplast expression of His-tagged GUS-fusions: a general strategy to overproduce and purify foreign proteins using transplastomic plants as bioreactors. *Mol. Breed*. 11: 49-58.

Li T K, Fox B S. (1999) Cholera toxin B subunit binding to an antigen-presenting cell directly co-stimulates cytokine production from a T cell clone. Int Immunol. 8:1849-56.

Limaye, A., V. Koya, S. M., and H. Daniell. (2006) Receptor mediated oral delivery green fluorescent protein expressed in transgenic chloroplasts into the mouse circulatory system. *FASEB* (in press)

Mason H., Haq T A., Clements J D., Arntzen C J. (1999) Edible vaccine protects mice against *Escherichia coZi* heat-labile enterotoxin (LT): potatoes expressing a synthetic LTB gene. Vaccine, Vol. 16, No. 13, pp. 1336-1343, 1998

Molina A, Herva-Stubbs S, Daniell H, Mingo-Castel A M, Veramendi J. (2004) High yield expression of a viral peptide animal vaccine in transgenic tobacco chloroplasts. *Plant Biotechnol. Journal* 2:141-153.

Nagata M, Santamaria P, Kawamura T, Utsugi T, Yoon J W. (1991) Evidence for the role of CD8+ cytotoxic T cells in the destruction of pancreatic beta-cells in nonobese diabetic mice. J. Immunol. 1994 Feb. 15; 152(4):2042-50.

Pozzilli P, Gisella Cavallo M. (2000a) Oral insulin and the induction of tolerance in man: reality or fantasy? Diabetes Metab Res Rev. September-October; 16(5):306-7.

Pozzilli P, Pitocco D, Visalli N, Cavallo M G, Buzzetti R, Crino A, Spera S, Suraci C, Multari G, Cervoni M, Manca Bitti M L, Matteoli M C, Marietti G, Ferrazzoli F, Cassone Faldetta M R, Giordano C, Sbriglia M, Sarugeri E, Ghirlanda G (2000b) No effect of oral insulin on residual beta-cell function in recent-onset type I diabetes (the IMDIAB VII). IMDIAB Group. *Diabetologia* 43:1000-1004

Prodromou C, Pearl L H. (1992) Recursive PCR: a novel technique for total gene synthesis. Protein Eng. December; 5(8):827-9.

Riedl S J, Shi Y. Molecular mechanisms of caspase regulation during apoptosis. *Nat Rev Mol Cell Biol*. 2004 November; 5(11):897-907

Ruiz, G. (2002) Optimization of codon composition and regulatory elements for expression of the human IGF-1 in transgenic chloroplasts. Master's Thesis, University of Central Florida, USA.

Ruiz O N, Hussein H, Terry N, Daniell H. (2003) Phytoremediation of organomercurial compounds via chloroplast genetic engineering. *Plant Physiol*. 132: 1344-1352.

Ruiz, O. & Daniell, H. (2005). Engineering Cytoplasmic male sterility via. The chloroplast Genome by expression of β-ketothiolase. *Plant Physio*. 138, 232-246.

Salmond R J, Luross J A, Williams N A. (2002) Immune modulation by the cholera-like enterotoxins. Expert Rev Mol. Med. October 1; 2002:1-16. Review.

Samsam M, Mi W, Wessig C, Zielasek J, Toyka K V, Coleman M P, Martini R (2003) The Wlds mutation delays robust loss of motor and sensory axons in a genetic model for myelin-related axonopathy. J. Neurosci. 1; 23(7):2833-9.

Singleton M L. (2003) Expression of CaF1 and LcrV as a fusion protein for development of a vaccine against *Yersisnia pestis* via chloroplast genetic engineering. Master's Thesis, University of Central Florida.

Skyler J S., Krishner J P., Wolfsdorf J., Cowie C., Plamer J P., Greenbaum C., Cuthbertson D., Rafkin-Mervis L E., Chase H P., and Leschek E. (2005) Effects of oral insulin in relatives of patients with type 1 diabetes. Diabetes Care 28: 1068-1076

Staub J M, Garcia B, Graves J, Hajdukiewicz P T, Hunter P, Nehra N, Paradkar V, Schlittler M, Carroll J A, Spatola L, Ward D, Ye G, Russell D A (2000) High-yield production of a human therapeutic protein in tobacco chloroplasts. *Nat. Biotechnol*. 18: 333-338.

Stern D B, Gruissem W (1987) Control of plastid gene expression: 3' inverted repeats act as mRNA processing and stabilizing elements, but do not terminate transcription. *Cell*. 51: 1145-57.

Strobel S, Mowat A M. (1998) Immune responses to dietary antigens: oral tolerance. Immunol Today. April; 19(4): 173-81. Review.

Sun, J-B., Holmgren J. Czerkinsky C. (1994). Cholera toxin B subunit: an efficient transmucosal carrier-delivery system for induction of peripheral immunological tolerance. *Proc Natl Acad. Sci. USA* 91: 10795-10799.

Tregoning J S, Nixon P, Kuroda H, Svab Z, Clare S, Bowe F, Fairweather N, Ytterberg J, van Wijk K J, Dougan G, Maliga P. (2003) Expression of tetanus toxin fragment C in tobacco chloroplasts. *Nucleic Acids Res*. 31: 1174-1179.

Watson J, Koya V, Leppla S, Daniell H. (2004) Expression of *Bacillus anthracis* protective antigen in transgenic chloroplasts of tobacco, a non-food/feed crop. *Vaccine* 22: 4374-4384.

Zhang Z J, Davidson L, Eisenbarth G, Weiner H L. (1991) Suppression of diabetes in nonobese diabetic mice by oral administration of porcine insulin. *Proc Natl Acad Sci USA*. November 15; 88 (22):10252-6

Example 2: Expression of a Cholera Toxin B Subunit-Rotavirus Enterotoxin Fusion Gene in Transgenic *Nicotiana tabacum* Chloroplast Introduction Rotavirus, the major cause of life-threatening infantile gastroenteritis, is a member of the Reoviridae family and is considered to be the single most important cause of virus-based severe diarrheal illness in infants and young children particularly 6 months to 2 years of age in industrialized and developing countries. Rotaviruses belong to the family Reoviridae and are spherical 70-nm particles. The virus genome contains 11 segments of double-stranded RNA, each encoding a viral capsid or nonstructural protein [1]. The identification of a rotavirus nonstructural protein gene (NSP4) encoding a peptide, which functions both as a viral enterotoxin and as a factor involved in the acquisition of host cell membrane during virus budding from cells, provides a new approach for mucosal immunization. NSP4 has been designated as the viral enterotoxin as it was demonstrated that a peptide derived from its cytoplasmic domain is enough to cause Diarrhea in 3-Day old mice [2]. Various critical functions of NSP4 at the molecular level have also been identified; it plays a major role in viral morphogenesis by functioning as an intracellular receptor to aid in the budding of subviral particles into the endoplasmic reticulum (ER) [3]. It has been demonstrated that NSP4 possesses membrane destabilization activity on ER by mobilizing intracellular calcium and hence increasing its levels in intestinal cells. It also affects the membrane trafficking from the ER to the Golgi complex with its ability to bind to the micro tubules [4]. NSP4 induced intracellular calcium mobilization may be responsible for some of the cellular aspects of rotavirus pathogenesis as this increase in intracellular calcium ultimately stimulates endogenous fluid secretory pathway in the intestinal mucosa [5]. These above attributes of C-terminal portion led to the use of the truncated form of NSP4 with 90 amino acids as a good candidate for rotavirus vaccine antigen instead of the full length NSP4. Cholera toxin B subunit (CTB) of *Vibrio cholera* has been shown to function efficiently as an adjuvant and carrier molecule for foreign proteins and especially for mucosal vaccines. Direct linking of small antigens with CTB results in specific targeting of the antigens to the mucosal immune system through its specific binding affinity to GM1 receptors of enterocytes and also increases the local antigen concentration at the mucosal surface. Hence the immune response to CTB-NSP4 fusion protein is expected to be lot stronger[6].

Presently there is no available vaccine for rotavirus included in national immunization systems, the only live tetravalent rhesus-human reassortant vaccine (RRV-TV; Rotashield) for rotavirus was licensed in 1998 in USA but withdrawn from market in 1999 for possible association with intussusception[7]. Among the various protein expression systems available, genetically engineered plants are considered to be most economical. As lot of investment is needed to establish and maintain the industrial facilities using fermentation or bioreactors when compared to the technology that is already available for harvesting and processing plants and plant products on a large scale [8, 9]. Plant-derived products are less likely to be contaminated with human pathogenic microorganisms than those derived from animal cells because plants don't act as hosts for human infectious agents 10. Recombinant proteins expressed in plant cells are naturally protected from degradation when taken orally 11. The levels of recombinant proteins expressed in transgenic plants by nuclear system have been observed to be less than 1% of total soluble protein which is considered to be commercially unfeasible for protein purification 8.

The inventors have realized that one of the most attractive alternative means for achieving higher expression levels of foreign proteins in plants is through the chloroplast transformation. Chloroplast transformation is considered to be an ideal system for expressing foreign proteins as it offers several advantages like high-level transgene expression 12, proper folding of proteins, multi-gene engineering in a single transformation event 12, 13, transgene containment via maternal inheritance [14, 15, 16, 17], lack of gene silencing, position effect due to site-specific transgene integration. Chloroplasts also possess the ability to accumulate any foreign proteins in large amounts that could otherwise be harmful if they were in the cytoplasm. For example CTB an oral subunit vaccine for cholera was not toxic when expressed in transgenic plastids in very high quantities which were otherwise toxic when expressed in leaves by nuclear transformation. Trehalose, a pharmaceutical industry preservative was toxic when accumulated in cytosol where as was non toxic when compartmentalized in plastids by chloroplast expression system[14,18].

The various vaccine antigens and therapeutic proteins have been successfully hyperexpressed via the chloroplast genetic engineering. Vaccine antigens that have already been expressed in the chloroplast include the Cholera toxin B-subunit (CTB) 15, the F1~V fusion antigen for plague 19, the 2L21 peptide from the Canine Parvovirus (CPV) 20, Anthrax Protective antigen (PA) 21, LecA protein as vaccine antigen for *Entamoeba histolytica* 22, NS3 protein as vaccine antigen for hepatitis C 23, C terminus of *Clostridium tetani* (TetC) (24, 25) and therapeutic proteins like Human Serum Albumin 26, Magainin 27, Interferon and Insulin like growth factor 28.

Plastid transformation has been proven to be highly successful in tobacco. The popularity of tobacco is due to the availability of well defined regulatory elements for the transgene expression. Tobacco being a non food, non feed crop carries a reduced risk of transgenic maternal or recombinant proteins contaminating feed and human food chains. One of the other advantages of tobacco crop is its ability to yield high biomass (produces in excess of 40 metric tones of leaf fresh weight per acre on multiple harvests annually) with low maintenance and cost[29,30]. For these attractive reasons tobacco plastid transformation has been a successful vehicle for the large scale production of human recombinant proteins and vaccines too.

The expression levels of CTB-NSP4 that were achieved in transgenic potato by nuclear expression was about 0.006% to 0.026% which is not feasible for purification 31. Hence the main objective of this project is to express the surface antigen CTB-NSP4$_{90}$ fusion gene in plants using the chloroplast expression system to achieve high levels of expression to enhance the protective efficacy and also develop a low cost vaccine for rotavirus.

Results

Construction of pLD-5'UTR-His-CTB-NSP4 Vector for Tobacco Chloroplast Transformation.

The pRSET vector with Histag-CTB-NSP4 cloned in its multiple cloning sites was a gift from Dr William H R Langridge, Loma Linda Univeristy School of Medicine. The goal was to clone the cassette into the universal chloroplast transformation vector, pLD-Ctv under the control of light regulated psbA 5'UTR regulatory sequence which enhances the translation of the genes. The Histag-CTB-NSP4 gene cassette in pRSET vector was digested with Nde I and EcoRI and cloned into p-bluescript containing the 5'UTR regulatory sequence as shown in FIG. 11C named as p-bluescript-5'UTR-Histag-CTB-NSP4. The p-bluescript containing the 5'UTR-Histag-CTB-NSP4 cassette was then digested with EcoRV and XbaI and was cloned into the universal chloroplast transformation vector, pLD-Ctv within the EcoRV and XbaI sites and was designated as pLD-AK as shown in FIG. 11D. The pLD vector contains the homologous recombination sequences (flanking sequences) that allowed the homologous recombination of the gene cassette (aadA, 5"UTR-His-CTB-NSP4) in between the trnI and trnA of the chloroplast genome 15. Downstream to the trnI, the vector provided the constitutive 16S rRNA promoter, which regulates the expression of aadA gene (aminoglycoside 3' adenyltransferase) that confers resistance to spectinomycin-streptomycin and the 5'UTR-His-CTB-NSP4 gene encoding the cholera toxin B subunit-rotavirus NSP4 enterotoxin fusion protein. Upstream to the trnA, the vector contains the 3'UTR which is a transcript stabilizer derived from the psbA gene.

After recovering in the dark for 48 hours from bombardment, leaves were cut into 5 mm$^2$ pieces and placed on RMOP 32 plates containing 500 μg/ml spectinomycin for Petite Havana, for the first round of selection as described in Daniell 33,34,35. From 10 bombarded Petit Havana leaves, about 20 green shoots appeared after 4 weeks. For second round of selection the leaves were cut into 2 mm$^2$ pieces and then transferred to fresh RMOP plates with 500 μg/ml spectinomycin for Petite Havana 33, 35.

The shoots that appeared during the second round of selection were tested positive for cassette integration into the chloroplast genome by PCR analysis, were grown in sterile jars containing fresh plant MSO medium with spectinomycin until the shoots grew to fill the jars. Then the plants were transferred to pots with soil containing no antibiotic. Potted plants were grown in a 16 hour light/8 hour dark photoperiod in the growth chamber at 26° C.

Transgene Integration in Chloroplast and Homoplasmy

Figure 11A:
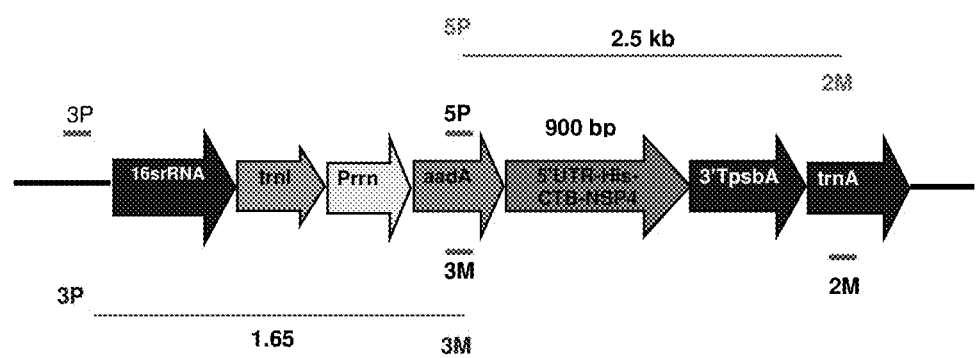
FIG. 11: PCR analysis of Wild type and putative transformants of pLD-5'UTR-His-CTB-NSP4. A: PCR using specific primers land within the native chloroplast genome (3P/3M) to yield a 1.65 kb product and 5P/2M primers to yield 2.5 kb product. B: Lane 1: 1 kb plus DNA ladder, Lane2: Negative control (Wild type) Lane 3-6: Transgenic lines of HisCTB-NSP4, Lane 7: Empty, Lane 8: Positive control (Interferon clone). C: Lane 1: 1 kb plus DNA ladder, Lane 2: Negative control (wild type), Lanes 3-6: Transgenic lines of HisCTB-NSP4, Lane 7: Empty, Lane 8: Positive control pLD 5'UTR-HisCTB-NSP4 plasmid.
Figure 11:
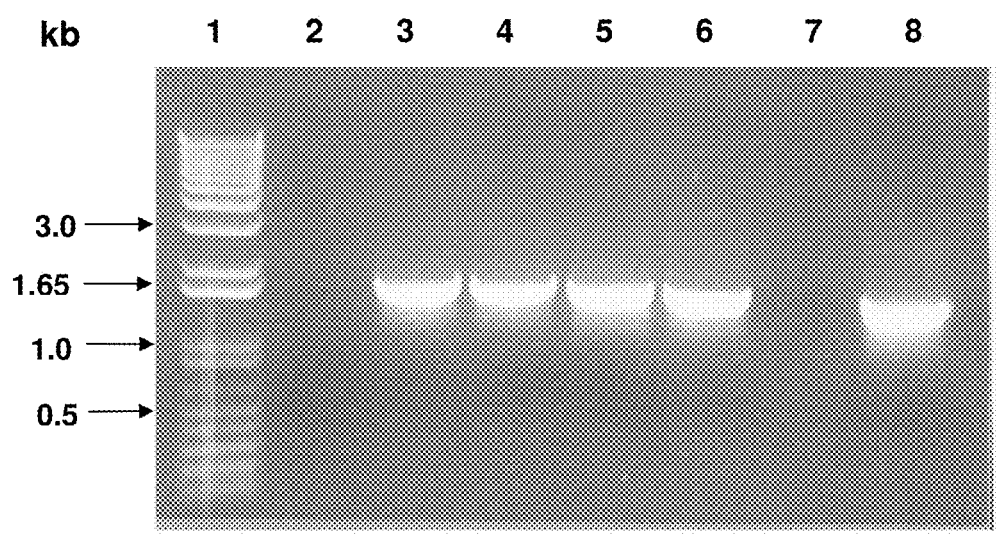
Figure 11:
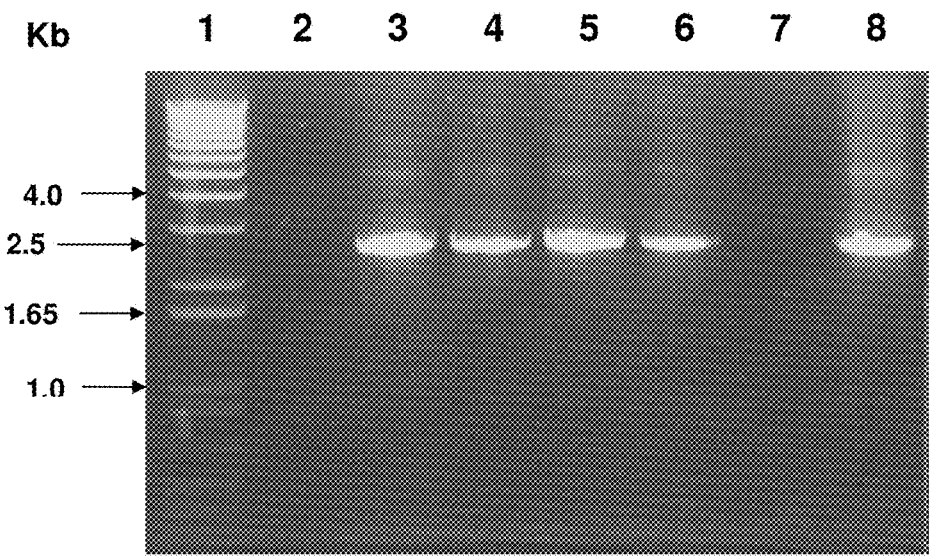

After bombardment of tobacco leaves with gold particles coated with plasmid DNA (pLD-5'UTR-His-CTB-NSP4), about 5 shoots/plate appeared after a period of 5-6 weeks. The shoots that were obtained on the RMOP selection medium could be due to any one of the three possible and two types of integration: chloroplast transgenic, nuclear transgenic or mutant shoots. Spontaneous mutation of the 16S rRNA gene, which confers resistance to spectinomycin in the ribosome, could allow plants to grow on spectinomycin without integration of the gene cassette which will result in the mutant shoot growth. The aadA gene in the gene cassette confers resistance to spectinomycin and hence the shoots with the integration of the gene cassette in either nuclear or chloroplast genome grow on the selection medium. True chloroplast transformants were distinguished from nuclear transformants and mutants by PCR analysis. Two primers, 3P and 3M were used to test for chloroplast integration of transgenes 15. 3P primer lands on the native chloroplast DNA in the 16S rRNA gene region and the 3M primer lands on the aadA gene as shown in FIG. 11A. Nuclear transformants were eliminated because 3P will not anneal and mutants were eliminated because 3M will not anneal. The 3P and 3M primers upon chloroplast integration of transgene will yield a product of 1.65 kb size fragment as shown in FIG. 11B.

The Integration of the aadA, 5'UTR-His-CTB-NSP4 gene and 3'psbA UTR, were additionally tested by using the 5P and 2M primer pair for the PCR analysis. The 5P and 2M primers annealed to the internal region of the aadA gene and the internal region of the trnA gene respectively as shown in FIG. 11A 15. The product size of a positive clone is of 2.5 kb for CTB-NSP4, while the mutants and the control do not show any product. FIG. 11C shows the result of the 5P/2M PCR analysis. After PCR analysis using both primer pairs, the plants were subsequently transferred through different rounds of selection on spectinomycin media to obtain a mature plant and reach homoplasmy.

Southern Analysis of Transgenic Plants

Figure 12:
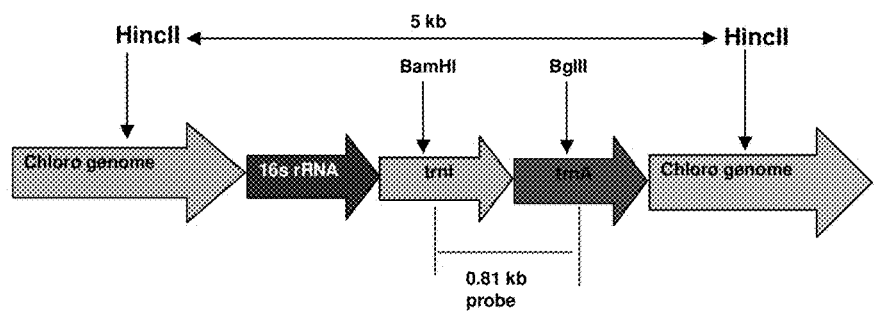
FIG. 12 Southern Blot analysis of CTB-NSP4 T0 plants. Schematic diagram of the products obtained from digestions of A: Wild type untransformed plants show a DNA fragment of 5 kb. B: Two DNA fragments of 4.3 kb and 2 kb indicate plants that are transformed with pLD-5'UTR-HisCTB-NSP4. C: A DNA fragment of 11 Kb is seen for transgenic lines with gene specific probe D: Southern with flanking sequence probe of CTB-NSP4 transgenic plants showing homoplasmy. Lane 1: 1 kb plus DNA ladder, Lane 2: Wild type, Lanes 3-8: CTB-NSP4 transgenic lines E: CTB-NSP4 gene specific probe showing the presence of CTB-NSP4 gene in the transgenic plants. Lane 1: 1 kb plus DNA ladder, Lane 2: Wild type, Lanes 3-6: CTB-NSP4 transgenic lines
Figure 12:
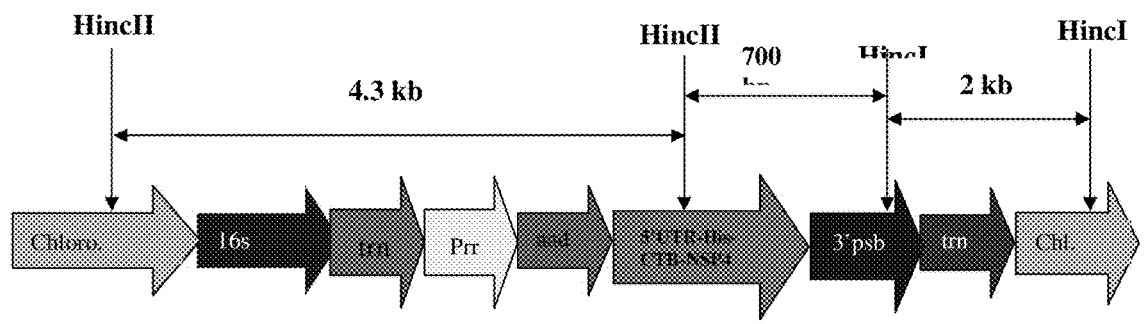
Figure 12:
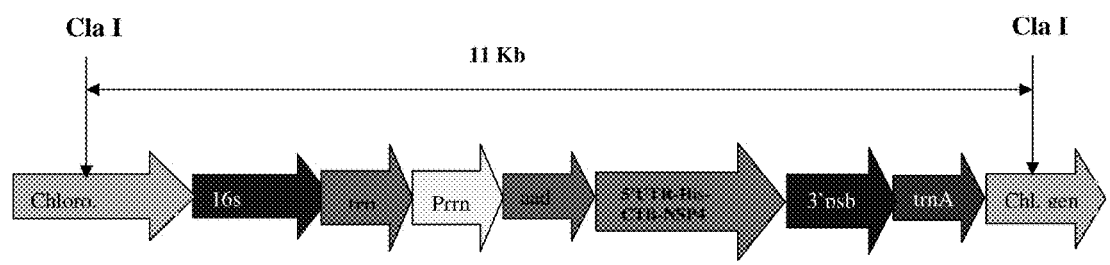
Figure 12:
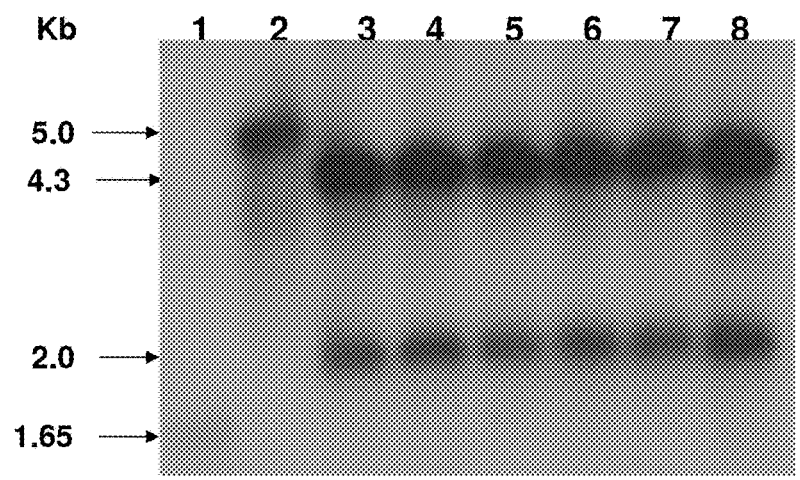
Figure 12:
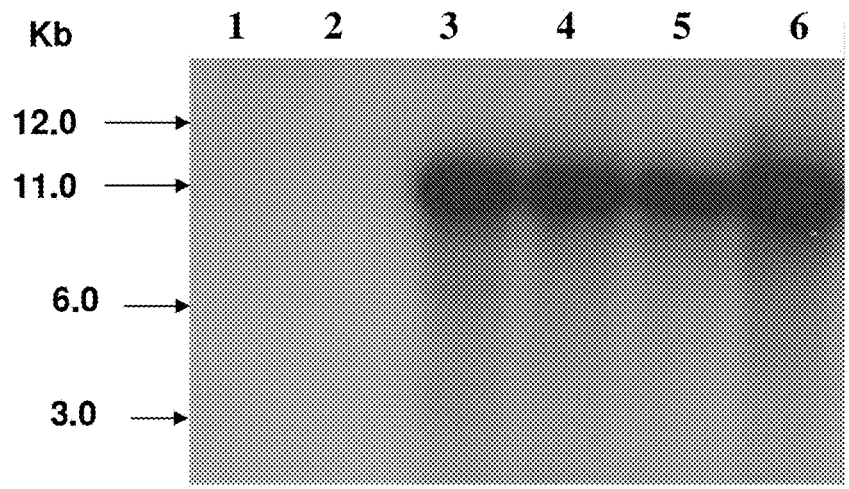

The plants that tested positive for the PCR analysis were moved through three rounds of selection and were then tested by Southern analysis for site specific integration of the transgene and homoplasmy. The DNA of the full regenerated clones growing in jars (third selection) was extracted and used for the Southern analysis. The flanking sequence probe of 0.81 kb in size allowed detection of the site-specific integration of the gene cassette into the chloroplast genome; this was obtained by double digesting the pUC-Ct vector that contained the trnI and trnA flanking sequences (FIG. 12A) with BamHI and BglII 15. FIG. 12B shows the HincII sites used for the restriction digestion of the plant DNA for pLD-5'UTR-Histag-CTB-NSP4. The transformed chloroplast genome digested with HincII produced fragments of 4.3 kb and 2.0 kb for pLD-5'UTR-Histag-CTB-NSP4, while the untransformed chloroplast genome that had been digested with HincII resulted in a 5.0 kb fragment (FIG. 12D). The flanking sequence probe can also show if homoplasmy of the chloroplast genome has been achieved through the three rounds of selection. The plants expressing CTB-NSP4 showed homoplasmy as there is no wild type band seen in transgenic lines within the levels of detection.

The gene specific probe CTB-NSP4 of size approx. 0.7 kb was used to show the specific gene integration producing a fragment of 11 kb when CTB-NSP4 transgenic plant DNA was digested with ClaI as shown in FIGS. 12C and 12E.

Immunoblot Analysis

Figure 13:
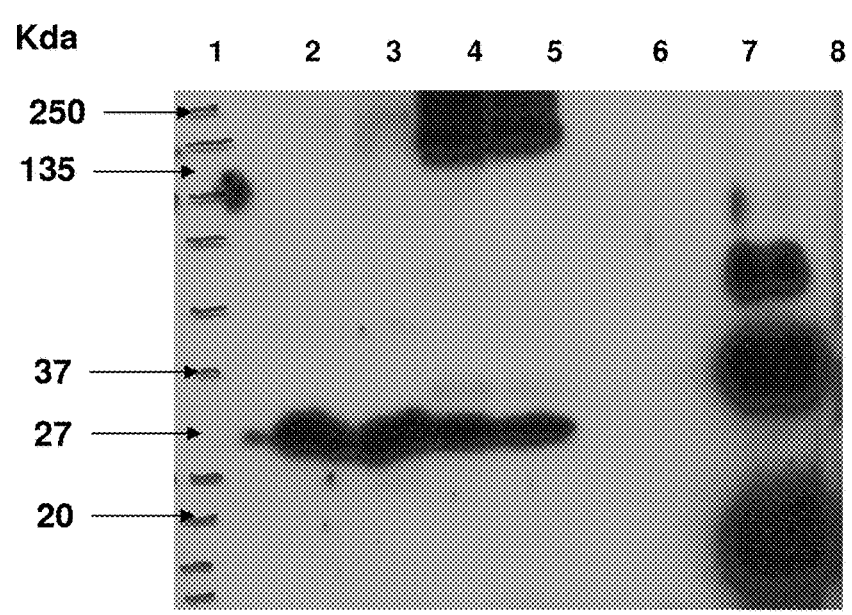
FIG. 13: Immunoblot analysis of crude plant extracts expressing CTB-NSP4. Lane 1: Molecular weight markers, Lane 2-3: Boiled T0 transgenic plant samples, Lane 4-5: Unboiled T0 transgenic plant samples (20 ug of crude plant extract was loaded). Lane 6: Wild type, Lanes 7: Empty, Lane 8: bacterial CTB-NSP4$_{90}$ fusion protein purified from Ecoli BL 21 cells (0.9 ug).

Crude protein extract of 20 ug, was loaded in each well of the SDS-PAGE. The rabbit anti-NSP4$_{90}$ antibodies (provided by Dr. William Langridge, Loma Linda Univ. of Loma Linda) were used to detect the 27 kDa and 135 kDa monomeric and pentameric forms CTB-NSP4 fusion protein (FIG. 13). The wild type plant (Petit havana) did not show any bands indicating that the anti-NSP4 antibodies did not cross react with any other proteins in the crude extract. As the CTB-NSP4 expression level was 2.45% of TSP in mature leaves, which indicates that there is 2.4 ug of the fusion protein in 100 ug of TSP. the total crude protein extract loaded in each well is 20 ug and so the expected amount of CTB-NSP4 fusion protein present in 20 ug of TSP will be about 0.6 ug. Hence each of the wells contains approximately about 0.6 ug of the CTB-NSP4 protein detected by the CTB-NSP4 antibodies.

Protein Quantification and Binding Affinity Using GM1 Binding Assay ELISA

Figure 14:
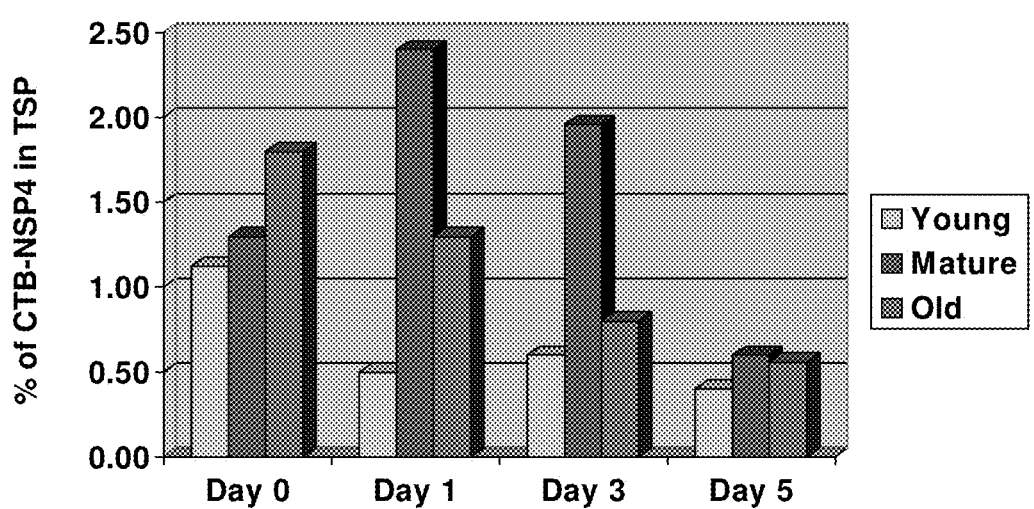
Figure 15A:
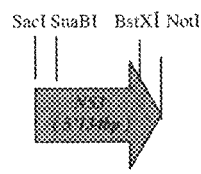
Figure 15B:
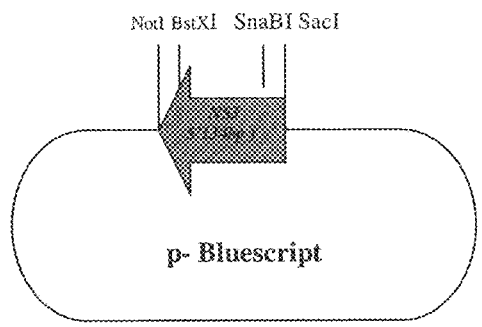
Figure 15C:
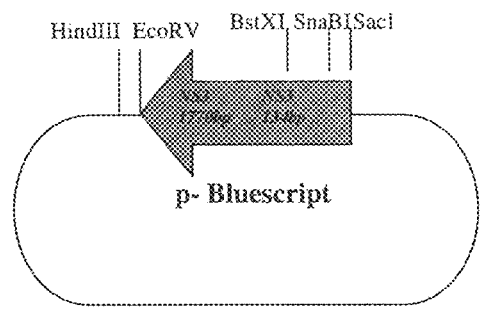
Figure 15D:
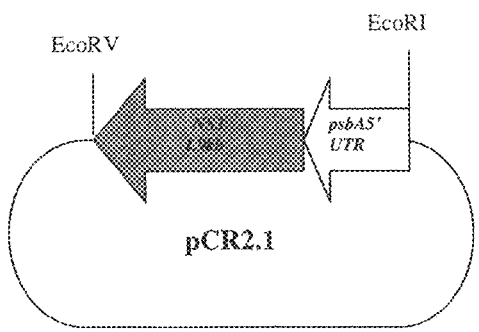
Figure 15E:
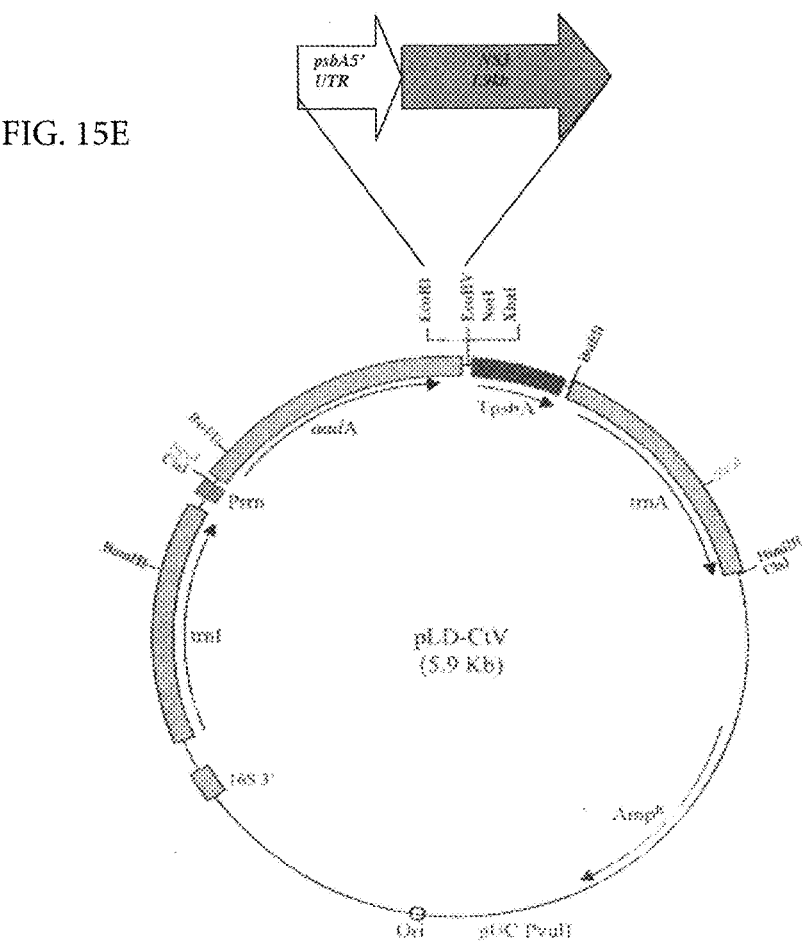

The levels of pentameric CTB-NSP4 fusion protein in transformed tobacco plants and its affinity for GM1-ganglioside was evaluated by quantitative GM1 ELISA. The standard curve has been obtained using different dilutions of purified CTB-NSP4. The dilutions were made in 0.01M phosphate buffered saline (PBS). The primary antibody used was Rabbit antibody raised against NSP4$_{90}$ protein expressed and purified from Ecoli BL21 cells and secondary antibodies were donkey anti-rabbit antibodies peroxidase conjugated. The percentage of CTB-NSP4 expressed was as a percent of total soluble protein calculated using the Bradford assay i.e. the percentage of CTB-NSP4 is inversely proportional to the TSP values. The CTB-NSP4 expression levels reached a maximum of 2.45% of the total soluble protein in the mature leaves after 1 Day of continuous light exposure due to increase in translation obtained under the control of light regulated psbA 5, UTR as shown in FIG. 14. The increased expression in mature leaves is due to more number of chloroplasts and high number of chloroplast genomes (up to 10,000 copies/cell) in the mature leaves. Also, the large size and more number of mature leaves per plant contributed to the higher levels of CTB-NSP4 in mature leaves.

Discussion

The pLD-5'UTR-Histag-CTB-NSP4 chloroplast transformation vector containing the aadA gene, CTB-NSP4 coding region and 3' psbA, integrates the transgene cassette into the transcriptionally active trnI-trnA spacer region of the chloroplast genome via homologous recombination. The site directed insertion of CTB-NSP4 into the chloroplast genome is achieved by homologous recombination between trnI-trnA regions of pLD-5'UTR-His-CTB-NSP4 and plastid genome which prevents any random integration of transgene that is usually observed with nuclear transformation. Achieving high expression of the CTB-NSP4 recombinant fusion protein in the chloroplast depends on various factors. First, the pLD-His-CTB-NSP4 vector is designed to integrate into the inverted repeat region of the chloroplast genome via homologous recombination. When the CTB-NSP4 fusion gene is inserted into the IR region, the copy number of the transgene gets doubled by a phenomenon know as copy correction that recruits the introduced transgene into another IR region 36,37). Increased copy number results in increased transcript levels resulting in higher protein accumulation 35, 12. Second, the psbA 5' UTR typically has stem loop structure which aid in transcript stability and is also a binding site for translation activation factors to enhance the binding of ribosomes to the mRNA for efficient translation. Also the translation of psbA mRNA is stimulated by light proposed to be mediated by a nuclear encoded protein. The binding of the nuclear encoded (RB) protein and psbA is directly dependent light which there by enhances the initiation of translation. The redox potential generated by light reactions of photosynthesis is used by chloroplast Protein Disulfide Isomerase system and thioredoxin which then activate the binding of translation activation factors to the ribosome binding sites in psbA 5' UTR thereby enhancing the translation in the presence of light 38. The expression of CTB-NSP4 in transgenic plant under continuous light showed an increase in expression at Day 1. The psbA 3' untranslated region (UTR) used for the regulation of transgene expression has potential role in post transcriptional stabilization by binding to different RNA binding proteins and help in enhancing translation of the foreign protein 14. Third, the pLD-His-CTB-NSP4 vector consists of a OriA site for origin of replication within trnI flanking region allowing to attain homoplasmy even in the first round of replication by increasing the number of templates for integration into the chloroplast genome (36, 37. To obtain an optimal production of the CTB-NSP4 fusion protein and transgene stability, it is essential to achieve homoplasmy through several rounds of selection on media containing spectinomycin. If homoplasmy is not achieved, it could result in heteroplasmy which leads to changes in the relative ratios of the two genomes upon cell division. The presence of heteroplasmic condition in a transgenic plant might retrograde back to the wild type eliminating the transgene in the absence of selection pressure in subsequent generations. The chimeric, aminoglycoside 3' adenyl transferase (aadA) gene, conferring resistance to spectinomycin was used as a selectable marker and its expression is driven by the 16S (Prrn) promoter (15, 39). Spectinomycin binds the 70S ribosome and inhibits translocation of peptidal tRNA's from the A site to the P site during protein synthesis. The aadA gene codes for the enzyme aminoglycoside 3' adenyltransferase, which transfers the adenyl moiety of ATP to spectinomycin and inactivating it. Fourth, chloroplast translation system provides the necessary enzymes for proper folding and disulphide bond formation. Chaperonins present in chloroplast are thought to aid in the folding and assembly of non native prokaryotic and eukaryotic proteins (15, 40). Reversible activation of genes that regulate expression in the chloroplast is the Protein Disulfide Isomerase (PDI) system composed of chloroplast polyadenylate-binding proteins that specifically bind to the 5'UTR of the psbA mRNA and are modulated by redox status through PDI (37). The ability of chloroplasts to form disulfide bonds and properly fold foreign proteins eliminates a major part of the costly downstream processing. The chloroplast expressed CTB-NSP4 fusion protein folded properly into functional pentameric form which was clearly seen on the immunoblot. The positive result in GM1 binding assay with CTB-NSP4 has reconfirmed the pentamer forms of CTB-NSP4 from transgenic tobacco chloroplasts.

Chloroplast transformants were distinguished from the nuclear transformants and mutants by PCR analysis. Southern blot analysis with gene specific CTB-NSP4 probe and flaking probe for chloroplast genome was done to confirm the site-specific integration of the gene cassette and also to determine the homo or heteroplasmy. High protein expression levels were obtained in the mature leaves after Day 1 of continuous light exposure of up to 2.45% of the total soluble protein which was quantified using the GM1 binding assay.

The present study reports the successful expression of the CTB-NSP4 fusion protein as pentameric forms. This opens the doors for the expression of CTB-NSP4 in carrot plastids so as to enable oral delivery of the vaccine antigen. The immunogenecity of the vaccine antigen needs to be tested in an animal model which is underway.

Materials and Methods

Construction of pLD-5'UTR-HisCTBNSP4 Vector for Transformation of Tobacco Chloroplast Initially the gene cassette Histag-CTB-NSP4 was cloned downstream to 5'UTR in p-bluescript between EcoRV and EcoRI sites. Then the final gene cassette containing the 5'UTR and His-CTB-NSP4 (approximate size 0.7 kb) were digested with EcoRV and XbaI and cloned into tobacco universal vector pLD-Ctv between EcoRV and XbaI.

Bombardment and Transgenic Plant Regeneration

Sterile *Nicotiana tabacum* cv. Petit Havana tobacco leaves were bombarded using the Bio-Rad PDS-1000/He biolistic device as previously described [32,33,35]. The bombarded leaves were allowed to incubate in dark for 48 hours to recover from tissue damage and then were placed on RMOP medium containing 500 ng/ml spectinomycin for two rounds of selection on plates and subsequently moved to jars with MSO medium containing 500 ng/ml spectinomycin[35].

Confirmation of Transgene Integration into the Chloroplast Genome

To confirm the transgene cassette integration into the chloroplast genome, PCR was performed using the primer pairs 3P (5'-AAAACCCGTCCTCGTTCGGATTGC-3' (SEQ ID NO: 2))-3M (5'-CCGCGTTGTTTCATCAAGC-CTTACG-3' (SEQ ID NO: 3)) 15 and the complete transgene integration was confirmed by PCR analysis using primer pairs 5P (5'-CTGTAGAAGTCACCATTGTTGTGC-3' (SEQ ID NO: 4)) and 2M (5'-GACTGCCCACCT-GAGAGC-GGACA-3' (SEQ ID NO: 5)) 15. The total DNA from putative transgenic and untransformed tobacco plants was isolated using Qiagen DNeasy Plant Mini Kit. The PCR reaction was set as follows: 150 ng of plant DNA, 1× Taq buffer, 0.5 mM dNTPs, 0.2 mM of primers each, 0.05 units/μl Taq polymerase. The amplification was set for 30 cycles with a program timed in the following way: 94° C. for 30 sec, 65° C. for 30 sec, and 72° C. for 30 sec for the 3P-3M primer pair and 72° C. for 1 min for the 5P-2M primer pair. Cycles were preceded by denaturation for 5 min at 94° C. and followed by a final extension for 7 min at 72° C. PCR products including the controls were loaded into a 0.8% agarose gel to confirm the results.

Southern Blot Analysis

The total plant DNA was digested with HincII and probed with Chloroplast flanking probe. The total plant DNA was also digested with ClaI in the similar manner and probed with CTB-NSP4 gene specific probe. The above set of digested samples was run on 0.7% agarose gel. The gels were soaked in 0.25 N HCl for 15 minutes and then rinsed 2 times with water. The gels were later soaked in transfer buffer (0.4 N NaOH, 1 M NaCl) for 20 minutes and then transferred overnight to a nitrocellulose membrane. The membranes were rinsed twice in 2×SSC (0.3 M NaCl, 0.03 M Sodium citrate), dried on filter paper, and then crosslinked in the GS GeneLinker (Stratagene, La Jolla, Calif.)[35]. The flanking sequence probe was made by digesting pUC-CT vector DNA with BamHI and BglII to generate a 0.81 kb probe lee et al. The CTB-NSP4 sequence of about 0.7 kb was used as gene specific probe. The probes were labeled with 32P using the ProbeQuant G-50 Micro Columns (Amersham, Arlington Heights, Ill.). The probes were hybridized with the membranes using Stratagene QUICK-HYB hybridization solution and protocol (Stratagene, La Jolla, Calif.).

Immunoblot Analysis

To detect the CTB-NSP4 fusion protein expression in transgenic tobacco plants the total protein was extracted from 100 mg of leaf tissue in 200 µl of plant extraction bufer (0.1% SDS, 100 mM NaCl, 200 mM Tris-HCl pH 8.0, 0.05% Tween 20, 400 mM sucrose, 2 mM PMSF). Similarly total protein from 100 mg of untransformed tobacco plant was also extracted to use as control. Both boiled (4 minutes) and unboiled samples of extracted protein with sample loading buffer were separated on 10% SDS/PAGE gel for one hour at 50V and then 3-4 hours at 80V for uniform separation. The proteins thus separated were transferred to a nitrocellulose membrane by electroblotting at 85V for one hour. The membrane was initially blocked with PTM (1×PBS, 0.05% Tween 20, and 3% dry milk) for one hour. Followed by incubation in P-T-M containing diluted (1:3000) rabbit anti-NSP4$_{90}$ antibody (provided by Dr Langridge, Univ of Loma Linda). Membranes were then washed with distilled water and transferred to P-T-M containing diluted (1:5000) goat derived anti-rabbit IgG antibody conjugated with alkaline phosphatase (AP) (Sigma, national immunization systems St. Louis, Mo.). Blots were washed three times with PBST for 15 minutes each time. Then washed with PBS for 10 minutes, followed by addition of chemiluminiscent substrate ((Pierce, Rockford, Ill.) for AP and incubating at room temp for 5 min for the chemiluminescence. Later the X-ray films were exposed to chemiluminescence and the films were developed in the film processor to visualize the bands.

Bradford Assay for Protein Quantification (Bio-Rad Manual).

The Bradford assay was used to determine the total protein from the plant extracts prepared as described above. This was used to determine the percent of CTB-NSP4 antigen in the total soluble protein extract (or % TSP). An aliquot of plant extract as prepared above was thawed on ice. Extraction buffer (15 mM Na$_2$CO$_3$, 35 mM NaHCO$_3$, 0.2 g NaN3, 0.1% Tween 20, and 5 mM PMSF adjusted to pH 9.6) was used to make Bovine Serum Albumin (BSA) standards ranging from 0.05 to 0.5 Plant extracts were diluted 1:10 and 1:20 with extraction buffer. 10 µl of each standard and 10 µl of each plant dilution was added to the wells of a 96 well microtiter plate (Cellstar) in duplicates. Bradford reagent (Biorad protein assay) was diluted 1:4 with distilled water as specified and 200 µl was added to each well. Absorbance was read. Comparison of the absorbance to known amounts of BSA to that of the samples was used to estimate the amount of total protein.

GM1 Binding (ELISA) Assay

The quantification and binding affinity of chloroplast derived CTB-NSP4 for GM1-ganglioside receptor in the plant crude extract was done using the GM1 ganglioside binding affinity (ELISA) as described by[41]. 100 mg of transgenic leaf samples (young, mature, old) and the wild type leaf samples (young, mature, old) were collected. The leaf samples were collected from plants exposed to regular lighting pattern (16 h light and 8 h dark), 1 Day, 3 Day and 5 Day continuous light exposure. The leaf samples were finely ground in liquid nitrogen, followed by collection of leaf powder into the eppendorf tube. Total soluble protein from the plant leaves was extracted in plant protein extraction buffer (15 mM Na$_2$CO$_3$, 35 mM NaHCO$_3$, 3 mM NaN$_3$, pH 9.6, 0.1% Tween, and 5 mM PMSF). The microtiter plate was coated initially with (100 µl/well) with monoganglioside-GM1 (Sigma) (3.0 µg/ml in bicarbonate buffer pH 9.6) and incubated overnight at 4° C. followed by washing three times with PBST (PBS and 0.05% Tween 20) and two times with dH$_2$O. As control, BSA (3.0 µg/ml in bicarbonate buffer pH 9.6) was coated in some wells. The wells were then blocked with 1% BSA in 0.01M phosphate buffer saline (PBS) (300 µl/well) for 2 h at 37° C. or incubate overnight at 4° C. followed by 3 washes with PBST and 2 washes with dH$_2$O. In order to check the protein concentration, the standards, test samples and antibody were diluted in coating buffer (15 mM Na$_2$CO$_3$, 35 mM NaHCO$_3$, 3 mM NaN$_3$, pH 9.6). The standards and protein samples (100 µl) were coated to 96-well polyvinyl chloride microtiter plate (Genstar) for 1 h at 37° C. or incubate overnight 4° C. followed by 3 washes with PBST and 2 washes with water. The primary rabbit anti-NSP4 antibody (provided by Dr. Langridge, Univ. of Loma Linda) diluted (1:1500) in 0.5% BSA in 1×PBS was loaded into wells and incubated for 2 h at 37° C. followed by washing steps and then again incubated with 100 µl of donkey anti-rabbit IgG-HRP conjugated antibody made in goat (American Qualex) (1:3000) diluted in 0.5% BSA in 1×PBS. The plate was then incubated for 2 h at 37° C. After the incubation the plate was washed thrice with PBST and twice with water. The wells were then loaded with 200 µl of 3,3,5,5-tetramethyl benzidine (TMB from American Qualex) substrate and incubated for 10-15 min at room temperature. The reaction was terminated by adding 50 µl of 2N sulfuric acid per well and the plate was read on a plate reader (Dynex Technologies) at 450 nm. (Modified form of protocol from Ausubel et al., 4$^{th}$ edition).

REFERENCES

1. Parashar U D, Hummelman E G, Bresee J S. Miller M A, Glass R I. (2003) Global illness and deaths caused by rotavirus disease in children. *Emerg Infect Dis* 9:565-572.
2. Ball J M, Tian P, Zeng C Q Y, Morris A P, Estes M K (1996). Age dependent diarrhea induced by rotavirus nonstructural glycoprotein. *Science.* 272: 101-104.
3. Tian P, Ball J M, Zeng C Q Y, Estes M K. (1997) The rotavirus nonstructural glycoprotein NSP4 possesses membrane destabilization activity. *J. Virol.* 70:6973-81.
4. Xu A, Bellamy R A, Taylor A J. 2000) Immobilization of the early secretory pathway by a virus glycoprotein that binds to microtubules. 19:6465-6474.
5. Dong Y, Zeng C Q-Y, Ball J M, Estes M K, Morris A P. (1997) The rotavirus enterotoxin mobilizes intracellular calcium in human intestinal cells by stimulating phospholipase C-mediated inositol 1,4,5-triphosphate production. PNAS 94:3960-65.
6. Yu J, Langridge H R. (2001) A plant-based multicomponent vaccine protects mice from enteric diseases. *Nat. Biotech.* 19: 548-552.
7. Kombo L A, Gerber M A, Pickering L K, Atreya C D, Breiman R F. (2001) Intussusception, Infection, and Immunization: summary of a workshop on rotavirus. *Pediatrics.* 108: 2.e37.
8. Daniell H, Streatfield S J, Wycoff K. (2001b) Medical molecular farming: production of antibodies, biopharmaceuticals and edible vaccines in plants. *Trends Plant Sci.* 6:219-26.
9. Daniell H, Muthukumar B, Lee S B. (2001a) Marker free transgenic plants: engineering the chloroplast genome without the use of antibiotic selection. *Curr Genet.* 39:109-116.

10. Giddings G, Allison G, Brooks D, Caryer A. (2000). Transgenic plants as factories for biopharmaceuticals. *Nat Biotechnol.* 18:1151-55.
11. Kong et al 2001
12. DeCosa B, Moar W, Lee S B, Miller M, Daniell H. (2001) Over expression of the Btcry2Aa2 operon in chloroplasts leads to formation of insecticidal crystals. *Nat. Biotechnol.* 19: 71-74.
13. Tania Q V, Ruiz N R, Daniell H. (2005). Characterization of Heterologous Multigene Operons in Transgenic Chloroplasts: Transcription, Processing and Translation. *Plant Physiol.* In press
14. Daniell H, Kumar S, Dufourmantel N (2005a) Breakthrough in chloroplast genetic engineering of agronomically important crops. *Trends Biotechnol.* 23:238-45.
15. Daniell H, Lee S B, Panchal T, Wiebe P O. (2001) Expression of cholera toxin B subunit gene and assembly as functional oligomers in transgenic tobacco chloroplasts. *J Mol. Biol.* 311: 1001-1009.
16. Daniell H. (2002) Molecular strategies for gene containment in transgenic crops. *Nat Biotechnol.* 20: 581-586.
17. Hagemann R. (2004) The sexual inheritance of plant organelles. H Daniell and C Chase, eds, Molecular biology and biotechnology of plant organelles, Kluwer Academic Publishers, Dordrecht, pp. 93-113.
18. Lee S B, Kwon H B, Kwon S J et al. (2003) Accumulation of trehalose within transgenic chloroplasts confers drought tolerance. *Mol. Breed.* 11: 1-13.
19. Singleton M L. (2003) Expression of CaF1 and LcrV as a fusion protein for development of a vaccine against *Yersisnia pestis* via chloroplast genetic engineering. Master's thesis, University of Central Florida.
20. Molina A, Herva-Stubbs S, Daniell H, Mingo-Castel A M, Veramendi J. (2004) High yield expression of a viral peptide animal vaccine in transgenic tobacco chloroplasts. *Plant Biotechnol. Journal* 2:141-153.
21. Watson J, Koya V, Leppla S, Daniell H. (2004) Expression of *Bacillus anthracis* protective antigen in transgenic chloroplasts of tobacco, a non-food/feed crop. *Vaccine* 22: 4374-4384.
22. Chebolu S. (2005) Expression of GAL/GALNAc lectin of *Entamoeba Histolytica* in transgenic chloroplast to develop a vaccine for amebiasis. Master's thesis, University of Central Florida.
23. Bhati A. (2005) Expression of Hepatitic C viral non structural 3 protein in transgenic chloroplast Master's thesis, University of Central Florida.
24. Tregoning J S, Nixon P, Kuroda H, Svab Z, Clare S. et al (2003) Expression of tetanus toxin fragment C in tobacco chloroplasts. *Nucleic Acids Res.* 31: 1174-1179.
25. Maliga P. (2003) Progress towards commercialization of plastid transformation technology. *Trends Biotechnol.* 21: 20-28.
26. Fernandez-San Millan A, Mingeo-Castel A M, Miller M, Daniell H. (2003) A chloroplast transgenic approach to hyper-express and purify human serum albumin, a protein highly susceptible to proteolytic degradation. *Plant Biotechnol J.* 1: 71-79.
27. DeGray G, Rajasekaran K, Smith F, Sanford J, Daniell H. (2001) Expression of an antimicrobial peptide via the chloroplast genome to control phytopathogenic bacteria and fungi. *Plant Physiol.* 127:852-862.
28. Staub J M, Garcia B, Graves J. et al (2000). High-yield production of a human therapeutic protein in tobacco chloroplasts. Nat Biotechnol 2000: 18:333-338.
29. Daniell H, Cohill P, Kumar S, Dufourmantel N, Dubald M. (2004a) Chloroplast genetic engineering. H Daniell and C Chase, eds, Molecular biology and biotechnology of plant organelles, Kluwer Academic Publishers, Dordrecht, pp. 423-468.
30. Fischer R, Stoger E, Schillberg S, Christou P, Twyman R M (2004). Plant based production of biopharmaceuticals. *Curr Opin Plant Bio.* 17:152-158.
31. Kim, J., Mayfield, S. (1997). Protein Disulfide Isomerase as a Regulator of Chloroplast Translational Activation. *Science.* 278:1954-1957.
32. Daniell H. Foreign gene expression in chloroplasts of higher plants mediated by tungsten particle bombardment. Methods Enzymol 1993; 217: 536-556.
33. Daniell, H. (1997). Transformation and foreign gene expression in plants mediated by microprojectile bombardment. *Meth Mol. Biol.* 62:453-488.
34. Guda C, Lee S B, Daniell H. (2000) Stable expression of biodegradable protein based polymer in tobacco chloroplasts. *Plant Cell Rep.* 19: 257-262.
35. Kumar, S., and Daniell. H. (2004). Engineering the chloroplast genome for hyper-expression of human therapeutic proteins and vaccine antigens. Methods Mol. Biol. 267, 365-383.
36. Devine A L, Daniell H. (2004) Chloroplast genetic engineering for enhanced agronomic traits and expression of proteins for medical/industrial applications. In S G Møller, ed, Plastids, Vol. 13. Blackwell publishing, Oxford, pp. 283-323
37. Daniell H, Ruiz O N, Dhingra A. (2004c). Chloroplast genetic engineering to improve agronomic traits. *Methods in Molecular Biology* 286: 111-137.
38. Zerges W (2000) Translation in chloroplasts. *Biochimie* 82:583-601.
39. Svab Z, Maliga P. (1993) High-frequency plastid transformation in tobacco by selection for a chimeric aadA gene. *Proc Natl Acad Sci USA.* 90: 913-917.
40. Daniell H, Chebolu S, Kumar S, Singleton M, Falconer R. (2005) Chloroplast-derived vaccine antigens and other therapeutic proteins. *Vaccine* 23:1779-1783.
41. Arakawa T, Cong D K X. Langridge W H R. (1998) Efficacy of a food-plant based oral cholera toxin B subunit vaccine. *Nat. Biotechnol.* 15:248-252. 16 292-297.

Example 3: Expression of Hepatitis C Virus Non Structural 3 Antigen in Transgenic Chloroplasts Hepatitis C virus infection is the major cause of acute hepatitis and chronic liver disease. An estimated 180 million people are infected globally (WHO). There is no vaccine available to prevent hepatitis C and treatment with antiviral drugs is expensive and is accompanied with various side effects. Therefore, there is an urgent need for the development of effective vaccine antigens and an efficacious HCV vaccine. The non-structural 3 protein of the hepatitis C virus is one of the most conserved and multifunctional protein of the virus and therefore is a good candidate for the development a HCV vaccine. Vaccine antigen production via chloroplast transformation system usually results in high expression levels and eliminates the possibility of contamination with viral vector sequences, human or animal pathogens. To express the HCV NS3 antigen in the chloroplast of *Nicotiana tabacum* var. Petit havana and LAMD-609, the NS3 gene (1.9 kb) was cloned into a chloroplast expression vector, pLD-ctv containing the 16S rRNA promoter, aadA gene coding for the spectinomycin selectable marker, psbA 5' & 3' untranslated regions to enhance translation in the light and trnI & trnA homologous flanking sequences for site specific integration into the chloroplast genome. Chloroplast integration of the NS3 gene was first confirmed by PCR. Southern blot analysis further confirmed site-specific gene integration and homoplasmy. The NS3 protein was detected in transgenic chloroplasts by Immunoblot analysis. The NS3 protein was further quantified by ELISA. Maximum expression levels of NS3 up to 2% in the total soluble protein were observed even in old leaves, upon 3-day continuous illumination. These results demonstrate successful expression of the HCV non-structural 3 antigen in transgenic tobacco chloroplasts.

Materials and Methods

N53-pcDNA3.1 Vector.

The plasmid encoding HCV NS3 protein (initial concentration of the plasmid-280 ng/ul in H2O) was sent cloned in the commercial plasmid pcDNA3.1/V5/His-TOPO (Invitrogen). A PCR product encoding NS3 had been inserted in this plasmid (in the cloning box) as described by the protocol supplied by the manufacturer. The plasmid encoded NS3 with a ATG and a Kozak sequence (5' end) and a TGA (3' end). The plasmid was transformed into Ultra competent XL1 Blue MRF' Tetracycline (tet) *E. coli* cells (Stratagene) that were endonuclease negative.

Preparation of Ultra Competent Cells (Rubidium Chloride Method).

The ultra competent cells were prepared using rubidium chloride method (http://www.nwfsc.noaa.gov/protocols-/rbcl.html). XL1 Blue MRF' (tet) *E. coli* cells (Stratagene) were made competent by the rubidium chloride method. The *E. coli* glycerol stock was streaked on the LB agar plate (1 liter LB broth, 15 grams agar), containing 12.5 ug/ml Tetracycline and incubated at 37° C. overnight. An isolated colony was picked and it was grown in 5 ml of Psi broth (per liter-5 g Bacto yeast extract, 20 g Bacto Tryptone, 5 g magnesium sulfate, pH 7.6) with 5 ug/ml Tetracycline and incubated at 37° C. for 12-16 hrs in a shaker at 225 rpm. From the overnight culture, 1 ml was taken and inoculated in 100 ml of Psi broth and was incubated at 37° C. for about 2 hours in a shaker at 225 rpm. After 2 hours, the O.D was checked at 550 nm and rechecked again after intervals, until the O.D reached 0.48. The culture was then kept on ice for 15 minutes and then the cells were centrifuged at 3000 g/5000 rpm for 5 minutes in a sorvall centrifuge. The supernatant was discarded and the pellet was resuspended in 40 ml cold TFB-I solution (per 200 ml-0.558 g Potassium acetate, 2.42 g rubidium chloride, 0.294 g calcium chloride, 2.0 g manganese chloride, 30 ml glycerol, pH 5.8). The cells were centrifuged at 3000 g/5000 rpm for 5 minutes. The supernatant was discarded and the cells were resuspended in 4 ml of TFB-II solution (per 100 ml-0.21 g MOPS, 1.1 g calcium chloride, 0.121 g rubidium chloride, 15 ml glycerol, pH 6.5) and then kept on ice for 15 minutes. The suspension was aliquoted (100 ul) and quick freezed in dry ice/liquid nitrogen and the aliquots were stored at −80° C.

Transformation of pcDNA3.1 Plasmid into Competent XL1 Blue MRF' (tet) *E. coli* Cells.

The competent cells were removed out of −80° C. and thawed on ice. 100 μl of competent cells were taken and 1 ul (100 ng) of plasmid pcDNA3.1 DNA was added and mixed by gently tapping. The cells were left on ice for 30 minutes, and the tube was gently tapped every 15 minutes. The cells were heat shocked at 42° C. for 90-120 seconds and then left on ice for 2 minutes, and then 900 μl LB broth was added to the cells and the cells were incubated at 37° C. at 225 rpm in a shaker for 45 minutes. The cells were pelleted by centrifugation at 13,000 rpm for 30 seconds and the supernatant was discarded. Almost 800 ul of supernatant was discarded and only approximately 100 ul was left. The remaining 100 ul of the cells were mixed well with the pellet. About 50 ul and 100 ul of the transformed cells and untransformed (control) were plated onto LB/amp agar plates (1 liter LB broth, 15 gr agar, 100 μg/ml ampicillin, pH 7) under the hood. Plates were covered and incubated 0/N at 37° C. (http://www.nwfsc.noaa.-gov/protocols-/rbcl.html).

Rapid Colony Screening by Cracking Method.

To check the colonies for the presence of plasmids, the Rapid Screen procedure by Promega was used. Sterile toothpicks were used for picking 8 colonies from the incubated LB agar plates to the bottom of an individual sterile microcentrifuge tube. 25 μl of 10 mM ethylene diamine tetra-acetic acid (EDTA), pH 8 was added to the tubes and vortexed to mix. Then 25 μl of fresh 2× cracking buffer (2N NaOH, 10% sodium dodecyl sulfate, 1M sucrose) was added to each colony and vortexed. The tubes were then incubated at 65° C. for 10 minutes and were cooled at room temperature. 1.5 μl of 4M KCl and 3.5 μl of 6× bromophenol blue (0.25% Bromophenol blue, 40% sucrose) was added to the tubes. The tubes were placed on ice for 5 minutes and centrifuged at 12,000 rpm for 3 minutes at room temperature. 20 μl of the supernatant form each tube was run on 0.8% agarose gel to visualize which of the selected colonies contained plasmids. Positive colonies were inoculated into 5 ml of fresh LB broth with 100 μg/ml amp and incubated overnight at 37° C. on shaker.

Midi-Prep of pcDNA3.1.

Inoculated a colony obtained from the plate in 50 ml of liquid LB broth, to which 50 μl of ampicillin (stock concentration; 100 mg/ml) was added and incubated at 37° C. for 12 hours in a shaker. 40 ml of the overnight culture was transferred to a clean 50 ml round bottom sorvall centrifuge tube. The cells were centrifuged for 10 minutes at 8000 rpm at 40 C. The supernatant was discarded. The pellet was resuspended by vortexing in 5 ml of Solution 1 (50 mM Glucose, 10 mM EDTA, 25 mM Tris, pH-8) with 5 ul of 100 mg/ml of RNAse freshly added to it. Solution II (500 ul of 2N NaOH, 100 ul of 10% SDS, 4400 ul of sterile water) which is a cell lysis solution was prepared freshly, added, and mixed by gently inverting the tube 6-8 times and the solution turned from milky to clear. Then 5 ml of Sol III (60 ml of 5M Potassium Acetate, 11.5 M glacial acetic acid, and 28.5 ml sterile dH2O) which is neutralizing solution was added to the clear solution and mixed well by inverting the tube 6-8 times and the solution precipitated. The solution was centrifuged for 15 minutes at 12,500 rpm at 40 C. The clear supernatant was poured into a new 50 ml Sorvall centrifuge tube. Cold absolute ethanol (24 ml) was added to the supernatant and mixed well by inverting the tube 6-8 times. The tube was then centrifuged for 10 minutes at 10,000 rpm at 40 C to pellet the plasmids. The supernatant containing contaminants was discarded. The pellet was washed with 12 ml of 70% ethanol and resuspended by shaking. The solution was centrifuged for 5 minutes at 10,000 rpm at 40 C. The supernatant was discarded and the pellet was dried in a speed vacuum or air-dried before resuspending the DNA pellet in 500 ul of TE (TE: 1M Tris, pH 8.0, 0.5M EDTA). The DNA sample was loaded in a 0.8% agarose gel and run at 60 volts for 30 minutes to check for plasmid isolation (Sambrook et al., 1989).

Phenol: Chloroform Extraction.

Plasmid DNA (500 ul) was taken and 250 ul Phenol and 250 ul Chloroform was added (1:1) and mixed well. The tube was then centrifuged at 14,000 rpm at 40 C for about 10 minutes. The supernatant was transferred to a new tube and 500 ul of Chloroform: IAA (Isoamyl alcohol) was added and centrifuged at 14,000 rpm at 40 C for 10 minutes. The supernatant was transferred to a new tube and 0.1 volume of 3M sodium acetate (pH: 5.2) was added. Absolute ethanol (900 ul) was added and mixed well by inverting several times and then centrifuged at 14,000 rpm, 40 C for 10 minutes. The supernatant was discarded and the pellet was rinsed with 70% ethanol (400 ul) and centrifuged for 10 minutes at 14,000 rpm at 40 C. The supernatant was discarded again and the pellet was dried in a speed vacuum or air-dried before resuspending the DNA pellet in Elution buffer, 10 mM Tris Cl, (Sambrook et al., 1989).

PCR Amplification of NS3 Gene.

The NS3 gene (first 134 bp) were amplified to introduce the Sac1 and SnaB1 restriction sites at the 5' terminal end and Not1 at the 3'end of the 134 bp of the NS3 gene for further subcloning. This was done to clone the 134 bp of the NS3 gene first into p-bluescript between Not1 and Sac1 sites. The primers used for amplification were the NS3-F primer (5'CAGTGTGGAGCTCTTGTACGTACCAC-CATGGCG3' (SEQ ID NO: 6)) and the NS3-R primer (5'TGGAGAGCACCTGCGGCCGCCCATCGACCTGG3' (SEQ ID NO: 7)). Primers (Invitrogen) were diluted with EB to give a 100 µM stock that was stored at 20° C. The PCR reaction was set up with 0.5 ul plasmid DNA (60 ng), 10×PCR buffer, 5.0 µl of 10 mM dNTP's, 1 µl of forward primer (NS3-F), 1 µl of reverse primer (NS3-R), 0.5 µl of Pfu polymerase and 37.0 µl of distilled, autoclaved H2O to a total volume of 50 µl.). Samples were carried through 35 cycles using the following temperatures and times: 94° C. for 5 minutes, 94° C. for 45 seconds, 56° C. for 45 seconds, 72° C. for 45 seconds, and followed by a 10-minute extension time at 72° C. The final PCR product (0.1 ul) was run on a 0.8% agarose gel to analyze the PCR products. The PCR product was purified using the PCR purification kit (Qiagen).

Ligation of the PCR Product (Sac1/SnaBI/NS3/Not1) into p-Bluescript Vector.

The PCR product was ligated into p-Bluescript cloning vector (Invitrogen) between NotI and SacI restriction sites. The ligation mixture consisted of 4 µl of PCR product after PCR purification, 16 ul of p-Bluescript, 0.5 ul of T4 DNA ligase, 6.0 ul of Ligase buffer, and 3.5 ul distilled, autoclaved H20 to a total of 30 ul total volume. The solution was gently mixed and incubated overnight at 12° C. Competent E. coli cells were taken from –80° C. freezer and thawed on ice and transformation was started immediately after cells thawed. 15 ul of the ligation mixture was mixed into a vial containing the 100 ul of E. coli competent cells and transformation was done as previously described (Sambrook et al., 1989).

Selection of Transformants.

The p-Bluescript cloning vector has the β-galactosidase gene (lacZ). Within this coding region is a multicloning site. Insertion of a fragment of foreign DNA into the multicloning site of p-Bluescript almost invariably results in production of an amino-terminal fragment that is not capable of α-complementation. Selective plates were made with LB agar with 100 ng/ml ampicillin and 12.5 µg/ml tetracycline. About 1 hour before transformation was complete, 40 µg/ml of 5-bromo-4-chloro-3-indolyl-β-D-galactoside (X-gal) was spread onto the top of the plates while under the hood. X-gal is a lactose analog that turns dark blue when it is hydrolyzed by β-galactosidase. After the X-gal dried (about 15 minutes), 40 µl of 100 mM of isopropyl-β-D-thiogalactoside (IPTG) was spread onto the plates. IPTG, another lactose analog, is a strong inducer of lacZ transcription but is not hydrolyzed by β-galactosidase. The plates were warmed 37° C. for 30 minutes and then the plates were streaked with 100 µl of the transformed bacterial cells were spread over the top of the agar. Allowed the plates to dry for 5 minutes, and then incubated the plates in an inverted position at 37° C. overnight. Colonies without an interrupting insert were blue because they had an active β-galactosidase. Colonies with an insert were white, so these were picked to culture, and midi-prep was done with the Midi-prep kit (Qiagen).

Sequencing of NS3 in p-Bluescript.

The PCR product in the plasmid (NS3-p-Bluescript) was sequenced using M13 forward (5'-TGACCGGCAG-CAAAATG-3' (SEQ ID NO: 8)) and M13 reverse (5'GGAAACAGCTATGACC-ATG-3' (SEQ ID NO: 9)) primers. Sequencing results confirmed that the fragment in the p-Bluescript vector was the NS3 gene.

Construction for pLD-AB-NS3 Vector for Transformation of Tobacco Chloroplasts.

The original vector pcDNA3.1 was digested with BstXI and EcoRV and the NS3 gene (remaining 1760 bp) was ligated between BstXI and EcoRV in p-Bluescript. The entire NS3 gene was digested from p-bluescript with SnaBI and HindIII and ligated in pCR2.1 vector downstream of the psbA 5'UTR. Finally, the pCR 2.1 vector containing the 5'UTR and the NS3 gene was digested with EcoRI and EcoRV (fragment size 2.1) and was cloned between the same sites in the universal vector pLD-AB-Ct.

Extraction of NS3 Protein from Transformed *E. coli* Cells.

5 ml of Terrific Broth (TB) containing 5 ul ampicillin (100 μg/nl) and tetracycline (50 μg/nl) was inoculated with the scrapping from the glycerol stock of *E. coli* transformed with pLD-AB-NS3 and incubated in a shaker at 37° C. for 10-12 hours. 5 ml of Terrific Broth (TB) with untransformed *E. coli* cells was used as a negative control. The buffers and gels used in this study were made from protocols in SDS-PAGE Buffer System (Laemmli, 1970). 800 μl of cultured cells were taken and centrifuged for 2 minutes at 12,000 rpm. The supernatant was discarded from pelleted *E. coli* cells and then washed with 1 ml of 1× Phosphate-Buffered Saline (PBS: 140 mM NaCl, 2.7 Mm KCl, 4 mM Na2HPO4, 1.8 mM KH2PO4, pH 7.2). The pellet was resuspended and then centrifuged for 1 minute at 13,000 rpm. The supernatant was then discarded. 50 μl of 1×PBS was added and mixed well. 50 μl of 2× loading buffer, also called Sample Buffer or SDS Reducing Buffer (1.25 ml of 0.5 M Tris-HCl, pH 6.8, 2.0 ml of 10% (w/v) SDS, 0.2 ml of 0.5% (w/v) bromophenol blue, 2.5 ml of glycerol, dH20 to a total volume of 9.5 ml, then add 50 μl of β-mercaptoethanol to the 9.5 ml) was added. The sample extracts were boiled for 4 minutes and then immediately loaded onto gels (Sambrook et al., 1989).

SDS-PAGE.

The buffers and gels used in this study were made from protocols in SDS-PAGE Buffer System below (Laemmli 1970). To detect the protein extracted from *E. coli* cells containing pLD-AB-NS3, SDS-PAGE gels were made in duplicate utilizing the following solutions: 1.) Bio-Rad (cat#161-0158), which is a 30% Acrylamide/Bis solution according to the ratio 37:5:1. 2.) The resolving buffer, which was used to make the lower portion of the gel: 1.5M Tris-HCl, pH 8.8. The pH was adjusted with 6N HCl and brought to a total volume of 150 ml with dH20. 3.) The stacking buffer that was used to make the stacking gel layered over the resolving gel and concentrated the samples at top of the resolving gel to improve resolution: 0.5M Tris-HCl, pH 6.8. 4.) Electrode buffer (1×) which was the gel running buffer. For 10× Electrode buffer: Dissolved 30.3 g Tris base, 144.0 g glycine and 10.0 g SDS into 1000 ml dH20. 5.) 2× loading buffer also called the Sample buffer and the SDS Reducing Buffer. 6.) 10% (w/v) Sodium Dodecyl Sulfate (SDS): 7.) N,N,N,N'-Tetra-methyl-ethylene diamine (TEMED) from BIO-RAD (cat#161-0800). 8.) 20% Ammonium Persulfate (APS): Dissolved 20 mg of APS into 1 ml dH20 and this solution can be stored at 4° C. for about a month. To make the 10% resolving gel, in 4.1 ml dH20, 3.3 ml of 30% Acrylamide/Bis, 2.5 ml of resolving buffer and 100 µl of 10% SDS was added. 40 µl of 20% APS and then 10 µl of TEMED was added to the gel mixture. The gel mixture was poured between the two, vertical, glass plates leaving about 1.5 cm at the top of glass plates for the stacking gel. The gel was allowed to polymerize for 20 minutes. To make the 4% stacking gel, in 6.1 ml dH20, 1.3 ml of 30% Acrylamide/Bis, 2.5 ml of the stacking buffer and 100 µl of 10% SDS was added. 40 µl of 20% APS and then 10 µl of TEMED was added to the gel mixture. The 4% gel mixture was layered on top of resolving gel and then the comb is inserted for the formation of wells. After polymerization for about 20 minutes, the comb is removed and put vertically into PAGE apparatus containing 1× Electrode (running) buffer. 20 µl of protein extract from pLD-AB-NS3 transformed and untransformed E. coli cells was loaded along with 10 ul protein marker. Gel was ran at 50V until samples stacked onto the top of the resolving gel, then ran gel at 80V for 2-3 hours so that protein marker bands could spread out sufficiently (Sambrook et al. 1989).

Transfer to Membranes and Immunoblot Analysis.

The separated proteins were transferred onto a 0.2 µm Trans-Blot nitrocellulose membrane (Bio-Rad) by electroblotting in Mini-Transfer Blot Module at 80V for 45 minutes in Transfer buffer (360 ml of 10× Electrode buffer, 360 ml of methanol, 0.18 grams of SDS, 1080 ml distilled H20). The membranes were taken out and rinsed with water and placed in blocking solution (100 ml 1×PBS, 100 µl of Tween 20, 5 g of non-fat, Carnation powdered milk) and incubated for an hour at room temperature in a shaker. The P-T-M was poured off and the Hepatitis C Virus (NS3)-specific primary mouse monoclonal antibody (HCV NS3 Ab-1, Clone MMM33, from Neomarkers) was added in the ratio of antibody: PTM as 1:1000 and incubated for 2 hours at room temperature in a shaker. Membranes were then washed with distilled water and transferred to P-T-M containing goat derived anti-mouse IgG antibody conjugated with Horseradish peroxidase (Sigma, St. Louis, Mo.), in the ratio of antibody: PTM as 1:10,000 and incubated for 1.5 hours at room temperature in shaker. Blots were washed three times with PBST for 15 minutes each time and then washed with only PBS for 10 minutes. Then 750 µl of 2× Stable Peroxidase Solution and 750 µl of 2× Luminol/Enhancer Solution (Pierce) was poured over the membrane and a film was developed in the to visualize the bands (Sambrook et al. 1989).

Sterilization of Seeds for Wild-type and T1.

For generating wild-type (untransformed) tobacco plants to use for bombardment, pods were picked from both varieties of tobacco when the pods were dry. The pods were broken under hood and then poured into labeled eppendorf about until about ⅓ full. To germinate seeds, fresh MSO (Murashige and Skoog, 1962) plates with no antibiotic were made. The sterilization solution consisted of 1.5% bleach (4 ml of 5.25% Chlorox bleach), 16 ml d/aH20, 0.05% Tween 20 (20 µl of Tween 20). 1.2 ml of the sterilization solution was added to each eppendorf and then vortexed for 20 minutes and then rinsed 7 times with sterile H20. Then the seeds were dried and then spread onto the surface of the MSO plates, covered and wrapped in parafilm. Put plates at 26° C. with a 16 hour photoperiod. For germination of T1, 1.2 ml of sterilization solution was added and sterilized as above, except the dry seeds were spread onto MSO plated with 500 µg/ml spectinomycin (Petit Havana) and 350 µg/ml to select for transformants (Kumar and Daniell, 2004).

Preparation of Tobacco Tissue Culture Media (RMOP and MSO Media).

The shoot-inducing RMOP media was made by adding one packet MS salts mixture, 30 gm sucrose, 1 ml benzylaminopurine, BAP (1 mg/ml stock); 100 ul napthalene acetic acid, NAA (1 mg/ml stock), 1 ml thiamine hydrochloride (1 mg/ml stock) to 1 L dH2O. The pH was adjusted to 5.8 with 1N KOH and 7.0 g/L phytagar was added to the mixture which was autoclaved, cooled and plated out under the hood (Kumar and Daniell, 2004). The root-inducing MSO media was prepared by adding 30 g sucrose and one packet (4.3 g) of Murashige & Skoog (MSO) salt mixture (Gibco BRL) to 1 L dH2O. The pH was adjusted to 5.8 with 1N KOH, then 7 g/L phytagar was added and the mixture was autoclaved (Kumar and Daniell, 2004).

Biolistic Transformation of Tobacco Leaf Chloroplast.

About 4 weeks prior to the planned bombardment, wild-type (untransformed) tobacco plants were micropropagated from seeds using sterile techniques. Two varieties of tobacco were generated for the bombardment: Petit Havana (model) and LAMD-609 (low nicotine hybrid produced by back-crossing a Maryland type variety, MD-609, to a low-nicotine producing burley variety, LA Burley 21 (Collins et al., 1974).

Preparation of the Gold Particles and DNA/Particle Suspension.

Fifty mg of gold particles (0.6 µm) were placed in a micro centrifuge tube and 1 ml of freshly prepared 70% ethanol was added. The mixture was vortexed for 3-5 minutes and incubated at room temperature for 15 minutes. The gold particles were pelleted by spinning for 5 seconds and then the supernatant was discarded. 1 ml of H2O was added to the particles and vortexed for a minute. Particles were allowed to sit for 1 minute and pulse centrifuged for 3 seconds. The supernatant was discarded and this was repeated three times. After the last spin, 50% glycerol was added to a concentration of 60 mg/ml. The gold particles were stored at −20° C. (Kumar and Daniell, 2004).

Coating DNA onto Macrocarriers.

The gold particles prepared in 50% glycerol (60 mg/ml) were vortexed for 5 minutes to resuspended the particles. Fifty ul of gold particles was removed and placed in a micro centrifuge tube. 10 ul (1 µg/nl) of the pLD-AB-NS3 vector DNA was added and quickly vortexed. Then, 50 ul of freshly prepared 2.5M CaCl2 (367.5 mg of CaCl2 into 1 ml of d/aH2O) was added and vortexed. Finally, 0.1M spermidine-free base (20 ul) was added and the tube was vortexed for 20 minutes at 4° C. 200 ul of absolute ethanol added to each tube and centrifuged for 2 seconds, then the ethanol was discarded. The wash was repeated 4 times. After the washes, the particles were resuspended in 40 ul of absolute ethanol and kept on ice (Kumar and Daniell, 2004).

Preparing the Biolistic Gun and Consumables.

Stopping screens, rupture disk holders, macrocarrier holders were autoclaved to ensure that they were sterile. Rupture disks and macrocarriers were washed in 50 ml of autoclaved H2O and 70% ethanol. The Bio-Rad PDS-1000/He (gene gun) shelves, macrocarrier holder, rupture disk holder were washed with 70% ethanol. After the pump under the hood was turned on, the main valve on the helium tank was opened and the valve controlling pressure to the gene gun was set to 13500 psi (Kumar and Daniell, 2004).

Bombardment.

The bombardment was performed as described previously (Daniell, 1997). Stopping screens were placed in macrocarrier holders. 6 ul of particle mixture was spread evenly onto the macrocarrier. The gold suspension was allowed to dry. One rupture disk was placed in the holder ring and screwed in place at the top of the vacuum chamber. The stopping screen and macrocarrier with the gold/DNA (in holder) were placed into the retaining assembly. The assembly was placed into the vacuum chamber. A piece of sterile whatman #1 filter paper was placed on solidified RMOP media in a petri dish. One leaf at a time was placed on the whatman paper abaxial side upwards. The petri dish with leaf was placed on a plastic holder and placed in the next to last slot in the vacuum chamber. The chamber door was closed and secured. The power switch for the gene gun was turned on. A vacuum was allowed to build to 28 psi in the bombardment chamber. When 28 psi was reached, the fire switch was pressed until the rupture disk ruptured (u1100 psi). After delivery of the gold particles with vector DNA, the vacuum was released and the Petri dish taken out and covered. The petri dishes were wrapped in aluminum foil and kept in the dark for 48 hours at room temperature to recover from the shock of bombardment (Kumar and Daniell, 2004).

Selection and Regeneration of Transgenic Lines.

After recovering in the dark for 48 hours from bombardment, leaves were cut into 5 mm2 squares and placed on a petri dish containing RMOP media containing spectinomycin. For Petite Havana, 500 ug/ml of spectinomycin was used and for LAMD-609, 350 ug/ml of spectinomycin was used for the first round of selection (with the abaxial side down). Four to six weeks later when the shoots appeared, they were cut into 2 mm2 pieces and transferred to fresh RMOP media with spectinomycin for the second round of selection (500 ug/ml for Petite Havana and 350 ug/ml for LAMD-609). During the second selection, the shoots that appeared and tested positive for cassette integration into the chloroplast by PCR analysis were grown in sterile glass jars containing fresh media with spectinomycin until the shoots grew to fill the jar. Then the plants were transferred to pots with soil containing no antibiotic. Potted plants were grown in a 16 hour light/8 hour dark photoperiod in the growth chamber at 26° C. (Kumar and Daniell, 2004).

Isolation of total plant genomic DNA from Tobacco Leaf.

The QIAGEN's DNeasy® Plant Mini Kit was used for isolating the total DNA from plant tissue as described in the Qiagen manual. 100 mg of the tissue was grounded in liquid nitrogen to a fine powder and was transferred to a cooled eppendorf and 400 ul of Buffer AP1 and 4 ul of RNase A stock solution (100 mg/ml) was added and vortexed. The mixture was incubated for 10 minutes at 65° C. and mixed about 2-3 times during incubation by inverting the tube. 130 ul of Buffer AP2 was added to the lysate, mixed, and then incubated on ice for 5 minutes. The lysate was applied to the QIAshredder spin column (lilac) sitting in a 2 ml collection tube and then centrifuged for 2 minutes. The flow-through was transferred to a new tube and 1.5 volumes of buffer AP3/E were added to the lysate and mixed immediately. 650 ul of the mixture was applied to the DNeasy mini spin column sitting in a 2 ml collection tube and then centrifuged for 1 minute at 8000 rpm. The DNeasy column was placed in a new 2 ml collection tube and 500 ul Buffer AW was added to the DNeasy column and centrifuged for 1 minute at 8000 rpm. The flow-through was discarded and collection tube was reused in the next step. 500 ul Buffer AW was added to the DNeasy column and centrifuged for 2 minutes at maximum speed to dry the membrane. The DNeasy column was transferred to a 2 ml microcentrifuge tube and 100 ul of preheated (65° C.) Buffer AE was directly added onto the DNeasy membrane. The membrane was incubated for 5 minutes at room temperature and then centrifuged at 8,000 rpm for 1 minute to elute the DNA. The DNA was kept at −20° C. for use in PCR and Southern analysis.

PCR Analysis of Integration into the Chloroplast Genome.

To confirm the transgene cassette integration into the chloroplast genome, two primers sets were designed and assigned numbers with the plus (P) being for the forward primer and minus (M) being for the reverse primer. The 3P/3M (3P: 5'-AAAACCCGTCCTCCGTTCGGAT-TGC-3' (SEQ ID NO: 11)) primer annealed to anneal to a unique portion of the chloroplast genome and 3M (5'-CCGCGTT-GTTTCATCAAGCCTTACG-3' (SEQ ID NO: 3)) annealed to the integrated aadA gene (Daniell et al, 2001b). For the PCR reaction, 200 ng of plant DNA, 5 µl of 10× buffer, 4 µl of 2.5 mM dNTP, 2 µl of each primer from the stock, 0.5 µl Taq DNA polymerase and H2O to make up the total volume to 50 ul. The amplification was carried for 25 cycles of the following reaction: 94° C. for 5 mins, 94° C. for 45 sec, and 65° C. for 45 sec, 68° C. for 1.5 min, 68° C. for 7 mins. To confirm the integration of gene of interest, PCR was performed using primer pairs 5P (5'-CTGTAGAAGTCACCAT-TGTTGTGC-3' (SEQ ID NO: 4) and 2M (5'-TGACTGC-CCACCTGAGAGCGGACA-3' (SEQ ID NO: 12)). The amplification was carried during 25 cycles of the following reaction: 95° C. for 5 mins, 95° C. for 1 min, and 68° C. for 1 min, 72° C. for 3 min, 72° C. for 10 mins. 5 ul of each PCR products including the controls were loaded into a 0.8% agarose gel to confirm the results. pLD-NS3 was used as the positive control and wild type petite Havana was used as a negative control.

Southern Blot Analysis.

These steps were performed as described in (Daniell et al., 2004a). The total DNA isolated from T0 plants as well as from untransformed tobacco plants with QIAGEN's DNeasy® Plant Mini Kit was digested as follows: 10 ul (2 ug) DNA from DNeasy, 3 µl of 10× buffer 3, 2 µl BglII enzyme (NEB), 14.7 µl sterile H2O, to a total volume of 30 µl. The digest was incubated O/N at 37° C. The digestion was separated on a 0.8% agarose at 50V for 3.5 hours. The gel was observed under UV light to verify the complete digestion of the plant DNA. The gel was soaked in 0.25N HCl (depurination solution) for 15 minutes in a continuous agitation. The depurination solution was discarded, and the gel was rinsed 2 times with sterile H2O for 5 minutes. The gel was then soaked in transfer buffer on a rotary shaker for 20 minutes. The transfer apparatus was assembled for the transfer of the DNA to Duralon-UV nylon membrane. Four pieces of the Whatman paper were cut slightly larger than the gel and the membrane. Two pieces of Whatman paper were dipped into the transfer solution and placed on three sponges placed in a large pyrex dish partially filled with transfer buffer. The gel was removed from the transfer buffer and inverted on the Whatman paper. The nylon membrane was soaked in water and then placed on the gel. Removed air bubble gently and arranged parafilm along all the side to prevent horizontal DNA transfer. A stack of ordinary paper towels onto the top of Whatman filter paper and then added a 500 g weight to encourage transfer. From the bottom of the pyrex dish the transfer was in the following order: sponges, 2 filter paper, gel, parafilm at edges, nylon membrane, 2 filter paper, paper towels and weight. The set up was left for transfer over night and the next day the membrane was washed on 2×SSC (3M NaCl, 0.3M Na citrate, H2O, the pH was adjusted with 1N HCl to 7 and water was added to 1 L) for 5 minutes. The membrane was air-dried and then cross-linked using the GS Gene Linker UV Chamber (BIO-RAD) at the C3 setting.

Generating and Labeling Probes.

The probes were prepared by the random primed $^{32}$P-labeling (Ready-to-go DNA labeling beads, Amersham Pharmacia). A pUC universal vector containing the chloroplast flanking sequences was used to generate the flanking probe. The restriction digest was set-up as follows: 20 µl of pUC-ct, 1 µl 10× buffer 3, 1 µl BamHI (NEB), 1 µl BglII (NEB), 0.3 µl of BSA, 6.7 µl of sterile H2O to a total volume of 30 µl. The reaction was incubated overnight at 37° C. The restriction digest for the gene specific probe was as follows: 20 µl of pLD-AB-NS3, 1 µl of EcoRI (NEB), 1 µl of EcoRV (NEB), 3 µl of 10× buffer #3 (NEB), 0.3 ul of BSA, 4.7 µl sterile H2O to a total volume of 30 The reaction was incubated O/N at 37° C. 45 µl of each probe was denatured at 94° C. for 5 minutes and then placed on ice for 3 minutes. The probes were added to the ready mix tube (Quantum G-50 Micro columns, Amersham) and gently mixed by flicking. 5 µl of α32P was added to the ready mix tube and then it was incubated at 37° C. for 1 hour. The resin in the G50 column was resuspended by vortexing. The cap was loosened and the bottom plug broken off. Then the column was placed in a microcentrifuge tube with the top cut off and centrifuged for 1 minute at 3000 rpm. The collection tube with the supernatant was discarded and the column was transferred to a new tube. The probes were added to the center of the resin and centrifuged for 2 minutes at 3000 rpm and then the column was discarded. The amount of labeled DNA probe to be used was determined.

Prehybridization, Hybridization and Washing of the Membrane.

For prehybridization, the membrane was washed with sterile water. The Quick Hyb solution was gently mixed by inverting and warmed. The membrane was placed in a bottle with the top facing in towards the solution and 5 ml of the pre-Hyb solution was added and incubated for 60 mins at 68° C. 100 µl of salmon sperm (10 mg/ml) was added to the labeled probes and the mixture was heated at 94° C. for 5 minutes. The probes were added to the pre-Hyb solution and the blot was incubated for 1 hour at 68° C. After hybridization, the membrane was removed from the bottle and washed twice in 50 ml of 2×SSC and 0.1% SDS for 15 minutes at room temperature. Then, the membrane was washed twice in 50 ml of pre-heated 0.1×SSC and 0.1% SDS for 15 minutes at 60° C. The membrane was then placed on top of Whatman filter paper for 30 minutes to dry and then wrapped in saran wrap. The membrane was exposed to film overnight, stored at −80° C. and then developed.

Plant Expression of NS3 and Immunoblot Analysis.

Petit Havana and LAMD-609 leaf sections were cut and 100 mg plant leaf tissue was weighed and grounded with liquid nitrogen in cold mortar and pestles and transferred to a microcentrifuge tube. Fresh plant extraction buffer (PEB: 60 ul of 5M NaCl, 60 ul of 0.5M EDTA (pH 8), 600 ul of 1M Tris-HCl (pH 8), 2 ul of Tween-20, 30 ul of 10% SDS, 3 ul of 14 mM β-mercaptoethanol (BME), 1.2 ml of 1M sucrose, 1 ml sterile H2O and 120 ul of 100 mM PMSF) was made and kept on ice. To make 100 mM of PMSF, 17.4 mg of powdered PMSF (Sigma) was weighed out, put into 1 ml of methanol and vortexed, and stored at up to 1 month at −20° C. 200 ul of PEB was added to each plant sample on ice and then samples were mixed for 3 minutes with a micropestle. The samples were centrifuged at 13,000 rpm for 10 mins to obtain the supernatant containing the soluble proteins. 20 µl of these extracts were mixed with 20 µl of sample loading buffer containing BME. Samples were then boiled for 5 minutes and loaded into SDS-PAGE gel. The procedure for the rest was identical to the protocol for *E. coli-expressed* NS3 and Immunoblot Analysis (see above sections).

Enzyme Linked Immuno Sorbant Assay (ELISA).

The levels of NS3 in transgenic LAMD-609 were calculated as a percentage of the total soluble protein of leaf extracts. The quantification of NS3 in the plant crude extract was done using the enzyme linked immunosorbant assay (ELISA). 100 mg of transgenic leaf samples (young, mature, old) and the wild type leaf samples (young, mature, old) were collected. The leaf samples were collected from plants exposed to regular lighting pattern (16 h light and 8 h dark), 3 day continuous light, and 5 day continuous light. The leaf samples were finely grounded in liquid nitrogen and the leaf powder was transferred into an eppendorf tube. To extract the protein, plant protein extraction buffer (15 mM Na2CO3, 35 mM NaHCO3, 3 mM NaN3, pH: 9.6, 0.1% Tween, 5 mM PMSF) was used to resuspended the leaf powder. In order to check the protein concentration, the standards, test samples and antibody were diluted in coating buffer (15 mM Na2CO3, 35 mM NaHCO3, 3 mM NaN3; pH: 9.6). The standards ranging from 50 to 500 ng/ml (500 ng/ml, 400 ng/ml, 300 ng/ml, 200 ng/ml, 100 ng/ml and 50 ng/ml) were made by diluting purified NS3 in coating buffer (stock: 1000 ng/ml). The standards and protein samples (100 µl) were coated to 96-well polyvinyl chloride microtiter plate (Cellstar) for 1 h at 37 C followed by 3 washes with PBST and 2 washes with water. Blocking was done with 3% fat-free milk in PBS and 0.1% Tween and incubated for 1 h followed by washing. The primary anti-NS3 antibody (Neomarkers) diluted (1:500) in PBST containing milk powder was loaded into wells and incubated for 1 h followed by washing steps and then again incubated with 100 µl of anti-mouse goat-HRP conjugated antibody (American Qualex, 1:5000) diluted in PBST containing milk powder. The plate was then incubated for 1 h at 37° C. After the incubation, the plate was washed thrice with PBST and twice with water. The wells were then loaded with 100 µl of 3,3,5,5-tetramethyl benzidine (TMB from American Qualex) substrate and incubated for 10-15 min at room temperature. The reaction was terminated by adding 50 µl of 2N sulfuric acid per well and the plate was read with a plate reader (Dynex Technologies) at 450 nm (Modified form of protocol from Ausubel et al., 4$^{th}$ edition).

Bradford Assay for Protein Quantification (Bio-Rad Manual).

The Bradford assay was used to determine the total protein from the plant extracts prepared as described above. This was used to determine the percent of NS3 antigen in the total soluble protein extract (or % TSP). An aliquot of plant extract as prepared above was thawed on ice. Extraction buffer (15 mM Na2CO3, 35 mM NaHCO3, 0.2 g NaN3, 0.1% Tween 20, and 5 mM PMSF adjusted to pH 9.6) was used to make Bovine Serum Albumin (BSA) standards ranging from 0.05 to 0.5 µg/µl. Plant extracts were diluted 1:20 and 1:30 with extraction buffer. 10 µl of each standard and 10 µl of each plant dilution were added to the wells of a 96 well microtiter plate (Costar) in duplicates. Bradford reagent (Biorad protein assay) was diluted 1:4 with distilled water as specified and 200 µl was added to each well. Absorbance was read. The comparison of the absorbance to known amounts of BSA to that of the samples was used to estimate the amount of total protein.

Results
Construction of pLD-5'UTR/NS3 Vector for Tobacco Chloroplast Transformation.

Figure 16:
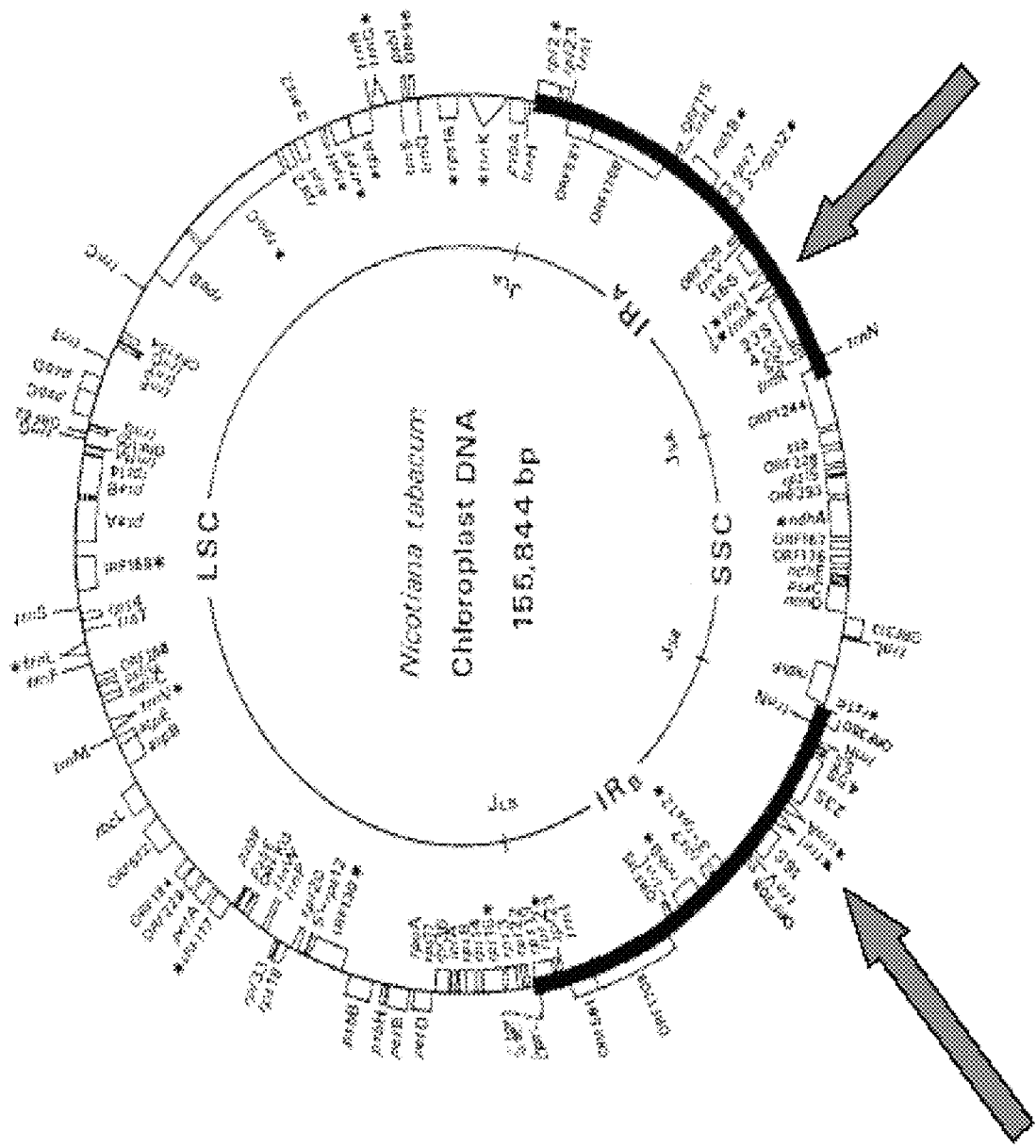
Figure 17:
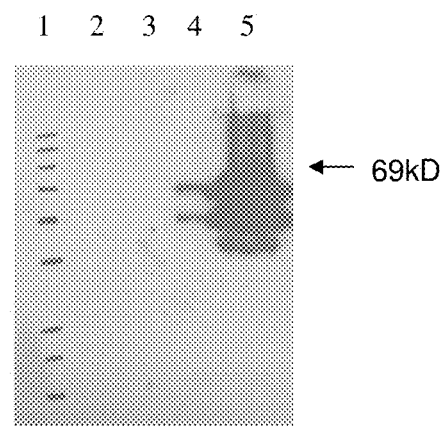

The NS3 gene (starting 134 bp) in pcDNA3.1D/V5-His-TOPO was PCR amplified and the restriction sites, SacI and SnaBI at the 5' end and NotI at the 3' end of the 134 bp of the NS3 gene were created for further subcloning. A PCR product of 134 bp in size was obtained by amplification. The PCR product was then digested with SacI and NotI and was ligated between the same sites in p-Bluescript II KS vector. The transformed colonies were selected as the pBluescript vector contains the LacZ gene for a complementation and blue/white selection. The ligated plasmid pBS-NS3 was isolated using midi-prep and the PCR product was sequenced. The sequence was compared with the original NS3 sequence sent by Dr. Lasarte. After confirming that the 5' of the NS3 gene (beginning 134 bp) was successfully cloned into pBluescript, the remaining NS3 gene (1770 bp) was digested from the original pcDNA3.1D/V5-His-TOPO vector with BstXI and EcoRV and ligated between the same sites in pBluescript vector. Therefore, the entire NS3 gene (1.9 kb) was cloned into p-Bluescript vector. The entire NS3 gene was digested with SnaBI and HindIII and cloned downstream of psbA 5'UTR in pCR2.1. Finally, the psbA 5'UTR and the NS3 gene were digested with EcoRV and EcoRI (fragment size 2.1 kb) from pCR2.1 and ligated into the final universal vector, pLD-AB-Ct. The 5.9 kb expression vector was developed with unique features facilitating the genetic engineering of plant chloroplasts (FIG. 16). The integration of cloned chloroplast DNA into the plastid genome occurs exclusively through site-specific homologous recombination and excludes the foreign vector DNA (Kavanagh et al., 1999). The pLD-AB-Ct uses trnA and trnI genes (chloroplast transfer RNAs coding for alanine and isoleucine) from the inverted repeat region of the tobacco chloroplast genome as flanking sequences for homologous recombination (Daniell, 1999). This chloroplast expression vector is considered universal because it can be used to transform the chloroplast genomes of not just tobacco, but several other plant species as well (Daniell, 1999). Therefore, this pLD-AB-Ct was successfully used as the backbone for the 5'UTR/NS3 cassette (FIG. 15).

Selection and Regeneration of Transgenic Lines.

Figure 18:
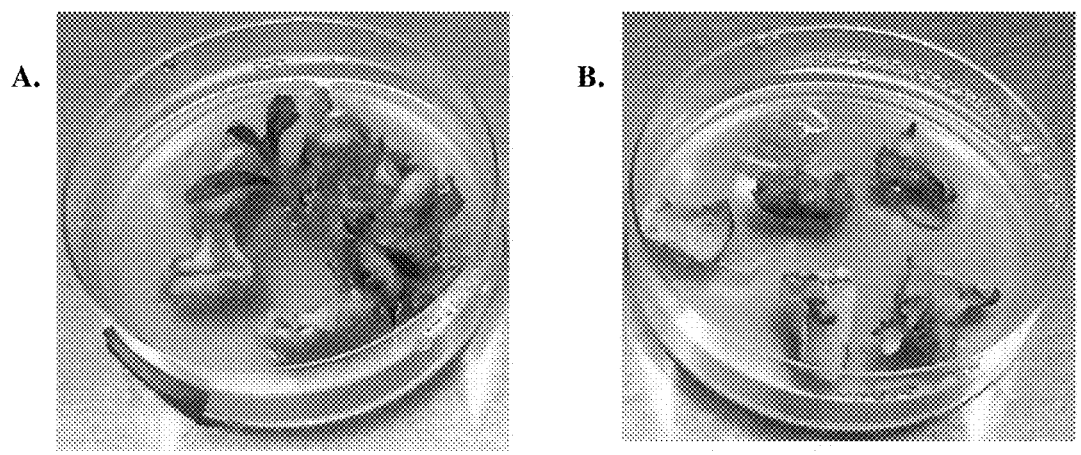

After recovering in the dark for 48 hours from bombardment, leaves were cut into 5 mm2 pieces and placed on RMOP (Daniell, 1993) plates containing 500 µg/ml spectinomycin for Petite Havana and 350 µg/ml for LAMD-650, for the first round of selection as described in Daniell (1997). From 10 bombarded Petit Havana leaves, 15 green shoots appeared after 4 weeks. From 10 bombarded LAMD leaves, 3 green shoots appeared within 7 weeks, so the shoots from the low-nicotine tobacco took longer to sprout and were less numerous. Untransformed cells appeared bleached on the antibiotic because they did not contain the aadA gene (FIG. 18). For second selection the shoots were cut into 2 mm² pieces and then transferred to fresh RMOP plates with 500 µg/ml and 350 µg/ml spectinomycin for Petite Havana and LAMD spectinomycin respectively (FIG. 19).

During the second round of selection, the shoots that appeared and tested positive for cassette integration into the chloroplast genome by PCR analysis were grown in sterile jars containing fresh plant media with spectinomycin until the shoots grew to fill the jars (FIG. 20A). Then the plants were transferred to pots with soil containing no antibiotic (FIG. 20B). Potted plants were grown in a 16 hour light/8 hour dark photoperiod in the growth chamber at 26° C.

PCR Analysis of Transgenic Lines.

Two primer sets were used to identify transgenic lines. The 3P/3M set, the 3P primer annealed to the chloroplast genome outside of the inserted cassette and the 3M primer annealed to the chimeric aadA gene (FIG. 21A). When both of the primers annealed, a 1.65 kb PCR product was observed, however, there was no PCR product in the untransformed (−) Petit Havana and LAMD line (FIG. 21B). In addition, no PCR product should be observed if the foreign gene cassette was integrated into the nuclear genome or if the plants were mutants lacking the aadA gene. Out of the 7 putative transgenic lines shown, all 7 were positive for insertion of the foreign gene cassette (FIG. 21B).

For the 5P/2M set, the 5P primer annealed to the chimeric aadA gene and the 2P primer annealed to trnA gene within the cassette (FIG. 22A). When both of the primers annealed, a 3.7 kb PCR product was observed, however, there was no PCR product in the untransformed (−) petit Havana or LAMD line (FIG. 22B). The correct size of PCR product (3.7 kb) indicated that the entire foreign gene cassette and not just the aadA gene had been integrated into the chloroplast genome (FIG. 22A).

Southern Blot Analysis of Transgenic Plants (T0).

Figure 24:
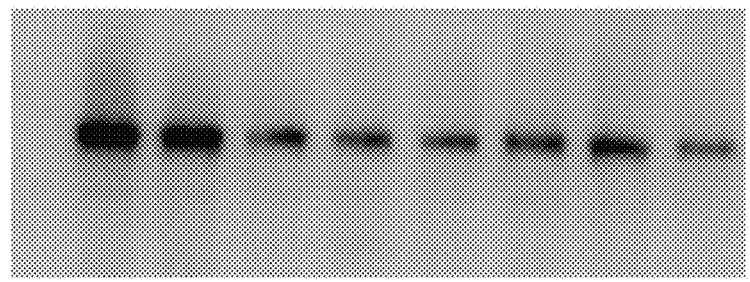

Southern blots were performed to confirm integration of the NS3 gene cassette utilizing two different DNA probes (FIG. 23 and FIG. 24). A 0.81 kb DNA fragment containing chloroplast-flanking sequences was used to probe a Southern blot to determine homoplasmy or heteroplasmy after bombardment with pLD-AB-NS3 (T0). This determination was also used to estimate chloroplasts genome copy number. BglII digested DNA from transformed plants produced a 5.2 kb and 2.7 kb fragment when probed with the 0.81 kb probe that hybridizes to the trnI and trnA flanking sequences (FIG. 23). Untransformed plant DNA from both tobacco varieties produced only a 4.47 kb fragment, indicating no integration of foreign DNA. Transgenic plant DNA (T0) produced only the 5.2 and 2.7 kb fragment in all transgenic plants indicating homoplasmy (contained only transformed chloroplast genomes).

The second probe used was a 2.1 kb 5'UTR/NS3 sequence that hybridized to a 2.7 kb fragment in transformed plants and no fragment was evident in untransformed plants (FIG. 24). All transgenic plants produced a 2.7 kb fragment corresponding to the NS3 sequence (FIG. 24).

Chloroplast-Synthesized NS3 and Immunoblot Analysis.

Figure 25:

Petit Havana and LAMD were bombarded with pLD-AB-NS3. Western blot analysis was performed on the leaf cell extracts. The total plant protein was separated using 10% sodium dodecyl sulfate polyacrylamide gel electrophoresis (SDS-PAGE). The NS3 protein was detected by mouse monoclonal antibody against NS3. Western blots detected NS3 protein at 69 kDa using chemiluminescense (FIG. 25A).

Quantification of Chloroplast-Synthesized NS3 by ELISA.

Figure 26:
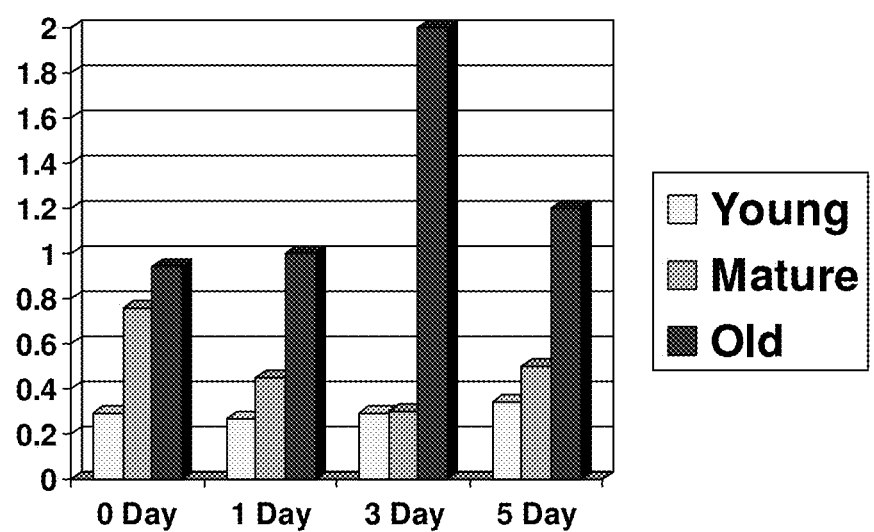

To quantify the amount of NS3 in transgenic Petit Havana and LAMD leaf extracts, an indirect enzyme-linked immunosorbent assay (ELISA) was used. The purified NS3 protein was used to make a six-point standard curve. 1 µl of the plant protein extracts were diluted into 20 ul and 30 ul of coating buffer to determine the dilution that would be in the linear range of NS3 standard curve. The primary antibody was anti-NS3 Mouse Monoclonal Antibody. The secondary antibody was Goat anti-mouse IgG conjugated to horseradish peroxidase. The addition of one step substrate (TMB) into the wells resulted in a color change that was eventually read on a plate reader with a 450 nm filter. The total soluble protein (tsp) in the plant leaf extracts was determined with a Bradford Bio-Rad Protein Assay. The levels of NS3 in transgenic LAMD were calculated as a percentage of the total soluble protein of leaf extracts (FIG. 26).

Discussion

Figure 27:
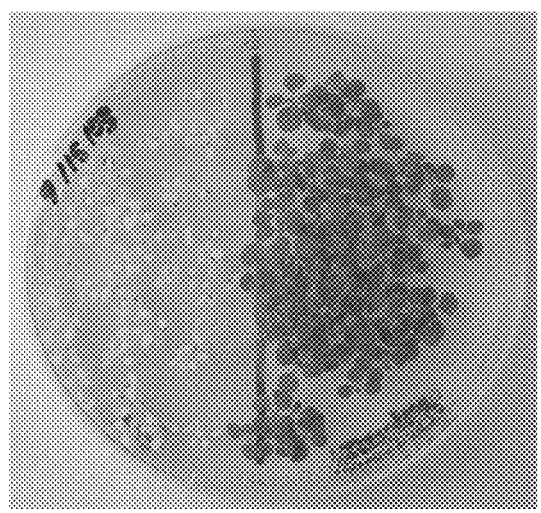

HCV vaccine development began recently with the use of recombinant HCV proteins as the immunogenic material (Choo et al., 1994). The initial candidate HCV vaccine developed in 1994, derived from the envelope glycoproteins (gpE1/E2) of HCV, with muramyl dipeptide adjuvants, induced high levels of neutralizing antibodies in chimpanzees and provided protection in a proportion of animals challenged with low doses of the homologous strain (Choo et al., 1994; Houghton et al., 1997). In the chimpanzees that were infected, the risk of persistent infection seemed to be reduced. Little new information about this candidate vaccine is available. Additional studies of a recombinant E1/E2 protein and peptide vaccine produced in insect cells (Esumi et al., 1999) also suggested that induced antibodies could neutralize low-level challenge with homologous HCV in the chimpanzee. In one DNA vaccine study utilizing chimpanzees, a plasmid encoding the E2 HCV protein was used as immunogen and elicited antibodies and immune response but on challenge with homologous HCV, sterilizing immunity could not be achieved (Forns et al, 2000). Other approaches to vaccine development have included the incorporation of HCV proteins into recombinant viruses (Siler et al., 2002; Brinster et al., 2002), the synthesis of HCV-like particles in insect cells (Lechmann et al., 2001), expression of the hypervariable-1-region of E2 in tobacco plants (Nemchinov et al., 2000) and DNA-based immunization (Brinster et al., 2001; Forns et al., 2000). Plant synthesized recombinant TMV/HCV HVR1 epitope/CTB induced a strong immune response when mice were immunized intranasally (Nemchinov et al., 2001). Plants infected with a recombinant tobacco mosaic virus engineered to express the hypervariable region 1 (HVR1) of HCV, the HVR1/CTB chimeric protein elicited both anti-CTB and anti-HVR1 serum which specifically bound to HCV virus-like particles. The HCV HVR1 epitope was also cloned into alfalfa mosaic virus (ALMV) coat protein and expressed in transgenic tobacco plants. The Plant-derived HVR1/ALMV-CP reacted with HVR1 and ALMV-CP specific monoclonal antibodies and immune sera from individuals infected with HCV (Nemchinov et al., 2001). A replication-deficient recombinant adenovirus expressing HCV NS3 protein was constructed. Mice immunized with this recombinant adenovirus were protected against challenge with a recombinant vaccinia virus expressing HCV polyprotein (Arribillaga et al, 2002).

The NS3 gene was introduced into pLD-Ct, the universal chloroplast expression vector, which was developed with unique features that facilitate chloroplast genetic engineering (FIG. 16). The 5' untranslated region (UTR) of the plastid psbA gene and its promoter were used to increase translation efficiency. The 5'UTR is involved in mRNA-rRNA interactions (between the mRNA ribosome-binding site and 16S r RNA 3' end) and interactions with translational-activating proteins that facilitate loading onto ribosomes (Maliga, 2002). The psbA gene encodes the D1 protein of photosystem II and is rapidly turned over in the chloroplasts (Eibl et al., 1999). The psbA 5'UTR is about 200 bp and contains a promoter. The 3' regulatory region (3'UTR) is important for mRNA stability and functions as an inefficient terminator of transcription. A unique short inverted repeat (IR) which can potentially fold into a stem loop structure at the 3'UTR probably act as a RNA processing signal rather than termination signal, playing a role in both RNA 3' end formation and stabilization (Hager and Bock, 2000). The pLD-Ct contains a chimeric aadA gene as a selectable marker, which encodes aminoglycoside 3'-adenylyltransferase. This enzyme catalyzes the covalent modification of aminoglycoside-type antibiotics and thereby inactivates them. The aadA protein catalyses the covalent transfer of an AMP residue from ATP to spectinomycin, thereby converting the antibiotic into an inactive from (adenyl-spectinomycin) that no longer inhibits protein biosynthesis on prokaryotic 70S ribosomes present in the chloroplast. The aadA gene is driven by a portion of the constitutive promoter of the chloroplast 16S rRNA operon (Prrn). The pLD-AB vector integrates the 16S rRNA promoter, aadA gene, 5'UTR, NS3 gene and 3'UTR cassette into the Inverted Repeat (IR) regions of the chloroplast genome between the homologous flanking sequences, trnI and trnA genes. The trnI and trnA intergenic spacer regions are highly conserved among higher plants (Guda et al., 2000). The pLD-Ct vector was constructed with a multiple cloning site downstream of the aadA gene and upstream of the TpsbA portion and flanked by chloroplast transfer RNA genes for isoleucine and alanine (trnI and trnA respectively). The plasmid can replicate autonomously because it contains a unique chloroplast origin of replication (Daniell, 1990; Kumar et al. 2004a, b) and ColE1 origin of replication that operates in *E. coli* (Glick and Pasternak, 1998). The translational apparatus of chloroplasts very much resembles that of prokaryotes, in that tRNAs, rRNAs, ribosomal proteins and the initiation and elongation factors exhibit strong similarity with their counterparts in *E. coli* (Brixey et al., 1997). As a way of testing the integrity of the NS3 cassette and its potential for protein expression, *E. coli* was transformed with pLD-AB-NS3. Western blot analysis performed on the *E. coli* cell lysates indicated the presence of NS3 protein at the expected size of 69 kDa (FIG. 17), while the untransformed *E. coli* cell lysates showed no protein. Since the protein synthetic machinery of chloroplasts is similar to that of *E. coli* (Brixey et al., 1997), the positive expression of NS3 suggested that it could be successfully expressed within transgenic chloroplasts. Two varieties of tobacco were bombarded with gold particles coated with pLD-AB-NS3 (Daniell, 1993). Petit Havana is the model tobacco variety because it is amenable to genetic engineering. The second variety of tobacco bombarded with pLD-AB-NS3 was LAMD-609. This tobacco hybrid contains 0.06% nicotine (Collin et al., 1974), which is at least 50-fold lower than the Petit Havana tobacco (3-4%). Tobacco is the easiest plant to genetically engineer and is widely used to test suitability of plant-based systems for bioproduction of recombinant proteins. Tobacco is ideal for transformation because of its ease for genetic manipulation and is an excellent biomass producer and a prolific seed producer (up to one million seeds produced per plant). Bombarded leaves were placed on RMOP medium containing no antibiotics and allowed to recover from bombardment in the dark for 48 hours (Daniell, 1993; Daniell, 1997; Daniell et al. 2004a).

After the recovery period, bombarded leaf discs were placed on selective plant medium containing 500 μg/ml of spectinomycin. Green shoots that emerged from the part of the leaf disc in contact with the medium were considered putative transformants because growth indicated that the aadA gene had been integrated into the chloroplast genome and was expressing functional enzyme. Each shoot (transgenic event) was subjected to a second round of selection (500 μg/ml of spectinomycin) in an effort to ensure that only transformed genomes existed in the cells of the transgenic lines (homoplasmy). A heteroplasmic condition is unstable and will result in loss of the transgene when the cell divides without selective pressure (Hager and Bock, 2000). A PCR method of screening putative transformants was utilized to distinguish chloroplast transformants from mutants and nuclear transformants (Daniell et al. 2004a). Only those transgenic lines with the appropriately sized PCR products were used in further characterizations. The Southern blot analysis utilized the integrity of DNA complimentary hybridization to identify specific sequences in the various plant genomes. Different positive transgenic lines (T0) were tested to confirm site-specific integration and to determine homoplasmy or heteroplasmy (FIGS. 26 & 27). The 810 bp flanking sequence probe confirmed that the NS3 gene cassette had been integrated into the chloroplast genome. An enzyme-linked immunosorbent assay (ELISA) utilizing 96-well microtiter plates, was used to quantify the amount of NS3 in transgenic LAMD-609 leaf extracts. The highest percentage of NS3 was 2% of total soluble protein, observed in the old leaves. In conclusion, this study reports successful expression of the HCV NS3 antigen in transgenic chloroplasts and the plant derived recombinant HCV vaccine antigen can potentially reduce expenses normally associated with the production and delivery of conventional vaccines and is a safe and inexpensive source for the production of HCV vaccine antigen.

REFERENCES

Alter M J. (1995) Epidemiology of hepatitis C in the west. *Semin Liver Dis.* 15: 5-14.

Arribillaga L, Cerio A, Sarobe P, Casares N, Gorraiz M, Vales A, Bruna-Romero O, Borras-Cuesta F, Paranhos-Baccala G, Prieto J, Ruiz J, Lasarte J J. (2002) Vaccination with an adenoviral vector encoding hepatitis C virus (HCV) NS3 protein protects against infection with HCV-recombinant vaccinia virus. *Vaccine* 21: 202-210.

Bedbrook J. R. and Bogorad, L. (1976) Endonuclease recognition sites mapped on the *Zea mays* chloroplast DNA. *Proc. Natl. Acad. Sci. USA* 73: 4309-4313.

Blowers A D, Bogorad L, Shark K B, and Sanford J C. (1989) Studies on *Chlamydomonas* chloroplast transformation: foreign DNA can be stably maintained in the chromosome. *Plant Cell* 1, 123-132.

Bogorad L. (2000) Engineering chloroplasts: an alternative site for foreign gene, proteins, reactions and products. TIBTECH 18, 257-263.

Botarelli P, Brunetto M R, Minutello M A. (1993) T-lymphocyte response to hepatitis C virus in different clinical courses of infection. *Gastroenterology* 104(2): 580-7.

Boynton J E, Gillham N R, Harris E H, Hosier J P, Johnson A M, Jones A R, Randolph-Anderson B L, Robertson D, Klein T M, Shark K B. (1988) Chloroplast transformation in *Chlamydomonas* with high velocity microprojectiles. *Science* 240: 1534-1538.

Bukh J, Forms X, Emerson S U, Purcell R H. (2001) Studies of hepatitis C virus in chimpanzees and their importance for vaccine development. *Intervirology* 44: 132-142.

Brinster C, Inchauspe G. (2001) DNA vaccines for hepatitis C virus. *Intervirology* 44: 143-153.

Brinster C, Chen M., Boucreux D, Paranhos-Baccala G, Liljestrom P, Lemmonier F, Inchauspe G. (2002) Hepatitis C virus non-structural protein 3-specific cellular immune responses following single or combined immunization with DNA or recombinant Semliki Forest virus particles. *J. Gen. Virol.* 83: 369-381.

Brixey M, Guda C, Daniell H. (1997) The chloroplast psbA promoter is more efficient in *E. coli* than the T7 promoter for hyper-expression of a foreign protein. Biotechnology Letters. 19, 395-400

Camps J, Castilla A, Ruiz J, Civveira M P, Prieto J. (1993) Randomised trial of lymphoblastoid alpha-interferon in chronic hepatitis C. Effects on inflammation, fibrogenesis and viremia. *J Hepatol* 17(3): 390-6.

Castanon S, Marin M S, Martin-Alonso J M, (2000) Immunization with potato plants expressing VP60 proteins protects against rabbit hemorrhagic disease virus. J *Virology* 73: 4452-55.

Cerny A, McHutchison J G, Pasquinelli C. (1995) Cytotoxic T lymphocyte response to hepatitis C virus-derived peptides containing the HLA A2.1 binding motif. *J Clin Invest* 95(2):521-30.

Choo Q. L. (1989) Isolation of a cDNA clone derived from a blood borne non-A, non-B viral hepatitis genome. *Science* 244: 359-362.

Choo Q L, Kuo G, Ralston R, Weiner A, Chien D, Van Nest G, Han J, Berger K, Thudium K, Kuo C, Kanospon J, McFarland J, Tarizi A, Ching K, Moss B, Cummins L B, Houghton M, Muchmore E. (1994) Vaccination of chimpanzees against infection by the hepatitis C virus. *Proc. Natl. Acad. Sci. USA* 91: 1294-1298.

Collins, Legg, Kasperbauer (1974). Tobbaco hybrid, LAMD-609. Crop Sci 14, 77-80.

Cooper S, Erickson A L, Adams E J. (1999) Analysis of a successful immune response against hepatitis C virus. *Immunity* 10 (4): 439-49.

Cowley D, Mackin R. (1996). Expression, purification and characterization of recombinant human proinsulin. *FEBS Letters* 402: 124-130.

Esumi M, Rikihisa T, Nishimura S, Goto J, Mizuno K, Zhou Y.-H., Shikata T. (1999) Experimental vaccine activities of recombinant E1 and E2 glycoproteins and hypervariable region 1 peptides of hepatitis C virus in chimpanzees. *Arch. Virol.* 144: 973-980.

Eibl C, Zou Z, Beck A, Kim M, Mullet J, Koop H. (1999). In vivo analysis of plastid psbA, rbcL and rpl32UTR elements by chloroplast transformation: tobacco plastid gene expression is controlled by modulation of transcript levels, and translational efficiency. *Plant J.* 19, 333-345

Daniell H., Ramanujan P, Krishnan M, Gnanam A, Rebeiz C A. (1983) In vitro synthesis of photosynthetic membranes: I. Development of photosystem I activity and cyclic phosphorylation. *Biochem. Biophys. Res. Comun.* 111: 740-749.

Daniell H, Krishnan M, Umabai U, Gnanam A. (1986) An efficient and prolonged in vitro translational system from cucumber etioplasts. *Biochem. Biophys. Res. Comun.* 135: 48-255.

Daniell H, McFadden B A. (1987) Uptake and expression of bacterial and cyanobacterial genes by isolated cucumber etioplasts. *Proc. Natl. Acad. Sci. USA,* 84: 6349-6353.

Daniell H, Vivekananda J, Neilsen B, Ye G N, Tewari K K, Sanford J C. (1990) Transient foreign gene expression in chloroplasts of cultured tobacco cells following biolistic delivery of chloroplast vectors. *Proc Natl Acad Sci USA.* 87: 88-92.

Daniell H, Krishnan M, McFadden B A. (1991) Expression of B-glucuronidase gene in different cellular compartments following biolistic delivery of foreign DNA into wheat leaves and calli. Plant Cell Reports. 9: 615-619.

Daniell H. (1993). Foreign gene expression in chloroplasts of higher plants mediated by tungsten particle bombardment. *Methods Enzymol.* 217: 536-556.

Daniell H. (1997). Transformation and foreign gene expression in plants mediated by microprojectile bombardment. *Meth Mol Biol*, 62: 453-488.

Daniell H, Datta R, Varma S, Gray S, and Lee S B. (1998) Containment of herbicide resistance through genetic engineering of the chloroplast genome. *Nature Biotechnology.* 16: 345-348.

Daniell H. (1999) Universal chloroplast integration and expression vectors, transformed plants and products thereof, World Intellectual Property Organization. WO 99/10513.

Daniell H, Streafield S J, Wycoff K. (2001). Medical molecular farming: production of antibodies, biopharmaceuticals and edible vaccines in plants. *Trends Plant Sci.,* 6(5): 219-26.

Daniell H, Lee S B, Panchal T, Wiebe P O. (2001a) Expression of the native cholera toxin B subunit gene and assembly of functional oligomers in transgenic tobacco chloroplasts. *Journal of Molecular Biology,* 311:1001-1009.

Daniell H, Muthukumar B, Lee S B. (2001b) Marker free transgenic plants: engineering the chloroplast genome without the use of antibiotic selection. *Curr Genet.,* 39(2):109-16.

Daniell H. (2002). Molecular strategies for gene containment in GM crops. *Nature Biotechnology,* 20: 581-586.

Daniell H, Dhingra, A. (2002a) Multiple gene engineering. *Current Opinion in Biotechnology,* 13:136-141.

Daniell H. (2004) Medical Molecular Pharming: Therapeutic recombinant antibodies biopharmaceuticals, and edible vaccines in transgenic plants engineered via the chloroplast genome. *Encyclopedia of Plant and Crop Science. In Press.*

Daniell H, Ruiz O N, Dhingra A. (2004a) Chloroplast genetic engineering to improve agronomic traits. *Methods in Molecular Biology* 286: 111-137.

Daniell H, Carmona-Sanchez O, Burns B B (2004b) Chloroplast derived antibodies, biopharmaceuticals and edible vaccines. In R Fischer and S Schillberg eds, Molecular Farming Weinheim: WILEY-VCH Verlag, pp. 113-133.

Daniell H, Chebolu S, Kumar S, Singleton M, Falconer R (2005) Chloroplast-derived vaccine and other therapeutic proteins. *Vaccine* 23: 1779-1783.

De Cosa B, Moar W, Lee S B, Miller M, Daniell H. (2001). Hyper-expression of Bt Cry2Aa2 operon in chloroplasts leads to formation of insecticidal crystals. *Nature Biotechnology,* 19: 71-74.

DeGray, G., Rajasekaran, K., Smith, F., Sanford, J., Daniell, H. (2001) Expression of an antimicrobial peptide via the chloroplast genome to control phytopathogenic bacteria and fungi. *Plant Physiology,* 127: 1-11.

Diepolder H M, Zachoval R, Homann R M, Wierenga E A, Santantonio T, Jung M C, Eichenlaub D, Pape G R. (1995) Possible mechanism involving T-lymphocyte response to nonstructural protein 3 in viral clearance in acute hepatitis C virus infection. *Lancet* 346: 1006-7.

Diepolder H M, Gerlach J T, Zachoval R, Homann R M, Jung M C, Wierenga E A, Scholz S, Santantonio T, Houghton M, Southwood S, Sette A, Pape G R. (1997) Immunodominant CD4+ T-cell epitope within nonstructural protein 3 in acute hepatitis C virus infection. *J Virol;* 71:6011-9.

El Attar A K, Shamloul A M, Shalaby A A, Riad B Y, Saad A, Mazyad H M and Keith J M (2004). Expression of chimeric HCV peptide in transgenic tobacco plants infected with recombinant alfalfa mosaic virus for development of a plant-derived vaccine against HCV. *African Journal of Biotechnology Vol.* 3 (11), pp. 588-594.

Erickson A L, Houghton M, Choo Q L, Weiner A J, Ralston R, Muchmore E, Walker C M. Hepatitis C virus-specific CTL responses in the liver of chimpanzees with acute and chronic hepatitis C. (1993) *J Immunol* 151: 4189-99.

Falconer R. 2002. *Expression of interferon alpha 2b in transgenic chloroplasts of a low-nicotine tobacco.* M.S. thesis, University of Central Florida, Orlando, Fla.

Fernandez-San Millan A, Mingo-Castel A, Daniell H. (2003) A chloroplast transgenic approach to hyper-express and purify human serum albumin, a protein highly susceptible to proteolytic degradation. *Plant Biotechnology Journal.* 1:71-79.

Ferrari C, Valli A, Galati L. (1994) T-cell response to structural and nonstructural hepatitis C virus antigens in persistent and self-limited hepatitis C virus infections. *Hepatology* 19 (2):286-95.

Forms X, Payette P J, Satterfield W, Eder G, Mushahwar I K, Govindarajan S, Davis H L, Emerson S U, Purcell R H, Bukh J. (2000). Vaccination of chimpanzees with plasmid DNA encoding the hepatitis C virus (HCV) envelope E2 protein modified the infection after challenge with homologous monoclonal HCV. *Hepatology* 32: 618-625.

Gillham N W (1994). Organelles genes and genomes. Oxford University Press, Oxford.

Glick B, Pasternak J. (1998) Molecular Biotechnology: Principles and Applications of Recombinant DNA. ASM Press, $2^{nd}$ edition.

Grakoui A, Wychowski C, Lin C, Feinstone S M, Rice C M (1993) Expression and identification of hepatitis C virus polyprotein cleavage products. *J Virol* 67: 1385-95.

Grakoui A, McCourt D W, Wychowski C, Feinstone Sm, Rice C M. (1993) A second hepatitis C virus-encoded proteinase. *Proc Natl Acad Sci USA* 10583-10587.

Gruener N H, Gerlach T J, Jung M C. (2000) Association of hepatitis C virus-specific CD8+ T cells with viral clearance in acute hepatitis C. *J Infect Dis* 181 (5):1528-36.

Guha C, Sha S J, Ghosh S, Lee S W, Roy-Chowdhury N, Roy-Chowdhury H. (2003) Molecular therapies for viral hepatitis. *BioDrugs.* 17: 81-91.

Guda C, Lee S B, Daniell H. (2000) Stable expression of biodegradable protein based polymer in tobacco chloroplasts. *Plant Cell Rep.* 19: 257-262.

Hager M., Bock R. (2000). Enslaved bacteria as new hope for plant biotechnologist. *Appl. Microbiology Biotechnol.* 54: 302-310.

Han D S, Hahm B, Rho H-M, Jang S K. (1995) Identification of the proteinase domain in NS3 of hepatitis C virus. *J Gen Virol.* 76: 985-993.

He X S, Rehermann B, Lopez-Labrador FX. Quantitative analysis of hepatitis C virus-specific CD8+ T cells in peripheral blood and liver using peptide-MHC tetramers. *Proc Natl Acad Sci USA,* 96 (10):5692-7.

Hoffmann R M, Diepolder H M, Zachoval R. (1995) Mapping of immunodominant CD4+ T lymphocyte epitopes of hepatitis C virus antigens and their relevance during the course of chronic infection. *Hepatology* 21(3):632-8.

Houghton M. Hepatitis C viruses. (1996) In: Fields B N, Knipe D M, Howley P M, editors. Fields Virology, 3rd edn. New York: Raven Press p. 1035-1058.

Houghton M, Choo Q L, Chien D, Kuo G, Weiner A, Coates S, Cousens L, Wininger M, Selby M, Ralston R, Berger K, Dong C, Crawford K, Tabrizi-Wright A, Purcell R H, Muchmore E, Morandi P, Rosa D, Abrignani S. (1997) Development of an HCV vaccine. In: Rizzetto, M., Purcell, R. H., Gerin, J. L., Verme, G. (Eds.), Viral Hepatitis and Liver Disease. Proceedings of the Ninth Triennial International Symposium of Viral Hepatitis and Liver Disease, Rome, Italy, 21-25 Apr. 1996. Edizioni Minerva Medica, Turin, pp. 656-659.

Invitrogen Catalog, 2000.

Kavanagh T, Thanh N, Lao N, McGrath N, Peter S, Horvath E, Dix P, Medgyest P. (1999). Homeologous Plastid DNA Transformation in Tobacco is Mediated by Multiple Recombination Events. *Genetics,* 152: 1111-1122.

Klein T M (1987) High velocity microprojectiles for delivering nucleic acids into living cells. *Nature* 327: 70-73.

Koff R S. Fulminant hepatitis due to HBV/HDV coinfection. Hosp Pract (Off Ed). 1987 Nov. 15; 22(11) 145-50.

Kong Q, Richter L, Yang Y, Arntzen C, Mason H, Thanavala Y. (2001). Oral immunization with hepatitis B surface antigen expressed in transgenic plants. *Proc. Natl. Acad. Sci. USA,* 20:11539-11544.

Kota M, Daniell H, Varma S, Garczynski S F, Gould F, William M J. (1999) Overexpression of the *Bacillus thuringiensis* (Bt) Cry2Aa2 protein in chloroplasts confers resistance to plants against susceptible and Bt-resistant insects. *Proc. Natl. Acad. Sci. USA* 96, 1840-1845.

Kumar S, Daniell H. (2004) Engineering the chloroplast genome for hyper-expression of human therapeutic proteins and vaccine antigens in recombinant protein protocols. *Methods Mol. Biol.* 267: 365-383.

Kumar S, Dhingra A, Daniell H. (2004a) Plastid-expressed betaine aldehyde dehydrogenase gene in carrot cultured cells, roots, and leaves confer enhanced salt tolerance. *Plant Physiol* 136: 2843-2854.

Kumar S, Dhingra A, Daniell H. (2004b) Stable transformation of the cotton plastid genome and maternal inheritance of transgenes. 2004 *Plant Mol Biol* 56: 203-216

Kurokohchi K, Akatsuka T, Pendleton C D (1996) Use of recombinant protein to identify a motif-negative human cytotoxic T-cell epitope presented by HLA-A2 in the hepatitis C virus NS3 region. *J Virol* 70 (1): 232-40.

Kusnadi A, Nikolov Z, Howard J. (1997) Production of Recombinant proteins in transgenic plants: Practical considerations. *Biotechnology and Bioengineering,* 56 (5), 473-484.

Kolodner R, Tewari, K K. (1979). Inverted repeats in chloroplast DNA from higher plants. *Proc. Natl. Acad. Sci. USA* 76: 41-45.

Laemmli U. (1970) Cleavage of structural proteins during the assembly of the head of bacteriophage T4. *Nature* 227: 680-685.

Lasarte J J, Garcia Granero M, Lopez A. (1998) Cellular immunity to hepatitis C virus core protein and the response to interferon in patients with chronic hepatitis C. *Hepatology* 28 (3): 815-22.

Lechmann M, Ihlenfeldt H G, Braunschweiger I. (1996) T- and B-cell responses to different hepatitis C virus antigens in patients with chronic hepatitis C infection and in healthy anti-hepatitis C virus-positive blood donors without viremia. *Hepatology* 24 (4): 790-5.

Lechmann M, Liang T J. (2000). Vaccine development for hepatitis C. *Semin Liver Dis.* 20 (2): 211-26.

Lechmann M, Murata K, Satoi J, Vergalla J, Baumert T F, Liang T J. (2001). Hepatitis C virus-like particles induce virus-specific humoral and cellular immune responses in mice. *Hepatology* 34: 417-423.

Lee S B, Kwon H B, Kwon S J, Park S C, Jeong M J, Han S E, Byun M O, Daniell H (2003) Accumulation of trehalose within transgenic chloroplasts confers drought tolerance. *Mol. Breeding,* 11: 1-13.

Leelavathi S, Reddy V S (2003) Chloroplast expression of His-tagged GUS-fusions: a general strategy to overproduce and purify foreign proteins using transplastomic plants as bioreactors. *Mol. Breeding,* 11: 49-58.

Lohmann V, Korner F, Koch J, Herian U, Theilmann L, Bartenschlager R. (1999) Replication of subgenomic hepatitis C virus RNAs in a hepatoma cell line. *Science* 285:110-113.

Lohmann V, Korner F, Dobierzewska A, Bartenschlager R, (2001). Mutations in hepatitis C virus RNAs conferring cell culture adaptation. *J. Virol.* 75: 1437-1449.

Maddrey W C. (1999) Safety of combination interferon alfa-2b/ribavirin therapy in chronic hepatitis C-relapsed and treatment-naive patients. *Semin Liver Dis.* 19 (Suppl 1): 67-75.

Maliga P. (2002) Engineering the plastid genome of higher plants. *Current Opinion in Plant Biology,* 5:164-172.

Martin W, Hermann R G. (1998) Gene transfer from organelles to the nucleus: how much, what happens, and why? *Plant Physiol.* 118, 9-17.

Mason H, Lam M, Arntzen C. (1992) Expression of hepatitis B surface antigen in transgenic plants. *Proc. Natl. Acad. Sci. USA.* 89: 11745-11749.

Mast E E, Alter M J, Margolis H S (2004). Strategies to prevent and control hepatitis B and C virus infections: a global perspective. *Vaccine.* 17(13-14):1730-3.

McHutchison J G, Poynard T. Combination therapy with interferon plus ribavirin for the initial treatment of chronic hepatitis C. (1999) *Semin Liver Dis* 19 (Suppl 1): 57-65.

Missale G, Bertoni R, Lamonaca V. (1996) Different clinical behaviors of acute hepatitis C virus infection are associated with different vigor of the anti-viral cell-mediated immune response. *J Clin Invest* 98 (3): 706-14.

Molina A, Herva-Stubbs S, Daniell H, Mingo-Castel A M, Veramendi J. (2004) High yield expression of a viral peptide animal vaccine in transgenic tobacco chloroplasts. *Plant Biotechnology, In Press.*

Mondelli M U, Cerino A, Boender P, Oudshoorn P, Middledorp J, Fipaldidni C, La Monica N, Habets W (1994) Significance of the immune response to a major, conformational B-cell epitope on the hepatitis C virus NS3 region defined by a human monoclonal antibody. *J Virol* 68: 4829-4836.

Moreira D, Le Guyader H, Phillippe H (2000). The origin of red algae and the evolution of chloroplasts. *Nature* 405: 69-72.

National Institutes of Health Consensus Development Conference Statement: Management of Hepatitis C. (2002b). *Hepatology* 36 (5 Suppl. 1), S3-S20.

Nemchinov L G, Liang T J, Rifaat M M, Mazyad H M, Hadidi A, Keith J M. (2001). Development of a plant-derived subunit vaccine candidate against hepatitis C virus. *Arch. Virol.* 145: 2557-2573.

Op De Beeck A, L. Cocquerel, J. Dubuisson. (2001) Biogenesis of hepatitis C virus envelope glycoproteins. *J. Gen. Virol.* 82: 2589-2595.

Polakos, N. K., Drane, D., Cox, J., Ng, P., Selby, M. J., Chien, D., O'Hagan, D. T., Houghton, M., Paliard, X. (2001). Characterization of hepatitis C virus core-specific immune responses primed in rhesus macaques by a non-classical ISCOM vaccine. *J. Immunol.* 166: 3589-3598.

Palmer J D (1985). Comparative organization of Chloroplast genomes. *Annu Rev genet* 19: 325-354.

Pape G R, Gerlach T J, Diepolder H M (1999). Role of the specific T-cell response for clearance and control of hepatitis C virus. *J Viral Hepatol* 6 (Suppl 1):36-40.

Purnell R. (1997) The hepatitis C virus: overview. *Hepatology* 26: 11S-45S.

Poynard T, Marcellin P, Lee S S (1998) Randomised trial of interferon alpha2b plus ribavirin for 48 weeks or for 24 weeks versus interferon alpha2b plus placebo for 48 weeks for treatment of chronic infection with hepatitis C virus. International Hepatitis Interventional Therapy Group (IHIT). *Lancet* 352 (9138):1426-32.

Ruiz O N, Hussein H, Terry N, Daniell H. (2003) Phytoremediation of organomercurial compounds via chloroplast genetic engineering. *Plant Physiol.* 132: 1-9.

Sambrook, Frish, Maniatis. (1989) Molecular cloning. A laboratory manual. 2nd edition. Cold spring harbor laboratory press.

Sanford J C (1991) An improved helium-driven biolistic device. *Technique* 3: 3-16.

Selby M J, Choo Q L, Berger K, Kuo G, Glazer E, Eckart M, Lee C, Chien D, Kuo C, Houghton M (1993) Expression, identification and subcellular localization of the proteins encoded by the hepatitis C viral genome. *J Gen Virol* 74: 1103-13.

Sidorov V A, Kasten D, Pang S Z, Hajdukiewicz P T, Staub J M. (1999) Technical advance: stable chloroplast transformation in potato: use of green fluorescent protein as a plastid marker. *Plant J.* 19: 209-216.

Siler C A, McGettigan J P, Dietzcshold B, Herrine S K, Dubuisson J, Pomerantz R J, Schnell M J (2002). Live and killed rhabdovirus-based vectors as potential hepatitis C vaccines. *Virology* 292: 24-34.

Singleton M L (2003). Expression of CaF1 and LcrV as a fusion protein for a vaccine against *Yersinia pestis* via chloroplast genetic engineering. MS thesis, University of Central Florida, USA.
Sharara A I, Hunt C M, Hamilton J D. (1996) *Ann. Intern. Med.* 125: 658-668.
Staub J M, Garcia B, Graves J. (2000) High-yield production of a human therapeutic protein in tobacco chloroplasts. *Nat. Biotechnol.* 18: 333-338.
Streatfield S J, Jilka J M, Hood E E, Turner D D, Bailey M R (2001) Plant-based vaccines: unique advantages. *Vaccine.* 19: 2742-2748.
Svab Z, Maliga P. (1993) High frequency plastid transformation in tobacco by selection for a chimeric aadA gene. *Proceedings of the National Academy of Sciences*, USA 90: 913-917.
Tacket C O, Mason H S, Losonsky G, Clements J D, Levine M M. (1998) Immunogenicity in humans of a recombinant bacterial-antigen delivered in transgenic potato. *Nat. Med.* 4 607-609.
Tacket C O, Mason H S, Losonsky G, Estes M K, Levine M M. (2000) Human immune responses to a novel norwalk virus vaccine delivered in transgenic potatoes. *J. Infect. Dis* 182: 302-305.
Tacket C O, Sztein M B, Losonsky G A, Wasserman S S, Estes M K (2003). Humoral, mucosal, and cellular immune responses to oral Norwalk virus-like particles in volunteers. *Clinimmunology* 108 (3): 241-7.
Takamizawa A, Mori C, Fuke I, Manabe S, Murakami S, Fujita J, Onishi E, Anodoh T, Yoshida I, Oakayama H. (1991) Structure and organization of the hepatitis C virus genome isolates from human carriers. *J. Virol.* 65: 1105-1113.
Tanaka T, Kato N, Cho M J, Shimotohno K. (1995) A novel sequence found at the 3' terminus of the hepatitis C virus genome. *Biochem Biophys Res Commun* 215: 744-749.
Thimme R, Oldach D, Chang K M. (2001) Determinants of viral clearance and persistence during acute hepatitis C virus infection. *J Exp Med* 194(10):1395-406.
Tomei L, Fulla C, Santolini E, De Francesco R, La Monica N (1993). NS3 is a serine proteinase required for processing of hepatitis C virus polyprotein. *J Virol* 67: 4017-4026.
Tuboly T, Yu W, Bailey A, Degrandis S, Du S. (2000) Immunogenicity of porcupine transmissible gastroenteritis virus spike protein expressed in plants. *Vaccine* 18: 2023-2028.
Vallari D S, Jett B W, Alter H J, Mimms L T, Holzman R, Shih J W (1992) Serological markers of posttransfusion hepatitis C viral infection. *J Clin Microbiol* 30: 552-556.
Vertuani S, Bazzaro M, Gualandi G, Micheletti F, Marastoni M, Fortini C, Canella A, Marino M, Tomatis R, Traniello S, Gavioli R. (2002) Effect of interferon-alpha therapy on epitope-specific cytotoxic T lymphocyte responses in hepatitis C virus-infected individuals. *Eur J. Immunol.* 32(1):144-54.
Viitanen P V, Devine A L. Kahn S, Deuel D L, Van Dyk D E, Daniell H. (2004) Metabolic Engineering via the Chloroplast Genome to Produce 4-Hydroxybenzoic Acid a Principle Monomer of Liquid Crystal Polymers. *Plant Physiol* 136(4):4048-60.
Walmsley A., & Arntzen, C. (2000) Plants for Delivery of Edible Vaccines. *Current Opinion in Biotechnology,* 11: 126-129.
Wang C, Siddiqui A. (1995) Structure and function of the hepatitis C virus internal ribosome entry site. *Curr Topics Microbiol Immunol* 203: 99-115.
Watson J, Koya V, Leppla S H, Daniell H. (2004) Expression of *Bacillus anthracis* protective antigen in transgenic chloroplasts of tobacco, a non-food/feed crop. *Vaccine* 22 (31-32): 4374-4384.
Wedemeyer H, Gagneten S, Davis A. (2001) Oral immunization with HCV-NS3 transformed *Salmonella*: induction of HCV-specific CTL in a transgenic mouse model. Gastroenterology 121(5):1158-66.
Wong J B. (2000) Estimating future hepatitis C morbidity, mortality and costs in the United States. *Am J Public Health* 90 (10): 1562-9.
World Health Organisation. Hepatitis C. (1997) *Wkly Epidemiol Rec* 72:65.
Wuest T, Both G, Prince A, Hofmann C, Loser P (2004) Recombinant ovine atadenovirus induces a strong and sustained T cell response against the hepatitis C virus NS3 antigen in mice. *Vaccine* 22: 2717-2721.
Ye G N, Daniell H, & Sanford J C. (1990) Optimization of delivery of foreign DNA into higher-plant chloroplasts. *Plant Mol. Biol.,* 15 (6): 809-819.
Zoubenko O V, Allison L A, Svab Z, Maliga P (1994) Efficient targeting of foreign genes into the tobacco plastid genome. *Nucleic Acids Res* 22: 3819-3824.

Example 4: Transgenic Chloroplast Expression of Soluble Modified Green Flourescent Protein and Interferon Alpha-5 Fusion Introduction The World Health Organization estimates that approximately 170 million people worldwide are infected with hepatitis C virus (HCV), with 3-4 million new cases each year, and that more than one third of the world's population is infected with hepatitis B virus (HBV). A large majority of HCV-infected patients have severe liver cirrhosis and currently there is no vaccine available for this disease. In addition, the rising cost of treatment for severe illnesses calls for the more economical production of therapeutic proteins. Alpha interferons have therapeutic uses, such as the inhibition of viral replication and cell proliferation, enhancement of the immune response, and most recently, the treatment of patients suffering from HCV. The Food and Drug Administration approved a specific subtype of interferon-α (IFNα2b) for the treatment of HCV. In an effort to produce another subtype of interferon-α (IFNα5, kindly provided by Dr. Jesus Prieto, Universidad De Navarra, Pamplona, Spain) in large quantities and free of contaminants for possible treatment options and oral delivery of HCV, a fusion of smGFP-IFNα5 has been expressed in transgenic chloroplasts of *Nicotiana tabacum* var. dark fire, by inserting the smGFP (745 bp) and IFNα5 (515 bp) genes into the chloroplast genome by homologous recombination. The pLD-BB1 vector contains smGFP with a C-terminal fusion to IFNα5 containing a furin cleavage site between the fusion proteins. The genes were cloned into a universal chloroplast vector, pLD-ctv containing the 16S rRNA promoter, aadA gene coding for the spectinomycin selectable marker, psbA 5' & 3' untranslated regions to enhance translation in the light and trnI & trnA homologous flanking sequences for site specific integration into the chloroplast genome. Chloroplast integration of the smGFP-IFNα5 genes was confirmed by PCR and Southern blot analysis. The smGFP-IFNα5 fusion protein expression was confirmed by immunoblot analysis and smGFP expression under UV light. Expression was quantified by ELISA. The smGFP-IFNα5 fusion protein is analyzed via in vivo studies. The expression of smGFP-IFNα5 transgenic chloroplasts will facilitate the development of a new and alternate treatment for HCV and possible oral delivery options with a lower cost of production.

Materials and Methods

Construction of the pLD-BB1 Vector

The IFNα5 gene was kindly provided by Dr. Jesus Prieto, Universidad De Navarra, Pamplona, Spain, within *Escherichia coli* expression vector designated pET-28b (Novagen). The smGFP gene was obtained from Ohio State University, within the plasmid vector psmGFP. The vector was transformed into Ultra competent XL1 Blue MRF' Tetracycline (tet) *E. coli* cells (Stratagene) that were endonuclease negative. The recombinant DNA techniques were carried out as detailed in Sambrook et al., 1989.

Preparation of Competent Cells

Ultra competent XL1 Blue MRF' (tet) *E. coli* cells were made competent by inoculating 50 ml of Luria Bertani (LB) broth (10 gr Tryptone, 5 gr yeast extract, 5 gr NaCl, pH 7.0, dH$_2$O to a liter) with 500 µl of cells and incubating at 37° C. overnight while shaking at 225 rpm using the Orbit Environ Shaker (Lab-Line). Once the Optical Density (OD) reading at 600 nm was between 0.4 and 0.6, the cells were transferred to several 14 ml falcon tubes, chilled on ice for 15 minutes. The cells were centrifuged at 8500 rpm for 6 minutes at 4° C. The subsequent *E. coli* pellet was resuspended in 25 ml of cold 50 mM CaCl$_2$, mixed by vortexing and then incubated on ice for 15 minutes. The cells were recentrifuged at 8500 rpm for 6 minutes at 4° C. The cells were resuspended into 1 ml of 50 mM CaCl$_2$ and 1 ml of 30% glycerol, then gently inverted 3 times. Competent cells were gently aliquoted into micro centrifuge tubes (200 µl/tube) being sure to keep everything cold at all times. Competent cells were labeled and stored at −80° C.

Midi-Prep of psmGFP

Inoculated *E. coli* containing psmGFP into 50 ml of liquid LB broth in a 250 ml flask. 25 µl of ampicillin (amp) stock (100 mg/ml) was added to the 50 ml LB above so that only the amp-resistant plasmids would grow. The flask was covered with aluminum foil and put in shaker at 37° C. for 16 hours to grow-up cells. 40 ml of the overnight culture was transferred to a clean 50 ml screw-cap centrifuge tube and spun down. The cells were centrifuged for 5 minutes at 5000 rpm. The Bio-Rad Midi-prep kit cat. #732-6120 was used for DNA isolation. The supernatant containing LB and cellular waste was discarded. 5 ml of cell resuspension solution was added to the pellet and vortexed until the cells were resuspended. 5 ml of cell lysis solution was added and mixed by inverting the tube 8 times. The solution turned from milky, light beige to clear, light beige. 5 ml of neutralization solution was added to the clear, beige solution and then the solution became a white precipitant. The solution was centrifuged for 10 minutes at 8000 rpm. The supernatant was poured into a new 50 ml screw-cap centrifuge tube. The quantum prep mix was resuspended by vigorously shaking. 1 ml of the quantum prep mix was added to the clear supernatant. The solution was swirled for 30 seconds to mix and then centrifuged for 2 minutes at 8000 rpm to pellet the plasmids. The supernatant containing contaminants was dissolved by the quantum prep mix and the pelleted plasmids remained 10 ml of wash buffer was added to pelleted plasmids and the matrix was resuspended in the wash buffer by shaking. The solution was centrifuged for 2 minutes at 8000 rpm and discarded the supernatant. The pellet was then resuspended in 600 µl of wash buffer and transferred to columns in collection tube provided by the kit. Columns were centrifuged for 30 seconds at 12,000 rpm at 4° C. and flow-through was discarded. Column was centrifuged for an additional 2 minutes at 12,000 rpm and then columns were transferred to sterile microcentrifuge tubes. 300 µl of Tris-EDTA (TE: 1M Tris, pH 8.0, 0.5M EDTA) was added to the column and centrifuged at 8000 rpm for 2 minutes at 4° C. The column was transferred to a fresh microcentrifuge tube and the same above step was repeated. The DNA was stored at −20° C.

Mini-Prep of pET28-IFNα5 by Rapid Plasmid Isolation

After cells had been growing for 12-16 hours at 37° C. in LB broth containing antibiotic, 1.5 ml of the cell suspension was put into an eppendorf and centrifuged at 13,000 rpm for 5 minutes. The supernatant was discarded. An additional 1.0 ml of the same cell suspension was added and the centrifugation was repeated and the supernatant was discarded. The pellet was resuspended in 100 µl of Solution I (GTE: 50 mM D-(+)-Glucose, 10 mM EDTA, 25 mM Tris, pH 8) and vortexed. 1 µl of 100 mg/ml Rnase was added to each tube and pulse vortexed. 200 µl of solution II (0.2NaOH, 10% SDS) was added and mixed by gently inverting 6 times. The mixture was left to sit for 3 minutes and then centrifuged at 13,000 rpm for 10 minutes at 4° C. The solution was pipetted into a fresh, labeled eppendorf. Then, added 1000 µl of cold 95% ethanol to each supernatant and vortexed briefly. The supernatant was centrifuged at 13,000 rpm at 4° C. for 17 minutes. The supernatant was removed and discarded, being careful not to dislodge the beige plasmid DNA in bottom of eppendorf. 500 µl of 70% cold ethanol was added and centrifuged for 5 minutes. The ethanol was removed and discarded and subsequently dried in the speed. The plasmid concentration and quality of DNA was measured by spectrophotometer. The DNA was stored at −20° C.

IFNα5 Amplification by Polymerase Chain Reaction (PCR)

Two primers were designed to amplify IFNα5 and include a furin cleavage site at the 5' end of the IFNα5 gene with the forward primer containing an EcoRV site and the reverse primer containing a Not I site for further subcloning. Primers were ordered from LIFE TECHNOLOGIES. When the primers arrived, they were reconstituted in TE to yield a 100 µM stock that was stored at −20° C. The PCR reaction contained 1.0 µl of pET28-IFNα5, 5 µl of 10×PCR buffer, 5.0 µl of 10 mM dNTP's, 0.5 µl of forward primer (Furin-IFNα5-F-EcoRV), 0.5 µl of reverse primer (Furin-IFNα5-R-NotI), 0.5 µl of Pfu polymerase and 36.5.0 µl of Rnase/Dnase Free H$_2$O to a total volume of 50 The PCR was performed as suggested by the manufacturer using the Gene Amp PCR system 2400 (Perkin-Elmer). Samples were carried through 30 cycles using the following temperatures and times: 94° C. for 1 minute, 55° C. for 1 minute, 72° C. for 1 minute. Cycles were preceded by denaturation at 94° C. for 3 minutes and followed by a 5 minute extension time at 72° C. The final PCR products were separated on a 0.8% agarose gel at 60 volts until dye reached bottom (about 50 minutes).

Extraction of the EcoRV/Furin/IFN α5/NotI PCR Product from the Gel

The QIAGEN QIA quick gel extraction kit was used to extract the PCR products from the agarose gel. The gel was placed on a flat UV light source and the appropriate DNA fragment (515 bp) was cut out using a sterile razor blade. The excised fragment was placed into a previously weighed microcentrifuge tube and reweighed to determine by difference weight of the cut out fragment. To the eppendorf containing the fragment, 3 volumes of Buffer QC to 1 volume of gel slice was added. The eppendorf was incubated at 50° C. for 10 minutes until the agarose melted and solublized. One volume of isopropanol was then added to the eppendorf. The mixture was added to a QIA quick spin column placed in a collection tube and then centrifuged for 1 minute at 12,000 rpm at room temperature. The flow-through was discarded and the column was centrifuged for an additional minute as above. The flow-through was discarded again and 750 µl of buffer PE was added to the column and centrifuged as above. The column was placed in a sterile microcentrifuge tube and 50 µl of elution buffer (EB) was added to the column and centrifuged for 1 minute at 12,000 rpm to elute the DNA (PCR product).

Ligation of the EcoRV/Furin/IFNα5/NotI PCR Product into pBKS vector

PCR products were eluted from the gel. The PCR products and the pBKS vector were restriction digested with EcoRV and NotI For digestion of pBKS, 2 µl of midi-prepped pBKS, 0.2 µl of 100× bovine serum albumin (BSA), 2 µl of 10× New England Bio-Labs (NEB) #3 buffer, 0.5 µl of EcoRV (NEB), 0.5 µl of Not I (NEB) and 14.8 µl of Rnase/Dnase Free H$_2$O to a total volume of 20 µl. This was done in duplicate to ensure enough DNA was available for the ligation reaction. The reaction was incubated at 37° C. overnight (O/N). For the PCR product digestion, 4 µl of purified PCR product (IFNα5), 0.2 µl of 100× bovine serum albumin (BSA), 2 µl of 10× New England Bio-Labs (NEB) #3 buffer, 0.5 µl of EcoRV (NEB), 0.5 µl of Not I (NEB) and 10.8 µl of Rnase/Dnase Free H$_2$O to a total volume of 20 This was done in duplicate to ensure enough DNA was available for the ligation reaction. The reaction was incubated at 37° C. overnight (O/N). Pulse vortexed the pBKS digestion, then added 4 µl of 6× bromophenol blue (bpb: 0.25% bromophenol blue, 40% w/v sucrose in d/a H$_2$O to a total volume of 10 ml) to the digestion. Loaded all 24 µl into well of 0.8% electrophoresis-grade agarose gel diluted into 1×TAE running buffer and then ran at 60 volts (V) for 60 minutes. Pulse vortexed the PCR product digestion, then added 4 µl of 6×bpb. Loaded all 24 µl into the well of a 0.8% agarose gel and electrophoresed at 60V for 60 minutes. The linearized pBKS DNA fragment and the PCR products were gel eluted. The duplicates were combined and the volume was reduced by vacuum to 25 µl. Ligated EcoRV/Furin/IFNα5/NotI into pBKS to complete pBKS-IFNα5 vector. For the ligation reaction, 4 µl of the pBKS backbone, 10 µl PCR product, 4 µl 5× Ligase Buffer (Invitrogen), 0.2 µl T4 Ligase (Invitrogen), 2 µl of Rnase/Dnase Free H$_2$O to a total reaction volume of 20 µl. The ligation mixture was incubated at 4° C., O/N. Transformed ligation mix containing pBKS-IFNα5 into competent XL1 Blue MRF' (tet) *E. coli* cells.

Transformation of pBKS-IFNα5 into Competent XL1 Blue MRF' (tet) *E. coli* Cells

Took out 100 µl of competent cells from −80° C. freezer and thawed in an ice bucket. 10 µl of DNA from ligation reaction was added to the competent cells and mixed gently. The mixture was allowed to stand on ice for a total of 30 minutes, gently rocking tube back and forth every 10 minutes. The cells were heat shocked at 42° C. for 45-50 seconds. The cells were left on ice for 2 minutes. 900 µl LB broth was added to each and incubated at 37° C. on 225 rpm shaker for 45 minutes. The cells were pelleted by centrifugation at 13,000 rpm for 45 seconds and 800 µl of the supernatant was discarded. The cells were resuspended in the remaining 100 µl of LB broth and plated out transformed and untransformed (control) onto X-gal/IPTG LB/amp agar plates (1 liter LB broth, 15 gr agar, 100 µg/ml ampicillin, pH 7) under the hood. Plates were covered and incubated 0/N at 37° C.

Selecting for Transformants

The pBKS cloning vector has a ColE1 origin of replication, ampicillin resistance, a DNA segment containing the lac promoter and the β-galactosidase α-fragment (lacZ). Within this coding region is a multiple cloning site that does not disrupt the reading frame, but must be used in a host cell that codes for the carboxy-terminal portion of the β-galactosidase gene so that an enzymatically active β-galactosidase protein can be formed. The cells that grow due to this α-complementation can be visually selected through a chromogenic test. Insertion of a fragment of foreign DNA into the multicloning site of pBKS almost invariably results in production of an amino-terminal fragment that is not capable of α-complementation. Selective plates were made with LB agar and 100 µg/ml of ampicillin About 1 hour before transformation was complete, 40 µg/ml of 5-bromo-4-chloro-3-indolyl-β-D-galactoside (X-gal) was spread onto the top of the plates while under the hood. X-gal is a lactose analog that turns dark blue when it is hydrolyzed by β-galactosidase. After the X-gal dried (about 15 minutes), 40 µl of 100 mM of isopropyl-β-D-thiogalactoside (IPTG) was spread onto the plates. IPTG, another lactose analog, is a strong inducer of lacZ transcription but is not digested/hydrolyzed by β-galactosidase. The plates were warmed 37° C. for 30 minutes and then the plates were streaked with 100 µl of the transformed bacterial cells were spread over the top of the agar. Allowed the plates to dry for 5 minutes, then incubated the plates in an inverted position at 37° C. overnight. Stored the plates after incubation at 4° C. for 3 hours to allow the blue color from the chromogenic process to develop fully. Colonies without an interrupting insert were blue because they had an active β-galactosidase. Colonies which had incorporated the insert were all white. These were picked to culture at 37° C. overnight and miniprepped as described in the previous section. The DNA was stored at −20° C. The vector was confirmed by restriction digestion analysis.

Amplification of smGFP by Polymerase Chain Reaction (PCR)

Two primers were designed to amplify smGFP and include specific restriction sites with the forward primer containing a HindIII and SnaBI site and the reverse primer containing an EcoRV site for further subcloning. Primers were ordered from LIFE TECHNOLOGIES. When the primers arrived, they were reconstituted in TE to yield a 100 µM stock that was stored at −20° C. The PCR reaction contained 3.0 µl of psmGFP, 5 µl of 10×PCR buffer, 1.0 µl of MgSO$_4$, 5.0 µl of 10 mM dNTP's, 1.0 µl of forward primer (smGFP-F-HindIII-SnaBI), 1.0 µl of reverse primer (smGFP-R-EcoRV), 0.5 µl of Pfx polymerase and 33.5.0 µl of Rnase/Dnase Free H$_2$O to a total volume of 50 µl. The PCR was performed as suggested by the manufacturer using the Gene Amp PCR system 2400 (Perkin-Elmer). Samples were carried through 30 cycles using the following temperatures and times: 94° C. for 15 seconds, 50° C. for 30 seconds, 68° C. for 1 minute. Cycles were preceded by denaturation at 94° C. for 5 minutes and followed by a 7 minute extension time at 68° C. After PCR, the vials were placed on ice and 1 unit of Taq polymerase was added to each tube and mixed. The vials were incubated at 72° C. for 10 minutes. The final PCR products were separated on a 0.8% agarose gel at 60 volts for about 50 minutes. The PCR product was then PCR purified using the QIAquick PCR purification kit (Qiagen).

Ligation of the smGFP PCR Product into pCR®2.1-TOPO®

*Thermus aquaticus* (Taq) polymerase has non-template dependent activity which preferentially adds a single deoxyadenosine (A) to the 3'-ends of a double stranded DNA molecule; therefore, most of the molecules PCR amplified possess single 3' A overhang. The linearized vector supplied with the kit has a single, overhanging 3' deoxythymidine (T) which allows the PCR product to ligate efficiently with the vector. TA cloning utilizes the complementarity between the PCR product 3'-A overhangs and vector 3'-T overhangs and is one of the simplest and most efficient methods for the cloning of PCR products (Zhou, 2000). The PCR products were ligated into pCR®2.1-TOPO® cloning vector (Invitrogen, 2000) that contained multiple restriction sites facilitating further subcloning. 2 µl of psmGFP PCR product was combined with 1 µl of dilute salt solution, 2 µl of Rnase/Dnase Free dH$_2$O and 1 µl of the pCR®2.1-TOPO® cloning vector. The solution was gently mixed and incubated 5 minutes at room temperature. Chemically competent *E. coli* cells (TOP10) were taken from −80° C. freezer and thawed on ice. The transformation was started immediately after cells thawed. The cells were removed and gently pipetted into a cold eppendorf on ice. 2 µl of the ligation mixture was added to an eppendorf containing the chemically competent cells and mixed gently without pipetting up and down. Then, the mixture was incubated on ice for 30 minutes. Heat shocked the cells for 30 seconds at 42° C. without any shaking. The mixture was immediately transferred to ice. Then 250 µl of warm SOC broth was added and allowed to incubate in the shaker horizontally (200 rpm) for 1 hour at 37° C.

Selecting for Transformants

The pCR®2.1-TOPO® cloning vector has a ColE1 origin of replication, kanamycin resistance, ampicillin resistance and a DNA segment containing the first 146 amino acids of the β-galactosidase gene (lacZ). Selective plates were made with LB agar and 50 µg/ml of kanamycin. About 1 hour before transformation was complete, 40 µg/ml of 5-bromo-4-chloro-3-indolyl-β-D-galactoside (X-gal) was spread onto the top of the plates while under the hood. X-gal is a lactose analog that turns dark blue when it is hydrolyzed by β-galactosidase. After the X-gal dried (about 15 minutes), 40 µl of 100 mM of isopropyl-β-D-thiogalactoside (IPTG) was spread onto the plates. IPTG, another lactose analog, is a strong inducer of lacZ transcription but is not digested/hydrolyzed by β-galactosidase. The plates were warmed 37° C. for 30 minutes and then the plates were streaked with 150 µl of the transformed bacterial cells were spread over the top of the agar. Allowed the plates to dry for 5 minutes, then incubated the plates in an inverted position at 37° C. overnight. Stored the plates after incubation at 4° C. for 3 hours to allow the blue color from the chromogenic process to develop fully. Colonies without an interrupting insert were blue because they had an active β-galactosidase. Colonies which contained an insert were all white so these were picked to culture. The culture was grown overnight at 37 C and miniprepped as described in the previous section. The DNA was confirmed by restriction digestion analysis and stored at −20° C.

Building the pCR®2.1-5'UTR Vector

Two primers were designed to amplify 5'UTR and include specific restriction sites with the forward primer containing an EcoRI site and the reverse primer containing an EcoRV site for further subcloning. Primers were ordered from LIFE TECHNOLOGIES. When the primers arrived, they were reconstituted in TE to yield a 100 µM stock that was stored at −20° C. The PCR reaction contained 1.0 µl of template DNA, 5 µl of 10×PCR buffer, 1.0 µl of MgSO$_4$, 5.0 µl of 10 mM dNTP's, 1.0 µl of forward primer (5'UTR-F-EcoRI), 1.0 µl of reverse primer (5'UTR-R-EcoRV), 0.5 µl of Pfx polymerase and 33.5.0 µl of Rnase/Dnase Free H$_2$O to a total volume of 50 µl. The PCR was performed as suggested by the manufacturer using the Gene Amp PCR system 2400 (Perkin-Elmer). Samples were carried through 30 cycles using the following temperatures and times: 94° C. for 15 seconds, 50° C. for 30 seconds, 68° C. for 30 seconds. Cycles were preceded by denaturation at 94° C. for 5 minutes and followed by a 7 minute extension time at 68° C. After PCR, the vials were placed on ice and 1 unit of Taq polymerase was added to each tube and mixed. The vials were incubated at 72° C. for 10 minutes. The final PCR products were separated on a 0.8% agarose gel at 60 volts for about 50 minutes. The PCR product was then PCR purified using the QIAquick PCR purification kit (Qiagen). The purified PCR product was cloned into pCR®2.1-TOPO® cloning vector (Invitrogen, 2000) as described in previous section. The transformants were selected and mini-prepped as described in previous section. The vector was confirmed by restriction digestion analysis.

Building the pLD-5'UTR Vector

A scraping of an *E. coli* glycerol stock containing the pLD expression vector which was developed by Lee and Daniell was grown up in 50 ml of liquid LB broth in a 250 ml flask. 25 µl of ampicillin (amp) stock (100 mg/ml) was added to the 50 ml LB broth. The flask was covered and put in shaker at 37° C. for 16 hours to grow-up cells. A midi-prep was performed as described in previous section. The vector was confirmed by restriction digestion analysis. For further subcloning, a restriction digestion was set up: 5.0 µl of pCR®2.1-5'UTR vector, 0.2 µl of 100× bovine serum albumin (BSA), 2.0 µl of 10× New England Bio-Labs (NEB) #3 buffer, 0.5 µl of EcoRV (NEB), 0.5 µl of EcoRI (NEB) and 11.8 µl of Rnase/Dnase Free H$_2$O to a total volume of 20 This was done in duplicate to ensure enough DNA was available for the ligation reaction. The reaction was incubated at 37° C. overnight (O/N). For the pLD restriction digestion, 1.0 µl of pLD vector, 0.2 µl of 100× bovine serum albumin (BSA), 2 µl of 10× New England Bio-Labs (NEB) #3 buffer, 0.5 µl of EcoRV (NEB), 0.5 µl of EcoRI (NEB) and 14.8 µl of Rnase/Dnase Free H$_2$O to a total volume of 20 µl. This was done in duplicate to ensure enough DNA was available for the ligation reaction. The reaction was incubated at 37° C. for 1 hour. Pulse vortexed the digestions, then added 4 µl of 6× bromophenol blue (bpb: 0.25% bromophenol blue, 40% w/v sucrose in d/a H$_2$O to a total volume of 10 ml) to each digestion. Loaded all 24 µl of each digestion into separate wells of 0.8% electrophoresis-grade agarose gel diluted into 1×TAE running buffer and then ran at 80 volts (V) for 60 minutes. The linearized pLD vector and the 5'-UTR DNA fragments were gel eluted in 50 µl of Rnase/Dnase Free H$_2$O and vacuum evaporated to a volume of 15 µl. Ligated the 5'UTR DNA fragment into pLD vector to complete pLD-5'UTR vector. For the ligation reaction, 15 µl of the pLD backbone and 5'UTR DNA fragment combined, 4 µl 5× Ligase Buffer (Invitrogen), and 1.0 µl T4 Ligase (Invitrogen) to a total reaction volume of 20 µl. The ligation mixture was incubated at 14° C., O/N. Transformed ligation mix containing pLD-5'UTR into competent XL1 Blue MRF' (tet) E. coli cells using SOC broth instead of LB broth as described in previous section. The transformation reaction was plated out onto LB/amp agar plates (1 liter LB broth, 15 gr agar, 100 µg/ml ampicillin, pH 7) under the hood. Plates were covered and incubated O/N at 37° C. 10 bacterial colonies were selected and cultured O/N at 37° C. and mini-prepped as described in the previous section. The DNA was confirmed by restriction digestion analysis and stored at −20° C.

Building the pBKS-smGFP-IFNα5 Vector

The pBKS-IFNα5 vector and the pCR®2.1-smGFP vector were thawed on ice. For further subcloning, a restriction digestion was set up: 2.0 µl of pCR®2.1-smGFP vector, 1.0 µl of 1× bovine serum albumin (BSA), 2.0 µl of 10× New England Bio-Labs (NEB) #2 buffer, 1.0 µl of EcoRV (NEB), 1.0 µl of HindIII (NEB) and 12.0 µl of Rnase/Dnase Free H$_2$O to a total volume of 20 µl. This was done in duplicate to ensure enough DNA was available for the ligation reaction. The reaction was incubated at 37° C. for 2 hours. For the pBKS-IFNα5 vector restriction digestion, 2.0 µl of pBKS-IFNα5 vector, 1.0 µl of 1× bovine serum albumin (BSA), 2 µl of 10× New England Bio-Labs (NEB) #2 buffer, 1.0 µl of EcoRV (NEB), 1.0 µl of HindIII (NEB) and 12.0 µl of Rnase/Dnase Free H$_2$O to a total volume of 20 µl. This was done in duplicate to ensure enough DNA was available for the ligation reaction. The reaction was incubated at 37° C. for 2 hours. Pulse vortexed the digestions, then added 4 µl of 6× bromophenol blue (bpb: 0.25% bromophenol blue, 40% w/v sucrose in d/a H$_2$O to a total volume of 10 ml) to each digestion. Loaded all 24 µl of each digestion into separate wells of 0.8% electrophoresis-grade agarose gel diluted into 1×TAE running buffer and then ran at 80 volts (V) for 60 minutes. The linearized vector and the smGFP DNA fragments were gel eluted in 50 µl of Rnase/Dnase Free H$_2$O and vacuum evaporated to a volume of 15 µl. Ligated the smGFP DNA fragment into pBKS-IFNα5 vector to complete pBKS-smGFP-IFNα5 vector. For the ligation reaction, 15 µl of the pBKS-IFNα5 backbone and smGFP DNA fragment combined, 4 µl 5× Ligase Buffer (Invitrogen), and 1.0 µl T4 Ligase (Invitrogen) to a total reaction volume of 20 µl. The ligation mixture was incubated at 14° C., O/N. Transformed ligation mix containing pBKS-smGFP-IFNα5 vector into competent XL1 Blue MRF' (tet) E. coli cells using SOC broth instead of LB broth as described in previous section. The transformation reaction was plated out onto LB/amp agar plates (1 liter LB broth, 15 gr agar, 100 µg/ml ampicillin, pH 7) under the hood. Plates were covered and incubated O/N at 37° C. 10 bacterial colonies were selected and cultured O/N at 37° C. Then, a mini-prep was performed as described in the previous section. The DNA was confirmed by restriction digestion analysis and stored at −20° C.

Building the pLD-5'UTR-smGFP-IFNα5 Vector

The pBKS-smGFP-IFNα5 vector and the pLD-5'UTR vector were thawed on ice. For further subcloning, a restriction digestion was set up: 5.0 µl of pLD-5'UTR vector, 2.0 µl of 10× New England Bio-Labs (NEB) #3 buffer, 2.0 µl of 1× bovine serum albumin (BSA) 1.0 µl of NotI (NEB), 1.0 µl of EcoRV (NEB) and 9.0 µl of Rnase/Dnase Free H$_2$O to a total volume of 20 µl. This was done in duplicate to ensure enough DNA was available for the ligation reaction. The reaction was incubated at 37° C. for 1 hour. For the pBKS-smGFP-IFNα5 restriction digestion, 5.0 µl of pBKS-smGFP-IFNα5 vector, 2.0 µl of 1× bovine serum albumin (BSA), 2 µl of 10× New England Bio-Labs (NEB) #4 buffer, 1.0 µl of NotI (NEB), and 10.0 µl of Rnase/Dnase Free H$_2$O to a total volume of 20 µl. This was done in duplicate to ensure enough DNA was available for the ligation reaction. The reaction was incubated at 37° C. for 1 hour. Then, 1.0 µl of SnaBI (NEB) was added and the reaction was incubated an additional 1 hour at 37° C. Pulse vortexed the digestions, then added 4 µl of 6× bromophenol blue (bpb: 0.25% bromophenol blue, 40% w/v sucrose in d/a H$_2$O to a total volume of 10 ml) to each digestion. Loaded all 24 µl of each digestion into separate wells of 0.8% electrophoresis-grade agarose gel diluted into 1×TAE running buffer and then ran at 80 volts (V) for 60 minutes. The linearized pLD-5'UTR vector and the smGFP-IFNα5 DNA fragments were gel eluted in 50 µl of Rnase/Dnase Free H$_2$O and vacuum evaporated to a volume of 15 µl. Ligated the smGFP-IFNα5 DNA fragment into pLD-5'UTR vector to complete pLD-BB1 vector (pLD-5'UTR-smGFP-IFNα5). For the ligation reaction, 15 µl of the pLD-5'UTR backbone and smGFP-IFNα5 DNA fragment combined, 4 µl 5× Ligase Buffer (Invitrogen), and 1.0 µl T4 Ligase (Invitrogen) to a total reaction volume of 20 µl. The ligation mixture was incubated at 14° C. for four hours. Transformed ligation mix containing pLD-BB1 into competent XL1 Blue MRF' (tet) E. coli cells using SOC broth instead of LB broth as described in previous section. The transformation reaction was plated out onto LB/amp agar plates (1 liter LB broth, 15 gr agar, 100 µg/ml ampicillin, pH 7) under the hood. Plates were covered and incubated O/N at 37° C. 15 bacterial colonies were selected and cultured O/N at 37° C. and mini-prepped as described in the previous section. The remaining 500 µl of each bacterial O/N cultures were placed on ice. The DNA was confirmed by restriction digestion analysis and stored at −20° C. Four positive clones were selected and the corresponding bacterial culture on ice was use to inoculate 50 ml of liquid LB broth/Amp/Spec (100 µg/ml of Ampicillin; 100 mg/ml Spectinomycin) in a 250 ml flask and covered. The cultures were placed in a shaker and incubated at 37° C. for 16 hours. The cultures were midi-prepped as described previously. The DNA was confirmed by restriction digestion analysis and stored at −20° C. Glycerol stocks were also made and stored at −80° C.

E. coli Expression of smGFP-IFNα5 and Immunoblot Analysis

Extraction of Protein from Transformed E. coli Cells

E. coli containing pLD-smGFP-IFNα5 was scraped off the top of the glycerol stock under the hood and inoculated 5 ml of Terrific Broth (TB) containing 25 µl of 100 mg/ml spectinomycin. Untransformed E. coli cells were added to 5 ml of Terrific Broth (TB) as a negative control. The inoculated broths were incubated in a shaker at 37° C. for 16 hours. 800 µl of cultured cells were placed in an eppendorf tube and centrifuged for 2 minutes. The supernatant was discarded. The pelleted cells were washed with 1 ml of 1× Phosphate-Buffered Saline (PBS: 140 mM NaCl, 2.7 Mm KCl, 4 mM $Na_2HPO_4$, 1.8 mM KH2PO4, pH 7.2) resuspend the pellet. Then, the suspension was centrifuged for 1 minute at 12,000 rpm and the supernatant was discarded. 50 µl of 1×PBS was added and mixed well. 50 µl of 2× loading buffer, also called Sample Buffer or SDS Reducing Buffer was added to the samples and the sample extracts were boiled for exactly 4 minutes. The samples were then immediately loaded onto polyacrylamide gels (Laemmli, 1970).

Solutions, Standards, and SDS-PAGE Gel

The solutions used in the immunoblot were as follows: (1) 1.5 M Tris-HCL, pH 8.8 resolving gel buffer (27.23 g Tris base in 80 ml water, adjusted the pH to 8.8 using 6N HCL and raised the volume to 150 ml. The solution was autoclaved and stored at 4° C.) (2) 0.5M Tris-HCl, pH 6.8 stacking gel buffer (6.0 g Tris base in 60 ml water, pH to 6.8 using 6N HCl and raised volume to 100 ml. Autoclaved and stored at 4° C.) (3) 10% SDS (10 g Sodium Dodecyl Sulfate and bring up volume to 100 ml with water and stored at room temperature) (Laemmli, 1970). (4) Acrylamide/Bis solution (from Bio-Rad cat#161-0158). (5) Sample loading buffer was an SDS reducing buffer (1.25 ml of 0.5 M Tris-HCl, pH6.8, 2.5 ml glycerol, 2.0 ml of 10% SDS and 0.2 ml of 0.5% Bromophenol blue in 3.55 ml $dH_2O$.) 25 µl of β-Mercapto ethanol was added to 475 µl of the sample buffer before use (Sambrook et al., 1989). (6) 10× Electrode running buffer (30.3 g Tris Base, 144.0 g glycine, 10.0 g SDS and water added to bring the volume to 1 L. The buffer was stored at 4° C.) (7) Transfer buffer (300 ml of 10× electrode buffer, 300 ml methanol, 900 ml water and 0.15 g SDS) (8) 20% APS (200 mg Ammonium persulfate in 1 ml water) (9) TEMED (N,N,N,N'-Tetra-methyl-ethylene diamine was purchased from BIO-RAD cat#161-0800) (10) 10×PBS (80 g NaCl, 2 g KCl, 26.8 g $Na_2HPO_4 \cdot 7 H_2O$, 2.4 g $KH_2PO4$ and water to a volume of 1 L with pH adjusted to 7.4 with HCl and autoclaved) (Laemmli, 1970).

PEG-Intron (Schering corporation) was used a standard. PEG-Intron is currently FDA approved to be used for Hepatitis C treatment and consists of recombinant IFNα2b conjugated to monomethoxy polyethylene glycol. The PEG portion weighs 12 kDa and IFNα2b weights 19,271 daltons. PEG-Intron's specific activity is $0.7 \times 10^8$ IU/mg protein. Pegylation of IFNα2b resulted in an increased half-life and lower blood clearance levels thereby reducing the dosing frequency compared to the non-pegylated form (Schering Corporation). Dilutions of the standard was made from aliquots of 160 µg/ml PEG-Intron stock stored at −4° C. 5 µl of the 160 µl/ml stock was mixed with 95 µl of Peg $H_2O$ and a 8 ng/µl working stock was made.

All apparatus (glass plates and combs) to be used in the experiment were cleaned using 70% ethanol. Two sets of plates were inserted into the plastic green clamps with the shorter plates to the front. The glass plates were leveled and locked into clamps. The apparatus was placed in a holder with a foam strip on the bottom to form a seal and to prevent leakage. The plates were checked for leaks with $dH_2O$ water and it was blotted out with filter paper. A 15% resolving gel was prepared in a 15 ml screw cap tube using 2.4 ml DDI $H_2O$, 5.0 ml of 30% Bio-Rad degassed Bis Acrylamide, 2.5 ml of 1.5 M pH8.8 Tris-HCL gel buffer, and 100 µl of 10% SDS. 50 µl of 20% APS and 10 µl TEMED were added to the mixture and swirled to mix. The gel was immediately pipetted into the glass plates leaving room at the top for the stacking to added later. A 0.1% SDS solution was used to fill the space in the plates on top of the gel to level and prevent bubbles. The gel polymerized in 20 minutes and filter paper was used to remove the 0.1% SDS solution. A 4% stacking gel was prepared using 6.1 ml DDI $H_2O$, 1.3 ml Acrylamide/Bis, 2.5 ml of 0.5M Tris-HCl, pH6.8 buffer, and 100 ul of 10% SDS. 50 µl of 20% APS and 10 µl TEMED were added to the mixture and swirled. The gel was immediately pipetted over the resolving gel until reaching the top of the glass plates. The 10 well combs were carefully inserted and checked to make sure bubbles were not formed. The gel polymerized in 20 minutes while the samples were prepared (Laemmli, 1970).

Equal volumes of the samples and the sample-loading buffer were mixed as well as the desired concentrations of the standards were prepared and also mixed with the sample-loading buffer. 15 µl of the protein extracts was used. After the stacking gel polymerized, the combs were removed and the plates were removed from the casting frame and placed in an electrode assembly. The assembly was locked and placed in a tank. The tank was filled with 1× running buffer inside and outside. All the samples and standards were boiled for 4 minutes and loaded carefully with a loading tip in to their respective wells. 5 µl of precision plus protein marker (Bio-Rad) was also loaded into one of the wells. The gel was run for an hour at 50 V or until the samples were stacked on top of the resolving gel and then run for 3-4 hours at 80 V (Sambrook et al., 1989).

Transfer of Protein to Membrane and Immunoblot Analysis

After running the gel the specified time, the glass plates were carefully separated and the stacking gel portion was removed. A glass dish was used to assemble the transfer apparatus. Transfer buffer was poured into the dish and the cassette was placed in it. A thin sponge was soaked in transfer buffer and placed on the black side of the cassette. The sponge was topped with a piece of wet filter paper cut to the same size. The gel was placed into the transfer buffer in the glass dish and carefully removed from the glass plate. The gel was placed on top of the filter paper and the bubbles were removed. A 0.2 µm Trans-Blot nitrocellulose membrane (Bio-Rad) was moistened and placed on top of the gel. Then, wet filter paper was placed on top of the membrane and a wet sponge placed on top of the paper. The cassette was closed. The assembly was placed into a mini transfer blot module containing an ice pack, a magnet and transfer buffer. The transfer process was run at 85V for 1 hour. After the transfer, the membrane was washed with water and stored overnight at −20° C. The next day, the membrane was removed from freezer and incubated in P-T-M (1×PBS, 0.1% Tween 20 and 3% Milk) at room temperature in a shaker for 1.5 hours. During the incubation period, a primary antibody solution was made by adding 5 µl of Mouse monoclonal antibody against Human Interferon Alpha (PBL labs 21100-2) to 15 ml P-T-M (1:3000 dilution). After the incubation period, the P-T-M was discarded from the membrane and the membrane was incubated in the primary antibody solution for 2 hours at room temperature in the shaker. During the incubation period, a secondary antibody solution containing 5 μl of Goat Anti-Mouse IgG conjugated peroxidase (Sigma, St. Louis, Mo.) in 20 ml P-T-M (1:4000 dilution) was prepared. After the incubation period, the primary antibody solution was discarded and the membrane was rinsed with water, two times. The membrane was then incubated for 1.5 hours in secondary anotbody solution. After the incubation period, the secondary antibody solution was discarded and the membrane was washed with P-T (1×PBS, 0.05% Tween 20) three times for 15 minutes each wash. A final wash with 1×PBS was done for 10 minutes. A chemiluminescent substrate solution for HRP (Pierce, Rockford, Ill.) was prepared by mixing 750 μl of Luminol Enhancer and 750 μl of stable peroxide in the darkroom. The chemiluminescent solution was added to the membrane and rinsed over the membrane several times. The chemiluminescent membrane was exposed to an X-ray film in the darkroom and developed in a film processor (Sambrook et al., 1989).

Bombardment of the pLD-BB1 Vector
Generation Media for Tobacco Plants

MSO media was prepared by adding 30 g sucrose and one 4.3 g packet of Murashige & Skoog (MSO) salt mixture (Gibco BRL) to 1 L dH$_2$O. The solution was mixed well and the pH was adjusted to 5.8 with 1N KOH. 7 g/L phytagar was added to a 1 L flask and the mixture was autoclaved. The autoclaved mixture was cooled slightly and poured into Petri dishes and allowed to solidify. The regeneration media of plants (RMOP) solution is prepared exactly like the MSO media with the addition of growth hormones and vitamins (1 ml benzylaminopurine, BAP (1 mg/ml stock); 100 □l napthalene acetic acid, NAA (1 mg/ml stock), 1 ml thiamine hydrochloride (1 mg/ml stock)) to interfere with root development; therefore, only shoots would be produced (Daniell, 1993; Daniell, 1997).

Preparation of Microcarriers

In a microcentrifuge tube, 50 mg of gold particles (0.6 μm) were placed and 1 ml of 70% ethanol was added. The mixture was vortexed and incubated at room temperature for 15 minutes. After the incubation, the mixture was centrifuged and the gold particles formed a pellet in the bottom of the tube. The supernatant was removed and discarded. Then, 1 ml of sterile H$_2$O was added to the particles and the tube was vortexed again. After vortexing, the particles were to rest 1 minute and then were centrifuged again for 3 seconds. The supernatant was removed and discarded. These steps were repeated three times. Then, 50% glycerol was added to a concentration of 60 mg/ml and the gold particles were stored at −20° C. 50 μl of gold particles was removed from the stock stored at −20° C. and placed in a microcentrifuge tube. 10 μl plasmid DNA (pLD-smGFP-IFNα5) was added to the gold particles. Then, 50 μl of 2.5M CaCl$_2$ (prepared that day, 367.5 mg of CaCl$_2$ into 1 ml of d/aH$_2$O) was added and vortexed. Finally, 0.1M spermidine (20 μl) was added. The tube was placed in 4° C. and vortexed for 20 minutes. The mixture was then washed by adding 200 μl of absolute ethanol to each tube, centrifuging for 2 s and the ethanol was discarded. The wash was repeated 4 times. Following the wash, the gold particles were resuspended using 30 μl of absolute ethanol. The microcentrifuge tubes were then placed on ice.

Microprojectile Bombardment

The macrocarrier holders and stopping screens were autoclaved to sterilize them. The macrocarriers and rupture disks were soaked in 70% ethanol for 15 minutes. The macrocarriers and rupture disks were then placed in a sterile Petri disk and allowed to air dry in the hood. The entire hood and all interior parts of chamber of the gene gun (Bio-Rad PDS-1000/He) were cleaned with 70% ethanol to sterilize them. The pump was turned on and the main valve of the helium tank was opened. The gene gun valve controlling pressure was allowed to reach 13500 psi and set. Stopping screens were placed in macrocarrier holders prior to adding the macrocarrier. Macrocarriers were placed in holders and 6 μl of particle mixture was spread evenly onto the macrocarrier. Five macrocarriers were used for every tube. The gold suspension was allowed to dry and the macrocarrier holders were placed in the launch assembly with gold particles facing downwards. One rupture disk was placed in its holder and screwed in place at the top of the vacuum chamber. The secure ring was screwed onto the launch assembly and the assembly placed in the chamber slot below the rupture disk holder. A piece of sterile whatman #1 filter paper was placed on solidified RMOP media in a petri dish. Each leave clipped from wild-type (untransformed) sterile plants in jars was taken from the middle of plant and only healthy leaves were choosen of medium size. One leaf at a time was placed on the whatman paper abaxial side upwards because the waxy, thick cuticle lowers transformation efficiency. The petri dish with leaf was placed on a plastic holder and placed in the next to last slot in the vacuum chamber. The chamber door was closed and secured. The power switch for the gene gun was turned on. A vacuum was allowed to build to 28 psi in the bombardment chamber. When 28 psi was reached, the fire switch was pressed until the rupture disk ruptured (~1100 psi). After delivery of the gold particles with vector DNA, the vacuum was released and the petri dish containing the leaf retrieved. After bombardment, covers were placed on petri dishes with the bombarded leaf abaxial side facing up and the dishes were wrapped in aluminum foil and kept in the dark for 48 hours to recover from the shock of bombardment.

Results

Figure 28:
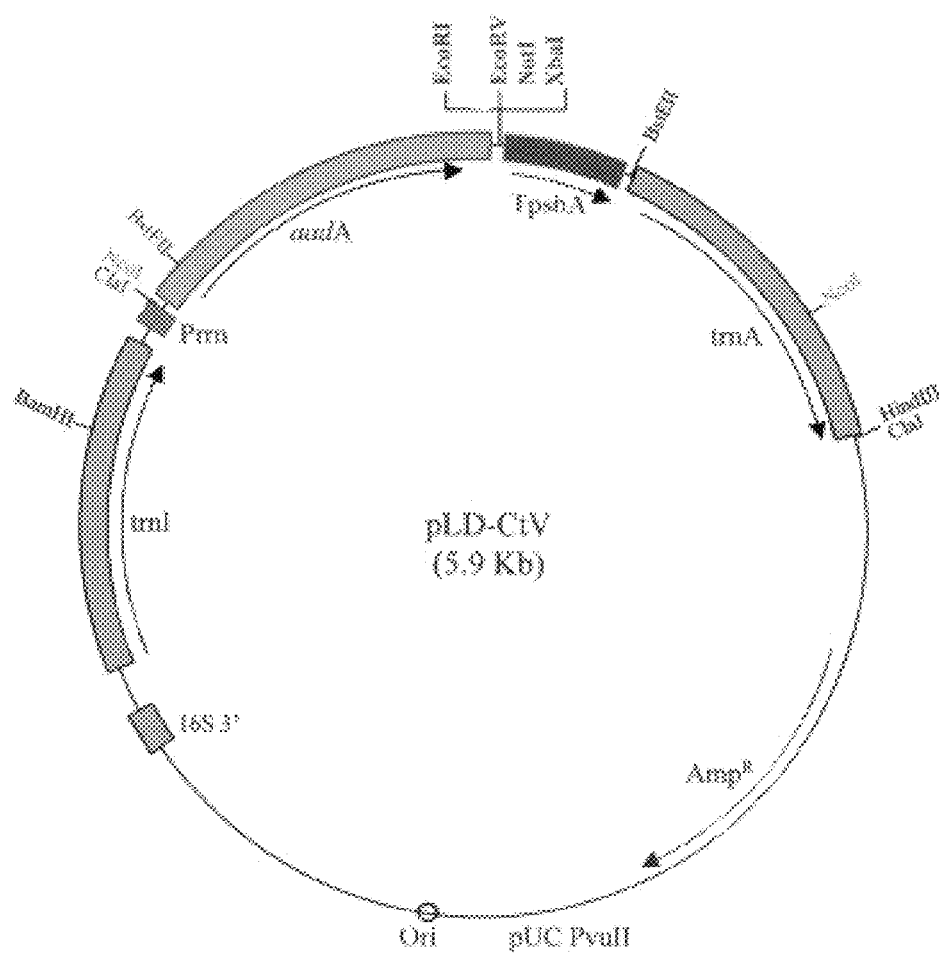
Figure 29:
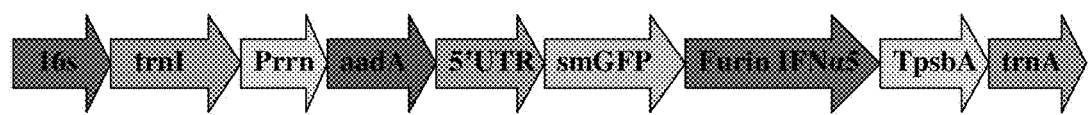

A 5.9 kb expression vector created by Lee and Daniell contain unique features facilitating the genetic engineering of plant chloroplasts (FIG. 28). Cloned chloroplast DNA is integrated into the plastid genome through site-specific homologous recombination allowing for the exclusion of vector DNA (Kavanagh et al., 1999). This universal chloroplast vector, pLD-CtV, contains the trnI & trnA homologous flanking sequences (chloroplast transfer RNAs coding for isoleucine and alanine) from the inverted repeat region of the chloroplast genome for site specific integration via homologous recombination (Daniell, 1999). The pLD-CtV also contains the 16S rRNA promoter, the aadA gene encoding spectinomycin resistance (selectable marker), and psbA3' untranslated region to enhance translation. The pLD-BB1 vector contains smGFP gene with a C-terminal fusion of the IFNα5 gene with a furin cleavage site between the fusion proteins cloned into the universal chloroplast vector, pLD-CtV (FIG. 29). Chloroplast integration of the smGFP-IFNα5 genes was confirmed by PCR and Southern blot analysis. The smGFP-IFNα5 fusion protein expression was confirmed by immunoblot analysis and smGFP expression under UV light. Expression was quantified by ELISA. The smGFP-IFNα5 fusion protein is being further analyzed via in vivo studies. The expression of smGFP-IFNα5 transgenic chloroplasts will facilitate the provision of a new and alternate treatment for HCV and possible oral delivery options with a lower cost of production.

Example 5: Evaluation of Chloroplast Derived Cholera Toxin B Subunit (CTB) and Green Fluorescent (GFP) Fusion Protein for Oral Delivery Many infectious diseases require booster vaccinations or multiple antigens to induce and maintain protective immunity. Advantages of plant-derived vaccines include the delivery of multiple antigens, low cost of production, storage & transportation, elimination of medical personnel and sterile injections, heat stability, antigen protection through bioencapsulation, the generation of systemic & mucosal immunity and improved safety via the use of a subunit vaccine and absence of human pathogens. In an effort to study the oral delivery of therapeutic proteins using the transmucosal carrier CTB, a fusion of CTB-smGFP was expressed in transgenic chloroplasts of Nicotiana tabacum var. petit Havana by inserting the CTB and smGFP genes into the chloroplast genome. The pLD-CTB-smGFP vector contains CTB with a C-terminal fusion to smGFP separated by a furin cleavage site. Both genes were inserted into a universal chloroplast vector, pLD-ctv containing the 16S rRNA promoter, the aadA gene coding for spectinomycin selectable marker gene, the psbA 5' & 3' untranslated regions to enhance translation in the light and trnI, trnA homologous flanking sequences for site specific integration into the chloroplast genome. Chloroplast integration of the CTB-smGFP genes was confirmed by PCR and Southern blot analysis. The CTB-smGFP fusion protein expression was confirmed by smGFP expression under UV light and immunoblot analysis. Expression level was quantified by ELISA. GM1-ganglioside binding assays confirmed that the chloroplast-derived CTB binds to the intestinal membrane receptor of cholera toxin, confirming correct folding and disulfide bond formation of CTB pentamers within transgenic chloroplasts. Functional studies are being carried out in mice to investigate the concept of bioencapsulation by plant cells by using smGFP as a visible marker as well as to test the ability of chloroplast-derived CTB to act as a transmucosal carrier of a reporter gene product. These investigations might facilitate the development of a novel cost effective oral delivery system for vaccines and therapeutic proteins.

One of the most challenging problems of human health management is the high cost of prescription drugs in developed countries and their lack of availability in developing countries. For example, interferon (IFN) alpha 2b is used for the treatment of viral diseases such as hepatitis C, as well as for certain cancers. However, IFN treatment for four months costs $26,000 in the United States, where more than forty-five million Americans do not have health insurance (1). Several hundred million people in developing countries are infected with hepatitis, but the daily income of one-third of the world population is less than $2 per day (1). The high cost of prescription drugs is due to a number reasons, including fermentation-based production (each fermenter costs several hundred million dollars to build), expensive purification and in vitro processing methods (such as column chromatography, disulfide bond formation) (2), the need for storage and transportation at low temperature and delivery via sterile injections requiring the involvement of hospitals and highly qualified health professionals (1). Therefore, new approaches to minimize or eliminate most of these expenses are urgently needed. Transgenic plants offer many advantages, including the feasibility of the oral delivery of foreign proteins, low cost of production, storage and transportation, heat stability and protection through bioencapsulation, elimination of the need for expensive purification, in vitro processing, and sterile injections (1-5). The generation of systemic and mucosal immunity (6) or induction of oral tolerance (7), improved safety, and absence of human pathogens (3) are other additional advantages (4, 5).

Chloroplast genetic engineering has recently become an attractive method for production of recombinant proteins (8, 9) because of high concentration of transgene expression [up to 47% of the total soluble protein (10)] due to the presence of 10,000 copies of the transgene per cell, which is uniquely advantageous for oral delivery of therapeutic proteins or vaccine antigens. It is also an environmentally friendly approach due to effective gene containment offered by maternal inheritance of chloroplast genomes in most crops (11, 12) or engineered cytoplasmic male sterility (13). Multigene engineering in a single transformation event (10μ, 14, 15) should facilitate delivery of polyvalent vaccines or expression of therapeutic proteins with multiple subunits.

Despite these advantages, a major limitation remains in the efficient delivery of plant-expressed therapeutic proteins across the intestinal mucus membrane, primarily because of poor permeability across the intestinal epithelial layer (16). Receptor-mediated oral delivery across the intestine might serve as a possible way to deliver not only vaccines but also biopharmaceutical proteins. Ganglioside M1 (GM1) receptors on the intestinal epithelial cells have been utilized by various pathogens such as *V. cholerae* to facilitate entry of cholera toxin, into the intestine. Crystal structures (17-19) of bacterial toxins like cholera toxin, (CT), heat-labile enterotoxin (LT), and *shigella* toxin show that they belong to AB5 subunit family. In CT, five identical (11.6 kDa) peptides assemble into a highly stable pentameric ring called the B subunit (58 kDa). The nontoxic B subunit (CTB) exhibits specific and high-affinity binding to the oligosaccharide domain of ganglioside GM1 (a lipid-based membrane receptor) and functions to tether the toxin to the plasma membrane of host cells (17, 20, 21). This receptor is present on the intestinal epithelium as well as motoneurons and sympathetic preganglionic neurons (22). GM1 sorts the CT into lipid rafts and a retrograde trafficking pathway to the endoplasmic reticulum, where the enzymatic subunit is transferred to the cytosol, probably by dislocation through the transloconsec61P (20).

To test the concept of receptor-mediated oral delivery of foreign proteins, the inventors have constructed a unique cholera toxin B-green fluorescent protein (CTB-GFP) fusion gene with a furin cleavage site between CTB and GFP and expressed the fusion protein in transgenic chloroplasts. Furin, a member of prohormone-proprotein convertases (23) (PCs), is a ubiquitously expressed protein found in the trans-Golgi network (TGN) (24, 25), endosomes, plasma membrane, and extracellular space (26). Furin cleaves protein precursors with narrow specificity following basic Arg-Xaa-Lys/Arg-Arg-like motifs (27). The furin cleavage site between CTB and GFP would, therefore, facilitate intracellular cleavage of the target protein (GFP).

Transgenic leaves expressing the CTB-GFP or IFNGFP fusion protein were fed to Balb/c mice to investigate receptor-mediated oral delivery of foreign protein using CTB as a transmucosal carrier across the intestinal epithelium. In this study, we show that CTB-GFP binds to the intestinal mucous membrane, including the lymphoid tissue. Experimental observations suggest that GFP is cleaved from CTB in the intestine through the action of furin and enters the mucosal vasculature. We show that GFP, but not CTB, is delivered to the liver and spleen of the CTB-GFP fed mice. No significant levels of GFP were observed in the liver and spleen of mice fed with IFN-GFP, which suggests that a transmucosal carrier is essential for efficient delivery of proteins across the intestinal lumen. Thus, CTB successfully delivers its fusion protein to the systemic circulation and supports the use of transmucosal carriers in the delivery of therapeutic proteins.

Materials and Methods
Construction of Chloroplast Vector

Figure 39:
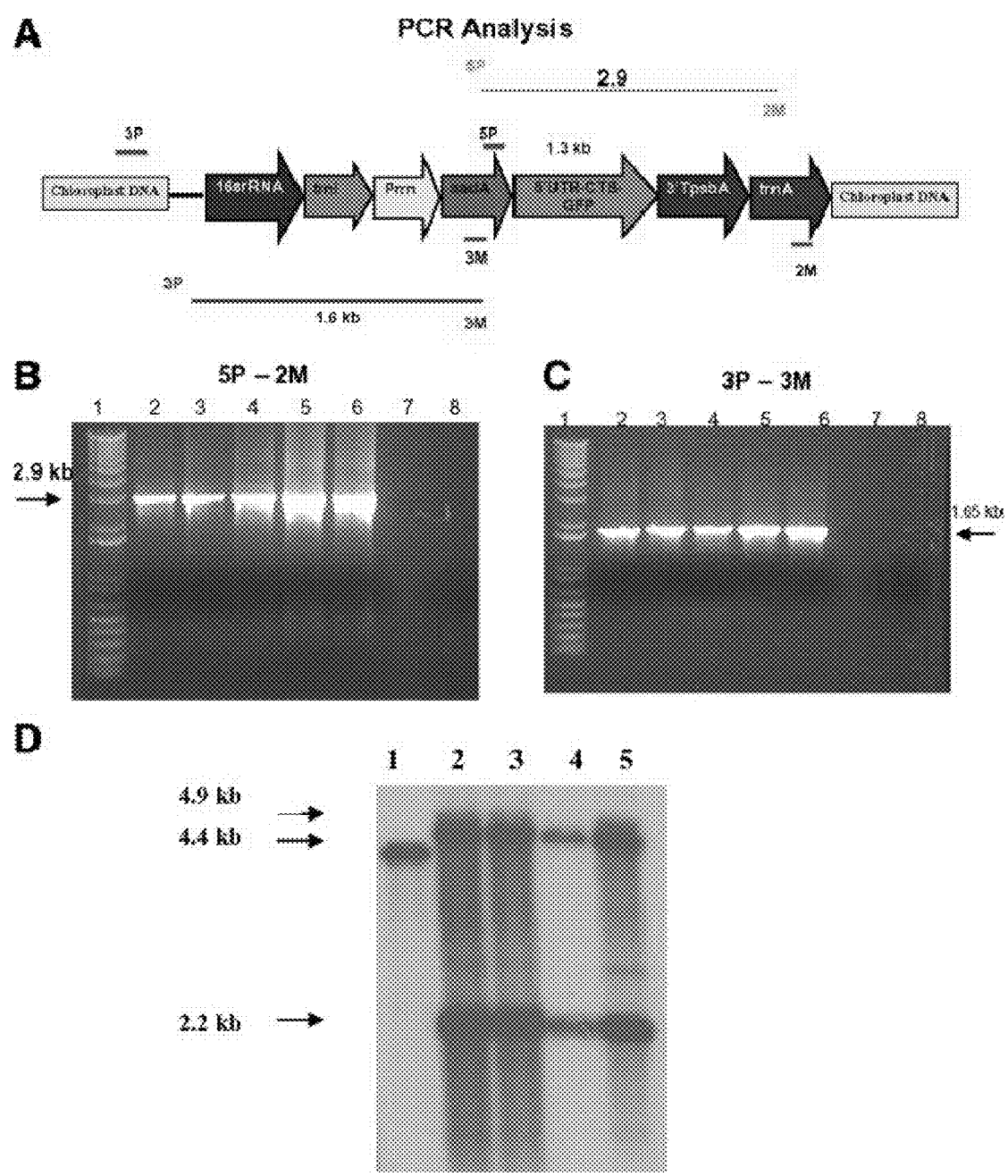

The pLD-CTB-GFP construct was based on the universal chloroplast vector pLD (FIG. 39) that has been used successfully in the inventors laboratory (28-31). CTB-GFP construct was engineered with a furin cleavage site, Pro-Arg-Ala-Arg-Arg (SEQ ID NO: 10), in between CTB and GFP. The constitutive 16 s rRNA promoter was used to drive transcription of the aadA and the CTB-GFP genes. The aminoglycoside 3_adenylyltransferase (aadA) gene conferring spectinomycin resistance was used as a selectable marker. The 5_-UTR from psbA, including its promoter, was engineered to enhance translation of the CTB-GFP because it has several ribosomal binding sites. The 3'UTR region conferred transcript stability. A GFP-IFN alpha5 fusion construct with a furin cleavage site between the two genes was created and expressed in Nicotiana tabacam chloroplasts, which served as a control molecule for the delivery of GFP without a transmucosal carrier.

Bombardment and Selection of Transgenic Plants

The Bio-Rad PDS-1000/He biolistic device was used to bombard pLD-CTB-GFP onto sterile Nicotiana tabacum cv. Petit Havana tobacco leaves, on the abaxial side as has been described previously (29, 30, 32). The bombarded leaves were incubated in the dark for 24 h and then placed on shooting media (RMOP) containing 500 µg/ml spectinomycin for two rounds of selection.

Pcr Analysis to Test Stable Integration

DNA was isolated from the transgenic shoots by using Qiagen DNeasy Plant Mini Kit, and PCR analysis was performed to confirm integration of the transgene in the inverted repeat regions of the chloroplast genome. PCR reactions were performed with two sets of primers, 3P/3M and 5P/2M (28).

The samples were denatured for 5 min at 95° C. followed by 30 cycles of the following temperatures: 95° C. for 1 min, 65° C. for 1 min, and 72° C. for 2 min and a 72° C. hold for 10 min after all 30 cycles were completed. After confirmation of transgenic plants, the shoots were then transferred to a rooting medium (MSO) with 500 µg/ml spectinomycin as a selective agent.

Southern Blot Analysis

Total plant DNA was digested with EcoR1, separated on a 0.7% agarose gel at 45V for 8 h, and then transferred to a nitrocellulose membrane. pUC-computed tomography vector DNA was digested with BamHI and BglII to generate a 0.8 kb probe, which was used as a flanking probe (28). After labeling the probe with P32, hybridization of the membranes was performed by using Stratagene QUICK-HYB hybridization solution and protocol (Stratagene, La Jolla, Calif.).

Western Blot Analysis

Approximately 100 mg of leaf tissue was ground in liquid nitrogen and resuspended in 500 µl of plant extraction buffer (0.1% SDS; 100 mM NaCl; 200 mM Tris-HCl, pH 8.0; 0.05% Tween 20; 400 mM sucrose; 2 mM PMSF). After centrifugation at 13,000 rpm for 5 min, the supernatant containing the extracted protein was collected. We boiled 10 µl of the plant extract along with 10 µl of sample loading buffer, which was then run on a 15% SDS-PAGE gel for 40 min at 50 V and then 2 h at 80 V. The protein was then transferred to nitrocellulose membrane for 1 h at 80 V. After blocking the membranes with PTM (1×PBS, 0.05% Tween 20, and 3% dry milk) for 1 h, we added polyclonal rabbit anti-CTB primary antibody (Ab) (Sigma) 1:3000 dilution.

Goat anti-rabbit IgG conjugated to alkaline phosphatase (Sigma) at a 1:5000 dilution was used as a secondary Ab.

Furin Cleavage Assay

Approximately 100 mg of leaf material was powdered in liquid nitrogen and resuspended in 500 µl of plant extraction buffer containing 15 mM Na2CO3, 35 mM NaHCO3, 3 Mm NaN3, 5 mM CaCl2, and 0.5% Triton-X, 2-mercaptoethanol at pH 6.0 and 7.0. We added 1 mM PMSF to some of the samples. After centrifugation at 13,000 rpm for 5 min, the supernatant containing the extracted protein was collected.

The extract (20 µl) was incubated at 30° C. for 4 h with 4 U of furin. A control group was also incubated at 30° C. for 4 h without furin. After 4 h, each sample was mixed with 20 µl sample loading buffer, boiled, and run on 12% SDS-PAGE gel for 45 min at 80 V and then 2 h at 100 V. The Western blot analysis was performed as per the procedure outlined above. Chicken anti-GFP Ab (Chemicon) at a 1:3000 dilution was used as the primary Ab, and alkaline phosphatase conjugated rabbit antichicken IgG (Chemicon) at a dilution of 1:5000 was used as a secondary Ab.

ELISA

The CTB-GFP quantification was done using the ELISA (ELISA). The standards and test samples were diluted in coating buffer (15 mM Na2CO3, 35 mM NaHCO3, 3 mM NaN3, pH 9.6). The standards, ranging from 50 to 500 ng, were made by diluting recombinant GFP in 1% PBS. The leaf samples were collected from plants exposed to regular lighting pattern (16 h light and 8 h dark), and total protein was extracted using plant protein extraction buffer. Standard GFP dilutions (100 µl) and protein samples were bound to a 96-well plate overnight at 4° C. The background was blocked with fat-free milk in PBST for 1 h at 37° C. followed by washing with PBST and water. Primary Ab used was polyclonal chicken anti-GFP Ab (Chemicon) diluted (1:3000) in PBST containing milk powder. Secondary Ab was HRP-conjugated rabbit anti-chicken IgG-secondary Ab (Chemicon) at a 1: 5000 dilution in PBST containing milk powder. For the color reaction, 100 µl of 3,3_,5,5_-tetramethyl benzidine (TMB from American Qualex) substrate was loaded in the wells and incubated for 10-15 min at room temperature. The reaction was stopped by addition of 50 µl of 2N sulfuric acid per well, and the plate was read on a plate reader (Dynex Technologies) at 450 nM.

GM1 Binding Assay

To test the functionality of CTB-GFP expressed in chloroplasts, a CTB-GM1 binding assay was performed. We coated 96-well plates with 100 µl of monosialoganglioside-GM1 (Sigma) (3.0 ng/ml in bicarbonate buffer) and incubated them overnight at 4° C. After washing with PBST and water, the standards and samples were incubated for 1 h at 37° C. The plate was blocked with 1% BSA in 1×PBS for 1 h at 37° C. Rabbit anti-CTB primary Ab (Sigma) and alkaline phosphatase (activating protein) conjugated goat anti-rabbit secondary Ab (Sigma) was used to detect the CTB binding to GM1 receptor. The plates were washed with PBST and water, and 200 µl of the substrate p-Nitrophenyl phosphate (PNPP) was added to the wells and incubated in the dark at 37° C. for 20 min The reaction was stopped by adding 50 µl of 3N NaOH, and the plates were read on a plate reader (Dynex Technologies) at 405 nM.

Animal Studies

Three groups of 5-week-old female Balb/c mice were fed with CTB-GFP, IFN alpha5-GFP (IFN-GFP), and wild-type (untransformed) plant leaf material. Leaves (350 mg) were powdered in liquid nitrogen, mixed with peanut butter, and fed to the mice, which had been starved overnight prior to this experiment. The mice were then gavaged for two more days, two times a day, with 40 mg of leaf material per gavage that was powdered with liquid nitrogen and mixed with 0.1M PBS (PBS). Five hours after the last gavage, the mice were sacrificed and perfused with 10 ml of PBS followed by 4% paraformaldehyde in PBS. Fresh frozen sections of the liver, spleen, ileum, and jejunum were collected according to Samsam et. al (33). Additional tissue was removed and immersed in Tissue Tec freezing medium (Vector labs) and immediately frozen in nitrogen-cooled isomethylbuthane (Sigma). Fixed tissue was cryoprotected by passing through 10, 20, and 30% sucrose solutions in PBS. Frozen sections (10_m thick) of various tissues were then made using a cryostat.

Fluorescence Microscopy and Immunohistochemistry for GFP, CTB, and Immune Cells

Frozen sections (10_m thick) of intestine, liver, and spleen were mounted with PBS and observed for GFP fluorescence using a Leica 4500 microscope Immunohistochemistry was performed in order to show the presence of GFP and/or CTB in various tissues. The slides were first blocked with 10% BSA (BSA) and 0.3% Triton-X 100. Polyclonal chicken anti-GFP (Chemicon) or polyclonal rabbit anti-CTB (Sigma) primary antibodies, at a concentration of 1:500 and 1:300, respectively, in 1% BSA and 0.3% Triton-X, were used for GFP or CTB localization of the tissues. Those sections processed for HRP conjugated secondary antibodies were blocked with a mixture of methanol/hydrogen peroxide 30% (2:1 ratio) to block the endogenous peroxidases. The secondary antibodies were horseradish peroxidase (HRP)-conjugated rabbit antichicken IgG (Chemicon) or HRP-conjugated goat anti-rabbit (Sigma). Tissue-bound peroxidase was developed by using the 3,3_diaminobenzidine (3,3_-diaminobenzidine) as a substrate to visualize the immunoreaction.

For macrophage localization of the tissues, rat monoclonal F4/80 Ab (Serotec) was used according to Berghoff et al. (34). The secondary Ab was Alexa-555 conjugated Goat antirat IgG (Molecular Probes). American hamster anti-CD11c primary Ab and anti-hamster Alexa-546 conjugated secondary Ab (Molecular Probes) were used to visualize dendritic cells in the intestine and other tissues. FITC-labeled anti-chicken IgG was used as a secondary Ab in such immunofluorescence staining to detect GFP in tissues.

Results

Confirmation of transgene integration into chloroplast genome

*Nicotiana tabacum* cv. Petit Havana leaves were bombarded with the pLD-CTB-GFP vector, and the leaves were grown on selective medium containing 500 mg/l spectinomycin. The resultant shoots were then screened for chloroplast transformants by PCR analysis by using primers 3P/3M, and 5P/2M (FIG. 39A-C). The 3P primer lands on the native chloroplast genome upstream of the site of integration, whereas the 3M primer lands on the aadA transgene producing a 1.65 kb PCR product. This analysis ruled out the nuclear transformants because 3P primer would not anneal and the spontaneous mutants are eliminated because 3M primer would not anneal.

To check for the presence of the transgene in the chloroplast, we performed the 5P-2M PCR analysis. The 5P primer lands on aadA gene and the 2M lands on the trnA coding sequence, which produces a 2.9 kb PCR product with CTB-GFP. This confirmed the site-specific integration of the CTB-GFP fusion gene in the inverted repeat regions of the chloroplast genome.

Southern Blot Analysis to Investigate Homoplasmy

To further confirm the integration of the transgene into the chloroplast genome and to determine whether homoplasmy had been achieved, Southern blot analysis was performed. Total plant DNA was digested with the enzyme EcoR1 and hybridized with a chloroplast flanking sequence probe (0.8 kb). Wild-type plants generated a 4.4 kb fragment, and transgenic plants generated 4.9 and a 2.2 kb fragments (FIG. 39D). All of the transgenic lines tested appeared to be homoplasmic (within the levels of detection), which means that all of the chloroplast genomes within plant cells contained the transgene CTB-GFP.

GFP Expression and Assembly of CTB-GFP Pentamers in Transgenic Lines

Figure 40:
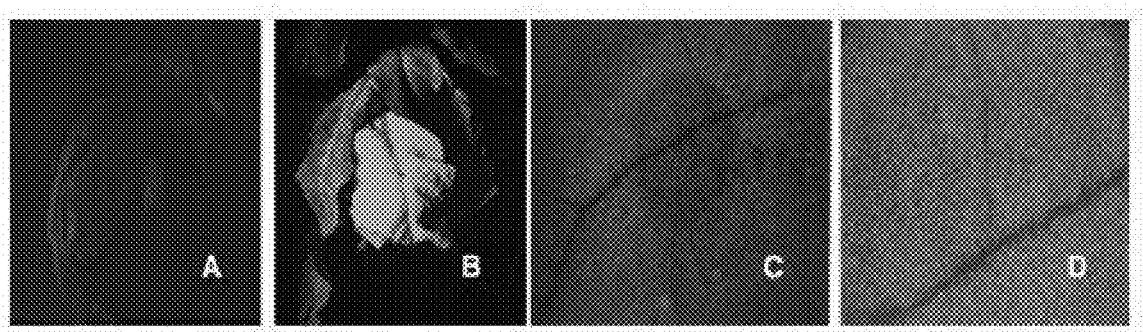

FIG. 40 shows the transgenic and wild-type (WT) plants. In FIG. 40B, the GFP expression of the transgenic plants can be seen under the UV light, which is not seen in the wild-type (untransformed) plant (FIG. 40A). FIG. 40C shows WT plant, and FIG. 40D, the CTB-GFP expressing plant under a low-magnification microscope. Expression of GFP is clearly evident in FIG. 40D. Western blot analysis was performed to investigate the expression of the fusion protein CTB-GFP in transgenic tobacco chloroplasts (FIG. 41A). The pentameric form (188 kDa) was observed in the unboiled samples of the transgenic plants, while predominantly the monomeric form (37.6 kDa) was detected in boiled samples.

Furin Cleavage Assay

The protease furin is present in the constitutive secretory pathway and on the cell surface of virtually all cells (35). An in vitro furin cleavage assay was performed on the CTB-GFP expressing plant extract to show that the engineered cleavage site (Arg-Ala-Arg-Arg (SEQ ID NO: 13)) was recognized by furin. As seen in FIG. 41 B, a 26 kDa polypeptide that corresponded with the recombinant GFP protein was observed in the samples that were incubated with furin, thus proving that furin could cleave CTB-GFP to release GFP. Furin cleavage occurred at both pH 6.0 and 7.0 in the samples with and without PMSF. Still, some protein did not get cleaved, probably because the amount of enzyme was not sufficient to cleave all the CTB-GFP protein present in the plant extract. The incubation time of 4 h might also have been insufficient. However, the presence of the cleaved GFP product in the samples incubated with furin confirms that the engineered furin cleavage site is functional. The introduction of furin consensus sequences at the Bchain/C-peptide and the C-peptide/A-chain interfaces of human proinsulin has been demonstrated to increase the processing of proinsulin to mature insulin in a wide variety of non-neuroendocrine cells, including fibroblasts, myoblasts, epithelial cells, and lymphocytes (36-42). As the furin cleavage site is also recognized by the endopeptidases PC2 and PC3/1, it is likely that CTB-GFP fusion protein is cleaved more efficiently during the process of receptor-mediated delivery.

Quantification of CTB-GFP

To quantify the amount of CTB-GFP fusion protein in transgenic tobacco leaves, ELISA (ELISA) was performed (FIG. 41B). A standard curve was obtained using different concentrations of recombinant GFP. The amount of CTB-GFP in the transgenic plants was compared with the known concentrations of the recombinant GFP (standard curve). Expression levels of CTBGFP ranged from 19.09 to 21.3% total soluble protein.

GM1 Binding Assay

The functionality of chloroplast-derived CTB-GFP was determined by its ability to bind to GM1 in an in vitro GM1 binding assay (FIG. 41C). GM1 binding assay showed that pentamers of CTB-GFP were formed. This finding confirms the correct folding and disulfide bond formation of CTB pentamers within transgenic chloroplasts because only the pentameric form of CTB can bind to GM1 (21).

Fluorescent Microscopy to Detect the Presence of GFP in the Tissue

Fixed tissue and fresh frozen sections of the liver, spleen, ileum, and jejunum were made from the three groups of mice fed with plants expressing CTB-GFP, IFN-GFP, and WT plants, respectively. In mice fed with CTB-GFP expressing plant leaf material, fluorescence microscopy showed the presence of GFP in intestinal mucosa and submucosa (FIG. 42A), the hepatocytes of the liver (FIG. 42D) as well as various cells of the spleen (FIG. 42G). In the mice fed with wild-type (untransformed) leaf material, no GFP fluorescence was observed (FIGS. 42B, E, and H). In the mice fed with IFN-GFP expressing plant leaf material, no GFP was detected in the liver or spleen (FIGS. 42F and I). Detection of GFP in the liver and spleen following oral delivery of CTB-GFP expressing plant leaf material, suggests the successful delivery of the protein across the intestinal lumen into the systemic circulation. Moreover, the lack of detection of a significant amount of GFP in the liver and spleen of mice fed with IFN-GFP expressing plants suggests that a transmucosal carrier such as CTB is required for delivery of an adequate amount of a macromolecule across the intestinal lumen into the systemic circulation.

Immunohistochemistry

Figure 42:
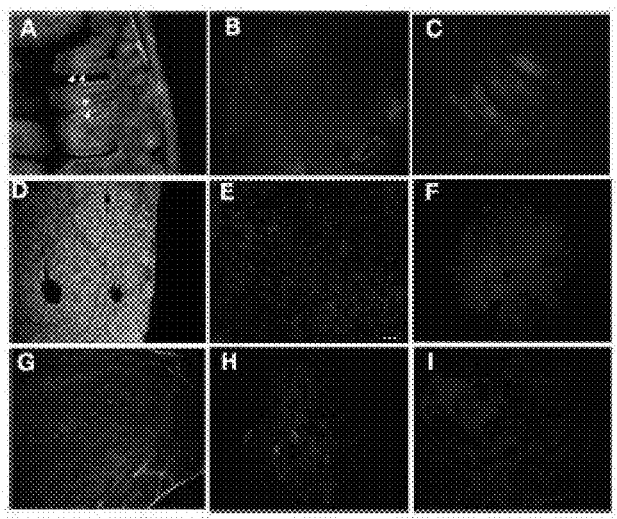
Figure 43:
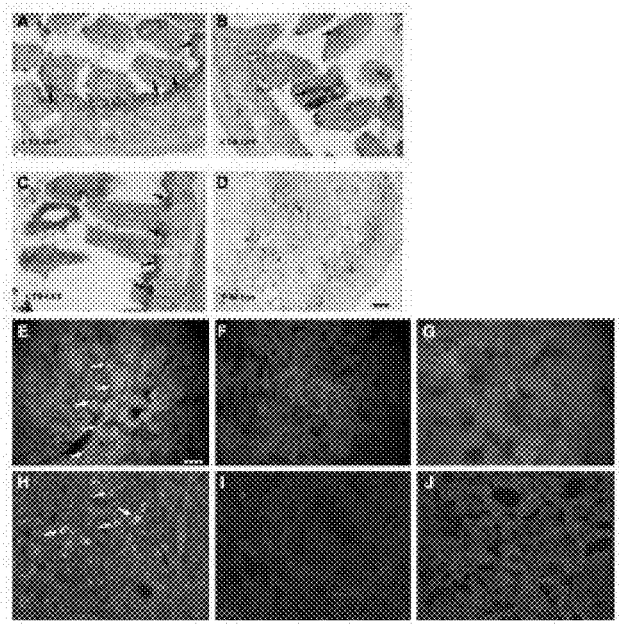

To confirm the fluorescent microscopy findings, immunostaining was performed with both CTB and GFP antibodies. In the intestine of the mice fed with CTBGFP, anti-GFP Ab detected GFP inside the epithelial cells of the villi of the intestine, in the crypts, as well as in the submucosal tissue (FIG. 43 A, C), which suggesting GFP uptake by lymphoid cells as well as the circulation. These results confirmed the previous microscopy findings (FIG. 42) and showed the presence of GFP in various tissues, confirming that GFP was successfully delivered to blood when transgenic leaf material was orally fed to the mouse. GFP immunoreactivity was detected in the liver and spleen (FIGS. 43E and H) in a similar pattern to that seen with fluorescence microscopy of the native tissue (FIGS. 42D and G). In the case of the mice fed with wild-type leaf material, no GFP was detected in any of the tissues (FIGS. 43F and I). In the mice fed with plants expressing IFN-GFP, GFP was not detected in the liver or spleen cells (FIGS. 43G and J).

To study the route of CTB in the body, we performed immunohistochemistry using anti-CTB antibodies. CTB was detected in the intestinal cells as well as inside the villi (FIG. 44A) in the lamina propia and the submucosa. It was, however, not detected in the liver (FIG. 44E), indicating that GFP is cleaved away from CTB and that, while GFP leaves the cell, CTB probably is translocated to the basolateral membrane of the cell. These results support the feasibility of CTB to act as a transmucosal carrier and orally deliver fused proteins via the intestinal cells. To localize the GFP and/or CTB in the gut associated lymphoid tissue (GALT) and other tissues, double staining for antigen-presenting cells such as macrophages or dendritic cells was performed. A double staining with F4/80 Ab for macrophages showed the presence of CTB inside macrophages (FIG. 44C). FIG. 44G shows macrophages associated with GFP, and FIG. 44I shows dendritic cells taking up the GFP. In either case, associations of GFP with these antigen presenting cells were found. Most of the macrophages were not associated with GFP, which is perhaps due to uptake by the blood and lymph circulation, while the CTB is translocated to the basolateral membrane and is associated with macrophages.

Discussion

In this study, detection of GFP and CTB in the intestinal mucosa (FIGS. 43, 44) suggests that CTB-GFP has been taken up by the enterocytes and the gut-associated lymphoid tissue (GALT). The CTB domain of the CTB-GFP forms the pentameric structure within chloroplasts through disulfide bond formation; pentameric form binds to the GM1 receptors on enterocytes and is endocytosed into the intestinal cells as endosomes (20). GM1 functions to concentrate CTB in detergent-insoluble, glycolipid-rich apical membrane microdomains called lipid rafts (43, 44). Binding to lipid rafts is required to couple the lipid-anchored protein with intracellular machinery for protein sorting and vesicular traffic (45, 46). After endocytosis, the CTB-GM1 complex trafficking occurs retrogradely through Golgi cisternae and/or TGN (20, 47) into the lumen of the endoplasmic reticulum (ER; 48). The GM1-CTB-GFP complex in the lipid rafts, targeted to the TGN, loses its endosomal covering. Within the TGN, ubiquitously expressed furin cleaves numerous polypeptide precursors as it gets activated. In eukaryotes, many essential secreted proteins and peptide hormones, enzymes, and neuropeptides are initially synthesized as proproteins (inactive precursors) and are activated by proteolytic cleavage by furin and other members of the prohormone-proprotein convertase (PCs, 23). Abundant experimental evidence indicates that the CTB-GFP protein with furin cleavage site in between the fusion protein gets cleaved and, as a result, the CTB and GFP separate. The CTB is taken into the ER and from there to the baso-lateral surface of the cell (transcytosis), where it remains membrane bound to GM1 receptor (20). The GFP molecule getting out of the TGN (presumeably membrane-bound) is exocytosed through the basolateral membrane and finds its way into extracellular fluid and into the submucosal vessels, including the lymphatic system. Due to the large-size fenestrations of the lymphatic vessels, lymphatics return over 3 L of fluid and _120 g of protein to the bloodstream every 24 h in an adult human (49).

Besides the entry of CTB-GFP through the GM1 ganglioside receptor, the M cells in intestinal epithelium covering the mucosa-associated lymphoid tissue in the digestive tract also serve as a port of entry of macromolecules and microorganisms by pinocytosis (50). Therefore, a small amount of CTB-GFP could be taken up by the GALT. This is shown in our study by CTB and GFP expression in the antigen presenting cells, including the macrophages as well as the dendritic cells in the intestinal lamina propia and submucosa. Similarly, a small amount of GFP associated with macrophages in the intestine of the INFGFP fed mice is likely to be taken up by the M cells nonspecifically. The IFN-GFP fusion protein also contains a furin cleavage site but, due to limited uptake by the intestinal epithelial cells, there is not a significant GFP transport to the tissues of the IFNGFP fed mice. The amount of CTB-GFP reaching the enterocytes via GM1 receptor is very high compared with the entry of IFN-GFP through M cells. This is quite evident due to the GFP detected in various organs of the CTB-GFP fed mice (FIGS. 43, 44). Presence of GFP and not CTB in the liver of CTB-GFP treated mice in our study (FIGS. 43, 44) suggests the cleavage of the CTB-GFP fusion protein in enterocytes and uptake of GFP into the vasculature of the lamina propia and the submucosa. CTB, however, might be translocated to the basolateral cell membrane and remain bound to GM1 (20).

The main goal of this study is to develop an efficient oral delivery of protein through GM1 receptor-mediated endocytosis. Moreover, furin cleavage site facilitates the cleavage of the candidate protein in the cell, so that it could be passed into the extracellular space and into the circulation. Internalization of GFP using receptor-mediated endocytosis suggests a possible way of protein delivery across the impermeable intestinal mucous membrane. Because of the rapid turnover of the intestinal epithelial cells (51) in humans (renewal of the intestinal epithelium occurs in every 3-6 d), repeated feeding of the CTB fused to a therapeutic protein is possible due to the continuous availability of GM1 receptors in the new epithelium. Moreover, Peterson and colleagues suggested a recycling mechanism for GM1 receptor as well (52).

One of the most challenging problems of human health management is the high cost of prescription drugs in developed countries and their lack of availability in developing countries. Such high cost of therapeutic proteins can be attributed to their production in fermentation-based system, expensive purification and processing methods, low-temperature storage, transportation, and sterile delivery using syringes through health professionals. Most of these expenses could be avoided by expressing therapeutic proteins in plant cells and through their oral delivery. This study shows internalization of CTB-GFP by the mouse intestinal mucosal cells as well as the antigen-presenting cells in the intestinal mucosa and submucosa. We also show the presence of GFP but not CTB in the liver of mice following oral delivery of CTB-GFP leaf material. Detection of both CTB and GFP in mouse intestinal cells following oral administration of CTB-GFP expressing leaf material shows that the recombinant protein has been protected from peptidases and/or acids by bioencapsulation (53) within the plant cells. Several vaccine antigens (28, 54-57) and human blood proteins (31, 58-60) have been expressed in transgenic chloroplasts and shown to be fully functional. The ability to express high levels of foreign proteins in plastids present within edible plant parts (61, 62) and the rapid turnover of intestinal epithelial cells (51) for recycling GM1 receptors make this approach a reality. This study facilitates the provision of low-cost production and delivery of human therapeutic proteins.

REFERENCES

1. Daniell, H., Carmona-Sanchez, O., and Burns, B. E. (2004) Chloroplast derived antibodies, biopharmaceuticals and edible vaccines. In *Molecular Farming* (Fischer, R. and Schillberg, S. eds) pp. 113-133, WILEY-VCH Verlag Publishers:Weinheim, Germany
2. Petridis, D., Sapidou, E., and Calandranis, J. (1995) Computer aided process analysis and economic evaluation for biosynthetic human insulin production—a case study. *Biotechnol. Bioeng* 48, 529-541
3. Giddings, G., Allison, G., Brooks, D., and Carter, A. (2000) Transgenic plants as factories for biopharmaceuticals. *Nat. Biotechnol.* 18, 1151-1155
4. Arntzen, C., Plotkin, S, and Dodet, B. (2005) Plant-derived vaccines and antibodies: potential and limitations. *Vaccine* 23, 1753-1756
5. Mason, H. S., Warzecha, H., Mor, T. and Arntzen, C. (2002) *Trends Mol. Med.* 8, 324
6. Mason, H. S., Haq, T. A., Clements, J. D., and Arntzen, C. J. (1998) *Vaccine* 16, 1336
7. Arakawa, T. Yu, J., Chong, D. K., Hough, J., Engen, P. C., and Langridge, W. H. (1998) *Nat. Biotechnol.* 16, 934
8. Grevich, J. J. and Daniell, H. (2005) Chloroplast genetic engineering: Recent advances and future perspectives. *Criti. Rev. Plant Sci.* 24, 83-107
9. Daniell, H., Kumar, S., and Dufourmantel, N. (2005) Breakthrough in chloroplast genetic engineering of agronomically important crops. *Trends Biotechnol.* 23, 238-245
10. De Cosa, B., Moar, W., Lee, S. B., Miller, M., and Daniell, H. (2001) Overexpression of the Btcry2Aa2 operon in chloroplasts leads to formation of insecticidal crystals. *Nat. Biotechnol.* 19, 71-74
11. Daniell, H. (2002) Molecular strategies for gene containment in transgenic crops. *Nat. Biotech.* 20, 581-587
12. Hagemann, R. (2004) The sexual inheritance of plant organelles. In *Molecular Biology and Biotechnology of Plant Organelles* (Daniell, H. and Chase, C. eds.) pp. 87-108. Springer, Dordrecht, The Netherlands
13. Ruiz, O. and Daniell, H. (2005) Engineering Cytoplasmic male sterility via the chloroplast genome by expression of _-ketothiolase. *Plant Physio.* 138, 232-246
14. Ruiz, O., Hussein, H., Terry, N. and Daniell, H. (2003) Phytoremediation of organomercurial compounds via chloroplast genetic engineering. *Plant Physiol.* 132, 1-9
15. Quesada-Vargas, T., Ruiz, O., and Daniell, H. (2005) Characterization of heterologous multigene operons in transgenic chloroplasts. Transcription, processing, and translation. *Plant Physiol.* 138, 1746-1762
16. Hamman, J. H., Enslin, G. M. and Kotze, A. F. (2005) *BioDrugs* 19, 165
17. Sixma, T. K., Pronk, S. E., Kalk, K. H., Wartna, E. S., van Zanten, B. A., Witholt, B., and Hol, W. G. (1991) Crystal structure of a cholera toxin-related heat-labile enterotoxin from *E. coli. Nature* 351, 371-377
18. Merritt, E. A. and Hol, W. G. (1995) AB5 toxins. *Curr. Opin. Struct. Biol.* 5, 165-71
19. Ling, H., Boodhoo, A., Hazes, B., Cummings, M. D., Armstrong, G. D., Brunton, J. L. and Read, R. J. (1998) Structure of the shiga-like toxin I B-pentamer complexed with an analogue of its receptor Gb3. *Biochemistry* 37, 1777-1788
20. Lencer, W. I. (2001) Microbes and microbial Toxins: paradigms for microbial-mucosal toxins. *V. Cholera*: invasion of the intestinal epithelial barrier by a stably folded protein toxin. *Am. J. Physiol. Gastrointest Liver Physiol.* 280, G781-786 21. Merritt, E. A., Sarfaty, S., van den Akker, F., L'Hoir, C., Martial J. A., Hol, W. G (1994) Crystal structure of cholera toxin B-pentamer bound to receptor GM1 pentasaccharide. *Protein Sci.* 3, 166-175
22. Alisky, J. M., Van de Wetering, C. I. and Davidson, B. L. (2002) Widespread dispersal of cholera toxin subunit b to brain and spinal cord neurons following systemic delivery. *Exprimental Neurol.* 178, 139-146
23. Nakayama, K. (1997) Furin: a mammalian subtilisin/Kex2p-like endoprotease involved in processing of a wide variety of precursor proteins. *Biochem. J.* 327, 625-635
24. Bosshart, H., Humphrey, J., Deignan, E., Davidson, J., Drazba, J., Yuan, L., Oorschot, V., Peters, P. J., and Bonifacino, J. S. (1994) The cytoplasmic domain mediates localization of furin to the TGN en route to the endosomal/lysosomal system. *J. Cell Biol.* 126, 1157-1172
25. Molloy, S. S., Thomas, L., VanSlyke, J. K., Stenberg, P. E. and Thomas, G. (1994) Intracellular trafficking and activation of the furin proprotein convertase: localization to the TGN and recycling from the cell surface. *EMBO J.* 13, 18-33

26. Mayer, G., Boileau, G. and Bendayan, M. (2004) The proprotein convertase furin colocalizes with caveolin-1 in the Golgi apparatus and endosomes of hepatocytes. *Cell Tissue Res.* 316, 55-63
27. Henrich. S., Cameron, A., Bourenkov, G. P., Kiefersauer, R., Huber, R., Lindberg, I., Bode, W., and Than, M. E. (2003) The crystal structure of the proprotein processing proteinase furin explains its stringent specificity. *Nat. Struct. Biol.* 10, 520-526
28. Daniell, H., Lee, S. B., Panchal, T. and Wiebe, P. O. (2001) Expression and assembly of the native cholera toxin B subunit gene as functional oligomers in transgenic tobacco chloroplasts. *J. Mol. Bio.* 311, 1001-1009
29. Daniell, H., Ruiz, O. N. and Dhingra, A. (2004) Chloroplast genetic engineering to improve agronomic traits. *Methods Mol. Biol.* 286, 111-137
30. Kumar, S, and Daniell, H. (2004) Engineering the chloroplast genome for hyperexpression of human therapeutic proteins and vaccine antigens in recombinant protein protocols. *Methods Mol. Biol.* 267, 365-383
31. Daniell H., Chebolu S., Kumar S., Singleton M., Falconer, R. (2005) Chloroplast-derived vaccine antigens and other therapeutic proteins. *Vaccine* 23, 1779-1783
32. Daniell, H. (1997) Transformation and foreign gene expression in plants mediated by microprojectile bombardment. *Methods Mol. Biol.* 62, 453-488
33. Samsam, M., Mi, W., Wessig, C., Zielasek, J., Toyka, K. V., Coleman, M. P., and Martini, R. (2003) The Wlds mutation delays robust loss of motor and sensory axons in a genetic model for myelin-related axonopathy. *J. Neurosci.* 23, 2833-2838
34. Berghoff, M., Samsam, M., Muller, M., Kobsar, I., Toyka, K. V., Kiefer, R., Maurer, M., and Martini, R. (2005) Neuroprotective effect of the immune system in a mouse model of severe dysmyelinating hereditary neuropathy: enhanced axonal degeneration following disruption of the RAG-1 gene. *Mol. Cell. Neurosci.* 28, 118-127
35. Taylor, N. A. W. J. Van De Ven, and J. W. Creemers. (2003) Curbing activation: proprotein convertases in homeostasis and pathology. *FASEB J.* 17, 1215-27
36. Groskreutz, D. J., Sliwkowski, M. X., and Gorman, C. M. (1994) Genetically engineered proinsulin constitutively processed and secreted as mature, active insulin. *J. Biol. Chem.* 269, 6241-6245
37. Hay, C. W., and Docherty, K. (2003) Enhanced expression of a furin-cleavable proinsulin. *J. Mol. Endocrinol.* 31, 597-607
38. Ito, M., Bujo H., Takahashi K., Arai T., Tanaka, I., and Saito, Y. (2005) Implantation of primary cultured adipocytes that secrete insulin modifies blood glucose levels in diabetic mice. *Diabetologia* 48, 1614-1620
39. Nishigori, T., Yanagita, M., and Takeuchi, T. (1996) Proinsulin cleaved by furin is processed to chromatographically mature insulin by carboxypeptidases in normeuroendocrine cells. *Peptides* 17, 789-796
40. Shaw, J. A., Delday M. I., Hart A. W., Docherty H. M., Maltin, C. A., and Docherty, K. (2002) Secretion of bioactive human insulin following plasmid-mediated gene transfer to non-neuroendocrine cell lines, primary cultures and rat skeletal muscle in vivo. *J. Endocrinol.* 172, 653-672
41. Short, D. K., Okada S., Yamauchi, K., and Pessin, J. E. (1998) Adenovirus-mediated transfer of a modified human proinsulin gene reverses hyperglycemia in diabetic mice. *Am. J. Physiol.* 275, E748-756
42. Yanagita, M., Nakayama, K., and Takeuchi, T. (1992) Processing of mutated proinsulin with tetrabasic cleavage sites to bioactive insulin in the non-endocrine cell line, COS-7. *FEBS Lett.* 311, 55-59
43. Orlandi, P. A. and Fishman, P. H. (1998) Filipin-dependent inhibition of cholera toxin: evidence for toxin internalization and activation through caveolae-like domains. *J. Cell Biol.* 141, 905-915
44. Brown, D. and Lendon, E. (2000) Structure and function of sphingolipid and cholesterol-rich membrane rafts. *J. Biol. Chem.* 275, 17220-17224
45. Lencer, W. I., Moe, S., Rufo, P. A. and Madara, J. L. (1995) Transcytosis of cholera toxin subunits across model human intestinal epithelia. *Proc. Natl. Acad. Sci. USA* 92, 10094-10098
46. Badizadegan, K., Wolf, A. A., Rodighiero, C., Jobling, M., Hirst, T. R., Holmes, R. K., and Lencer, W. I. (2000) Floating cholera toxin into epithelial cells: functional association with caveolaelike detergent-insoluble membrane microdomains. *Int. Med. Microbiol.* 290, 403-408
47. Feng, Y., Jadhav, A. P., Rodighiero, C., Fujinaga, Y., Kirchhausen, T., and Lencer, W. I. (2004) Retrograde transport of cholera toxin from the plasma membrane to the endoplasmic reticulum requires the TGN but not the Golgi apparatus in Exo2-treated cells. *EMBO Rep.* 5, 596-601
48. Fujinaga, Wolf, A. A., Rodighiero, C., Wheeler, H., Tsai, B., Allen, L., Jobling, M. G., Rapoport, T., Holmes, R. K., and Lencer, W. I. (2003) Gangliosides that associate with lipid rafts mediate transport of cholera and related toxins from the plasma membrane to endoplasmic reticulum. *Mol. Biol. Cell.* 12, 4783-4793
49. Granger, D. N. (1997) Essential medical physiology; 2nd edition (Leonard R. Johnson, ed.); pp. 217-225; Lippincott-Raven, Philadelphia
50. Jepson, M. A. and Clark, M. A. (1998) Studying M cells and their role in infection. *Trends Microbiol.* 6, 359-365
51. Heath, J. P. (1996) Epithelial cell migration in the intestine. *Cell Biol. Int.* 20, 139-146
52. Boonyarattanakalin, S, Martin, S. E., Dykstra, S. A., and Peterson, B. R. (2004) Synthetic mimics of small Mammalian cell surface receptors. *J. Am. Chem. Soc.* 126, 16379-16386
53. Kong, Q., Richter, L., Yang, Y. F., Arntzen, Mason, H. S., and Thanavala, Y. (2001) Oral immunization with hepatitis B surface antigen expressed in transgenic plants. *Proc. Natl. Acad. Sci. USA* 98, 11539-11544
54. Koya, V., Moayeri, M., Leppla, S. H., and Daniell, H. (2005) Plant based vaccine: mice immunized with chloroplast-derived anthrax protective antigen survive anthrax lethal toxin challenge. *Infect. Immun.* 73, 8266-8274
55. Watson J., Koya V., Leppla, S., and Daniell, H. (2004) Expression of *Bacillus anthracis* protective antigen in transgenic chloroplasts of tobacco, a non-food/feed crop. *Vaccine* 22, 4374-4384
56. Molina A., Daniell H., Mingo-Castel, A., and Veramendi, J. (2004) High-yield expression of a viral peptide animal vaccine in transgenic tobacco chloroplasts. *Plant Biotech. J.* 2, 141-153
57. Molina A., Veramendi, J., and Hervas-Stubbs, S. (2005) Induction of neutralizing antibodies by a tobacco chloroplast derived vaccine based on a B cell epitope from canine parvo virus. *Virology* 342, 266-275
58. Fernandez-San Millan, Mingeo-Castel A., Miller, M., and Daniell, H. (2003) A chloroplast transgenic approach to hyperexpress and purify Human Serum Albumin, a protein highly susceptible to proteolytic degradation. *Plant Biotech. J.* 1, 71-79

59. DeGray, G., Rajasekaran K., Smith F., Sanford, J., and Daniell, H. (2001) Expression of an antimicrobial peptide via the chloroplast genome to control phytopathogenic bacteria and fungi. *Plant Physiol.* 127, 852-862
60. Leelavathi, S., and V. S. Reddy. (2003) Chloroplast expression of His-tagged GUS-fusions: a general strategy to overproduce and purify foreign proteins using transplastomic plants as bioreactors. *Molec. Breed.* 11, 49
61. Lelivelt, C. L., McCabe, M. S., Newell, C. A., Desnoo, C. B., vanDun, K. M., Birch-Machin, I., Gray, J. C., Mills, K. H., and Nugent, J. M. (2005) Stable plastid transformation in lettuce (*Lactuca sativa* L.). *Plant Mol. Biol.* 58, 763-74
62. Kumar, S., Dhingra, A., and Daniell, H. (2004) Plastid-expressed betainealdehyde dehydrogenase gene in carrot cultured cells, roots, and leaves confers enhanced salt tolerance. *Plant Physiol.* 136, 2843-2854

Example 6: Characterization of Heterologous Multigene Operons in Transgenic Chloroplasts: Transcription, Processing And Translation Introduction Plastid genes in higher plants are mainly organized as operons, of which more than sixty have been described in the tobacco chloroplast genome (Sugita and Sugiura, 1996). These may group genes of related or unrelated functions, the former being the most common (Barkan, 1988; Rochaix, 1996). Most of these genes are transcribed into polycistronic precursors that may be later processed and modified to render the transcripts competent for translation (Eibl et al., 1999; Barkan & Goldschmidt-Clermont, 2000; Monde et al., 2000b).

The processing mechanisms for translation regulation in chloroplast genes of higher plants are still largely unknown. The general consensus is that most native primary transcripts require processing in order to be functional (Barkan, 1988; Zerges, 2000; Meierhoff et al., 2003), and that post-transcriptional RNA processing of primary transcripts represents an important control of chloroplast gene expression (Hashimoto et al., 2003; Nickelsen, 2003). However, it is believed that more than one pathway may be involved in transcript processing (Danon, 1997; Choquet and Wollman, 2002).

For example, several studies have shown that the regulation of gene expression in the chloroplast relies more on RNA stability than on transcriptional regulation (Deng and Gruissem, 1987; Jiao et al., 2004). In chloroplast, such stability is mainly influenced by the presence of 5' untranslated regions, or UTRs (Eibl et al., 1999; Zou et al., 2003), nucleus-encoded factors (Lezhneva and Meurer, 2004) and 3'UTRs (Adams and Stern, 1990; Chen and Stern, 1991), without which rapid degradation or low accumulation of primary transcripts has been observed. The role of plastid 3'UTRs differs from the role of its bacterial counterparts by being more involved in transcript stability and less involved in the effective termination of transcription (Stern and Gruissem, 1987).

Translation has also been a crucial step in the regulation of gene expression, as in many cases protein levels in the chloroplast did not correlate with steady-state transcript abundance (Monde et al., 2000b). Therefore, the transcription of native chloroplast operons and their post-transcriptional and translational patterns have been the target of several studies which showed that intercistronic processing enhanced translation of chloroplast operons, including the maize psbB and pet clusters (Barkan, 1988; Barkan et al., 1994). In addition, different species may experience various processing mechanisms for the same gene cluster. For example, species such as *Arabidopsis* (Meierhoff et al., 2003), tobacco (Monde et al., 2000a) and spinach (Westhoff and Herrmann, 1988) have a different mechanism than maize for the translation of petD, which depends mainly upon the establishment of dicistrons and tricistrons of this gene. Alternative processing of the polycistron containing the petD gene, which produces monocistronic petD, causes the degradation of the transcript, inhibiting translation (Meierhoff et al., 2003; Tanaka et al., 1987; Monde et al., 2000a, b). In contrast, in *Chlamydomonas*, nearly all chloroplast genes appear to be transcribed as monocistronic mRNAs, with translation being an essential regulatory step of gene expression (Rochaix et al., 1989; Zerges and Rochaix, 1994). Other mechanisms, such as editing, which can produce alternate start codons, have been linked to alternative processing and to a complete different translation pattern (Hirose and Sugiura, 1997; del Campo et al., 2002). These examples provide evidence of different modifications of primary transcripts for efficient translation in chloroplasts.

Traditionally, plant genetic engineering had involved the introduction of single genes through nuclear transformation. In the past decade, the introduction of multiple genes has also been successful through this approach, allowing the incorporation of complete metabolic pathways (Ma et al., 1995; Nawrath et al., 1994; Ye et al., 2000). However, this approach required a long process of integration of individual transgenes followed by breeding to reconstruct the desired pathways. Additionally, transgene segregation from nuclear transformed plants may be possible in subsequent generations, which may result in loss of function of the introduced pathway. Furthermore, plant nuclear genes are typically transcribed monocistronically, which requires separate promoter sequences for each of the introduced genes. Expression of foreign genes may also be influenced by position effects and gene silencing, causing levels of gene expression to vary among independent transgenic lines (Daniell and Dhingra, 2002).

On the other hand, plant genetic engineering through chloroplast transformation presents several additional advantages over nuclear transformation, such as their ability to efficiently transcribe and translate operons (DeCosa et al., 2001; Lossl et al., 2003; Ruiz et al., 2003), as well as to confer hyperexpression capability (Daniell et al., 2004c). In addition, chloroplasts are able to accumulate foreign proteins that are toxic in the cytoplasm, such as cholera toxin □ subunit (Daniell et al., 2001), trehalose (Lee et al., 2003), and xylanase (Leelavathi et al., 2003), without any deleterious effects, due to the compartmentalization of transgene products (Bogorad, 2000). Concerns about position effect are also eliminated due to site-specific integration of transgenes via homologous recombination of chloroplast DNA flanking sequences (Daniell et al., 2002), and because chloroplasts are maternally inherited in most crops, the risk of outcrossing transgenes to related species through pollen is minimized (Daniell, 2002). Additionally, transformation of plastids in non-green tissues, such as carrot roots, offer promising options for oral delivery of vaccine antigens (Kumar et al., 2004a).

As foreign genes are engineered into operons, the resulting transcript differs from the native operons by lacking native intergenic sequences. These sequences are removed during cloning or by PCR amplification of the coding sequences. The effect of such modifications in the transcription and translation of heterologous operons has not yet been investigated. Therefore, the purpose of this study is to examine the transcription, processing and translation of several foreign operons engineered via the chloroplast genome. The results of this investigation provide sufficient evidence that suggests that engineered polycistrons in chloroplast transgenic lines are efficiently translated and that processing into monocistrons is not required to obtain overexpression of transgenes. Additionally, the role of 5'UTRs and 3'UTRs in post-transcriptional modifications, translation, and transcript stability are addressed. Addressing questions on polycistron translation as well as the sequences required for processing and transcript stability are essential for chloroplast metabolic engineering.

Results

Multigene Engineering via the Tobacco Chloroplast Genome

Multigene engineering via the chloroplast genome has been achieved by using several different foreign genes, promoters, and 5' and 3' regulatory sequences (Daniell et al., 2004a; Kumar and Daniell, 2004). Chloroplast transgenic lines analyzed in this study were genetically engineered with multigene cassettes that contained the following basic features; the aadA (aminoglicoside 3'-adenylyltransferase) gene, which confers resistance to spectinomycin and help in transgenic plant selection (Goldschmidt-Clermont, 1991), downstream from the constitutive chloroplast 16S ribosomal RNA gene promoter (Prrn). The heterologous gene or genes of interest were inserted downstream of the aadA gene and were flanked at the 3' end by the psbA 3' untranslated region (3'UTR), which is involved in mRNA abundance and stability in the chloroplast (Deng and Gruissem, 1987; Stern and Gruissem, 1987). In some cases, the heterologous gene was also engineered to contain the psbA promoter and 5' regulatory sequence (5' untranslated region; 5'UTR) to enhance translation (Eibl et al., 1999; Fernandez-San Millan et al., 2003; Dhingra et al., 2004, Watson et al., 2004). The multigene cassettes were flanked at the 5' and 3' by sequences homologous to the tobacco chloroplast trnI (tRNA Ile) and trnA (tRNA Ala) genes, respectively, which allow site-specific integration by homologous recombination into the inverted repeat region of the chloroplast genome (Daniell et al., 1998). More than thirty genes have been successfully integrated and expressed at this transcriptionally active spacer region (Daniell et al., 2004a, b). In this study, the following foreign genes were inserted into the basic expression cassettes: human serum albumin (hsa), cholera toxin β subunit (ctxB), ctxB-gfp (green fluorescent protein) fusion, Bacillus thuringiensis insecticidal protein (cry2Aa2) along with the associated chaperonin protein (orf2) and orf1, and trehalose phosphate synthase (tps1). The transgenic lines engineered to express CRY insecticidal protein contained the entire cry2Aa2 native operon.

Transcription and Translation of the cry2Aa2 Operon

The chloroplast transgenic lines transformed with the transgene cassette containing the aadA gene and the complete cry2Aa2 operon (ORF1,2-Cry2Aa2 lines) were used to study the transcriptional and translational patterns of a heterologous operon in transgenic chloroplasts. This operon comprises the orf1, orf2, and cry2Aa2 genes under the transcriptional regulation of the Prrn promoter (FIG. 45A). Several transcripts were anticipated based on transcription initiation at the engineered promoter (Prrn promoter) and the native 16S ribosomal RNA promoter (native Prrn) in transgenic lines (FIG. 45A). Northern blot analyses of three independent lines harboring the cry2Aa2 operon revealed that the predicted 4.9 kilonucleotide (knt) polycistron, which contained all four transgenes (aadA-orf1-orf2-cry2Aa2), was the most abundant transcript detected with the cry2Aa2 specific probe (FIG. 45B, c). Interestingly, the cry specific probe also revealed a shorter transcript of about 2.4 knt; which was about the same size as the cry2Aa2 gene (FIG. 45B, a), suggesting that this transcript could be the cry2aA2 monocistron. Densitometric analyses of the foreign mRNA transcripts revealed that the cry2Aa2 monocistron and the aadA-orf1-orf2-cry2Aa2 polycistron had similar abundances (FIG. 45C, a,c), indicating that processing in the intergenic region between orf2 and cry2Aa2 occurred in about 50 percent of the polycistrons transcribed from the Prrn promoter (FIG. 45A, B a, c). Another prominent 7.4 knt transcript was predicted, based on the calculation of the length of the coding sequence, initiating at the native 16S Prrn promoter (FIG. 45B, e). A low intensity ~6.0 knt transcript detected (FIG. 45B, d) may be produced by read-through of the transcript starting at the Prrn promoter and terminating downstream of the engineered 3' UTR. The low intensity ~3.5 knt transcript (FIG. 45B, b) terminates at the same location as the 6.0 knt transcript, although it is smaller due to the processing between orf2 and cry2Aa2. Because this fragment only contained the cry gene and the sequences downstream from the 3'UTR, it could not be detected with the aadA probe (FIG. 45D). The read-through transcripts processed downstream of the 3'UTR represent an average of 27.3±3% of those produced in these transgenic lines (FIG. 45B, b, d).

Northern blot analyses with the aadA specific probe confirmed the results observed with the cry2Aa2 probe. The predicted 4.9 knt polycistron that harbors the aadA gene plus the complete cry operon was detected as expected (FIG. 45D, c). Although the predicted 2.5 knt tricistron (FIG. 45D, f) containing the aadA gene plus the orf1 and 2 was expected due to processing between the orf2 and the cry2Aa2 genes, a transcript of a similar intensity to that of the polycistron was observed instead (FIG. 45D, c, f). Densitometric analyses revealed a 1 to 1 ratio of the polycistron (aadA-orf1-orf2-cry2Aa2) versus the aadA-orf1-orf2 tricistron (FIG. 45E, c,f), due to processing in the intergenic region between orf2 and cry2Aa2 (FIG. 45A). These results showed that the two transcripts produced by the processing in the intergenic region between cry2Aa2 and orf2 resulted in transcripts with a similar abundance to the complete polycistron containing all four genes and the 3'UTR (FIGS. 45C, a,c and FIGS. 45E, f and c, respectively). The fact that the tricistron containing the aadA, orf1 and orf2 genes did not contain a chloroplast 3'UTR but still was very stable, suggests that polycistrons are stable in the chloroplast even in the absence of 3'UTRs. The results obtained by using the orf1-orf2 fragment (orf1,2) as a probe, confirmed the detection of the aadA-orf1-orf2 tricistron (predicted 2.5 knt), indicating effective processing at the intergenic region between orf2 and cry2Aa2 (FIG. 45F, f). Other transcripts of larger size were also observed and corresponded to those obtained with the cry2Aa2 gene-specific probe (FIG. 45 F, d,e).

Northern blots were also performed on the cry2Aa2 transgenic lines using the psbA 3'UTR probe (FIG. 51B). Results revealed a pattern similar to that obtained with the cry2Aa2 gene-specific probe, as well as the presence of the endogenous psbA transcript. In the case of the cry2Aa2 operon, transcripts were in much lower proportion to the native psbA operon. Because the native psbA and the heterologous cry2Aa2 operon are driven by different promoters, transcript abundance cannot be quantitatively compared. In contrast to the results obtained in FIG. 45B, only the major transcripts (a and c) were detected.

Polysome fractionation assays of the cry2Aa2 operon support polycistron translation, as the larger transcripts corresponding in size to the complete operon (from the prrn promoter) were observed mainly in the lower fractions of the sucrose gradients, when hybridized with the cry2Aa2 probe (FIG. 46A) and with the orf1,2 probe (FIG. 46B). Additionally, smaller transcripts corresponding in size to the cry2Aa2 gene processed from the rest of the operon also appear associated to polysomes, suggesting that processing may also occur and could be coupled to translation. Puromycin release controls confirm that the polycistronic transcripts found in the lower fractions were indeed associated to polyribosomes (FIG. 46C).

Western blot analyses revealed that the Cry2Aa2 (65 kDa; F1G. 45H) and the ORF2 proteins (45 kDa; FIG. 45) were highly expressed in the transgenic lines. The abundant expression of the orf2 confirmed that polycistrons were efficiently translated without the need for processing into monocistrons.

Transcription and Translation of the hsa Operon

Chloroplast transgenic lines transformed with 3 different multigene constructs, all containing the human serum albumin (hsa) gene, were used to study transcription, translation and posttranscriptional modifications (FIG. 47A). The Prrn promoter drives the operon downstream in all three constructs. The first transgenic line (referred to as RBS-HSA) has an operon formed by the aadA gene, followed by the hsa gene, whereas the second transgenic line (5'UTR-HSA) harbored an expression cassette that contained the aadA gene under the transcriptional regulation of the Prrn promoter, as well as the hsa gene under the transcriptional regulation of the psbA promoter and the translational enhancement of the 5' psbA UTR. This transgenic line was predicted to produce a monocistronic hsa transcript (FIG. 47A). Finally, the third transgenic line (ORF-HSA) contained a four-gene operon formed by the aadA, and hsa genes, as well as the orf1 and orf2 sequences of the cry2Aa2 operon from the bacterium Bacillus thuringiensis (FIG. 47A).

Northern blot analyses of the RBS-HSA lines with the hsa and the aadA probes revealed that the most abundant transcript was a dicistron of a predicted 2.8 knt (aadA-hsa, FIG. 47B, D, b), followed by two polycistronic transcripts: one transcribed from the native 16S Prrn promoter of an expected size of 5.3 knt (FIG. 47B, D, h), and the 3.2-knt transcript transcribed (FIG. 47B, D, d) from the engineered Prrn promoter, terminating downstream of the 3'UTR of the gene cassette. No monocistrons were detected in these RBS-HSA transgenic lines. Quantification of transcripts from the northern blots obtained with the hsa probe revealed that the polycistrons transcribed from the engineered Prrn promoter accounted for 65.5±3% of the transcript detected in these lines (FIG. 47C). The polycistrons terminating downstream of the 3'UTR in the trnA region and the one transcribed from the native 16S Prrn were 24.9±2. and 9.6±1% of the total transcripts, respectively (FIG. 47C, d, h). Values for the northern analysis performed with the aadA probe were similar, with 61.8±3% for the polycistron transcribed from the engineered Prrn promoter, 31.7±3% and 6.5±0.3% for the read-through transcript and the polycistron transcribed from the native promoter, respectively (FIG. 47E, b, d, h). This analysis shows that there is abundant read-though transcription.

The ORF-HSA transgenic lines also showed a similar transcription pattern with respect to the RBS-HSA line when probed with the hsa or aadA probe. When hybridized with the orf1,2 probe, the same pattern to that obtained with the aadA probe was observed, and no processing was detected between orf2 and the hsa gene (FIG. 47F, lanes 7-9). The most abundant transcript was the polycistron containing all four genes (predicted size of 4.4 knt), which was transcribed from the engineered Prrn promoter, representing 68.1±2%, 65.5±1% and 43.3±4% of the total transcripts detected with the hsa, aadA or orf1,2 probes, respectively (FIG. 47B, D, F, f). Additionally, the predicted 6.9 knt polycistron originating at the Prrn native promoter was also detected (FIG. 47D, k) and this represented 6.8±0.4% of the polycistrons (FIG. 47E, k). A ~5.2 knt transcript (FIG. 47B, D, F, g) obtained from the engineered 16S Prrn and processed downstream of the 3'UTR was also observed. This transcript was about 27.7±1.% and 31.9±2% of the polycistrons detected with the aadA or hsa probes (FIG. 47C, g, and E, g), respectively, and 44.2±1% of those detected with the orf1,2 probe (FIG. 47G, g). Finally, transgenic lines engineered with the aadA-5'UTR-hsa construct produced transcripts about 200 nt longer than the transgenic lines transformed with the aadA-hsa construct (FIG. 47B, D, c, e). This increase in transcript size is due to the presence of the psbA 5'UTR and promoter. Additionally, this transgenic line produced an abundant hsa monocistron (2.1 knt) that accounted for approximately 50% of the total transcript detected with the hsa probe (FIG. 47B, C a); this transcript was not detected with the aadA, nor with the orf1,2 probes, (FIG. 47D, lanes 7-9). The polycistrons transcribed from the engineered Prrn and native promoter were 28.7±3% and 9.4±2% of the transcripts produced (FIG. 47E, g, k) Similar transcript abundance was detected in northern blot analyses in which the aadA probe was used (FIG. 47E, g, k). Furthermore, read-through transcripts processed downstream of the transgene cassette, in the trnA native gene, were detected (FIG. 47B, D letters e, j). The combined abundance of these transcripts was 15.5% (FIG. 47C, e, j), whereas the overall polycistron abundance in this transgenic line was as much as the monocistronic transcript.

When RNA from the different transgenic hsa lines were hybridized with the psbA 3'UTR probe, a pattern similar to that obtained with the hsa gene-specific probe was observed (FIG. 51A). Because the native psbA transcript was also detected, the abundance of both native and heterologous operons could be observed. However, endogenous versus heterologous transcript abundance could only be compared among transcripts that were regulated by the same psbA promoter (FIG. 51A, lanes 4-6a). The results showed that the 5'UTR-HSA monocistronic transcript was approximately 1.6 times as abundant as that of the native psbA. This may be due to the effect of gene dosage, as the trangene is integrated into the inverted repeat region, whereas the psbA gene is located in the large single copy region.

Western blot analyses of the different constructs showed expression of the HSA monomer (66 kDa) and dimer (132 kDa) in the transgenic lines harboring the 5'UTR-hsa and the orf1,2-hsa constructs (FIG. 47H). Transgenic lines expressing the monocistrons showed expression levels similar to the ORF-HSA transgenic line, in which only polycistrons were translated. The abundant translation of ORF2 protein (45 kDa) from the aadA-orf1-orf2-hsa transgenic lines (FIG. 47I), which only transcribed tricistrons and polycistrons, support the view that polycistrons are highly stable in the chloroplast and can be efficiently translated without further processing. This was also observed in polysome fractionation assays, in which larger polycistronic transcripts of the ORF-HSA lines were detected in the lower fractions of the gradient (data not shown). Expression of the hsa gene in the transgenic line ORF-HSA at levels similar to the ones produced by the psbA-5'UTR-hsa transgenic lines, suggest a similar translation efficiency for heterologous polycistrons and monocistrons in the chloroplast (FIG. 47H).

The accumulation of human serum albumin in transgenic lines aadA-orf1-orf2-hsa was monitored under different photoperiods and developmental stages by performing ELISA analyses. These experiments were conducted to determine whether hsa expression under the cry 5'UTR, which is a heterologous 5'UTR, is light dependent or developmentally regulated. The data obtained from the analysis of cell extracts from young, mature and old leaves exposed to periods of 0, 4, 8, and 16 hours of light, revealed no significant differences among age of leaf or among different periods of illumination. Therefore, HSA accumulation in this transgenic line regulated by a heterologous 5' UTR is independent of light regulation and is free of cellular control (FIG. 48).

Transcription and Translation of the tps1 Operon

The tps1 gene coding for trehalose phosphate synthase was engineered into a two-gene operon, formed by the aadA and the tps1 genes, and transcribed from the engineered Prrn promoter (RBS-TPS1 lines) (FIG. 49A). Northern blot analyses with either the tps1-specific or aadA-specific probes detected the expected 2.7 knt dicistron (aadA-tps1) as the most prominent transcript (FIG. 49B, D, a). Densitometric analyses of the northern blots showed that the aadA-tps1 dicistron accounted for 43.3±3% of the total transcripts detected by the tps1 probe, and 59.8±5% of the total transcript when the aadA probe was used (FIG. 49C, a, and E, a). A predicted 5.2 knt polycistron observed in the northern blots with either the tps1 and aadA probes (FIGS. 49B, c and D, c), is transcribed from the native 16S Prrn (FIG. 49A, c). Additionally, the tps1 probe detected less abundant polycistrons of about 3.5 knt (FIG. 49B, D, b) and ~6.5 knt (FIG. 49B, d), transcribed from the engineered Prrn promoter and the native 16S Prrn promoter, respectively, terminating downstream of the 3'UTR. The 3.5-knt polycistron was also detected by the aadA probe. Transcripts that ended in the trnA intron region (downstream of the engineered 3'UTR) were also detected in the cry (FIGS. 45B, b and D, e) and hsa transgenic lines (FIG. 47B, d, e, g; D d, e, g, and F, g), indicating that this region may contain different processing sequences. The transcripts processed at the trnA location account for about 37% of the total transcripts detected in the transgenic lines (FIG. 49C b, d and E, b). Transcripts longer than the 6.5 knt polycistrons may terminate at undetermined locations and these were not quantified densitometrically. No monocistron was detected in the northern blots with the tps1 probe nor with the aadA probe, indicating that the polycistron is not being processed in these transgenic lines, whereas the larger transcripts detected are likely to be read-through.

Northern blot analyses performed using the psbA 3'UTR probe (FIG. 51C, lanes 1-3), revealed a pattern consistent to that obtained using the gene-specific tps1 probe (see FIG. 49B). In addition, the native psbA transcript was also detected and was similar in abundance to the aadA/tps1 dicistron (FIG. 51C, a). However, transcript abundance cannot be quantitatively compared because they are regulated by different promoters. Larger, less abundant transcripts (FIG. 51C, b-c) were also detected with the gene-specific tps1 probe (see FIG. 49B), and may correspond to read-through transcripts.

Western blot analyses performed to detect the trehalose phosphate synthase revealed efficient translation of polycistrons, as shown by the abundant accumulation of a 65 kDa polypeptide corresponding to this protein (FIG. 49F).

Because no monocistrons for tps1 or aadA were detected in the northern blot analyses, hyperexpression of TPS1 should thus be the result of efficient translation of polycistrons in transgenic chloroplasts.

Transcription and Translation of the ctb Operon

RNA from chloroplast transgenic lines transformed with the aadA-ctxb (referred to as RBS-CTB lines) or 5'UTR-ctxb-gfp fusion constructs (5'UTR-CTB-GFP lines) were also analyzed by northern blots. The RBS-CTB lines showed dicistrons and polycistrons, whereas the 5'UTR-CTB-GFP transgenic lines showed monocistrons along with several polycistrons. Predicted dicistrons of 1.3 knt (FIGS. 50B, a and D, a) and 2.3 knt (FIGS. 50B, d and D, d) transcribed from the engineered Prrn promoter were detected with either the ctxb or aadA probe. Additionally, polycistrons transcribed from the native 16S Prrn were observed in both transgenic lines. In the RBS-CTB transgenic lines, the aadA-ctxb polycistron was of a predicted size of 3.8 knt (FIGS. 50B, f and D, f), while in the 5' UTR-CTB-GFP transgenic line aadA-5'-UTR-ctxb-gfp polyciston was 4.8 knt (FIGS. 50B, g and D, g); both polycistrons code for four genes (16 rRNA gene, trnI gene plus the two heterologous genes). Polycistronic transcripts of higher molecular weight appear to terminate downstream from the engineered 3'UTR (FIG. 50B, D, i, h), as well as the transcripts of ~2.2 knt (FIG. 50A,B, c) and ~3.5 knt (FIG. 50A,B,e), obtained from the engineered Prrn promoter and processed downstream of the 3'UTR in the gene construct. The cxtb-gfp monocistron of 1.4 knt (FIG. 50B, b) was detected with the ctxb probe but not with the aadA probe; besides this transcript, no other monocistron was detected in these analyses. Its average relative abundance was 42.1±3% of the total heterologous transcripts in the 5'UTR-CTB-GFP transgenic lines (FIG. 50C, b), while the total combined abundance of the polycistrons averaged 56% (FIG. 50C, d, g), with the polycistron transcribed from the engineered Prm accounting for 22.9±1% of the total transcripts (FIG. 50C, d). For the RBS-CTB transgenic line, 100% of the transcripts were polycistrons, of which the most abundant transcript was the aadA-ctxB dicistron, (about 45% of the total transcripts), followed by approximately 30% of the polycistron transcribed from the engineered Prrn and processed downstream at the trnA gene (FIG. 50D, a. c and E, a, c).

Additional northern blot analyses performed with the psbA 3'UTR probe (FIG. 51D) revealed a transcript pattern consistent to that obtained with the ctxB gene-specific probe (see FIG. 50B). Furthermore, the native psbA transcript was also detected. Because the size of the aadA/ctxb dicistron (1.25 knt) is similar to that of the endogenous psbA (1.3 knt), they could not be distinguished from each other. However, this may account for the increase in transcript abundance observed in relation to the native psbA transcript (FIG. 51D, lanes wt and 1-3a*). Due to similar reasons, the increase in transcript abundance of the native psbA transcript observed on the 5'UTR-CTB-GFP transgenic lines (FIG. 51D, lanes 4-6b*) could be due to the presence of the ctxb-gfp monocistron (1.4 knt). Although, the native psbA and the ctxb-gfp genes are regulated by the same psbA promoter, transcript abundance could be quantitatively compared. However, because both transcripts are similar in size, comparison between these native and heterologous transcripts was not possible.

The western blot analyses showed that transgenic lines expressing either CTB or CTB-GFP fusion produced large amounts of either protein (FIG. 50F, G). CTB protein was detected as a higher molecular weight polypeptide (trimer of 35 kDa) than the $E.\ coli$ expressed CTB (FIG. 50F). High protein level was also detected for the gfp-ctxB fusion protein (FIG. 50G), which was detected in the monomeric form (45 kDa). Interestingly, expression levels in both transgenic lines were similar, even though in the aadA-5'UTR-ctxb-gfp transgenic line the more abundant transcript was the monocistron. This again suggests that polycistrons are translated as effectively as monocistrons.

Discussion

The chloroplast genome has been engineered with single genes to confer useful agronomic traits including herbicide resistance (Daniell et al., 1998), insect resistance (McBride et al., 1995; Kota et al., 1999, De Cosa et al., 2001), disease resistance (DeGray et al., 2001), drought tolerance (Lee et al., 2003), salt tolerance (Kumar et al., 2004a), and phytoremediation (Ruiz et al., 2003). Recent success in transforming the chloroplast genome of several major crops, including cotton (Kumar et al., 2004b) and soybean (Dufourmantel et al., 2004) has opened this field for commercial development. Because most of the desired traits require multigene engineering, it is important to understand transcription, posttranscriptional changes and translation of heterologous polycistrons within plastids.

Transcript analyses performed in this study repeatedly confirmed that different transgenic lines harboring multigenic operons generated polycistrons as the most abundant transcript form, along with monocistronic mRNA. This observation is further supported by the polysome fractionation assays performed on the cry2Aa2 samples, in which larger transcripts were collected from the fractions associated to polyribosomes. Smaller transcripts were observed mainly in the upper fractions of the gradient, suggesting that polycistrons may be preferentially translated without processing. Similar results were obtained after stripping the membranes and re-probing with the orf1,2 probe. Polycistronic polysomal RNA has been previously reported in native chloroplast operons, as well as multiple open reading frames simultaneously translated from polycistions (Barkan, 1988), however, in such case, polycistronic transcripts were less abundant than monocistrons. In the case of the cry2Aa2 operon, ribosome-associated polycistrons were in much higher abundance than the monocistronic transcripts, suggesting that the heterologous operon is preferentially translated as a polycistronic unit. Similar results were observed with chloroplast transgenic lines harboring the aadA-orf1-orf2-hsa operon (data not shown). These observations contrast with the general consensus for native chloroplast translation mechanisms (Barkan, 1988; Barkan et al., 1994; Zerges, 2000; Meierhoff et al., 2003), thus showing that multigene operons engineered into the chloroplast genome do not necessarily require processing of polycistrons to monocistrons or dicistrons for efficient translation.

Processing was observed in the native cry2Aa2 operon, between orf2 and the cry2Aa2 genes on the transgenic lines. However, this event did not occur between orf1 and orf2 of this operon, or at intergenic sequences of the other engineered operons studied. The fact that processing occurred only in the cry2Aa2 5'UTR suggests that this intergenic sequence might contain unique information required for processing. By using computer simulation, it was observed that the heterologous bacterial intergenic transcript sequences, may form secondary structures. Evidence for the protection of chloroplast RNA by 5'UTRs has been previously discussed (Drager et al., 1998), as well as the role of 5'UTR secondary structures in RNA stability (Zou et al., 2003). Additionally, previous reports have shown that, intergenic sequences forming stable secondary structures that mask the ribosome-binding site, may affect the translation of the downstream gene (Barkan et al., 1994; Hirose and Sugiura 1997; Del Campo et al., 2002). These observations offer the possibility of further studies involving the role of intergenic secondary structures of native and heterologous operons in post-transcriptional processes.

Transgenic lines harboring the engineered aadA-orf1-orf2-hsa operon showed no difference in HSA accumulation in response to light or dark conditions, in contrast to those transformed with the hsa gene and native psbA 5' UTR. This suggests that the translation enhancement observed is not light-dependent. Thus, the heterologous cry2aA2 operon UTR region is independent of nuclear and chloroplast control, unlike the psbA regulatory sequences (Fernandez San Millan, et al., 2003; Zerges, 2004). Such heterologous UTRs have played a major role in transgene expression in non-green tissues, such as carrot roots (Kumar et al., 2004a), or in non-green cultured cells (Kumar et al., 2004 a, b), to facilitate transformation of recalcitrant crops.

Data shown here supports the idea that engineered operons in the chloroplast, which do not carry any intergenic sequences capable of forming stable secondary structures, can be translated very efficiently and do not require processing into monocistrons in order to be translated. The processing observed in the cry2Aa2 transgenic lines may be due to endonucleolytic cleavage of a region in the intergenic sequence, but it does not indicate that this processing has to occur in order for translation to take place. An interesting observation is that the aadA-orf1-orf2 tricistron produced by the processing event does not contain a 3' UTR region, yet this transcript is as abundant as the polycistrons, which contain the 3'UTR and are efficiently translated. This shows that polycistrons may be stable in the chloroplast, even in the absence of the 3'UTR.

In chloroplasts, all of the genes in the 16S rrn operon, including the trnA, trnI, as well as 23S, 4.5S and 5S rrn genes (which are downstream of the integrated transgenes), are transcribed from the native Prrn promoter. Therefore, disruption of these polycistrons by the insertion of the foreign operon due to effective termination at the 3' untranslated regions would mean that the trnA and other downstream genes would not be transcribed, affecting chloroplast protein synthesis. However, this was not the case; all the transgenic lines grew similar to the wild type plants, indicating that the read-through transcripts formed by the insertion of foreign operons were sufficient for optimal ribosome synthesis in chloroplasts. Read-through transcripts processed at the trnA region accounted for about 26 to 39% of the total heterologous transcripts in all transgenic lines tested whereas, in HSA-expressing transgenic lines, this percentage was between 15% and 32%. Introns within the trnA gene undergo splicing and other posttranscriptional modifications in order to produce the functional trnA (Barkan et al., 2004). Therefore, such processing may modify polycistronic transcripts that read through from the 3'UTR psbA engineered in these chloroplast vectors. Additionally, larger polycistrons were also detected, although these were not quantified.

The transcript profile for the transgenic lines 5'UTR-hsa and 5'UTR-ctxb-gfp, (the only two transgenic lines in this study that transcribed monocistrons) was very similar The monocistronic transcripts accounted for about 42% to 50% of the total heterologous transcripts examined. The total polycistronic levels in these two transgenic lines, including read-through transcripts were between 50% and 57%. In all the transgenic lines that did not transcribe monocistrons, the most abundant transcript was transcribed from the engineered Prm promoter, terminating at the 3'UTR, which accounted for 43% to 59% of the total transcripts detected.

Data generated by analyzing the different transcripts with the psbA 3'UTR probe not only supported the previous results observed with the gene-specific probes, but also allowed comparison with the native psbA transcripts. In two transgenic lines (5'UTR-HSA and 5'UTR-CTB-GFP), the psbA 5'UTR was used upstream of the genes of interest. In such cases, endogenous versus heterologous transcript abundance could be quantitatively compared, unless the 5'utr-ctxb-gfp transcript was similar in size to the native psbA gene. Comparison of the native psbA and 5'utr-hsa transcripts showed a greater abundance (1.6 times) of the heterologous transcript. This could be attributed to gene dosage, as the heterologous operons are integrated into the inverted repeat region, whereas the native psbA gene is located in the single-copy region. In addition, transcript abundance was variable among the remaining heterologous operons regulated by the 16S prrn promoter. Variability could be attributed to differences in mRNA stability, as well as in the level of posttranscriptional processing of the primary transcripts (Barkan and Goldschmidt-Clermont, 2000; Monde et al., 2000b; del Campo et al., 2002).

The ability to engineer foreign genes without promoters or other regulatory sequences has several advantages. Also, repeated sequences may cause deletion of the transgene (Iamtham and Day, 2000). Observations reported here show evidence for transcription and processing of heterologous operons. While endogenous polycistrons require processing for effective translation, this is not required for expression of foreign operons. Native polycistrons require chloroplast specific 3'UTRs for stability, which is not always required for heterologous polycistrons. Untranslated regions in native transcripts are regulated by nuclear factors, whereas heterologous transcripts have not been shown to be dependent of such regulations. Specific nuclear-encoded factors recognize sequences in native transcripts for the processing of primary mRNA (Barkan, 2004). This is not the case in foreign operons where heterologous sequences can be recognized and processed by the chloroplast posttranscriptional machinery. Finally, in both native and foreign operons there are abundant read-through transcripts that allow the expression of genes downstream of 3'UTRs. Addressing questions of the translation of polycistrons and sequences required for transcript processing and stability is essential for chloroplast metabolic engineering. Knowledge of such factors would enable engineering pathways that will not be under the complex post-transcriptional regulatory machinery of the chloroplast.

One of the primary advantages of using heterologous sequences for increasing gene expression is the lack of cellular control over these sequences, allowing the enhancement of transgene expression in green and non-green tissues. Recently, the use of the g10 5'UTR facilitated the transformation of non-green plastids of carrot (Kumar et al., 2004a). Additionally, the use of a gene cassette containing the selectable marker genes under the regulation of heterologous UTRs, increased transformation efficiency and facilitated cotton plastid transformation (Kumar et al., 2004b). Recent accomplishments in the transformation of agronomically important species through somatic embryogenesis using species-specific chloroplasts vectors, also broadens the possibility of extending this technology to crops that have been, until now, recalcitrant to chloroplast transformation (Dufourmantel et al., 2004; Kumar et al., 2004a; Kumar et al., 2004b; Daniell et al 2005).

In this study, we report the translation of polycistronic transcripts without processing, the expression of multigene operons independently of cellular control, and the stability of heterologous polycistrons lacking a 3'UTR. These results suggest that it is possible to effectively express multiple genes via the chloroplast genome without significant intervention of chloroplast regulation. The findings of this study facilitate multigene engineering via the plastid genome in both green and non-green plastids. One embodiment of the invention relates to a vector suitable for integration into the chloroplast genome that comprises multigene operons, a plant stably transformed with such a vector and a method of transforming a plant with such a vector.

The results reported here are the first attempts to understand multigene engineering in transgenic plastids.

Materials and Methods

Chloroplast Transformation, Selection and Characterization of Transgenic Plants

The chloroplast transformation, selection and characterization of the transgenic lines used in this study have been previously reported (Daniell et al., 2001; De Cosa et al., 2001; Lee et al., 2003; Fernandez-San Millan et al., 2003) with the exception of the ctb-gfp transgenic lines. Sterile tobacco leaves were bombarded using the Bio-Rad PDS-1000/He biolistic device as described previously (Daniell, 1997; Daniell et al., 2004a, b).

Chloroplast Expression Vector Carrying the hsa Gene.

The pLDA-sdHSA vector was constructed by inserting the hsa gene (1.8 kb) into EcoRI/NotI sites of the multiple cloning site of the chloroplast transformation vector (pLD-ctv). This construct contained the hsa gene and a ribosome binding site sequence (ggagg) upstream of the gene. For the pLDA-5'UTR-hsa vector, the promoter and 5'UTR (205 bp) from psbA gene were amplified by PCR from tobacco chloroplast DNA and then sequenced. The subsequent in-frame cloning of the promoter/5'UTR upstream and hsa gene into pLD-ctv vector by EcoRI/NotI digestion produced the functional gene cassette.

Chloroplast Expression Vector Carrying the ctxB Gene.

A ribosome binding site (GGAGG) was engineered five bases upstream of the start codon of the ctxB gene. The PCR product was then cloned into pCR2.1 vector (Invitrogen) and subsequently cloned into the chloroplast transformation vector (pLD-ctv) after the sequencing of the open reading frame. The pLD vector carrying the ctxB gene was used for successive transformation of tobacco chloroplast genome according to the published protocol.

Chloroplast Expression Vector Carrying the tps1 Gene.

The yeast trehalose phosphate synthase (tps1) gene was inserted into the XbaI site of the universal chloroplast expression (pCt) vector between the aadA selection marker gene for spectinomycin resistance and the psbA terminator to form the final pCt-tps1 vector.

Chloroplast Expression Vector Carrying the Cry2Aa2 Operon.

The cry2Aa2 operon from the HD-1 strain (Delattre et al., 1999) was inserted into the universal chloroplast expression vector, pLD ctv, to form the final shuttle vector pLD-BD Cry2Aa2 operon (De Cosa et al., 2001). This vector contains the 16S ribosomal RNA (rRNA) promoter (Prrn) upstream of the aadA gene (aminoglycoside 3'-adenylyltransferase) for spectinomycin resistance, the three genes of the cry2Aa2 operon, and the psbA terminator from the 3' region of the chloroplast photosystem II gene.

Plant Transformation

Tobacco leaves were transformed by particle bombardment (Bio-Rad PDS-1000He device), using 0.6 nm gold microcarriers coated with the pCt-TPS1 chloroplast expression vector, and delivered at 1,100 psi with a target distance of 9 cm (Daniell, 1997). The bombarded leaves were selected on RMOP medium containing 500 ng/ml spectinomycin to regenerate the transformants, as previously described (Kumar and Daniell, 2004; Daniell et al., 2004a)

Northern-Blot Analysis

Total plant RNA from untransformed tobacco (var. Petit Havana) and from three clones of $T_1$ chloroplast transgenic tobacco plants, was isolated by using the RNeasy Mini Kit (Qiagen, Valencia, Calif.) and protocol. Northern blot analyses were performed essentially as follows. Total RNA (1 µg) per plant sample was resolved in a 1.2% (w/v) agarose/formaldehyde gel at 55 V for 2.5 h. The RNA was transferred overnight to a nitrocellulose membrane by capillarity. The next day, the membrane was rinsed twice in 2×SSC (0.3 M NaCl and 0.03 M sodium citrate), dried on Whatman paper, and then cross-linked in the GS Gene Linker (Bio-Rad, Hercules, Calif.) at setting C3 (150 njouls).

The probes used for northern blot analyses were obtained as follows: the aadA (aminoglycoside 3' adenylyl transferase) probe was obtained by BstEII/XbaI restriction digestion of plasmid pUC19-16S/aadA; the ctxB (cholera toxin β-subunit) and tps1 (trehalose phosphate synthase) probes were obtained by XbaI restriction digestion of plasmids pSBL-CTB and pSBL-TPS1, respectively. The Cry2Aa2 (*Bacillus thuringiensis* insecticidal protein) probe was obtained by XbaI digestion of plasmid pSBL-ctv-CryIIA. The hsa (human serum albumin) probe was obtained by EcoRV/NotI digestion of plasmid pCR2.1 ATG-HSA. Finally, the orf 1,2 probe was obtained by EcoRI digestion of plasmid pCR2.1 ORF1,2 and the psbA 3'UTR probe was obtained by pstI/XbaI digestion of plasmid pLD-ctv.

Probes were radio labeled with $^{32}P$ dCTP by using Ready Mix® and Quant G-50® micro columns for purification (Amersham, Arlington Heights, Ill.). Prehybridization and hybridization were performed using the Quick-Hyb® solution (Stratagene, La Jolla, Calif.). The membrane was then washed twice for 15 min at room temperature in 2×SSC with 0.1% (w/v) SDS, followed by two additional washes at 60° C. (to increase the stringency) for 15 min with 0.1×SSC with 0.1% (w/v) SDS. Radiolabeled blots were exposed to x-ray films and then developed in the Mini-Medical Series x-ray film processor (AFP Imaging, Elmsford, N.Y.). When required, membranes were stripped by applying boiling 0.1% SSC and 0.1% SDS to the membrane, washing for 15 minutes, and repeating before re-hybridizing with a different probe.

Relative transcript levels within each lane were measured by spot densitometry (Alphaimager 3300, Alpha Innotech, San Leandro, Calif.) on radiograms from the different northern blot analyses, except those obtained using the psbA 3'UTR probe. The former are shown as percentage of abundance within each line and therefore comparison among lines cannot be made. For the blots obtained by hybridization with the psbA 3'UTR probe, transcript abundance was quantified by using the wild-type native psbA transcript, to which a value of 1 was assigned. All other transcripts show values greater or smaller than 1, depending on abundance in relation to the wild-type psbA transcript, and are shown as additive values in each line. Average transcript abundance was calculated among corresponding clones and the standard deviation was determined Polysomal Fractionation Assays Approximately 0.3 grams of leaf material from transgenic tobacco harboring the cry2Aa2 operon were thoroughly ground in liquid nitrogen and resuspended in polysome extraction buffer (Barkan, personal communication). The ground tissue was treated according to the protocol described by Barkan (1988), with some modifications. The samples were treated with 0.5% sodium deoxycholate and loaded onto 15%-55% sucrose gradients and centrifuged at 45,000 rpm for 65 minutes (Beckmann rotor SW52Ti). Fractions were collected from the bottom of the tube onto microcentrifuge tubes containing 50 µl 5% SDS and 0.2M EDTA, up to a volume of about 500 µl for each fraction. Polysomal RNA was extracted with phenol:chloroform:isoamyl-alcohol (25:24:1), followed by ethanol precipitation. The resulting pellets were resuspended in RNase-free TE buffer (pH 8.0) and stored at −80° C., or loaded onto denaturing 1.2% agarose-formaldehyde gels (5 µl from each fraction). Northern blot analyses were then performed as described above. Blots were hybridized with cry2Aa2 and orf1,2 probes.

To provide further evidence that the RNA obtained from the bottom fractions of the sucrose gradient corresponded to polysome-associated RNA, a puromycin-release control was included. Before treatment with sodium deoxycholate, samples were treated with 150 µl of 2M KCl and 170 µl of puromycin (3 mg/ml stock) and incubated 10 minutes at 37° C. Sodium deoxycholate was then added to 0.5%, and the samples were incubated 5 minutes on ice before loading onto the sucrose gradient. RNA extraction and Northern blot analyses were performed as described above. The blots were hybridized with the aadA and orf1,2 probes.

Western-Blot Analyses

Protein samples were obtained from 100 mg of leaf material from the same wild type and transgenic lines used in the Northern analyses by grinding the tissue to a fine powder in liquid nitrogen. Subsequent homogenization in 200 µl plant protein extraction buffer (100 mM NaCl, 10 mM EDTA, 200 mM Tris-HCl, 0.05% (w/v) Tween-20, 0.1% (w/v) SDS, 14 mM β-mercaptoethanol (BME), 400 mM sucrose and 2 mM phenylmethylsulfonyl fluoride) was performed, followed by a centrifugation step at 15.7×g for 1 minute to remove solids. The *Bacillus thuringiensis* Cry2Aa2 protein was extracted from 100 mg of transgenic leaf material by adding 200 µl of 50 mM NaOH to solubilize the Cry protein from the crystals formed in the transgenic plants, and centrifuged at 10,000×g for 1 minute to remove cell debris. Total protein concentrations for the samples were determined by Bradford assay (Bio-Rad Protein Assay) with bovine serum albumin as the protein standard.

Approximately 60 µg of total soluble protein was loaded onto 12% v/v SDS-polyacrylamide gels and separated by electrophoresis. The separated proteins were then transferred to a nitrocellulose membrane (Bio-Rad, Hercules, Calif.). The membrane was blocked for 1 hr with PTM buffer: 1×PBS (phosphate buffer solution), 0.05% (v/v) Tween-20 and 3% (w/v) non-fat dry milk The membranes were probed with primary and secondary antibodies as follows: for 2 hrs with primary antibody, then rinsed with water twice and probed with secondary antibody for 1.5 hrs. Finally, the membranes were washed 3 times for 15 minutes with PT buffer (1×PBS, 0.05% (v/v) Tween-20) and one time with 1×PBS for 10 minutes, followed by incubation in Lumi-Phos® WB (Pierce, Rockford, Ill.) reagent for the alkaline phosphatase reaction or SuperSignal (Pierce) reagent for horseradish peroxidase (HRP) reaction.

Film exposure took place for 1, 3, 5 or 10 minutes, depending on the strength of the signal of each blot. The antibodies used and their respective dilutions were the following: anti-cry2A (Envirologix, Portland, Me.), dilution 1:3,000; anti-ORF2 (Moar et al., 1989), dilution 1:1,000;

anti-HSA (Sigma, St. Louis, Mo.), dilution 1:3,000; anti-CTB (Sigma), dilution 1:2,500; anti-PA (Dr. Stephan Leppla, NIH), dilution 1:30,000. Secondary antibodies were used as follows: alkaline phosphatase conjugated anti-rabbit antibody (Sigma) was used to probe against every primary antibody with the exception of anti-PA which was probed with HRP conjugated anti-mouse antibody; dilutions of 1:5,000 anti-rabbit antibody were used for anti-HSA, anti-ORF2 and anti-Cry2A, for anti-CTB the dilution was 1:4,000. Anti-mouse antibody was used in a 1:5,000 dilution.

ELISA Quantification

The Human Albumin Quantitation Kit (Bethyl Laboratories) was used for ELISA quantification. Leaf material (100 mg) of the aadA-orf1-orf2-hsa transgenic line was ground in liquid nitrogen and resuspended in 700 µl of 50 mM NaOH. The leaf extracts were then diluted to fit in the linear range of the provided HSA standard. Absorbance was read at 450 nm. The DC protein assay (Bio-Rad) was used to determine total soluble protein concentration following the manufacturer's protocol.

REFERENCES

Adams C C, Stern D B (1990) Control of mRNA stability in chloroplasts by 3' inverted repeats: effects of stem and loop mutations on degradation of psbA mRNA in vitro. Nucleic Acids Res 18: 6003-6010.

Barkan A (1988) Proteins encoded by a complex chloroplast transcription unit are each translated from both monocistronic and polycistronic mRNAs. EMBO J. 7: 2637-2644.

Barkan A (2004) Intron splicing in plant organelles. In H Daniell, C Chase eds, Molecular Biology and Biotechnology of Plant Organelles, Kluwer Academic Publisher, The Netherlands, pp. 291-318.

Barkan A, Goldschmidt-Clermont M (2000) Participation of nuclear genes in chloroplast gene expression. Biochimie 82: 559-572.

Barkan A, Walker M, Nolasco M, Johnson D (1994) A nuclear mutation in maize blocks the processing and translation of several chloroplast mRNAs and provides evidence for the differential translation of alternative mRNA forms. EMBO J. 13: 3170-3181.

Bogorad L (2000) Engineering chloroplasts: an alternative site for foreign genes, proteins, reactions and products. Trends Biotechnol 18: 257-263.

Bruick R K, Mayfield S P (1999) Light-activated translation of chloroplast mRNAs. Trends Plant Sci 4: 190-195.

Chen H C, Stern D B (1991) Specific ribonuclease activities in spinach chloroplasts promote mRNA maturation and degradation. J Biol Chem 266: 24205-11

Choquet Y, Wollman F A (2002) Translational regulations as specific traits of chloroplast gene expression. FEBS letters 529: 39-42.

Daniell H (1997) Transformation and foreign gene expression in plants mediated by microprojectile bombardment. Methods Mol Biol 62: 453-488.

Daniell H (2002) Molecular strategies for gene containment in transgenic crops. Nat Biotechnol 20: 581-586.

Daniell H, Dhingra A (2002) Multigene engineering: dawn of an exciting new era in biotechnology. Curr Opin Biotech 13: 136-141.

Daniell H, Carmona-Sanchez O, Burns B B (2004b) Chloroplast derived antibodies, biopharmaceuticals and edible vaccines. In R Fischer, S Schillberg eds, Molecular Farming, WILEY-VCH Verlag, Winheim, pp. 113-133.

Daniell H, Cohill P R, Kumar S, Dufourmantel N, Dubald M (2004c) Chloroplast genetic engineering. In H Daniell, C Chase, eds, Molecular Biology and Biotechnology of Plant Organelles, Kluwer Academic Publishers, The Netherlands, pp. 437-484.

Daniell H, Datta R, Varma S, Gray S, Lee S B (1998) Containment of herbicide resistance through genetic engineering of the chloroplast genome. Nature Biotechnol 16: 345-348.

Daniell H, Khan M S, Allison L (2002) Milestones in chloroplast genetic engineering: an environmentally friendly era in biotechnology. Trends Plant Sci 7: 84-91.

Daniell H, Kumar, S, Dufourmantel, N (2005) Breakthrough in chloroplast genetic engineering of agronomically important crops. Trends Biotechnol 23:238-245.

Daniell H, Lee S B, Panchal T, Wiebe P O (2001) Expression of the native cholera toxin B subunit gene and assembly as functional oligomers in transgenic tobacco chloroplasts. J Mol Biol 311: 1001-1009.

Daniell H, Ruiz O N, Dhingra A (2004a) Chloroplast genetic engineering to improve agronomic traits. Methods Mol Biol 286: 111-137.

Danon A (1997) Translational regulation in the chloroplast. Plant Physiol 115: 1293-1298.

DeCosa B, Moar W, Lee S B, Miller M, Daniell H (2001) Overexpression of the Bt cry2Aa2 operon in chloroplasts leads to formation of insecticidal crystals. Nature Biotechnol 19: 71-74.

DeGray G, Rajasekaran K, Smith F, Sanford J, Daniell H (2001) Expression of an antimicrobial peptide via the chloroplast genome to control phytopathogenic bacteria and fungi. Plant Physiol 127: 852-862.

Del Campo E M, Sabater B, Martin M (2002) Post-transcriptional control of chloroplast gene expression. Accumulation of stable psaC mRNA is due to downstream RNA cleavages in the ndhD gene. J Biol Chem 277: 36457-36464.

Delattre D, Rang C, Lecointe N, Royer M, Delecluse A, Moar W J Frutos R (1999) Expression of orf1 from the *Bacillus thuringiensis* NRD-12 cry2Aa1 Operon. Current Microbiology, 39:9-13.

Deng X W, Gruissem W (1987) Control of plastid gene expression during development: the limited role of transcriptional regulation. Cell 8: 379-87.

Dhingra A, Portis A R Jr., Daniell H (2004) Enhanced translation of a chloroplast-expressed RbcS gene restores small subunit levels and photosynthesis in nuclear RbcS antisense plants. Proc Natl Acad Sci USA 101: 6315-6320.

Drager R G, Girard-Bascou J, Choquet Y, Kindle K L, Stern D B (1998) In vivo evidence for 5'-3' exoribonuclease degradation of an unstable chloroplast mRNA. Plant Journal 13:85-96.

Dufourmantel N, Pelissier B, Garcon F, Peltier J M, Tissot G (2004) Generation of fertile transplastomic soybean. Plant. Mol. Biol. 55: 479-489.

Eibl C, Zou Z, Beck A, Kim M, Mullet J, Koop H U (1999) In vivo analysis of plastid psbA, rbcL and rpl32 UTR elements by chloroplast transformation: tobacco plastid gene expression is controlled by modulation of transcript levels and translation efficiency. The Plant J 19: 333-345.

Fernandez-San Millan A, Mingo-Castel A, Miller M, Daniell H (2003) A chloroplast transgenic approach to hyper-express and purify human serum albumin, a protein highly susceptible to proteolytic degradation. Plant Biotechnol J 1: 71-79.

Goldschmidt-Clermont M (1991) Transgenic expression of aminoglycoside adenine transferase in the chloroplast: a selectable marker for site-directed transformation of *chlamydomonas*. Nucleic Acids Research 19: 4083-4089.

Hashimoto M, Endo T, Peltier G, Tasaka M, Shikanai T (2003) A nucleus-encoded factor, CRR2, is essential for the expression of chloroplast ndhB in *Arabidopsis*. Plant J 36: 541-549.

Hirose T, Sugiura M (1997) Both RNA editing and RNA cleavage are required for translation of tobacco chloroplast ndhD mRNA: a possible regulatory mechanism for the expression of a chloroplast operon consisting of functionally unrelated genes. EMBO J. 16: 6804-6811.

Iamtham S, Day A (2000) Removal of antibiotic resistance genes from transgenic tobacco plastids. Nature Biotechnol 18:1172-1176.

Jiao H S, Hicks A, Simpson C, Stern D B (2004) Short dispersed repeats in the *Chlamydomonas* chloroplast genome are collocated with sites for mRNA 3' end formation. Curr Genet. 45: 311-22.

Kota M, Daniell H, Varma S, Garczynski S F, Gould F, William M J (1999) Overexpression of the *Bacillus thuringiensis* (Bt) Cry2Aa2 protein in chloroplasts confers resistance to plants against susceptible and Bt-resistant insects. Proc Natl Acad Sci USA 96: 1840-1845.

Kumar S, Daniell H (2004) Engineering the chloroplast genome for hyper-expression of human therapeutic proteins and vaccine antigens. Methods Mol Biol 267: 365-383.

Kumar S, Dhingra A, Daniell H (2004a) Plastid expressed betaine aldehyde dehydrogenase gene in carrot cultured cells, roots and leaves confers enhanced salt tolerance. Plant Physiol 136: 2843-2854.

Kumar S, Dhingra A, Daniell H (2004b) Manipulation of gene expression facilitates cotton plastid transformation by somatic embryogenesis and maternal inheritance of transgenes. Plant Mol Biol 56: 203-216.

Lee S B, Kwon H B, Kwon S J, Park S C, Jeong M J, Han S E, Byun M O, Daniell H (2003) Accumulation of trehalose within transgenic chloroplasts confers drought tolerance. Mol Breed 11: 1-13.

Leelavathi S, Gupta N, Maiti S, Ghosh A, Reddy V S (2003) Overproduction of an alkali- and thermo-stable xylanase in tobacco chloroplasts and efficient recovery of the enzyme. Mol Breed 11: 59-67.

Lezhneva L, Meurer J (2004) The nuclear factor HCF145 affects chloroplast psaA-psaB-rps14 transcript abundance in *Arabidopsis thaliana*. The Plant Journal 38: 740-753.

Lossl A, Eibl C, Harloff H J, Jung C, Koop H U (2003) Polyester synthesis in transplastomic tobacco (*Nicotiana tabacum* L.): significant contents of polyhydroxybutyrate are associated with growth reduction. Plant Cell Rep 21: 891-899.

Ma J K, Hiatt A, Hein M, Vine N D, Wang F, Stabila P, van Dolleweerd C, Mostov K, Lehner T (1995) Generation and assembly of secretory antibodies in plants. Science 268: 716-719

McBride K E, Svab Z, Schaaf D J, Hogan P S, Stalker D M, Maliga P (1995) Amplification of a chimeric *Bacillus* gene in chloroplasts leads to an extraordinary level of an insecticidal protein in tobacco. Bio/Technology 13: 362-365.

Meierhoff K, Felder S, Nakamura T, Bechtold N, Schuster G (2003) HCF152, an *Arabidopsis* RNA binding pentatricopeptide repeat protein involved in the processing of chloroplast psbB-psbT-psbH-petB-petD RNAs. Plant Cell 15: 1480-1495.

Moar W. J, Trumble J T, Federici B A (1989) Comparative toxicity of spores and crystals from the NRD-12 and HD-1 strains of *Bacillus thuringiensis* subsp. *kurstaki* to neonate beet armyworm (Lepidoptera:Noctuidae). J. Econ. Entomol. 82: 1593-1603.

Monde R A, Greene J C, Stern D B (2000a) Disruption of the petB-petD intergenic region in tobacco chloroplasts affects petD RNA accumulation and translation. Mol Gen Genet. 263: 610-8.

Monde R, Schuster G, Stern D B (2000b) Processing and degradation of chloroplast mRNA. Biochimie 82: 573-582.

Nawrath C, Poirier Y, Somerville C (1994) Targeting of the polyhydroxybutyrate biosynthetic pathway to the plastids of *Arabidopsis thaliana* result in high levels of polymer accumulation. Proc Natl Acad Sci 91: 12760-12764.

Nickelsen J (2003) Chloroplast RNA-binding proteins. Curr Genet. 43: 392-399.

Rochaix J D (1996) Post-transcriptional regulation of chloroplast gene expression in *Chamydomonas reinhardtii*. Plant Mol Biol 32: 327-341.

Rochaix J D, Kuchka M, Mayfield S, Schirmer-Rahire M, Girard-Bascou J, Bennoun P (1989) Nuclear and chloroplast mutations affect the synthesis or stability of the chloroplast psbC gene product in *Chlamydomonas reinhardtii*. EMBO J. 8: 1013-1021.

Ruiz O N, Hussein H, Terry N, Daniell H (2003) Phytoremediation of organomercurial compounds via chloroplast genetic engineering. Plant Physiol. 132: 1344-1352.

Stern D B, Gruissem W (1987) Control of plastid gene expression: 3' inverted repeats act as mRNA processing and stabilizing elements, but do not terminate transcription. Cell 51:1145-57.

Sugita M, Sugiura M (1996) Regulation of gene expression in chloroplasts of higher plants. Plant Mol Biol 32: 315-26.

Tanaka M, Obokata J, Chunwongse J, Shinozaki K, Sugiura M (1987) Rapid splicing and stepwise processing of a transcript from the psbB operon in tobacco chloroplast: Determination of the intron sites in petB and petD. Mol Gen Genet. 209: 427-431.

Watson J, Koya V, Leppla S H, Daniell H (2004) Expression of *Bacillus anthracis* protective antigen in transgenic tobacco chloroplasts: development of an improved anthrax vaccine in a non-food/feed crop. Vaccine 22: 4374-4384.

Westhoff P, Herrmann R G (1988) Complex RNA maturation in chloroplasts. The psbB operon from spinach. Eur J Biochem 171: 551-64.

Widner W R Whiteley H R (1989) Two highly related insecticidal crystal proteins of *Bacillus thuringiensis* subsp. *Kurstaki* possess different host range specificities. Journal of Bacteriology 171:965-974.

Ye X, Al-Babili S, Kloti A, Zhang J, Lucca P, Beyer P, Potrykus I (2000) Engineering the provitamin A (□-carotene) biosynthetic pathway into (carotenoid-free) rice endosperm. Science 287: 303-305.

Zerges W. (2000) Translation in chloroplasts. Biochimie 82: 583-601.

Zerges W, Rochaix J D (1994) The 5' leader of a chloroplast mRNA mediates the translational requirements for two nucleus-encoded functions in *Chlamydomonas reinhardtii*. Mol Cell Biol 14: 5268-5277.

Zerges W (2004) The regulation of translation and protein complex assembly in the plastids. In H Daniell and C Chase eds, Molecular Biology and Biotechnology of Plant Organelles, Kluwer Academic Publisher, The Netherlands, pp. 343-379.

Zou, Z, Eibl, C, Koop, H U (2003) The stem-loop region of the tobacco psbA 5'UTR is an important determinant of mRNA stability and translation efficiency. Mol Genet Genomics 269: 340-349.

Example 7: Efficacy and Functionality of Chloroplast-Derived Anthrax Protective Antigen Introduction Anthrax, a fatal bacterial infection, is caused by *Bacillus anthracis*, a gram-positive spore-forming organism. It is a zoonotic disease transmitted from animals to humans. CDC lists *Bacillus anthracis* as a category A biological agent due to its severity of impact on human health, high mortality rate, acuteness of disease, and potential for delivery as a biological weapon. The disease is acquired when spores enter the body through the skin or by inhalation or ingestion. Virulent strains of *B. anthracis* contain plasmids pX01, which carries genes encoding the toxins, and pX02, which encodes the poly-Dglutamic acid capsule. Plasmid pX01 carries the genes pagA, lef, and cya that encode the protective antigen (PA), lethal factor (LF), and edema factor (EF), respectively. The term "protective antigen" is derived because of this protein's ability to elicit a protective immune response against anthrax. None of these proteins is toxic when administered individually to cells or animals. However, PA in combination with EF, known as edema toxin, causes edema. Similarly, PA in combination with LF forms lethal toxin (LT) (1, 5).

PA is the primary immunogen and key component of human vaccines produced and licensed in the United Kingdom and United States. The current U.S. vaccine (BioThrax; BioPort Corp.) consists of an alum-absorbed, formalin-treated culture supernatant of a toxigenic, nonencapsulated strain of *B. anthracis*. The British anthrax vaccine is produced from supernatant of a static culture of the Sterne strain, a nonencapsulated toxigenic variant of *B. anthracis*, adsorbed to aluminum salts. These vaccines contain predominantly PA, but also small quantities of LF and trace amounts of EF (31). These traces of LF and EF may contribute to the vaccine side effects, such as local pain and edema (19), and relatively high rates of local and systemic reactions, including inflammation, flu-like symptoms, malaise, rash, arthralgia, and headache (14, 29). Therefore, an effective expression system that can provide a clean, safe, and efficacious vaccine is required. Recombinant PA has been expressed in *Escherichia coli* (15), *Lactobacillus casei* (32), and *Salmonella enterica* serovar Typhimurium (6). Expression of PA in plants through chloroplast transformation has several advantages over bacterial and mammalian expression systems. Foreign proteins have been expressed at extraordinarily high levels in transgenic chloroplasts due to the presence of 10,000 copies of the chloroplast genomes per cell. These include A T-rich proteins such as Cry2a (67% AT) at 47% of the total soluble protein (TSP) (11), cholera toxin B chain fusion protein (59% AT) at 33% TSP (23), and human serum albumin (66% AT) up to 11.1% TSP (12). Therefore, we first tested the feasibility of expressing PA in transgenic chloroplasts (30), but no further studies were possible because no tag was used in that study to facilitate purification. In addition to high levels of transgene expression, there are several other advantages to chloroplast genetic engineering. Several genes can be introduced in a single trans-formation event to facilitate development of multivalent vaccines (11, 28). Gene silencing is a common concern in nuclear transformation, but this has not been observed in transgenic chloroplasts in spite of hyperexpression of transgenes (11).

There is minimal risk of animal or human pathogens contaminating the vaccine as seen with mammalian expression systems. Additionally, chloroplast expression systems minimize cross-pollination of the transgene due to the maternal inheritance of the chloroplast genome (8). In this study, we expressed PA with a histidine tag in transgenic chloroplasts, characterized the resultant transgenic plants, and performed immunization studies. We compared the efficacy of the plant-derived PA with that of PA derived from *B. anthracis* in both in vitro and in vivo studies.

Materials and Methods

Construction of pLD-VK1 Vector for Chloroplast Transformation.

The six histidine tag (SEQ ID NO: 14) and the factor Xa cleavage site with NdeI and XhoI restriction sites were introduced N terminal to pagA using PCR (FIG. 52a). The PCR-amplified region was sequenced and shown to match corresponding pagA database sequences (accession no. AY700758). The PCR product was then cloned into pCR2.1 vector containing the psbA 5' untranslated region (UTR). Finally, the fragment containing the 5' UTR, His tag, and pagA was cloned into tobacco universal vector pLD-ctv to produce pLD-VK1 (FIG. 52a).

Leaf Bombardment and Selection Protocol.

Microprojectiles coated with plasmid DNA (pLD-VK1) were bombarded into *Nicotiana tabacum* var. petit Havana leaves using the biolistic device PDS1000/He (Bio-Rad) as described elsewhere (9). Following incubation at 24° C. in the dark for 2 days, the leaves were cut into small (~5 mm by 5 mm) pieces and placed abaxial side up (five pieces/plate) on selection medium (RMOP [regeneration medium of plants] containing 500 mg/liter spectinomycin dihydrochloride [9]). Spectinomycin-resistant shoots obtained after about 6 weeks were cut into small pieces (~2 mm by 2 mm) and placed on plates containing the same selection medium.

Confirmation of Transgene Integration into the Chloroplast Genome.

To confirm the transgene cassette integration into the chloroplast genome, PCR was performed using the primer pairs 3P (5'-AAAACCCGTCCTCCGTTCGGATTGC-3' (SEQ ID NO: 11)) and 3 M (5'-CCGCGTTGTTTCAT-CAAG-CCTTACG-3' (SEQ ID NO: 3)) (10), and to confirm the integration of gene of interest, PCR was performed using primer pairs 5P (5'-CTGTAGAAGTCACCATTGTTGTGC-3' (SEQ ID NO: 4)) and 2 M (5'-TGACT GCCCACCTGA-GAGCGGACA-3' (SEQ ID NO: 12)) (10).

Southern Blot Analysis.

Two micrograms of plant DNA per sample (isolated using DNeasy kit) digested with BglII was separated on a 0.7% (wt/vol) agarose gel and transferred to a nylon membrane. The chloroplast vector DNA digested with BglII and BamHI generated a 0.8-kb probe homologous to the flanking sequences. Hybridization was performed using the Ready-To-Go protocol (Pharmacia).

Immunoblot Analysis.

Transformed and untransformed leaves (100 mg) were ground in liquid nitrogen and resuspended in 500 µl of extraction buffer (200 mM Tris-HCl, pH 8.0, 100 mM NaCl, 10 mM EDTA, 2 mM phenylmethylsulfonylfluoride). Leaf crude extracts, boiled (4 min) or unboiled, in sample buffer (Bio-Rad) were subjected to sodium dodecyl sulfate-polyacrylamide gel electrophoresis (SDS-PAGE). Thirty percent acrylamide Bis solution (Bio-Rad) was used to make the 10% gels. The gel was run in 1× electrode buffer (10× electrode buffer is 30.3 g Tris base, 144.0 g glycine, and 10.0 g SDS added to 1,000 ml distilled water). The separated proteins were then transferred to nitrocellulose, and Western blot analyses was performed using anti-PA primary antibody (Immunochemical labs) diluted in phosphate-buffered saline (PBS)-0.1% Tween-3% milk powder (PTM) (1:20,000) and secondary horseradish peroxidase (HRP)-conjugated goat anti-mouse immunoglobulin G (IgG) (Sigma) diluted in PTM (1:5,000) followed by washing with PBS and finally incubated with Lumiphos WB (Pierce) as a substrate for HRP at room temperature for 5 min for chemiluminescence.

ELISA for PA.

Leaf samples (100 mg of young, mature, or old leaves) were collected from plants exposed to regular (16 h of light and 8 h of dark) or continuous illumination. The extraction buffer (15 mM $Na_2CO_3$, 35 mM $NaHCO_3$, 3 mM $NaN_3$, pH 9.6, 0.1% Tween, 5 mM phenylmethylsulfonyl fluoride) was used to isolate plant protein. All dilutions were made in the coating buffer (15 mM $Na_2CO_3$, 35 mM $NaHCO_3$, 3 mM $NaN_3$, pH 9.6). Antibodies were used at dilutions similar to those in the Western blotting protocol. Wells were then loaded with 100 μl of 3,3,5,5-tetramethylbenzidine (TMB; American Qualex) substrate and incubated for 10 to 15 min at room temperature. The reaction was terminated by adding 50 μl of 2 N $H_2SO_4$ per well, and the plate was read on a plate reader (Dynex Technologies) at 450 nm.

Purification of His-Tagged PA by Affinity Chromatography.

His affinity chromatography using nickel-chelate-charged columns (Amersham Biosciences) was used to purify His-tagged PA as per the manufacturer's protocol. The buffers used for purification include the following: binding buffer, 20 mM $Na_2HPO_4$, 0.5 M NaCl, 10 mM imidazole, pH 7.4; elution buffer, 20 mM $Na_2HPO_4$, 0.5 M NaCl, 0.5 M imidazole, pH 7.4; and Ni-loading eluent, 100 mM $NiSO_4$ solution (Sigma). Protein samples were analyzed for PA using enzyme-linked immunosorbent assay (ELISA). Eluate fractions containing purified PA were pooled together and dialyzed against PBS, pH 7.4, using dialysis cassettes (molecular weight, 10,000; Pierce) and concentrated using Centricon 10,000-molecularweight-cutoff ultrafiltration units (Millipore) following the manufacturer's protocols.

Macrophage Lysis Assay.

Macrophage lysis assays were performed on the crude leaf extracts, partially purified chloroplast-derived PA, and *B. anthracis*-derived PA. RAW264.7 macrophage cells were plated in 96-well plates in 120 μl Dulbecco's modified Eagle's medium and grown to 50% confluence. The plant samples or solutions containing 20 μg/ml of the purified PA proteins were diluted serially 3.14-fold in a separate 96-well plate and then transferred onto the RAW264.7 cells in such a way that the top row had plant extract at a 1:50 dilution and PA at 0.4 μg/ml. Cells were incubated with LT for 2.5 h, and the cell viability was assessed by addition of MTT [3-(4,5-dimethylthiazo-2-yl)-2,5-diphenyltetrazolium bromide] (Sigma, St. Louis, Mo.) at a final concentration of 0.5 mg/ml. Cells were then further incubated with MTT for 40 min, and the blue pigment produced by viable cells was dissolved by aspirating the medium and adding 50 μl/well of a mixture containing 0.5% (wt/vol) SDS and 25 mM HCl in 90% (vol/vol) isopropanol and shaking the plates for 5 min prior to reading at 570 nm using a microplate reader. Control plates received medium with no LF to test toxicity of plant material and buffers.

Immunization Studies in Mice.

The immunization studies were conducted in accordance with federal and institutional guidelines. Seven groups of five female 6- to 7-week-old BALB/c mice (Charles River) were immunized subcutaneously (s.c.; 5 μg PA) at two sites (100 μl per site) on day 0. The groups include mice immunized with (i) chloroplast-derived PA (CpPA) with adjuvant, (ii) chloroplast-derived PA (CpPA) alone, (iii) Std. PA derived from *B. anthracis* with adjuvant, (iv) Std-PA alone (26), (v) PA plant leaf crude extract with adjuvant, or (vi) wild-type plant leaf crude extract with adjuvant and (vii) unimmunized mice. The measurement of PA adsorbed to alhydrogel was done as described previously (20). Booster doses were administered on day 14, day 28, and day 140. Blood was drawn from the retro-orbital plexus 15 days after the third and fourth doses (i.e., on days 43 and 155 of post-initial immunization). The blood samples were allowed to stay undisturbed for 2 h at room temperature, stored at 4° C. overnight, and centrifuged at 3,000 rpm for 10 min to extract the serum.

ELISA to Detect the Anti-PA IgG Antibodies in the Serum Samples.

Ninety-six well microtiter ELISA plates were coated with 100 μl/well of PA standard at a concentration of 2.0_g/ml in PBS, pH 7.4. The plates were stored overnight at 4° C. The serum samples from the mouse were serially diluted (1:100 to 1:640,000). Plates were incubated with 100 μl of diluted serum samples for 1 h at 37° C. followed by washing with PBS-Tween. The plates were then incubated for 1 h at 37° C. with 100 μl of HRP-conjugated goat anti-mouse IgG (1:5,000 dilution of 1-mg/ml stock). TMB was used as the substrate, and the reaction was stopped by adding 50 μl of 2 M sulfuric acid. The plates were read on a plate reader (Dynex Technologies) at 450 nm. Titer values were calculated using a cutoff value equal to an absorbance difference of 0.5 between immunized and unimmunized mice (25).

Toxin Neutralization Assays.

Sera from immunized mice were tested for neutralization in the macrophage cytotoxicity assay described above. LT (PA plus LF) was added at 50 ng/ml in Dulbecco's modified Eagle's medium to 96-well plates (100 μl/well, except 150 μl in first well). Serum from each mouse was diluted directly into the LT plates starting at 1:150 and proceeding in 3.14-fold dilutions. Each serum was tested in triplicate. Following a 30-min incubation of sera with toxin, 90 μl of the mixture was moved to a 96-well plate containing RAW264.7 cells grown to 90% confluence and incubated for 5 h at 37° C. MTT was then added (final concentration, 0.5 mg/ml), and cell death was assessed as described above. Neutralization curves were plotted, and 50% effective concentrations (EC50s) were calculated for the averaged data from each mouse serum using GraphPad Prism 4.0 software.

Toxin Challenge in Mice.

Groups of five mice with various immunization treatments described above were injected intraperitoneally with 150 μg LT (150 μg LF plus 150 μg PA) in sterile PBS (1 ml). Mice were monitored every 8 h for signs of malaise and mortality.

Results and Discussion

Chloroplast Vector Design.

The pLD-VK1 vector (FIG. 52*a*) contains homologous sequences that facilitate recombination of the pag gene cassette between the trnI and trnA genes of the native chloroplast genome (9). The constitutive 16S rRNA promoter regulates expression of the aadA (aminoglycoside 3' adenyltransferase) gene. The pagA gene is regulated by the psbA promoter and 5' and 3' UTRs. The psbA 5'UTR has several sequences for ribosomal binding that act as a scaffold for the light-regulated proteins involved in ribosomal binding to enhance translation (12), and the psbA 3'UTR serves to stabilize the transcript.

Demonstration of Transgene Integration.

Several shoots appeared 5 to 6 weeks after the bombardment of tobacco leaves with gold particles coated with the pLD-VK1 plasmid DNA (FIG. 52a). There are three genetic events that can lead to survival of shoots on the selective medium: chloroplast integration, nuclear integration, or spontaneous mutation of the 16S rRNA gene to confer resistance to spectinomycin in the ribosome. True chloroplast transformants were distinguished from nuclear transformants and spontaneous spectinomycin resistance mutants by PCR. Previously described primers, 3P and 3M, were used to test for chloroplast integration of transgenes (9). The 3P primer anneals to the native chloroplast genome within the 16S rRNA gene. The 3M primer anneals to the aadA gene (FIG. 52a). Nuclear transformants could be distinguished because 3P will not anneal and mutants were identified because 3M will not anneal. Thus, the 3P and 3M primers will only yield a product (1.65 kb) from true chloroplast integrants (FIG. 52c).

The integration of the transgenes was further tested by using the 5P and 2M primer pairs for PCR analysis. The 5P and 2M primers anneal to the internal region of the aadA gene and the internal region of the trnA gene, respectively, as shown in FIG. 52a (9). The product size of a positive clone is 3.9 kb for PA, while the mutants and the control do not show any product. FIG. 52d shows the result of the 5P/2M PCR analysis. After PCR analysis using both primer pairs, the transgenic plants were subsequently transferred through different rounds of selection to obtain mature plants and reach homoplasmy.

Southern Blot Analysis of Transgenic Plants.

The plants that tested positive by PCR analysis were moved through three rounds of selection and were then evaluated by Southern analysis. The flanking sequence probe (0.81 kb, FIG. 52b) allowed detection of the site-specific integration of the gene cassette into the chloroplast genome (9). FIG. 52a shows the BglII sites used for the restriction digestion of the chloroplast DNA for pLD-VK1. The transformed chloroplast genome digested with BglII produced fragments of 5.2 kb and 3.0 kb for pLDVK1 (FIG. 52e), while the untransformed chloroplast genome that had been digested with BglII formed a 4.4-kb fragment. The flanking sequence probe can also show if homoplasmy of the chloroplast genome had been achieved through the three rounds of selection. The plants expressing PA showed slight degree of heteroplasmy in one or two transgenic lines, as few of the wild-type genomes were not transformed. This is not uncommon and could be eliminated by germinating seeds on stringent selection medium containing 500 µg/ml spectinomycin. The gene-specific probe with a size of approximately 0.52 kb was used to show the specific gene integration producing a 3-kb fragment containing the pagA gene as shown in FIG. 52f.

Immunoblot Detection of PA Expression.

To determine whether the transgenic plants were producing PA, immunoblot analysis was performed on leaf extracts. Probing blots with anti-PA monoclonal antibody revealed full-length 83-kDa protein (FIG. 53a). PA has protease-sensitive sequences at residues 164 and 314 that are easily cleaved by trypsin and chymotrypsin, respectively, resulting in polypeptides of 63 kDa and 20 kDa (for trypsin) or 47 kDa and 37 kDa (for chymotrypsin).

The absence of these or other such bands demonstrates that PA is intact within the chloroplast (FIG. 53a). The supernatant samples from wild-type plants did not show any band, indicating that anti-PA antibodies did not cross-react with any plant proteins in the crude extract.

Quantification of PA using ELISA.

The PA protein expression levels of pLD-VK1 plants of T0 generation reached up to 4.5% of TSP in mature leaves under normal illumination conditions (16 h of light and 8 h of dark, FIG. 53b). The psbA regulatory sequences, including the promoters and UTRs, have been shown to enhance translation and accumulation of foreign proteins under continuous light (12). Therefore, the pLD-VK1 transgenic lines were exposed to continuous light an expression patterns were determined on days 1, 3, 5, and 7 (FIG. 53b). PA expression levels reached a maximum of 14.2% of the TSP in mature leaves at the end of day 5 and the expression levels declined to 11.7% TSP on day 7. The larger amount of PA in mature leaves is probably due to the high number of chloroplasts in mature leaves and the high copy number of chloroplast genomes (up to 10,000 copies per cell). The decrease in PA expression in bleached old leaves could be due to degradation of the proteins during senescence. These results show that approximately 1.8 mg PA can be obtained per gram fresh weight of mature leaf upon exposure to 5-day continuous illumination. Thus, approximately 150 mg of PA can be obtained from a single plant and with 8,000 tobacco plants on an acre of land, 1.2 kg of PA can be obtained per single cutting of tobacco plant (petit Havana variety, Table 1). Upon three cuttings in a year, a total of 3.6 kg of PA can be obtained. Assuming a loss of 50% during purification and 5 µg PA per dose (current vaccine dose is in a range of 1.75 to 7 µg PA) (17), a total of 360 million doses of vaccine can be obtained per acre of land. The commercial cultivar yields 40 metric tons biomass of fresh leaves as opposed to 2.2 tons in experimental cultivar petit Havana (7). Therefore, the commercial cultivar is expected to give 18-fold-higher yields than the experimental cultivar. Thus an acre of land grown with transgenic tobacco plants would yield vaccine sufficient for a very large population.

Functional Analysis of PA with Macrophage Cytotoxicity Assay.

FIG. 54a shows the Coomassie-stained gel of crude leaf extracts and various purification fractions and the absence of PA in the flowthrough. The expression level of PA is so high that it can be observed in a Coomassie-stained gel even in crude plant extracts. FIG. 54b is a Coomassie-stained gel showing fractions of purified and concentrated chloroplast derived PA used for immunization studies. Supernatant samples from crude extracts of plant leaves expressing PA and partially purified chloroplast-derived PA were tested for functionality in vitro using the well-defined macrophage lysis assay (16). The transgenic plants were shown to produce fully functional PA (FIG. 55). Crude extracts of wild-type tobacco plant and plant extraction buffer were used as negative controls. The crude extract of plant leaves expressing PA had activity equal to that of a 20-µg/ml solution of purified B. anthracis-derived PA. These results show that the PA expressed in plants has high functional activity.

Immunization of BALB/c Mice.

Having confirmed that the chloroplast-derived PA has in vitro biological activity comparable to that of the B. anthracis-derived PA, we proceeded further to investigate the functionality in vivo. For this, seven groups each consisting of five mice were injected s.c. with 5 µg of the antigen on days 0, 14, 28, and 140. The group 1 and group 2 mice, immunized with chloroplast-derived partially purified PA and with B. anthracis-derived fully purified PA, respectively, both adsorbed to alhydrogel adjuvant, showed comparable IgG immune titers of about 1:300,000 (FIG. 56a).

These observations are comparable to those of earlier studies where anti-PA titers up to 1:250,000 were observed in guinea pigs immunized with PA along with adjuvant (4). The observation that the chloroplast-derived PA and PA derived from *B. anthracis* show comparable immune responses suggests that the plant-derived PA has been properly folded and was fully functional. The group that received partially purified chloroplast-derived PA without adjuvant showed titers ranging from 1:10,000 to 1:40,000, while the mice that received PA derived from *B. anthracis* without adjuvant showed titers of 1:80,000 to 1:160,000. Previous studies showed that mice immunized s.c. with recombinant PA (rPA) derived from *B. anthracis* along with the adjuvant had significant antibody titers, while no significant immune response was observed in the group immunized with PA alone (13). Similarly, guinea pigs immunized s.c. with rPA derived from *B. subtilis* did not elicit a significant IgG immune response, while rPA with alhydrogel adjuvant showed significant levels of IgG titers above 1:15,000 (20). Taken together, these studies show that PA alone may not be a potent immunogen to elicit a significant immune response and therefore all currently used anthrax vaccines contain an adjuvant.

The difference between the immune responses between the two groups immunized with chloroplast-derived PA and *B. anthracis*-derived PA could be due to differences in the purities of the proteins. The level of purity was extremely high in PA derived from *B. anthracis* because of the use of anion-exchange and gel filtration chromatography and fast protein liquid chromatography (FPLC) to eliminate the breakdown products of the PA (21), whereas chloroplast-derived PA was purified by affinity chromatography without using protease inhibitors. In the presence of adjuvant, PA binds to the alhydrogel via electrostatic forces (21), making it more stable against proteolytic degradation. Differences in the titer values of the groups that received PA with and without adjuvant were probably due to depot effect (2) and due to the alhydrogel's nonspecific priming of the immune system. The group that received transgenic plant crude extracts expressing PA with adjuvant showed IgG titers ranging from 1:40,000 to 1:80,000. In spite of significant levels of impurities in the crude extract, this group showed good immune titers, confirming high expression levels of PA in transgenic leaves.

Toxin Neutralization Assay of Serum Samples.

In order to evaluate the functionality of the IgG antibodies produced in response to the immunization, sera from the mice were tested for their ability to neutralize PA and thereby protect macrophages against LT killing Toxin neutralization assays were performed on two different sets of sera. The first set was drawn 15 days after the third immunization dose (day 43 of post initial immunization), and the second set was drawn 15 days after the fourth immunization dose (day 155 of post-initial immunization). Sera obtained after the third dose (FIG. 56b) showed similar neutralization titers for the mice immunized with chloroplast-derived PA or *B. anthracis*-derived PA when both proteins were administered with adjuvant (1:10,000 to 1:100,000). These observations are in agreement with the results obtained in earlier studies where neutralization titers of 20,000 to 70,000 were obtained when guinea pigs were immunized with PA derived from *B. anthracis* along with adjuvant (4). However, titers were slightly higher for *B. anthracis*-derived PA used in conjunction with adjuvant in bleeds after the fourth immunization (FIG. 56c). The mice immunized with chloroplast-derived PA alone showed significantly smaller neutralization titers (between 1:100 and 1:1,000) than the mice immunized with *B. anthracis*-derived PA alone (1:10,000 to 1:200,000 after the third immunization and 1:10,000 to 1:50,000 after the fourth immunization, FIGS. 56b and c). Mice immunized with the crude extracts of PA-expressing leaves showed strong neutralization titers, ranging from 1:500 to 1:7500, with the exception of a single mouse after the fourth immunization (FIG. 56c). Control mice immunized with wild-type plant leaf crude extract or PBS did not show any immune response or neutralization ability. Generally, the average neutralization titers compared among different groups showed similar distribution patterns to that of the average anti-PA immune titers determined by the ELISA. These results show that there is good correlation between the anti-PA antibody levels and neutralization titers.

Toxin Challenge of BALB/c Mice.

We proceeded to test the immunized mice for their ability to survive challenge with 1.5×100% lethal dose (LD100) of LT (22). Mice immunized with the chloroplast or *B. anthracis*-derived PA with adjuvant survived the toxin challenge. Mice immunized with crude extracts of plants expressing PA showed a significant survival rate of 80%, confirming high PA expression levels. In this group, 4 out of 5 mice showed neutralization titers above 1:1,000. These studies demonstrate the immunoprotective properties of chloroplast-derived PA against anthrax LT challenge. The single mouse in this group that showed a neutralization titer below 1:150 may have been the one to succumb. None of the mice immunized with chloroplast-derived PA without adjuvant survived (FIG. 57), as expected from their low neutralization titers (FIGS. 56b and c). The comparison of neutralization titers to mouse challenge survival for all the groups seems to indicate neutralization titers at and above 1:1,000 result in protection against challenge with greater than LD100 doses of LT. These results prove the immunogenic and immunoprotective properties of plant-derived *B. anthracis* PA. Prior studies did not investigate functionality of plant-derived PA in animal studies (3, 30). The production of anti-PA IgG antibodies combined with in vitro neutralization and toxin challenge studies shows that immunization with transgenic chloroplast-derived PA is highly effective. Plant-derived recombinant PA is free of EF and LF and easy to produce, without the need for expensive fermenters. Even with 50% loss during purification, 1 acre of transgenic plants can produce 360 million doses of functional anthrax vaccine. Our studies open the door for possible oral immunization through feeding of edible plant parts like carrot roots, which should effectively stimulate the mucosal immune system as well as a systemic immune response, thereby offering better protection against pathogens that attack through mucosa. Delivering vaccines in edible plants can potentially eliminate existing vaccine purification and processing steps, cold storage and transportation requirements, and the need for health professionals for vaccine delivery. Although foreign genes have been expressed in chromoplasts of edible plant parts (18), there is no report of expressing vaccine antigens in non-green plastids present within edible tissues so far. In addition to maternal inheritance of transgenes engineered via the chloroplast genomes (8), cytoplasmic male sterility has been developed as another fail-safe mechanism for biological containment of transgenes (27). Furthermore, successful engineering of several foreign operons via the chloroplast genome (24) has opened the door for development of multivalent vaccines.

REFERENCES

1. Ascenzi, P., P. Visca, G. Ippolito, A. Spallarossa, M. Bolognesi, and C. Montecucco. 2002. Anthrax toxin: a tripartite lethal combination. FEBS Lett. 531:384-388.

2. Audibert, F. 2003. Adjuvants for vaccines, a quest. Int. Immunopharmacol. 3:1187-1193.
3. Aziz, M. A., S. Singh, P. Anand Kumar, and R. Bhatnagar. 2002. Expression of protective antigen in transgenic plants: a step towards edible vaccine against anthrax. Biochem. Biophys. Res. Commun 299:345-351.
4. Cohen, S., I. Mendelson, Z. Altboum, D. Kobiler, E. Elhanany, T. Bino, M. Leitner, I. Inbar, H. Rosenberg, Y. Gozes, R. Barak, M. Fisher, C. Kronman, B. Velan, and A. Shafferman. 2000. Attenuated nontoxinogenic and non-encapsulated recombinant Bacillus anthracis spore vaccines protect against anthrax. Infect. Immun 68:4549-4558.
5. Collier, R. J., and J. A. Young. 2003. Anthrax toxin. Annu. Rev. Cell Dev. Biol. 19:45-70.
6. Coulson, N. M., M. Fulop, and R. W. Titball. 1994. Bacillus anthracis protective antigen, expressed in Salmonella typhimurium SL 3261, affords protection against anthrax spore challenge. Vaccine 12:1395-1401.
7. Cramer, C. L., J. G. Boothe, and K. K. Oishi. 1999. Transgenic plants for therapeutic proteins: linking upstream and down stream strategies. Curr. Top. Microbiol. Immunol. 240:95-118.
8. Daniell, H. 2002. Molecular strategies for gene containment in transgenic crops. Nat. Biotechnol. 20:581-587.
9. Daniell, H., A. Dhingra, and O. N. Ruiz. 2004. Chloroplast genetic engineering to confer desired plant traits. Methods Mol. Biol. 286:111-137.
10. Daniell, H., S. B. Lee, T. Panchal, and P. O. Wiebe. 2001. Expression of cholera toxin B subunit gene and assembly as functional oligomers in transgenic tobacco chloroplasts. J. Mol. Biol. 311:1001-1009.
11. DeCosa, B., W. Moar, S. B. Lee, M. Miller, and H. Daniell. 2001. Overexpression of the Btcry2Aa2 operon in chloroplasts leads to formation of insecticidal crystals. Nat. Biotechnol. 19:71-74.
12. Fernandez-San Millan, A., A. M. Mingeo-Castel, M. Miller, and H. Daniell. 2003. A chloroplast transgenic approach to hyper-express and purify human serum albumin, a protein highly susceptible to proteolytic degradation. Plant Biotechnol. J. 1:71-79.
13. Gaur, R., P. K. Gupta, A. C. Banerjea, and Y. Singh. 2002. Effect of nasal immunization with protective antigen of Bacillus anthracis on protective immune response against anthrax toxin. Vaccine 20:2836-2839.
14. Geier, D. A., and R. M. Geier. 2002. Anthrax vaccination and joint related adverse reactions in light of biological warfare scenarios. Clin. Exp. Rheumatol. 20:217-220.
15. Gupta, P., S. M. Waheed, and R. Bhatnagar. 1999. Expression and purification of the recombinant protective antigen of Bacillus anthracis. Protein Expr. Purif. 16:369-376.
16. Hanna, P. C., D. Acosta, and R. J. Collier. 1993. On the role of macrophages in anthrax. Proc. Natl. Acad. Sci. USA 90:10198-10201.
17. Kaufmann, A. F., M. I. Meltzer, and G. P. Schmid. 1997. The economic impact of a bioterrorist attack: are prevention and postattack intervention programs justifiable? Emerg. Infect. Dis. 3:83-94.
18. Kumar, S., A. Dhingra, and H. Daniell. 2004. Plastid-expressed betainealdehyde dehydrogenase gene in carrot cultured cells, roots, and leaves confers enhanced salt tolerance. Plant Physiol. 136:2843-2854.
19. Leppla, S. H., J. B. Robbins, R. Schneerson, and J. Shiloach. 2002. Development of an improved vaccine for anthrax. J. Clin. Investig. 109:141-144.
20. McBride, B. W., A. Mogg, J. L. Telfer, M. S. Lever, J. Miller, P. C. Turnbull, and L. Baillie. 1998. Protective efficacy of a recombinant protective antigen against Bacillus anthracis challenge and assessment of immunological markers. Vaccine 16:810-817.
21. Miller, J., B. W. McBride, R. J. Manchee, P. Moore, and L. W. J. Baillie. 1998. Production and purification of recombinant protective antigen and protective efficacy against Bacillus anthracis. Lett. Appl. Microbiol. 26:56-60.
22. Moayeri, M., N. W. Martinez, J. Wiggins, H. A. Young, and S. H. Leppla. 2004. Mouse susceptibility to anthrax lethal toxin is influenced by genetic factors in addition to those controlling macrophage sensitivity. Infect. Immun 72:4439-4447.
23. Molina, A., S. Herva-Stubbs, H. Daniell, A. M. Mingo-Castel, and J. Veramendi. 2004. High yield expression of a viral peptide animal vaccine in transgenic tobacco chloroplasts. Plant Biotechnol. J. 2:141-153.
24. Quesada-Vargas, T., O. N. Ruiz, and H. Daniell. 2005. Characterization of heterologous multigene operons in transgenic chloroplasts: transcription, processing, translation. Plant Physiol. 138:1746-1762.
25. Quinn, C. P., V. A. Semenova, C. M. Elie, S. Romero-Steiner, C. Greene et al. 2002. Specific, sensitive, and quantitative enzyme-linked immunosorbent assay for human immunoglobulin G antibodies to anthrax toxin protective antigen. Emerg. Infect. Dis. 8:1103-1110.
26. Ramirez, D. M., S. H. Leppla, R. Schneerson, and J. Shiloach. 2002. Production, recovery and immunogenicity of the protective antigen from a recombinant strain of Bacillus anthracis. J. Ind. Microbiol. Biotechnol. 28: 232-238.
27. Ruiz, O. N., and H. Daniell. 2005. Engineering cytoplasmic male sterility via the chloroplast genome. Plant Physiol. 138:1232-1246.
28. Ruiz, O. N., H. Hussein, N. Terry, and H. Daniell. 2003. Phytoremediation of organomercurial compounds via chloroplast genetic engineering. Plant Physiol. 132:1344-1352.
29. Sever, J. L., A. I. Brenner, A. D. Gale, J. M. Lyle, L. H. Moulton et al. 2002. Safety of anthrax vaccine: a review by the Anthrax Vaccine Expert Committee (AVEC) of adverse events reported to the Vaccine Adverse Event Reporting System (VAERS). Pharmacoepidemiol. Drug Saf. 11:189-202.
30. Watson, J., V. Koya, S. H. Leppla, and H. Daniell. 2004. Expression of Bacillus anthracis protective antigem in transgenic chloroplasts of tobacco, a non-food/feed crop. Vaccine 22:4374-4384.
31. Whiting, G. C., S. Rijpkema, T. Adams and M. J. Corbel. 2004. Characterisation of adsorbed anthrax vaccine by two-dimensional gel electrophoresis. Vaccine 22:4245-4251.
32. Zegers, N. D., E. Kluter, H. van Der Stap, E. van Dura, P. van Dalen, M. Shaw, and L. Baillie. 1999. Expression of the protective antigen of Bacillus anthracis by Lactobacillus casei: towards the development of an oral vaccine against anthrax. J. Appl. Microbiol. 87:309-314.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

What is claimed is:

1. A method of retarding the development of diabetes in a subject in need thereof comprising providing a composition comprising a Cholera toxin subunit B (CTB) proinsulin (Pins) fusion polypeptide and at least one chloroplast genome having a transgene inserted therein that encodes said fusion polypeptide and administering to said subject said composition; wherein said fusion polypeptide comprises pro-insulin consisting of an insulin A-chain, an insulin B-chain and an insulin C-peptide; and a furin cleavage site located between said CTB and proinsulin on the fusion polypeptide, said furin site increasing the efficiency of processing of proinsulin to mature insulin during receptor mediated delivery, said Cholera toxin subunit B proinsulin fusion polypeptide being effective to increase recruitment of IL-10 or IL-4 producing cells to the pancreas and induce tolerance in said subject.

2. The method of claim 1, wherein said fusion polypeptide comprises a furin cleavage site located between said insulin A-chain and said insulin C-peptide.

3. The method of claim 1, wherein said fusion polypeptide comprises a furin cleavage site located between said insulin B-chain and said insulin C-peptide.

4. The method of claim 1, wherein said fusion polypeptide is effective to reduce expression of caspase-3 and apoptosis in pancreatic beta cells in said subject.

5. The method of claim 4 comprising determining caspase-3 levels following delivery of said fusion protein to said subject.

* * * * *